US010253027B2

(12) United States Patent
Hartz et al.

(10) Patent No.: US 10,253,027 B2
(45) Date of Patent: Apr. 9, 2019

(54) ARYL LACTAM KINASE INHIBITORS

(71) Applicant: Bristol-Myers Squibb Company, Princeton, NJ (US)

(72) Inventors: Richard A. Hartz, Middletown, CT (US); Vijay T. Ahuja, Princeton, NJ (US); Joanne J. Bronson, Durham, CT (US); Carolyn Diane Dzierba, Middletown, CT (US); John E. Macor, Washington Crossing, PA (US); Susheel Jethanand Nara, Mumbai (IN); Ramkumar Rajamani, Woodbridge, CT (US)

(73) Assignees: Bristol-Myers Squibb Company, Princeton, NJ (US); Syngene International Limited, Bangalore (IN); Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/902,868

(22) PCT Filed: Jul. 1, 2014

(86) PCT No.: PCT/US2014/045075
§ 371 (c)(1),
(2) Date: Jan. 5, 2016

(87) PCT Pub. No.: WO2015/006100
PCT Pub. Date: Jan. 15, 2015

(65) Prior Publication Data
US 2016/0152621 A1 Jun. 2, 2016

Related U.S. Application Data

(60) Provisional application No. 61/843,588, filed on Jul. 8, 2013.

(51) Int. Cl.
| | | |
|---|---|---|
| *C07D 487/04* | (2006.01) |
| *C07D 409/10* | (2006.01) |
| *C07D 233/61* | (2006.01) |
| *C07D 401/12* | (2006.01) |
| *C07D 401/10* | (2006.01) |
| *C07D 263/32* | (2006.01) |
| *C07D 213/56* | (2006.01) |
| *C07D 285/12* | (2006.01) |
| *C07D 277/30* | (2006.01) |
| *C07D 213/73* | (2006.01) |
| *C07D 213/65* | (2006.01) |
| *C07D 249/08* | (2006.01) |
| *C07D 233/54* | (2006.01) |
| *C07D 249/06* | (2006.01) |
| *C07D 237/08* | (2006.01) |
| *C07D 213/72* | (2006.01) |
| *C07D 213/16* | (2006.01) |
| *C07D 285/08* | (2006.01) |
| *C07D 231/12* | (2006.01) |
| *C07D 213/62* | (2006.01) |
| *C07D 277/20* | (2006.01) |
| *C07D 213/61* | (2006.01) |
| *C07D 263/30* | (2006.01) |
| *C07D 413/12* | (2006.01) |
| *C07D 417/12* | (2006.01) |

(52) U.S. Cl.
CPC ......... *C07D 487/04* (2013.01); *C07D 213/16* (2013.01); *C07D 213/56* (2013.01); *C07D 213/61* (2013.01); *C07D 213/62* (2013.01); *C07D 213/65* (2013.01); *C07D 213/72* (2013.01); *C07D 213/73* (2013.01); *C07D 231/12* (2013.01); *C07D 233/54* (2013.01); *C07D 233/61* (2013.01); *C07D 237/08* (2013.01); *C07D 249/06* (2013.01); *C07D 249/08* (2013.01); *C07D 263/30* (2013.01); *C07D 263/32* (2013.01); *C07D 277/20* (2013.01); *C07D 277/30* (2013.01); *C07D 285/08* (2013.01); *C07D 285/12* (2013.01); *C07D 401/10* (2013.01); *C07D 401/12* (2013.01); *C07D 409/10* (2013.01); *C07D 413/12* (2013.01); *C07D 417/12* (2013.01)

(58) Field of Classification Search
CPC .. C07D 487/04; C07D 213/65; C07D 401/12; C07D 249/08; C07D 233/61; C07D 213/73; C07D 263/32; C07D 213/56; C07D 409/10; C07D 401/10; C07D 285/12; C07D 277/30; C07D 213/61; C07D 213/62; C07D 237/08; C07D 413/12; C07D 417/12; C07D 249/06; C07D 213/72; C07D 263/30; C07D 277/20; C07D 285/08; C07D 213/16; C07D 233/54; C07D 231/12; C07D 5/12; C07D 216/16
See application file for complete search history.

(56) References Cited

U.S. PATENT DOCUMENTS 4,317,827 A * 3/1982 Lesher ................. C07D 213/40
514/357

FOREIGN PATENT DOCUMENTS

| CN | 1733708 | 2/2006 |
| JP | 2007-217408 | 8/2007 |

(Continued)

OTHER PUBLICATIONS

RN 1309036-92-7.*

(Continued)

*Primary Examiner* — Kortney L. Klinkel
*Assistant Examiner* — Ibrahim D Bori
(74) *Attorney, Agent, or Firm* — Pamela A. Mingo

(57) ABSTRACT

The present disclosure is generally directed to compounds which can inhibit AAK1 (adaptor associated kinase 1), compositions comprising such compounds, and methods for inhibiting AAK1.

6 Claims, No Drawings

(56) References Cited

FOREIGN PATENT DOCUMENTS

| WO | WO 96/21464 | 7/1996 |
|---|---|---|
| WO | WO 03/086325 A2 | 10/2003 |
| WO | WO 2004/056745 A2 | 7/2004 |
| WO | WO 2004/072018 A1 | 8/2004 |
| WO | WO 2005/000309 A2 | 1/2005 |
| WO | WO 2006/012227 A2 | 2/2006 |
| WO | WO 2007/026910 A2 | 3/2007 |
| WO | WO 2007/117715 A2 | 10/2007 |
| WO | WO 2009/075874 A1 | 6/2009 |
| WO | WO 2009/079009 A1 | 6/2009 |
| WO | WO 2011/044195 A1 | 4/2011 |
| WO | WO 2011/044212 A1 | 4/2011 |
| WO | WO 2011/044225 A1 | 4/2011 |
| WO | WO 2013/134036 A1 | 9/2013 |
| WO | WO 2013/134336 A2 | 9/2013 |
| WO | WO 2014/022167 A1 | 2/2014 |
| WO | WO 2014/130258 A1 | 8/2014 |
| WO | WO 2015/026574 A1 | 2/2015 |
| WO | WO 2015/038112 A1 | 3/2015 |
| WO | WO 2015/116060 A1 | 8/2015 |
| WO | WO 2015/116492 A1 | 8/2015 |
| WO | WO 2015/153720 A1 | 10/2015 |
| WO | WO 2016/022312 A1 | 2/2016 |
| WO | WO 2016/053794 A1 | 4/2016 |

OTHER PUBLICATIONS

Chouliaras et al (Progress in Neurobiology, 2010, 90, 498-510).*
RN1308935-23-0 (Year: 2011).*
Buonanno, A., "The neuregulin signaling pathway and schizophrenia: From genes to synapses and neural circuits", Brain Research Bulletin, vol. 83, pp. 122-131 (2010).
Conner, S.D. et al., "AAK-1 Mediated µ2 Phosphorylation is Stimulated by Assembled Clathrin", Traffic, vol. 4, pp. 885-890 (2003).
Conner, S.D. et al., "Identification of an adaptor-associated kinase, AAK1, as a regulator of clathrin-mediated endocytosis", The Journal of Cell Biology, vol. 156, No. 5, pp. 921-929 (2002).
Greenwood, T.A. et al., "Analysis of 94 Candidate Genes and 12 Endophenotypes for Schizophrenia", Am. J. Psychiatry, vol. 168, No. 9, pp. 930-946 (2011).
Henderson, D.M. et al., "A Novel AAK1 Splice Variant Functions at Multiple Steps of the Endocytic Pathway", Molecular Biology of the Cell, vol. 18, pp. 2698-2706 (2007).
Jaaro-Peled, H. et al., "Review of Pathological Hallmarks of Schizophrenia: Comparison of Genetic Models with Patients and Nongenetic Models", Schizophrenia Bulletin, vol. 36, No. 2, pp. 301-313 (2010).
Jackson, A.P. et al., "Clathrin promotes incorporation of cargo into coated pits by activation of the AP2 adaptor µ2 kinase", The Journal of Cell Biology, vol. 163, No. 2, pp. 231-236 (2003).
Kuai, L. et al., "AAK1 Identified as an Inhibitor of Neuregulin-1/ErbB4-Dependent Neurotrophic Factor Signaling Using Integrative Chemical Genomics and Proteomics", Chemistry & Biology, vol. 18, pp. 891-906 (2011).
Latourelle, J.C. et al., "Genomewide association study for onset age in Parkinson disease", BMC Medical Genetics, 10:98 (2009).
Motley, A.M. et al., Functional Analysis of AP-2 α and µ2 Subunits, Molecular Biology of the Cell, vol. 17, pp. 5298-5308 (2006).
Ricotta, D. et al., "Phosphorylation of the AP2 µ subunit by AAK1 mediates high affinity binding to membrane protein sorting signals", The Journal of Cell Biology, vol. 156, No. 5, pp. 791-795 (2002).
Wen, L. et al., "Neuregulin 1 regulates pyramidal neuron activity via ErbB4 in parvalbumin-positive interneurons", Proc. Natl. Acad. Sci. USA, vol. 107, No. 3, pp. 1211-1216 (2010).
Ryan Scientific Chemical Catalog, Chem Abstracts RN 1308368-50-4.
Ryan Scientific Chemical Catalog, Chem Abstracts RN 1308935-23-0.
Registry(STN), Sep. 1, 2009, CAS registry No. 1178946-97-8.

* cited by examiner

ARYL LACTAM KINASE INHIBITORS

CROSS-REFERENCE TO RELATED APPLICATIONS

This application claims the benefit of U.S. Provisional Application Ser. No. 61/843,588, filed on Jul. 8, 2013, which is hereby incorporated by reference in its entirety.

The present disclosure is generally directed to compounds which can inhibit adaptor associated kinase 1 (AAK1), compositions comprising such compounds, and methods for inhibiting AAK1.

Adaptor associated kinase 1 (AAK1) is a member of the Ark1/Prk1 family of serine/threonine kinases. AAK1 mRNA exists in two splice forms termed short and long. The long form predominates and is highly expressed in brain and heart (Henderson and Conner, *Mol. Biol. Cell.* 2007, 18, 2698-2706). AAK1 is enriched in synaptosomal preparations and is co-localized with endocytic structures in cultured cells. AAK1 modulates clatherin coated endocytosis, a process that is important in synaptic vesicle recycling and receptor-mediated endocytosis. AAK1 associates with the AP2 complex, a hetero-tetramer which links receptor cargo to the clatherin coat. The binding of clatherin to AAK1 stimulates AAK1 kinase activity (Conner et. al., *Traffic* 2003, 4, 885-890; Jackson et. al., *J. Cell. Biol.* 2003, 163, 231-236). AAK1 phosphorylates the mu-2 subunit of AP-2, which promotes the binding of mu-2 to tyrosine containing sorting motifs on cargo receptors (Ricotta et. al., *J. Cell Bio.* 2002, 156, 791-795; Conner and Schmid, *J. Cell Bio.* 2002, 156, 921-929). Mu2 phosphorylation is not required for receptor uptake, but phosphorylation enhances the efficiency of internalization (Motely et. al., *Mol. Biol. Cell.* 2006, 17, 5298-5308).

AAK1 has been identified as an inhibitor of Neuregulin-1/ErbB4 signaling in PC12 cells. Loss of AAK1 expression through RNA interference mediated gene silencing or treatment with the kinase inhibitor K252a (which inhibits AAK1 kinase activity) results in the potentiation of Neuregulin-1 induced neurite outgrowth. These treatments result in increased expression of ErbB4 and accumulation of ErbB4 in or near the plasma membrane (Kuai et. al., *Chemistry and Biology* 2011, 18, 891-906). NRG1 and ErbB4 are putative schizophrenia susceptibility genes (Buonanno, *Brain Res. Bull.* 2010, 83, 122-131). SNPs in both genes have been associated with multiple schizophrenia endophenotypes (Greenwood et. al., *Am. J. Psychiatry* 2011, 168, 930-946). Neuregulin 1 and ErbB4 KO mouse models have shown schizophrenia relevant morphological changes and behavioral phenotypes (Jaaro-Peled et. al., *Schizophrenia Bulletin* 2010, 36, 301-313; Wen et. al., *Proc. Natl. Acad. Sci. USA.* 2010, 107, 1211-1216). In addition, a single nucleotide polymorphism in an intron of the AAK1 gene has been associated with the age of onset of Parkinson's disease (Latourelle et. al., *BMC Med. Genet.* 2009, 10, 98). These results suggest that inhibition of AAK1 activity may have utility in the treatment of schizophrenia, cognitive deficits in schizophrenia, Parkinson's disease, neuropathic pain, bipolar disorder, and Alzheimer's disease.

In a first aspect the present disclosure provides a compound of formula (I)

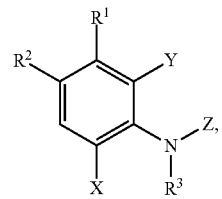

or a pharmaceutically acceptable salt thereof, wherein:

$R^1$ is selected from $C_1$-$C_3$alkoxy, $C_1$-$C_3$alkyl, cyano, $diC_1$-$C_3$alkylamino, halo, $haloC_1$-$C_3$alkoxy, $haloC_1$-$C_3$alkyl, hydroxy, and thienyl;

$R^2$ is selected from

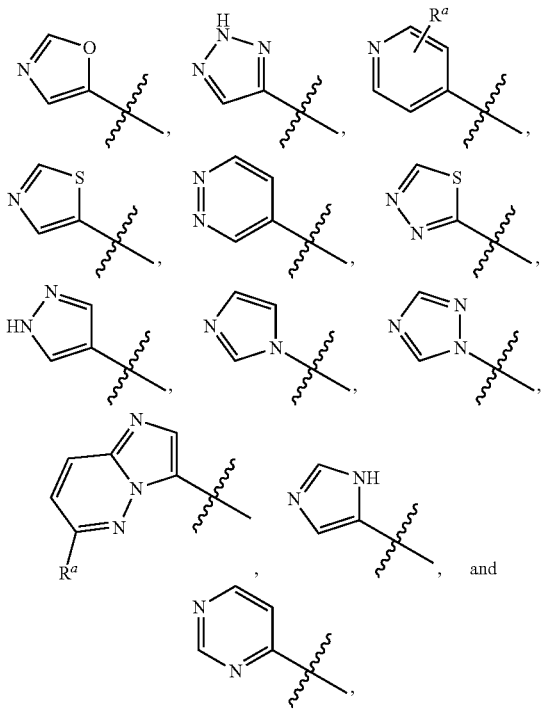

wherein $R^a$ is selected from hydrogen, $C_1$-$C_3$alkoxy, $C_1$-$C_3$alkylamino, $C_1$-$C_3$alkylcarbonylamino, amino, and halo;

$R^3$ is selected from hydrogen and $C_1$-$C_3$alkyl;

X is selected from hydrogen, $C_1$-$C_3$alkoxy, $C_1$-$C_3$alkyl, cyano, halo, $haloC_1$-$C_3$alkyl,

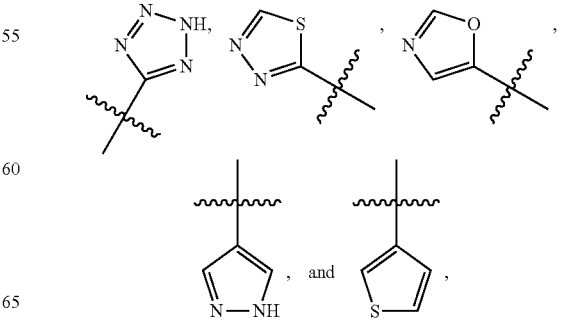

Y is selected from hydrogen and halo;

Z is selected from

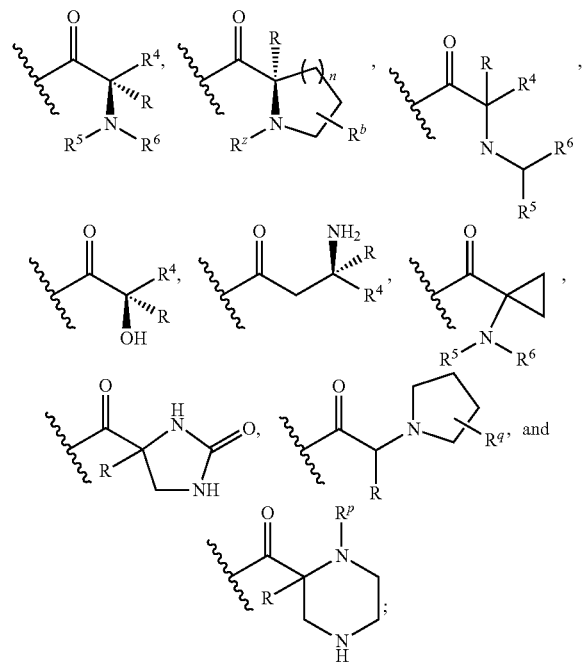

wherein n is 1 or 2;

R is selected from hydrogen and $C_1$-$C_3$alkyl;

$R^4$ is selected from $C_2$-$C_6$alkyl, $C_3$-$C_6$cycloalkyl, ($C_3$-$C_6$cycloalkyl)$C_1$-$C_3$ alkyl, $C_{1-3}$ alkylthio$C_{1-3}$ alkyl, hydroxy$C_1$-$C_6$alkyl, and halo$C_1$-$C_6$alkyl;

$R^5$ and $R^6$ are independently selected from hydrogen, $C_1$-$C_3$alkyl, $C_1$-$C_3$alkylsulfonyl, $C_3$-$C_6$cycloalkyl optionally substituted with an amino group, heterocyclyl, heterocyclyl$C_1$-$C_3$alkyl, phenyl$C_1$-$C_3$alkyl, phenyl$C_1$-$C_3$alkylsulfonyl, and phenylsulfonyl; wherein the heterocyclyl, the heterocyclyl part of the heterocyclyl$C_1$-$C_3$alkyl, and the phenyl part of the phenyl$C_1$-$C_3$alkyl, phenyl$C_1$-$C_3$alkylsulfonyl, and the phenylsulfonyl are optionally substituted with one group selected from $C_1$-$C_3$alkyl, halo, hydroxy; or $R^5$ and $R^6$, together with the nitrogen atom to which they are attached, form a five- or six-membered heterocyclic ring optionally containing a second nitrogen atom and optionally substituted with an amino group;

$R^b$ is selected from hydrogen, $C_1$-$C_3$alkoxy, $C_1$-$C_3$alkyl, halo, and halo$C_1$alkyl;

$R^p$ is selected from hydrogen and $C_1$-$C_3$alkyl;

$R^q$ is selected from hydrogne and oxo; and $R^z$ is selected from hydrogen, $C_1$-$C_3$alkyl, and $C_1$-$C_3$alkylcarbonyl;

or a pharmaceutically acceptable salt thereof.

In a first embodiment of the first aspect R and $R^3$ are hydrogen.

In a second embodiment of the first aspect X and Y are independently selected from hydrogen and halo.

In a third embodiment of the first aspect $R^1$ is $C_1$-$C_3$alkoxy.

In a fourth embodiment of the first aspect Z is

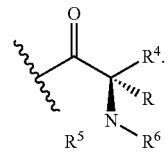

In a fifth embodiment of the first aspect $R^2$ is

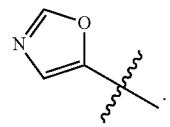

In a sixth embodiment of the first aspect, X and Y are independently selected from hydrogen and halo; $R^1$ is $C_1$-$C_3$alkoxy; and Z is

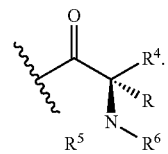

In a second aspect the present disclosure provides a composition comprising a compound of formula (I), or a pharmaceutically acceptable salt thereof, and a pharmaceutically acceptable salt thereof.

In a third aspect the present disclosure provides a method of inhibiting adaptor associated kinase 1 (AAK1) activity, comprising contacting AAK1 with a compound of formula (II)

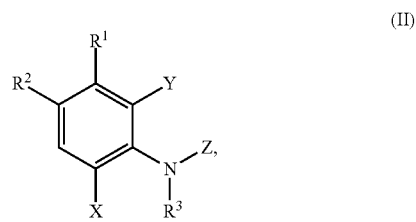

or a pharmaceutically acceptable salt thereof, wherein:

$R^1$ is selected from hydrogen, $C_1$-$C_3$alkoxy, $C_1$-$C_3$alkyl, cyano, di$C_1$-$C_3$ alkylamino, halo, halo$C_1$-$C_3$alkoxy, halo$C_1$-$C_3$alkyl, hydroxy, and thienyl;

$R^2$ is selected from

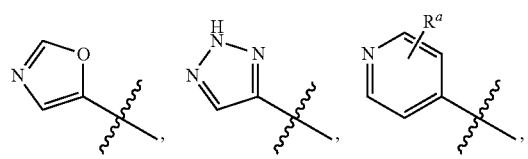

-continued

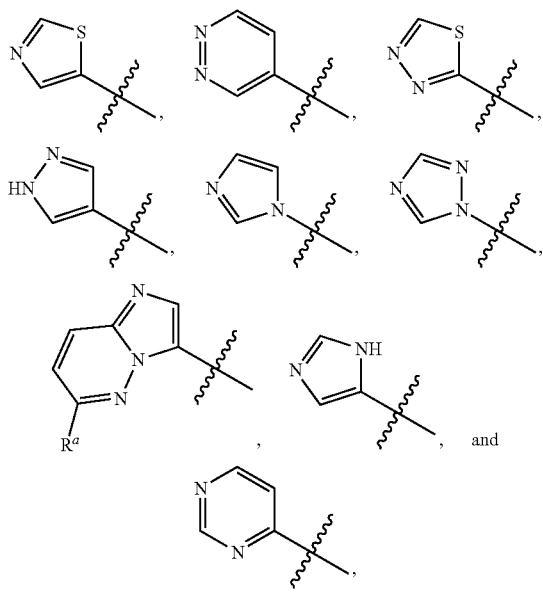

wherein R$^a$ is selected from hydrogen, C$_1$-C$_3$alkoxy, C$_1$-C$_3$alkylamino, C$_1$-C$_3$ alkylcarbonylamino, amino, and halo;

R$^3$ is selected from hydrogen and C$_1$-C$_3$alkyl;

X is selected from hydrogen, C$_1$-C$_3$alkoxy, C$_1$-C$_3$alkyl, cyano, halo, haloC$_1$-C$_3$ alkyl,

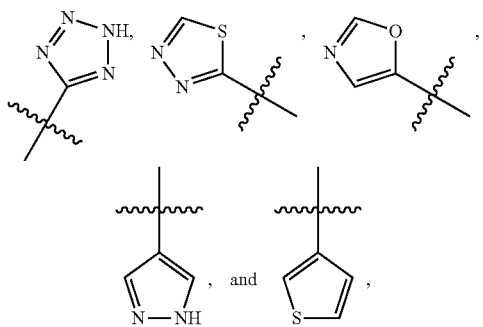

Y is selected from hydrogen and halo;

Z is selected from

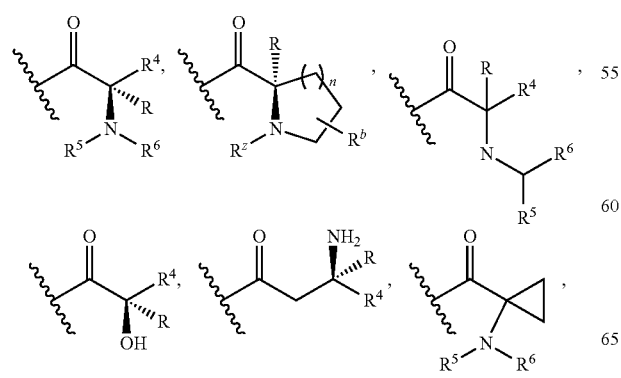

-continued

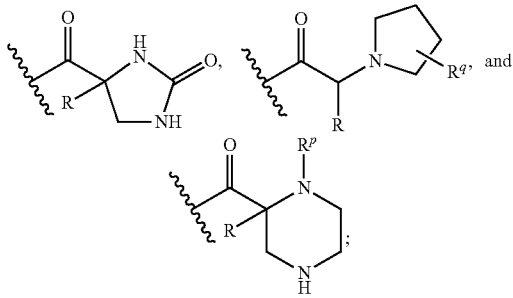

wherein n is 1 or 2;

R is selected from hydrogen and C$_1$-C$_3$alkyl;

R$^4$ is selected from C$_2$-C$_6$alkyl, C$_3$-C$_6$cycloalkyl, (C$_3$-C$_6$cycloalkyl)C$_1$-C$_3$ alkyl, C$_{1-3}$ alkylthioC$_{1-3}$ alkyl, hydroxyC$_1$-C$_6$alkyl, and haloC$_1$-C$_6$alkyl;

R$^5$ and R$^6$ are independently selected from hydrogen, C$_1$-C$_3$alkyl, C$_1$-C$_3$alkylsulfonyl, C$_3$-C$_6$cycloalkyl optionally substituted with an amino group, heterocyclyl, heterocyclylC$_1$-C$_3$alkyl, phenylC$_1$-C$_3$alkyl, phenylC$_1$-C$_3$alkylsulfonyl, and phenylsulfonyl; wherein the heterocyclyl, the heterocyclyl part of the heterocyclylC$_1$-C$_3$alkyl, and the phenyl part of the phenylC$_1$-C$_3$alkyl, phenylC$_1$-C$_3$alkylsulfonyl, and the phenylsulfonyl are optionally substituted with one group selected from C$_1$-C$_3$alkyl, halo, hydroxy; or R$^5$ and R$^6$, together with the nitrogen atom to which they are attached, form a five- or six-membered heterocyclic ring optionally containing a second nitrogen atom and optionally substituted with an amino group;

R$^b$ is selected from hydrogen, C$_1$-C$_3$alkoxy, C$_1$-C$_3$alkyl, halo, and haloC$_1$alkyl;

R$^p$ is selected from hydrogen and C$_1$-C$_3$alkyl;

R$^q$ is selected from hydrogne and oxo; and

R$^z$ is selected from hydrogen, C$_1$-C$_3$alkyl, and C$_1$-C$_3$alkylcarbonyl;

or a pharmaceutically acceptable salt thereof.

In a fourth aspect the present disclosure provides a method for treating or managing a disease or a disorder mediated by AAK1 activity, the method comprising administering to a patient in need thereof a therapeutically effective amount of a compound of formula (II)

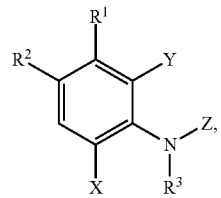

(II)

or a pharmaceutically acceptable salt thereof, wherein:

R$^1$ is selected from hydrogen, C$_1$-C$_3$alkoxy, C$_1$-C$_3$alkyl, cyano, diC$_1$-C$_3$alkylamino, halo, haloC$_1$-C$_3$alkoxy, haloC$_1$-C$_3$alkyl, hydroxy, and thienyl;

$R^2$ is selected from

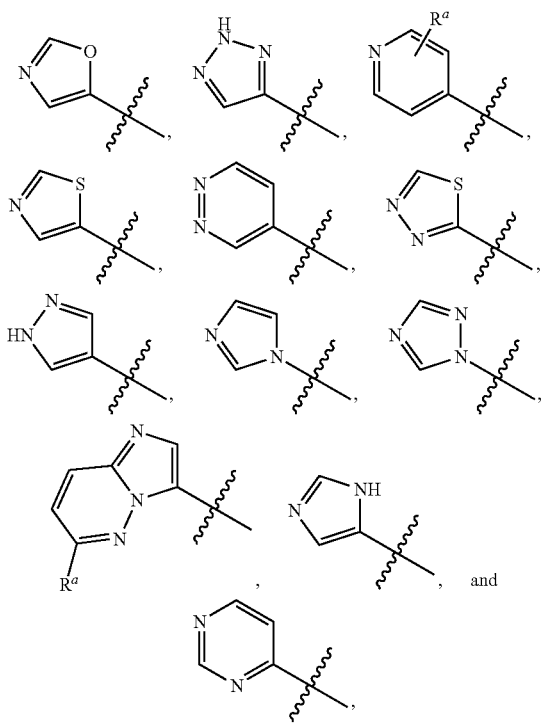

wherein $R^a$ is selected from hydrogen, $C_1$-$C_3$alkoxy, $C_1$-$C_3$alkylamino, $C_1$-$C_3$ alkylcarbonylamino, amino, and halo;

$R^3$ is selected from hydrogen and $C_1$-$C_3$alkyl;

X is selected from hydrogen, $C_1$-$C_3$alkoxy, $C_1$-$C_3$alkyl, cyano, halo, halo$C_1$-$C_3$ alkyl,

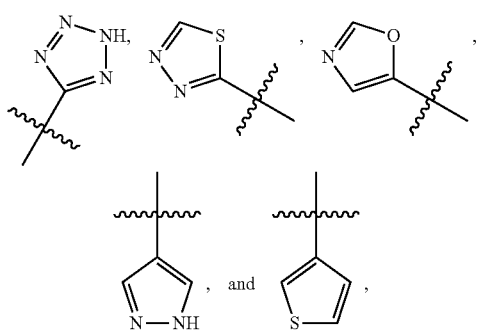

Y is selected from hydrogen and halo;
Z is selected from

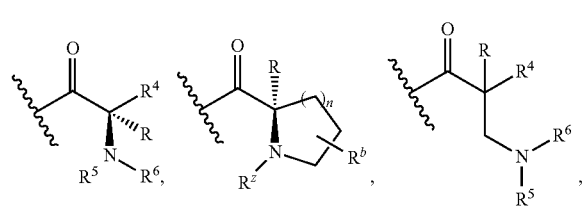

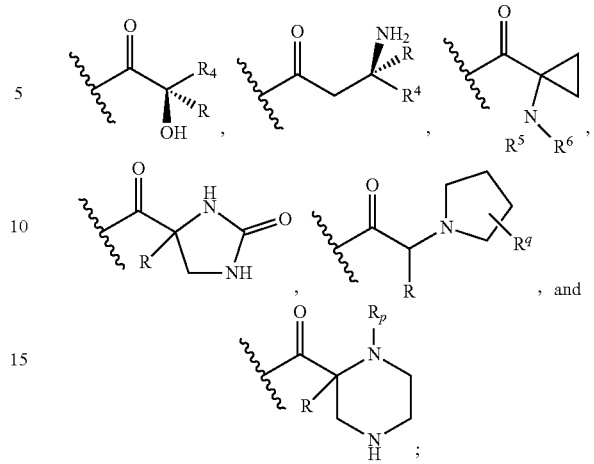

wherein
n is 1 or 2;
R is selected from hydrogen and $C_1$-$C_3$alkyl;
$R^4$ is selected from $C_2$-$C_6$alkyl, $C_3$-$C_6$cycloalkyl, ($C_3$-$C_6$cycloalkyl)$C_1$-$C_3$ alkyl, $C_{1-3}$ alkylthio$C_{1-3}$ alkyl, hydroxy$C_1$-$C_6$alkyl, and halo$C_1$-$C_6$alkyl;

$R^5$ and $R^6$ are independently selected from hydrogen, $C_1$-$C_3$alkyl, $C_1$-$C_3$alkylsulfonyl, $C_3$-$C_6$cycloalkyl optionally substituted with an amino group, heterocyclyl, heterocyclyl$C_1$-$C_3$alkyl, phenyl$C_1$-$C_3$alkyl, phenyl$C_1$-$C_3$alkylsulfonyl, and phenylsulfonyl; wherein the heterocyclyl, the heterocyclyl part of the heterocyclyl$C_1$-$C_3$alkyl, and the phenyl part of the phenyl$C_1$-$C_3$alkyl, phenyl$C_1$-$C_3$alkylsulfonyl, and the phenylsulfonyl are optionally substituted with one group selected from $C_1$-$C_3$alkyl, halo, hydroxy; or $R^5$ and $R^6$, together with the nitrogen atom to which they are attached, form a five- or six-membered heterocyclic ring optionally containing a second nitrogen atom and optionally substituted with an amino group;

$R^b$ is selected from hydrogen, $C_1$-$C_3$alkoxy, $C_1$-$C_3$alkyl, halo, and halo$C_1$alkyl;

$R^p$ is selected from hydrogen and $C_1$-$C_3$alkyl;

$R^q$ is selected from hydrogne and oxo; and $R^z$ is selected from hydrogen, $C_1$-$C_3$alkyl, and $C_1$-$C_3$alkylcarbonyl;

or a pharmaceutically acceptable salt thereof.

In a first embodiment of the first aspect the disease or disorder is selected from Alzheimer's disease, bipolar disorder, pain, Parkinson's disease, and schizophrenia. In a second embodiment of the first aspect the pain is neuropathic pain. In a third embodiment of the first aspect neuropathic pain is fibromyalgia or peripheral neuropathy.

Other aspects of the present disclosure may include suitable combinations of embodiments disclosed herein.

Yet other aspects and embodiments may be found in the description provided herein.

This disclosure is based, in part, on the discovery that AAK1 knockout mice exhibit a high resistance to pain. That discovery prompted research that ultimately led to the discovery of AAK1 inhibitors, compositions comprising them, and methods of their use.

The description of the present disclosure herein should be construed in congruity with the laws and principals of chemical bonding. In some instances it may be necessary to remove a hydrogen atom in order to accommodate a substituent at any given location.

It should be understood that the compounds encompassed by the present disclosure are those that are suitably stable for use as pharmaceutical agent.

As used in the present specification, the following terms have the meanings indicated:

All patents, patent applications, and literature references cited in the specification are herein incorporated by reference in their entirety. In the case of inconsistencies, the present disclosure, including definitions, will prevail.

As used herein, the singular forms "a", "an", and "the" include plural reference unless the context clearly dictates otherwise.

In some instances, the number of carbon atoms in any particular group is denoted before the recitation of the group. For example, the term "$C_{1-6}$ alkyl" denotes an alkyl group containing one to six carbon atoms. Where these designations exist they supercede all other definitions contained herein.

The term "alkenyl," as used herein, refers to The term "alkenyl," as used herein, refers to a straight or branched chain group containing at least one carbon-carbon double bond.

The term "alkoxy," as used herein, refers to an alkyl group attached to the parent molecular moiety through an oxygen atom.

The term "alkyl," as used herein, refers to a group derived from a straight or branched chain saturated hydrocarbon.

The term "alkylamino," as used herein refers to —NHR, wherein R is an alkyl group.

The term "alkylcarbonyl," as used herein, refers to an alkyl group attached to the parent molecular moiety through a carbonyl group.

The term "alkylcarbonylamino," as used herein, refers to —NHR wherein R is an alkylcarbonyl group.

The term "alkylsulfonyl," as used herein, refers to an alkyl group attached to the parent molecular moiety through a sulfonyl group.

The term "alkylthioalkyl," as used herein, refers to an alkyl group attached to the parent molecular moiety through a thioalkyl group.

The term "amino," as used herein, refers to —NH$_2$.

The term "carbonyl," as used herein, refers to —C(O)—.

The term "cyano," as used herein, refers to —CN.

The term "cycloalkyl," as used herein, refers to a saturated monocyclic hydrocarbon ring system having zero heteroatoms. Representative examples of cycloalkyl groups include, but are not limited to, cyclopropyl, cyclopentyl, and cyclohexyl.

The term "(cycloalkyl)alkyl," as used herein, refers to an alkyl group substituted with one, two, or three cycloalkyl groups.

The term "dialkylamino," as used herein refers to —NR$_2$, wherein each R is an alkyl group. The alkyl groups may be the same or different.

The term "halo," as used herein, refers to Br, Cl, F, and/or I.

The term "haloalkoxy," as used herein, refers to a haloalkyl group attached to the parent molecular moiety through an oxygen atom.

The term "haloalkyl," as used herein, refers to an alkyl group substituted by one, two, three, or four halogen atoms.

The term "heterocyclyl," as used herein, refers to a four-, five-, or six-membered ring containing one, two, or three heteroatoms independently selected from nitrogen, oxygen, and sulfur. The four-membered rings have zero double bonds, the five-membered rings have zero to two double bonds, and the six-membered rings have zero to three double bonds.

The term "heterocyclylalkyl," as used herein, refers to a heterocyclyl group attached to the parent molecular moiety through an alkyl group.

The term "hydroxy," as used herein, refers to —OH.

The term "hydroxyalkyl," as used herein, refers to a hydroxy group attached to the parent molecular moiety through an alkyl group.

The term "phenylalkyl," as used herein, refers to a phenyl group attached to the parent molecular moiety through an alkyl group.

The term "phenylalkylsulfonyl," as used herein, refers to a phenylalkyl group attached to the parent molecular moiety through a sulfonyl group.

The term "phenylsulfonyl," as used herein, refers to a phenyl group attached to the parent molecular moiety through a sulfonyl group.

The term "sulfonyl," as used herein, refers to —SO$_2$—.

The term "thioalkyl," as used herein, refers to a thiol group attached to the parent molecular moiety through an alkyl group.

The term "thiol," as used herein, refers to —SH.

Asymmetric centers may exist in the compounds of the present disclosure. It should be understood that the disclosure encompasses all stereochemical isomeric forms, or mixtures thereof, which possess the ability to inhibit AAK1. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, or direct separation of enantiomers on chiral chromatographic columns. Starting compounds of particular stereochemistry are either commercially available or can be made and resolved by techniques known in the art.

Certain compounds of the present disclosure may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

The term "compounds of the present disclosure", and equivalent expressions, are meant to embrace compounds of formula (I), and pharmaceutically acceptable enantiomers, diastereomers, and salts thereof. Similarly, references to intermediates are meant to embrace their salts where the context so permits.

The present disclosure is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the disclosure can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

The compounds of the present disclosure can exist as pharmaceutically acceptable salts. The term "pharmaceutically acceptable salt," as used herein, represents salts or zwitterionic forms of the compounds of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use. The salts can be prepared during the final isolation and purification of the compounds or separately by reacting a suitable nitrogen atom with a suitable acid. Representative acid addition salts include acetate, adipate, alginate, citrate, aspartate, benzoate, benzenesulfonate, bisulfate, butyrate, camphorate, camphorsulfonate; digluconate, dihydrobromide, diydrochloride, dihydroiodide, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine. Other representative organic amines useful for the formation of base addition salts include ethylenediamine, ethanolamine, diethanolamine, piperidine, and piperazine.

One embodiment of this disclosure encompasses methods of inhibiting adaptor associated kinase 1 (AAK1), both in vitro and in vivo, which comprise contacting AAK1 with a compound of formula I or a pharmaceutically acceptable salt thereof.

When it is possible that, for use in therapy, therapeutically effective amounts of a compound of formula (I), as well as pharmaceutically acceptable salts thereof, may be administered as the raw chemical, it is possible to present the active ingredient as a pharmaceutical composition. Accordingly, the disclosure further provides pharmaceutical compositions, which include therapeutically effective amounts of compounds of formula (I) or pharmaceutically acceptable salts thereof, and one or more pharmaceutically acceptable carriers, diluents, or excipients.

Unless otherwise indicated, a "therapeutically effective amount" of a compound is an amount sufficient to provide a therapeutic benefit in the treatment or management of a disease or condition, or to delay or minimize one or more symptoms associated with the disease or condition. The term "therapeutically effective amount" can encompass an amount that improves overall therapy, reduces or avoids symptoms or causes of a disease or condition, or enhances the therapeutic efficacy of another therapeutic agent.

The term "therapeutically effective amount," as used herein, refers to an amount of a compound or compounds sufficient to provide a therapeutic benefit in the treatment or management of a disease or condition, or to delay or minimize one or more symptoms associated with the disease or condition. A "therapeutically effective amount" of a compound means an amount of therapeutic agent, alone or in combination with other therapies, that provides a therapeutic benefit in the treatment or management of the disease or condition. The term "therapeutically effective amount" can encompass an amount that improves overall therapy, reduces or avoids symptoms or causes of a disease or condition, or enhances the therapeutic efficacy of another therapeutic agent. When applied to an individual active ingredient, administered alone, the term refers to that ingredient alone. When applied to a combination, the term refers to combined amounts of the active ingredients that result in the therapeutic effect, whether administered in combination, serially, or simultaneously. The compounds of formula (I) and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the present disclosure there is also provided a process for the preparation of a pharmaceutical formulation including admixing a compound of formula (I), or a pharmaceutically acceptable salt thereof, with one or more pharmaceutically acceptable carriers, diluents, or excipients. The term "pharmaceutically acceptable," as used herein, refers to those compounds, materials, compositions, and/or dosage forms which are, within the scope of sound medical judgment, suitable for use in contact with the tissues of patients without excessive toxicity, irritation, allergic response, or other problem or complication commensurate with a reasonable benefit/risk ratio, and are effective for their intended use.

Pharmaceutical formulations may be presented in unit dose forms containing a predetermined amount of active ingredient per unit dose. Dosage levels of between about 0.01 and about 250 milligram per kilogram ("mg/kg") body weight per day, preferably between about 0.05 and about 100 mg/kg body weight per day of the compounds of the present disclosure are typical in a monotherapy for the prevention and treatment of disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Treatment may be initiated with small dosages substantially less than the optimum dose of the compound. Thereafter, the dosage is increased by small increments until the optimum effect under the circumstances is reached. In general, the compound is most desirably administered at a concentration level that will generally afford effective results without causing any harmful or deleterious side effects.

When the compositions of this disclosure comprise a combination of a compound of the present disclosure and one or more additional therapeutic or prophylactic agent, both the compound and the additional agent are usually present at dosage levels of between about 10 to 150%, and more preferably between about 10 and 80% of the dosage normally administered in a monotherapy regimen.

Compounds of the disclosure may be administered in combination with one or more additional therapeutic or prophylactic agents. For example, when used for the treatment of pain, possible additional agents include immunosuppressive agents, anti-inflammatory agents, and/or other agents used in the treatment of pain.

Immunosuppressants suitable for use in the methods and compositions of this disclosure include those known in the art. Examples include aminopterin, azathioprine, cyclosporin A, D-penicillamine, gold salts, hydroxychloroquine, leflunomide, methotrexate, minocycline, rapamycin, sulfasalazine, tacrolimus (FK506), and pharmaceutically acceptable salts thereof. A particular immunosuppressant is methotrexate.

Additional examples of immunosuppressants include anti-TNF antibodies, such as adalimumab, certolizumab pegol, etanercept, and infliximab. Others include interleukin-1 blockers, such as anakinra. Others include anti-B cell (CD20) antibodies, such as rituximab. Others include T cell activation blockers, such as abatacept.

Other immunosuppressants include inosine monophosphate dehydrogenase inhibitors, such as mycophenolate mofetil (CellCept®) and mycophenolic acid (Myfortic®).

Anti-inflammatory drugs suitable for use in the methods and compositions of this disclosure include those known in the art. Examples include glucocorticoids and NSAIDs. Examples of glucocorticoids include aldosterone, beclometasone, betamethasone, cortisone, deoxycorticosterone, dexamethasone, fludrocortisones, hydrocortisone, methylprednisolone, prednisolone, prednisone, triamcinolone, and pharmaceutically acceptable salts thereof.

Examples of NSAID include salicylates (e.g., aspirin, amoxiprin, benorilate, choline magnesium salicylate, diflunisal, faislamine, methyl salicylate, magnesium salicylate, salicyl salicylate, and pharmaceutically acceptable salts thereof), arylalkanoic acids (e.g., diclofenac, aceclofenac, acemetacin, bromfenac, etodolac, indometacin, nabumetone, sulindac, tolmetin, and pharmaceutically acceptable salts thereof), arylpropionic acids (e.g., ibuprofen, carprofen, fenbufen, fenoprofen, flurbiprofen, ketoprofen, ketorolac, loxoprofen, naproxen, oxaprozin, tiaprofenic acid, suprofen, and pharmaceutically acceptable salts thereof), arylanthranilic acids (e.g., meclofenamic acid, mefenamic acid, and pharmaceutically acceptable salts thereof), pyrazolidine derivatives (e.g., azapropazone, metamizole, oxyphenbutazone, phenylbutazone, sulfinprazone, and pharmaceutically acceptable salts thereof), oxicams (e.g., lornoxicam, meloxicam, piroxicam, tenoxicam, and pharmaceutically acceptable salts thereof), COX-2 inhibitors (e.g., celecoxib, etoricoxib, lumiracoxib, parecoxib, rofecoxib, valdecoxib, and pharmaceutically acceptable salts thereof), and sulphonanilides (e.g., nimesulide and pharmaceutically acceptable salts thereof).

Other agents used in the treatment of pain (including but not limited to neuropathic and inflammatory pain) include, but are not limited to, agents such as pregabalin, lidocaine, duloxetine, gabapentin, carbamazepine, capsaicin, and other serotonin/norepinephrine/dopamine reuptake inhibitors, and opiates (such as oxycontin, morphine, and codeine).

In the treatment of pain caused by a known disease or condition, such as diabetes, infection (e.g., herpes zoster or HIV infection), or cancer, compounds of the disclosure may be administered in combination with one or more additional therapeutic or prophylactic agents directed at the underlying disease or condition. For example, when used to treat diabetic neuropathy, compounds of the disclosure may be administered in combination with one or more anti-diabetic agents, anti-hyperglycemic agents, hypolipidemic/lipid lowering agents, anti-obesity agents, anti-hypertensive agents and appetite suppressants. Examples of anti-diabetic agents include biguanides (e.g., metformin, phenformin), glucosidase inhibitors (e.g., acarbose, miglitol), insulins (including insulin secretagogues and insulin sensitizers), meglitinides (e.g., repaglinide), sulfonylureas (e.g., glimepiride, glyburide, gliclazide, chlorpropamide, and glipizide), biguanide/glyburide combinations (e.g., Glucovance), thiazolidinediones (e.g., troglitazone, rosiglitazone, and pioglitazone), PPAR-alpha agonists, PPAR-gamma agonists, PPAR alpha/gamma dual agonists, glycogen phosphorylase inhibitors, inhibitors of fatty acid binding protein (aP2), glucagon-like peptide-1 (GLP-1) or other agonists of the GLP-1 receptor, dipeptidyl peptidase IV (DPP4) inhibitors, and sodium-glucose co-transporter 2 (SGLT2) inhibitors (e.g., dapagliflozin, canagliflozin, and LX-4211).

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s). Oral administration or administration by injection are preferred.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phopholipids, such as cholesterol, stearylamine, or phophatidylcholines.

The compounds of formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research* 1986, 3(6), 318.

Pharmaceutical formulations adapted for topical administration may be formulated as ointments, creams, suspensions, lotions, powders, solutions, pastes, gels, sprays, aerosols, or oils.

Pharmaceutical formulations adapted for rectal administration may be presented as suppositories or as enemas.

Pharmaceutical formulations adapted for nasal administration wherein the carrier is a solid include a course powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

The term "patient" includes both human and other mammals.

Unless otherwise indicated, the terms "manage," "managing", and "management" encompass preventing the recurrence of the specified disease or disorder in a patient who has already suffered from the disease or disorder, and/or lengthening the time that a patient who has suffered from the disease or disorder remains in remission. The terms encompass modulating the threshold, development and/or duration of the disease or disorder, or changing the way that a patient responds to the disease or disorder.

The term "treating" refers to: (i) preventing a disease, disorder or condition from occurring in a patient that may be predisposed to the disease, disorder, and/or condition but has not yet been diagnosed as having it; (ii) inhibiting the disease, disorder, or condition, i.e., arresting its development; and (iii) relieving the disease, disorder, or condition, i.e., causing regression of the disease, disorder, and/or condition.

This disclosure is intended to encompass compounds having Formula (I) when prepared by synthetic processes or by metabolic processes including those occurring in the human or animal body (in vivo) or processes occurring in vitro.

The abbreviations used in the present application, including particularly in the illustrative schemes and examples which follow, are well-known to those skilled in the art. Some of the abbreviations used are as follows: TosMIC for tosylmethyl isocyanide; HATU for O-(7-azabenzotriazol-1-yl)-N,N,N',N'-tetramethyluronium hexafluorophosphate; BOP for benzotriazol-1-yloxytris(dimethylamino)phosphonium hexafluorophosphate; EDC or EDCI for 1-(3-dimethylaminopropyl)-3-ethylcarbodiimide hydrochloride; TBTU for O-benzotriazol-1-yl-N,N,N',N'-tetramethyluronium tetrafluoroborate; THF for tetrahydrofuran; MeOH for methanol; DIEA or i-Pr$_2$NEt for N,N-diisopropylethylamine; DMF for N,N-dimethylformamide; Me for methyl; Ph for phenyl; dba for dibenzylideneacetone; EtOH for ethanol; DME for 1,2-dimethoxyethane; TBAF for tetrabutylammonium fluoride; TEA or Et$_3$N for triethylamine; Ac for acetyl; SPhos for 2-dicyclohexylphosphino-2',6'-dimethoxybiphenyl; XPhos for 2-dicyclohexylphosphino-2',4',6'-triisopropylbiphenyl; dppf for 1,1'-bis(diphenylphosphanyl)ferrocene; DMAP for N,N-dimethylaminopyridine; NMP for N-methylpyrrolidone; BOC or Boc for tert-butoxycarbonyl; RT or rt or r.t. for room temperature or retention time (context will dictate); $t_R$ for retention time; DIBAL or DIBAL-H for diisobutylaluminum hydride; TPAP for tetrapropylammonium perruthenate; NBS for N-bromosuccinimide; min for minutes; h for hours; MeCN or ACN for acetonitrile; TFA for trifluoroacetic acid; DEA for diethylamine; LDA for lithium diisopropylamide; DCM for dichloromethane; and PMHS for polymethylhydrosiloxane.

EXAMPLES

The present disclosure will now be described in connection with certain embodiments which are not intended to limit its scope. On the contrary, the present disclosure covers all alternatives, modifications, and equivalents as can be included within the scope of the claims. Thus, the following examples, which include specific embodiments, will illustrate one practice of the present disclosure, it being understood that the examples are for the purposes of illustration of certain embodiments and are presented to provide what is believed to be the most useful and readily understood description of its procedures and conceptual aspects.

The compounds of the present disclosure may be prepared using the reactions and techniques described in this section as well as other synthetic methods known to those of ordinary skill in the art. The reactions are performed in solvents appropriate to the reagents and materials employed and suitable for the transformation being effected. Also, in the description of the synthetic methods described below, it is to be understood that all proposed reaction conditions, including choice of solvents, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

Compounds of formula 5 are prepared by the methods outlined in Scheme 1. Treatment of 2 with TosMIC in the presence of a base such as potassium carbonate in a solvent such as methanol affords 5-phenyloxazoles 3. Reduction of the nitro group in 3 is accomplished using standard conditions such as, but not limited to, H$_2$ and Pd/C, zinc with ammonium chloride, or tin chloride in an appropriate solvent such as methanol or ethanol at temperatures ranging from 0° C. to 100° C. to give compounds of formula 4. Compounds of formula 4, are coupled with a carboxylic acid containing either an amine or an alcohol group using standard peptide coupling reagents such as HATU, BOP, EDC, or TBTU in the presence of a base such as N,N-diisopropylethylamine and a solvent such as THF at temperatures ranging from 20° C. to 80° C. to form compounds of formula 5. Alternatively, compounds of formula 4 can be coupled with an acid chloride to form compounds of formula 5.

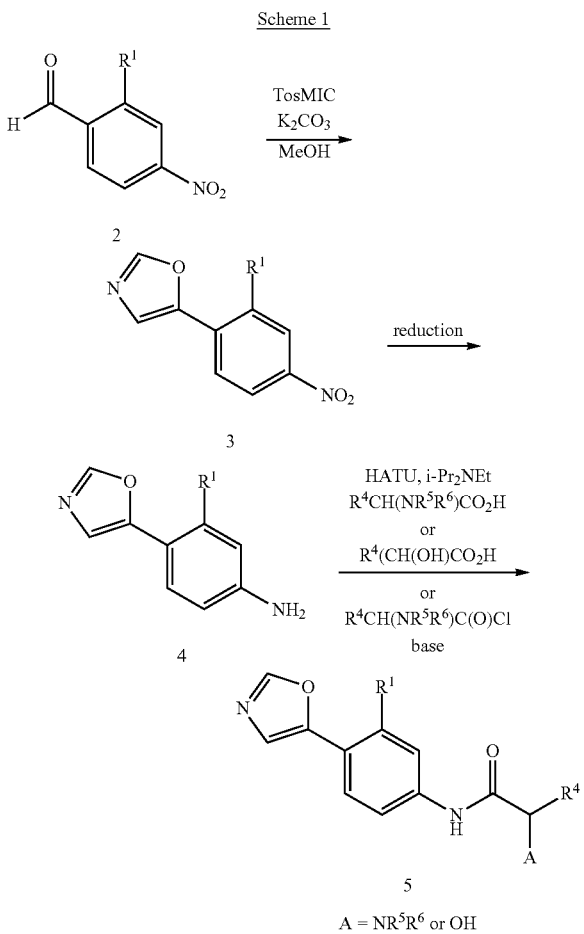

If the amide side chain designated as "X" in compounds of formula (I) contains a protected amine or another functional group that is protected, the protecting group is removed as shown in Scheme 2 by treating the substrate with the appropriate reagents as described in *Protective Groups in Organic Synthesis* (Greene, Wuts; 3$^{rd}$ ed., 1999, John Wiley & Sons, Inc.) to provide compounds of formula 7.

Scheme 2

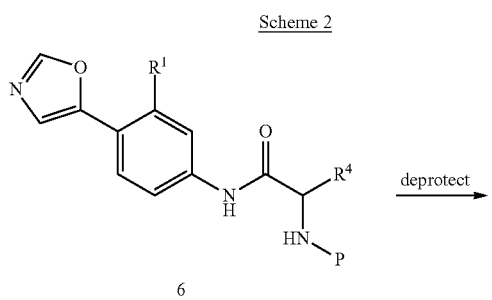

P = protecting group

Compounds of formula 9 are prepared, as shown in Scheme 3, by treatment of compounds of formula 6 with a base such as barium hydroxide in the presence of an alkylating agent such as an alkyl halide in a solvent such as DMF to form compounds of formula 8. The protecting group is then removed as described in Scheme 2 to provide compounds of formula 9.

Scheme 3

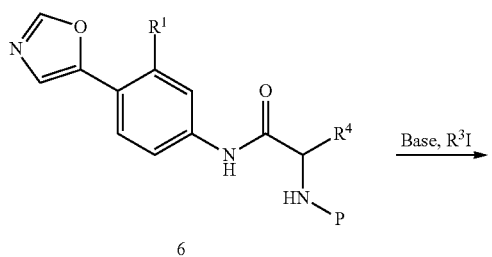

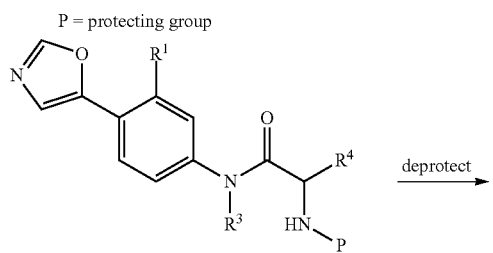

Compounds of formula 11 are prepared, as shown in Scheme 4, by treatment of compounds of formula 6 with a halogenating reagent such as N-chlorosuccinimide, N-bromosuccinimide, or N-iodosuccinimide in a solvent such as THF or DMF to afford compounds of formula 10. The protecting group is then removed as described in Scheme 2 to provide compounds of formula 11.

The skilled person will appreciate that incorporation of alkyl groups at $R^3$ in compounds of formula (I) wherein $R^2$ represents groups other than the oxazol-5-yl group can be carried out using the conditions described for the conversion of 6 to 8. Likewise, the skilled person will appreciate that incorporation of halo groups at either Y or Z or at both Y and Z in compounds of formula (I) wherein $R^2$ represents groups other than the oxazol-5-yl group can be carried out using the conditions described for the conversion of 6 to 10. In addition, it is recognized that the above steps may be used in combination. For example, compounds of formula 8 or related compounds wherein other groups may replace the oxazol-5-yl group can be treated with a reagent to incorporate a halogen at either Y or Z or at both Y and Z.

Scheme 4

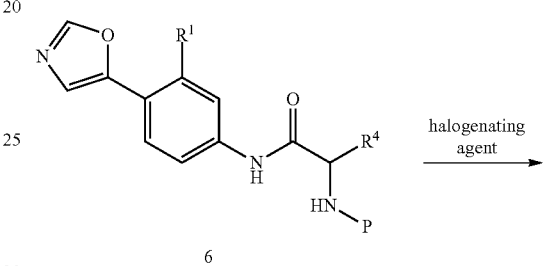

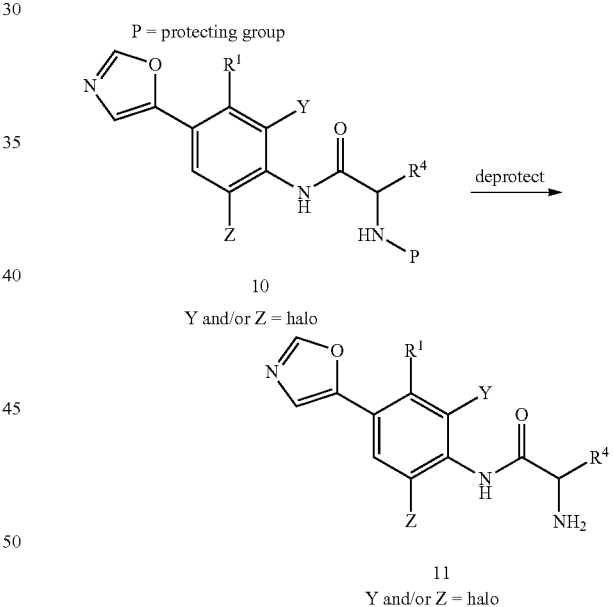

Compounds wherein $R^1$=OH can be prepared from compounds of formula 12 as shown in Scheme 5.

Scheme 5

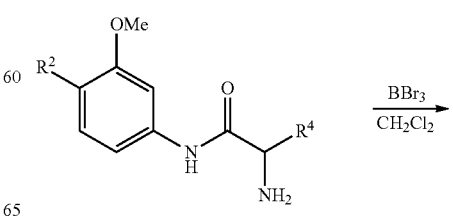

-continued

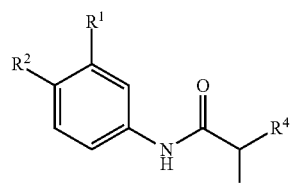

13

Alternatively, compounds of formula 7 are prepared by the methods outlined in Scheme 6. Compound 14 is prepared according to the procedure described in Org. Syn. 1943; Collect. Vol. 2, pp 441-443 wherein 14 is treated with chromium (VI) oxide in the presence acid and acetic anhydride followed by heating the resultant intermediate in a mixture of sulfuric acid and aqueous ethanol. Treatment of 15 with TosMIC in the presence of a base such as potassium carbonate in a solvent such as methanol affords 16. Reduction of the nitro group in 16 is accomplished using standard conditions that will not cleave the bromide-carbon bond such as, but not limited to, zinc with ammonium chloride or tin chloride in an appropriate solvent such as methanol or ethanol at temperatures ranging from 0° C. to 100° C. to give compound 17. Compound 17 is coupled with a carboxylic acid using standard peptide coupling reagents such as HATU, BOP, EDC, or TBTU in the presence of a base such as N,N-diisopropylethylamine and a solvent such as THF at temperatures ranging from 20° C. to 80° C. to furnish compound 18. Alternatively, compound 17 can be coupled with an acid chloride. The bromide at $R^1$ can optionally be replaced with other substituents by using a palladium catalyzed coupling reaction, including in reaction conditions familiar to those skilled in the art such as a Suzuki reaction, Stille reaction, or Negishi reaction. Representative reaction conditions for incorporation of various substituents at $R^1$ include reaction of 18 with an aryl, heteroaryl, methyl, or vinyl boronic acid in the presence of a base such as sodium carbonate and a catalyst such as $Pd(PPh_3)_4$, $Pd_2(dba)_3$, or $PdCl_2(PPh_3)_2$ in a solvent such as toluene, dichloroethane, THF, DMF, methanol, ethanol, water or a combination thereof at temperatures ranging from 20° C. to 150° C. to give compound 6. The protecting group is then removed as described in Scheme 2 to provide compounds of formula 7.

Scheme 6

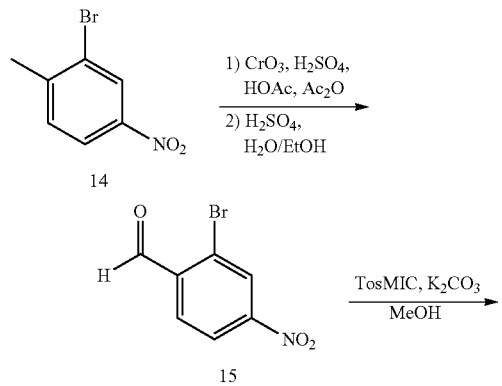

-continued

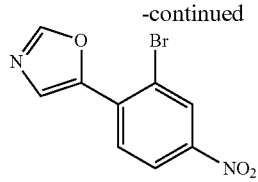

16

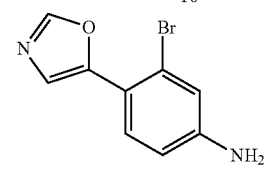

17

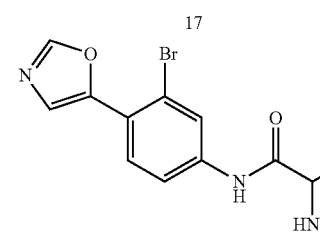

18

P = protecting group

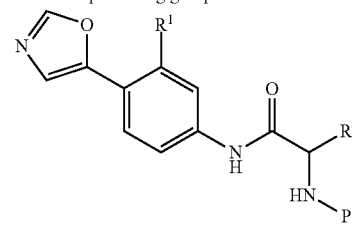

6

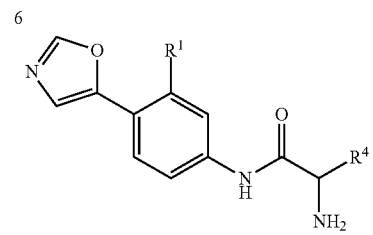

7

Alternatively, compounds of formula 7 with various substituents at $R^1$ are prepared as shown in Scheme 7. The bromide of 15 is replaced with other substituents by using a palladium catalyzed coupling reaction, including reaction conditions familiar to those skilled in the art such as a Suzuki reaction, Stille reaction, or Negishi reaction. Representative reaction conditions for incorporation of various substituents at $R^1$ include reaction of 15 with an aryl, heteroaryl, vinyl, or methyl boronic acid in the presence of a base such as sodium carbonate and a catalyst such as $Pd(PPh_3)_4$, $Pd_2(dba)_3$, or $PdCl_2(PPh_3)_2$ in a solvent such as toluene, dichloroethane, THF, DMF, methanol, ethanol, water or a combination thereof at temperatures ranging from 20° C. to 150° C. to form compounds of formula 2. The coupling reaction can be carried out by heating the reaction mixture using standard laboratory methods or by heating the reaction mixture in a microwave. Treatment of compounds of formula 2 with TosMIC in the presence of a base such as potassium carbonate in a solvent such as methanol affords compounds of formula 3. Reduction of the nitro group in 3 is accomplished using standard conditions such as, but not limited to, H$_2$ and Pd/C, zinc with ammonium chloride, or tin chloride in an appropriate solvent such as methanol or ethanol at temperatures ranging from 0° C. to 100° C. to give compounds of formula 4. A skilled person will appreciate that if R$^1$=vinyl, reduction of the nitro group with H$_2$ and a palladium catalyst will also reduce the vinyl group to furnish the product where R$^1$=ethyl. Compounds of formula 4 are then coupled with a carboxylic acid using standard peptide coupling reagents such as HATU, BOP, EDC, or TBTU in the presence of a base such as N,N-diisopropylethylamine and a solvent such as THF at temperatures ranging from 20° C. to 80° C. to provide compounds of formula 6. Alternatively, compounds of formula 4 can be coupled with an acid chloride. The protecting group is then removed as described in Scheme 2 to provide compounds of formula 7.

Compounds of formula 24 wherein R$^1$ contains an ether-linked substituent are prepared by the methods shown in Scheme 8. The methoxy group in compounds of formula 19 is demethylated by treating the substrate with a Lewis acid such as boron tribromide in a polar aprotic solvent such as dichloromethane, dichloroethane, or toluene at temperatures ranging from −78° C. to 80° C. to form the phenol intermediate of formula 20. Alkylation of the phenol is carried out by treating compounds of formula 20 with a base such as, but not limited to, potassium carbonate, sodium carbonate, sodium hydroxide, or sodium hydride and an electrophile in the presence of a polar solvent such as DMF, THF, or DME at temperatures ranging from 0° C. to 150° C. to furnish compounds of formula 21. Reduction of the nitro group in 21 is accomplished using standard conditions such as, but not limited to, H$_2$ and Pd/C, zinc with ammonium chloride, or tin chloride in an appropriate solvent such as methanol or ethanol at temperatures ranging from 0° C. to 100° C. to give compounds of formula 22. Compounds of formula 22 are then coupled with a carboxylic acid using standard peptide coupling reagents such as HATU, BOP, EDC, or TBTU in the presence of a base such as N,N-diisopropylethylamine and a solvent such as THF at temperatures ranging from 20° C. to 80° C. to form compounds of formula 23. Alternatively, compounds of formula 23 can be coupled with an acid chloride. The protecting group is then removed as described in Scheme 2 to provide compounds of formula 24.

Scheme 7

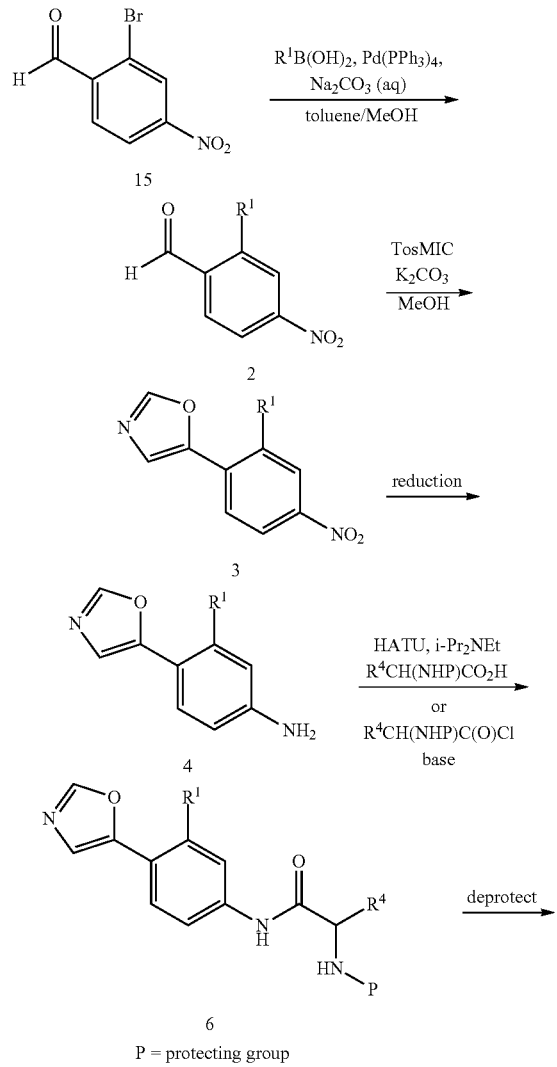

Scheme 8

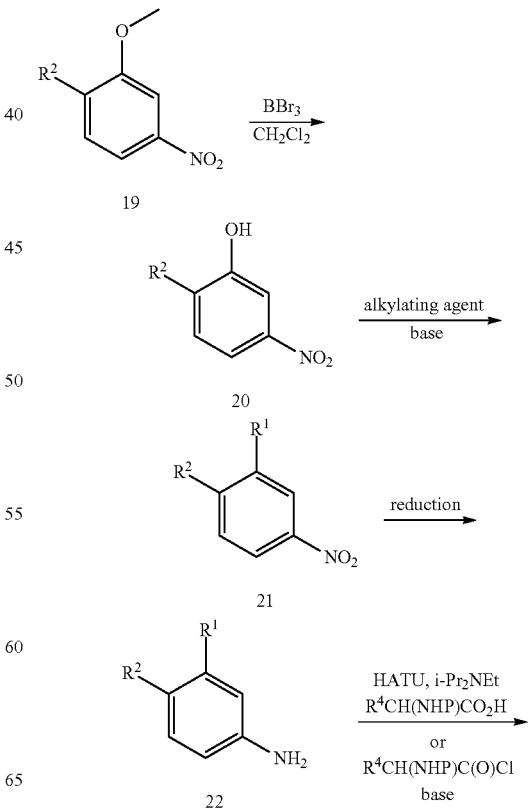

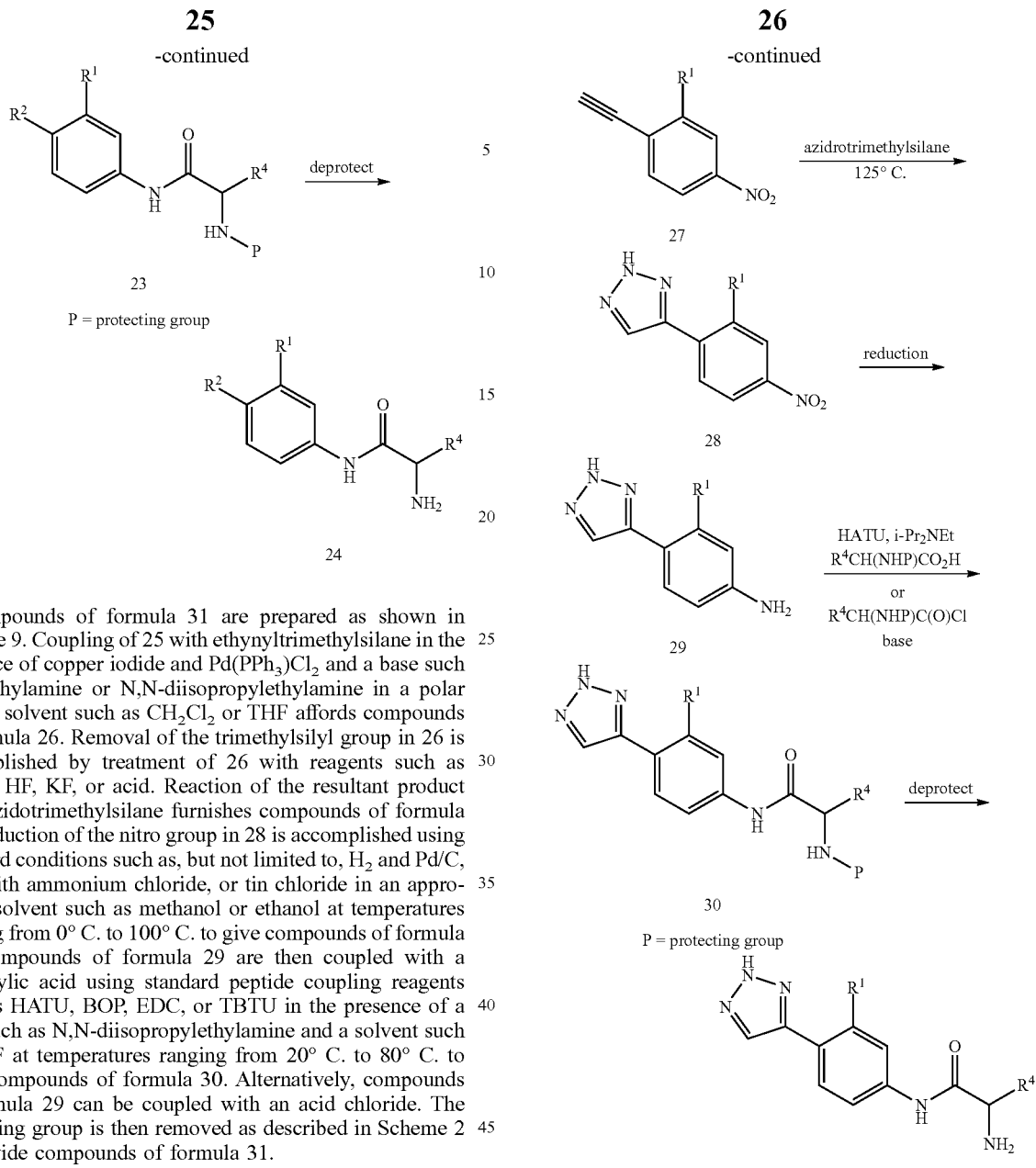

Compounds of formula 31 are prepared as shown in Scheme 9. Coupling of 25 with ethynyltrimethylsilane in the presence of copper iodide and Pd(PPh$_3$)Cl$_2$ and a base such as triethylamine or N,N-diisopropylethylamine in a polar aprotic solvent such as CH$_2$Cl$_2$ or THF affords compounds of formula 26. Removal of the trimethylsilyl group in 26 is accomplished by treatment of 26 with reagents such as TBAF, HF, KF, or acid. Reaction of the resultant product with azidotrimethylsilane furnishes compounds of formula 28. Reduction of the nitro group in 28 is accomplished using standard conditions such as, but not limited to, H$_2$ and Pd/C, zinc with ammonium chloride, or tin chloride in an appropriate solvent such as methanol or ethanol at temperatures ranging from 0° C. to 100° C. to give compounds of formula 29. Compounds of formula 29 are then coupled with a carboxylic acid using standard peptide coupling reagents such as HATU, BOP, EDC, or TBTU in the presence of a base such as N,N-diisopropylethylamine and a solvent such as THF at temperatures ranging from 20° C. to 80° C. to form compounds of formula 30. Alternatively, compounds of formula 29 can be coupled with an acid chloride. The protecting group is then removed as described in Scheme 2 to provide compounds of formula 31.

Scheme 9

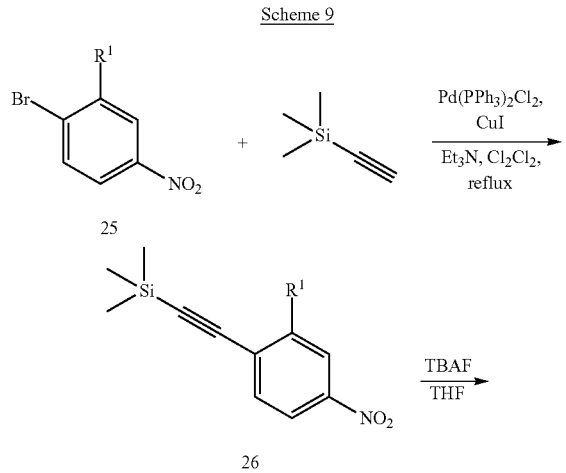

Various aryl and heteroaryl groups are incorporated at the R$^2$ position in compounds of formula (I) using the methods outlined in Schemes 10-13 below. In Scheme 10, compounds of formula 32 are coupled with a carboxylic acid using standard peptide coupling reagents such as HATU, BOP, EDC, or TBTU in the presence of a base such as N,N-diisopropylethylamine and a solvent such as THF at temperatures ranging from 20° C. to 80° C. to form compounds of formula 33. Alternatively, compounds of formula 32 can be coupled with an acid chloride. Coupling of compounds of formula 33 with aryl or heteroarylboronic acids in the presence of a palladium catalyst such as Pd(PPh$_3$)$_4$ or Pd(OAc)$_2$ and a base such as sodium carbonate, cesium carbonate, potassium carbonate, or potassium phosphate in the presence or absence of a ligand such as SPhos or XPhos and in a solvent such as DME, DMF, toluene, THF, dioxane, methanol, ethanol, butanol or water or a combination thereof at temperatures ranging from 20° C. to 150° C. furnishes compounds of formula 34. The coupling reaction is carried out by heating the reaction mixture using standard laboratory methods or by heating the reaction mixture in a microwave. The protecting group is then removed as described in Scheme 2 to provide compounds of formula 35.

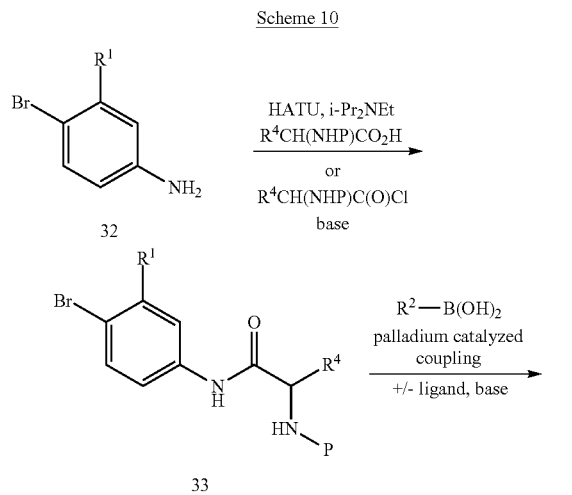

Alternatively, as shown in Scheme 11, various aryl and heteroaryl groups are incorporated at the $R^2$ position in compounds of formula 35 by first coupling compounds of formula 25 with aryl and heteroarylboronic acids in the presence of a palladium catalyst such as $Pd(PPh_3)_4$ or $Pd(OAc)_2$ and a base such as sodium carbonate, cesium carbonate, potassium carbonate, or potassium phosphate in the presence or absence of a ligand such as SPhos or XPhos and in a solvent such as DME, DMF, toluene, THF, dioxane, methanol, ethanol, butanol or water or a combination thereof at temperatures ranging from 20° C. to 150° C. furnishes compounds of formula 21. The coupling reaction is carried out by heating the reaction mixture using standard laboratory methods or by heating the reaction mixture in a microwave. Compounds of formula 21 wherein the heterocycle comprising $R^2$ contains an NH group within the ring are optionally alkylated on the nitrogen using a base such as sodium hydride and an alkylating agent such as an alkyl iodide or an alkyl bromide in the presence of a polar aprotic solvent such as DMF, DME, THF or toluene at temperatures ranging from 20° C. to 150° C. Reduction of the nitro group in 21 is accomplished using standard conditions such as, but not limited to, $H_2$ and Pd/C, zinc with ammonium chloride, or tin chloride in an appropriate solvent such as methanol or ethanol at temperatures ranging from 0° C. to 100° C. to give compounds of formula 22. Compounds of formula 22 are then coupled with a carboxylic acid using standard peptide coupling reagents such as HATU, BOP, EDC, or TBTU in the presence of a base such as N,N-diisopropylethylamine and a solvent such as THF at temperatures ranging from 20° C. to 80° C. to form compounds of formula 34. Alternatively, compounds of formula 34 can be coupled with an acid chloride. The protecting group is then removed as described in Scheme 2 to provide compounds of formula 35.

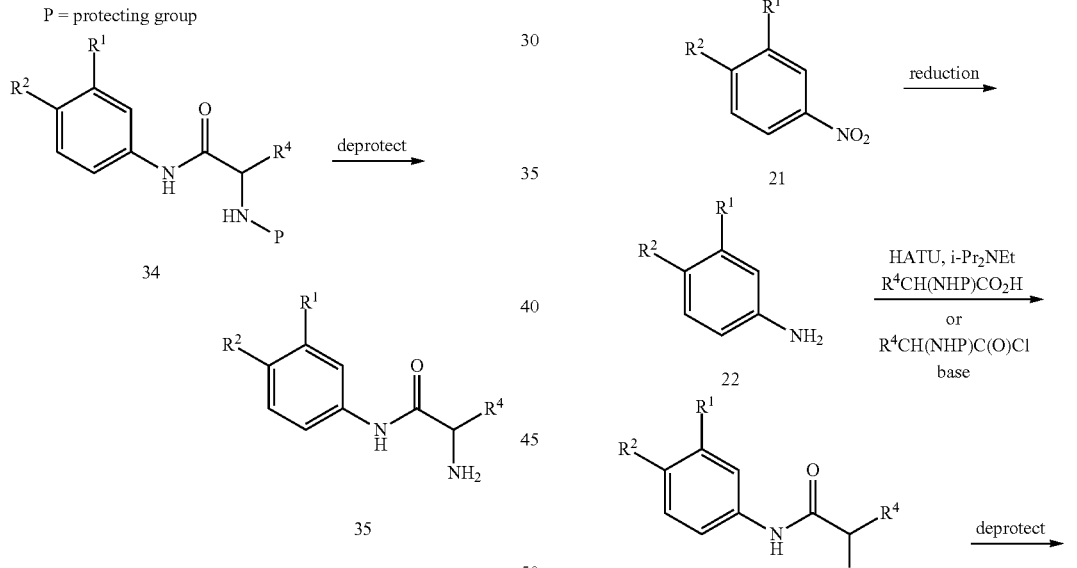

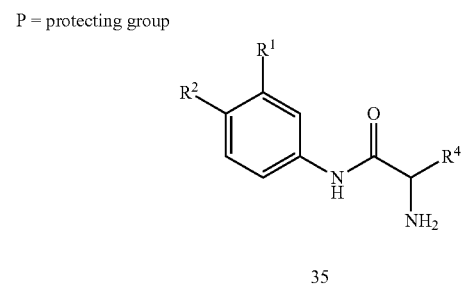

Alternatively, as shown in Scheme 12, compounds of formula 35 are prepared by a method wherein the nature of the coupling partners is reversed. Compounds of formula 33 are converted to the corresponding boronate ester (36) by treatment of 33 with bis(pinacolato)diboron in the presence of a palladium catalyst such as $PdCl_2$(dppf) and a base such as potassium acetate or potassium phosphate in a solvent such as dioxane, THF, or toluene at temperatures ranging from 20° C. to 150° C. Coupling of compounds of formula 36 with aryl and heteroaryl halides in the presence of a palladium catalyst such as $PdCl_2$(dppf) and a base such as cesium carbonate, potassium phosphate, or potassium acetate in a solvent such as DMF or dioxane at temperatures ranging from 20° C. to 150° C. furnishes compounds of formula 34. The coupling reaction is carried out by heating the reaction mixture using standard laboratory methods or by heating the reaction mixture in a microwave. The skilled person will also recognize that the aryl tin intermediate corresponding to 36 can also be prepared and used in the coupling reaction using conditions commonly used for a Stille coupling to form compounds of formula 34. The protecting group is then removed as described in Scheme 2 to provide compounds of formula 35.

Alternatively, as shown in Scheme 13, compounds of formula 35 are prepared by first converting compounds of formula 25 to the corresponding boronate ester (37) by treatment of 25 with bis(pinacolato)diboron in the presence of a palladium catalyst such as $PdCl_2$(dppf) and a base such as potassium acetate or potassium phosphate in a solvent such as dioxane, THF, or toluene at temperatures ranging from 20° C. to 150° C. Alternatively, compounds of formula 25 can be converted to the corresponding alkyltin (37) by treatment of 25 with hexamethylditin in the presence of a palladium catalyst such as $Pd(PPh_3)_4$ in a solvent such as dioxane at temperatures ranging from 50° C. to 150° C. Coupling of compounds of formula 37 with aryl and heteroaryl halides is carried out in the presence of a palladium catalyst such as $PdCl_2$(dppf), $Pd(OAc)_2$, or $Pd(PPh_3)_4$ and a base such as cesium carbonate, potassium carbonate, potassium phosphate, or potassium acetate with or without the addition of tetrabutylammonium bromide in a solvent such as DMF or dioxane at temperatures ranging from 20° C. to 150° C. to furnish compounds of formula 21. When compounds of formula 21 are synthesized according to the method of Deng et al (Org. Lett. 2009, 11, 345-347) additives such as dppf and CuCl are also employed in addition to a palladium catalyst. The coupling reaction is carried out by heating the reaction mixture using standard laboratory methods or by heating the reaction mixture in a microwave. Reduction of the nitro group in 21 is accomplished using standard conditions such as, but not limited to, $H_2$ and Pd/C, zinc with ammonium chloride, or tin chloride in an appropriate solvent such as methanol or ethanol at temperatures ranging from 0° C. to 100° C. to give compounds of formula 22. Compounds of formula 22 are then coupled with a carboxylic acid using standard peptide coupling reagents such as HATU, BOP, EDC, or TBTU in the presence of a base such as N,N-diisopropylethylamine and a solvent such as THF at temperatures ranging from 20° C. to 80° C. to form compounds of formula 34. Alternatively, compounds of formula 22 can be coupled with an acid chloride. The protecting group is then removed as described in Scheme 2 to provide compounds of formula 35.

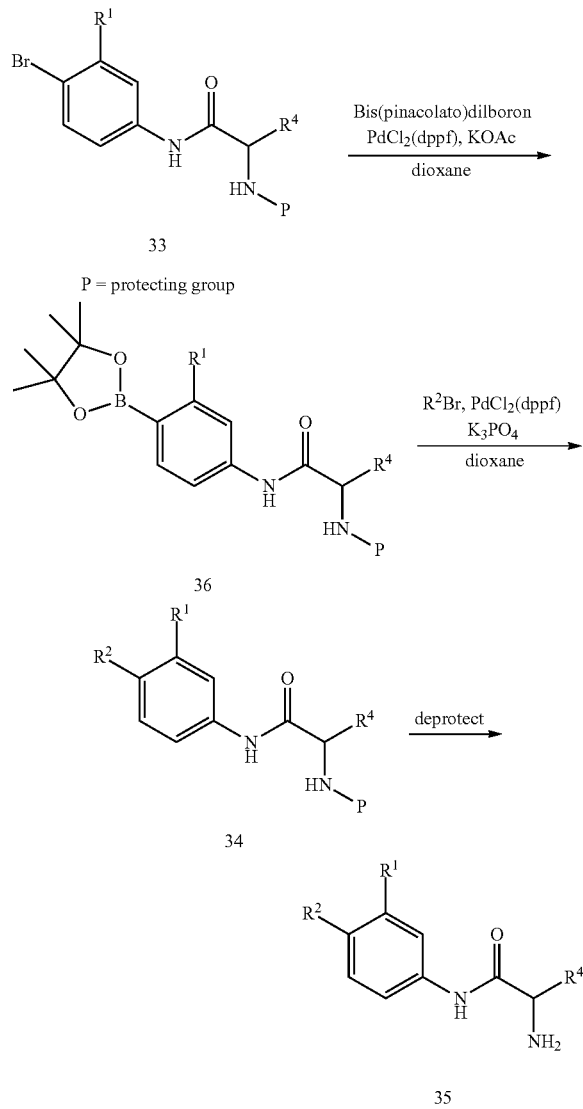

Scheme 12

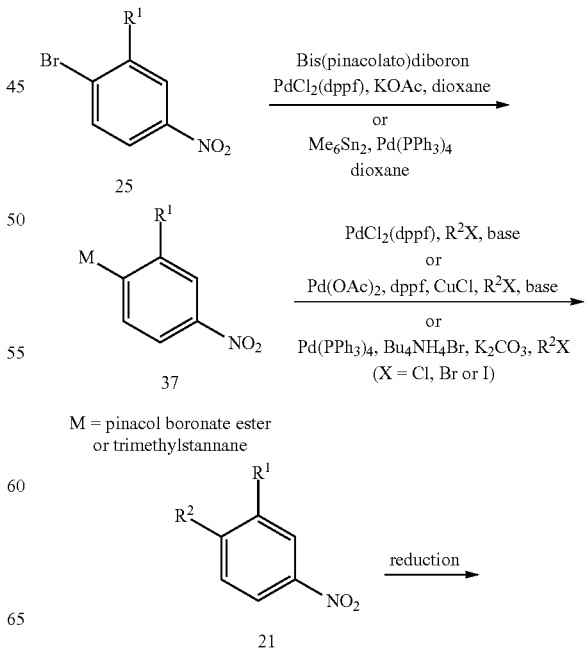

Scheme 13

-continued

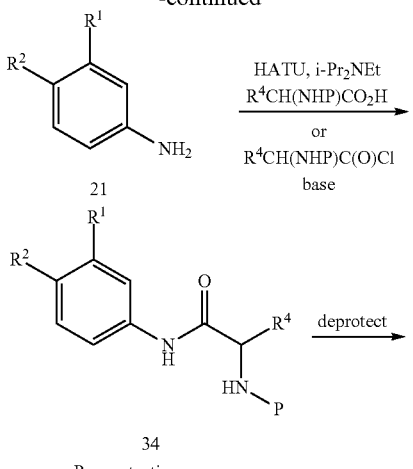

34
P = protecting group

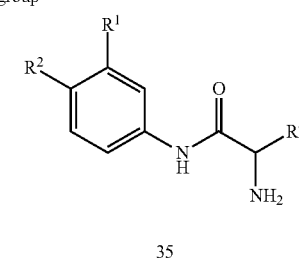

35

An intermediate used for the preparation of compounds of formula 35 wherein $R^2$ is a heteroaryl group and is attached to the central phenyl ring via a nitrogen atom is prepared by the method in Scheme 14. Compounds of formula 25 are treated with a nitrogen containing heterocycle wherein there is a protonated nitrogen in the ring (e.g., imidazole), copper iodide, L-histadine, and potassium carbonate in DMSO as described by Shreedhar et al (*J. of Mol. Catalysis A: Chemical* 2007, 265, 183-185). The mixture is heated at 100° C. to furnish compounds of formula 21. Compounds of formula 35 are prepared from compounds of formula 21 as described in Scheme 13.

Scheme 14

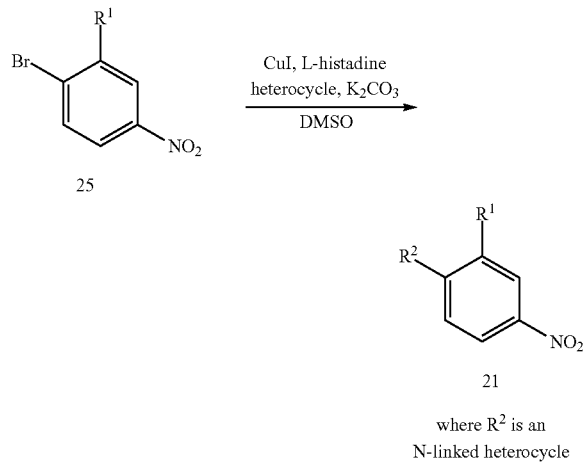

where $R^2$ is an N-linked heterocycle

Compounds of formula (I) wherein substituent "X" contains a mono or disubstituted amine can be prepared according to the methods shown in Scheme 15. Compounds of formula 22 are coupled with a carboxylic acid using standard peptide coupling reagents such as HATU, BOP, EDC, or TBTU in the presence of a base such as N,N-diisopropylethylamine and a solvent such as THF at temperatures ranging from 20° C. to 80° C. to form compounds of formula 38. Alternatively, compounds of formula 22 can be coupled with an acid chloride. The bromide in compounds of formula 38 is displaced with amines in the presence of a base such as N,N-diisopropylethylamine or triethylamine in a polar solvent such as DMF, acetonitrile, acetone, THF, or DMSO at temperatures ranging from 25° C. to 120° C. to form compounds of formula 39. If either $R^5$ or $R^6$ contain a functional group that is protected, the protecting group is removed by treating the substrate with the appropriate reagents as described in *Protective Groups in Organic Synthesis* (Greene, Wuts; $3^{rd}$ ed., 1999, John Wiley & Sons, Inc.).

Scheme 15

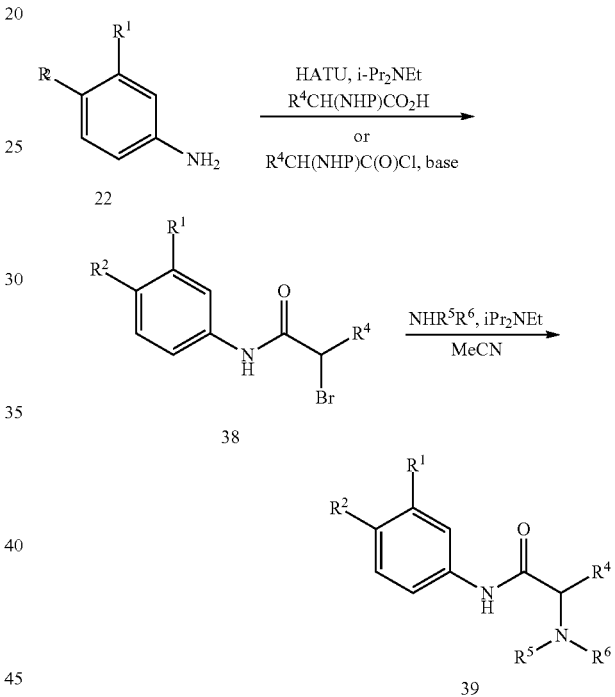

Compounds of formula 45 can be prepared by the methods shown in Scheme 16. Coupling of compounds of formula 25 with a heteroarylboronic acid in the presence of a palladium catalyst such as $Pd(PPh_3)_4$, $(PPh_3)_2PdCl_2$, or $Pd(OAc)_2$ and a base such as sodium carbonate, cesium carbonate, potassium carbonate, or potassium phosphate in the presence or absence of a ligand such as SPhos or XPhos and in a solvent such as DME, DMF, toluene, THF, dioxane, methanol, ethanol, butanol or water or a combination thereof at temperatures ranging from 20° C. to 150° C. furnishes compounds of formula 40. The coupling reaction is carried out by heating the reaction mixture using standard laboratory methods or by heating the reaction mixture in a microwave. Compounds of formula 41 can be formed from adducts 40 using a Buchwald reaction. This reaction can be carried out in the presence of a palladium catalyst such as palladium(II)acetate, a phosphine ligand such as 1,3-bis (diphenylphosphino)propane, and a base such as sodium tert-butoxide in a solvent such as toluene, dioxane, or THF at temperatures ranging from 20° C. to 180° C. It is recognized that a variety of palladium catalysts, phosphine ligands, and bases can be used to carry out this transformation. A detailed summary of various conditions that can be used for this reaction is described by Surry and Buchwald (*Chem. Sci.* 2011, 2, 27-50). Reduction of the nitro group in 41 is accomplished using standard conditions such as, but not limited to, $H_2$ and Pd/C, zinc with ammonium chloride, or tin chloride in an appropriate solvent such as methanol or ethanol at temperatures ranging from 0° C. to 100° C. to give compounds of formula 42. Compounds of formula 42 are then coupled with a carboxylic acid using standard peptide coupling reagents such as HATU, BOP, EDC, or TBTU in the presence of a base such as N,N-diisopropylethylamine and a solvent such as THF at temperatures ranging from 20° C. to 80° C. to form compounds of formula 43. Alternatively, compounds of formula 42 can be coupled with an acid chloride. Removal of the benzyl group can be carried out using conditions such as, but not limited to, $H_2$ and Pd/C or ammonium formate and Pd/C to furnish 44. The protecting group is then removed as described in Scheme 2 to provide compounds of formula 45.

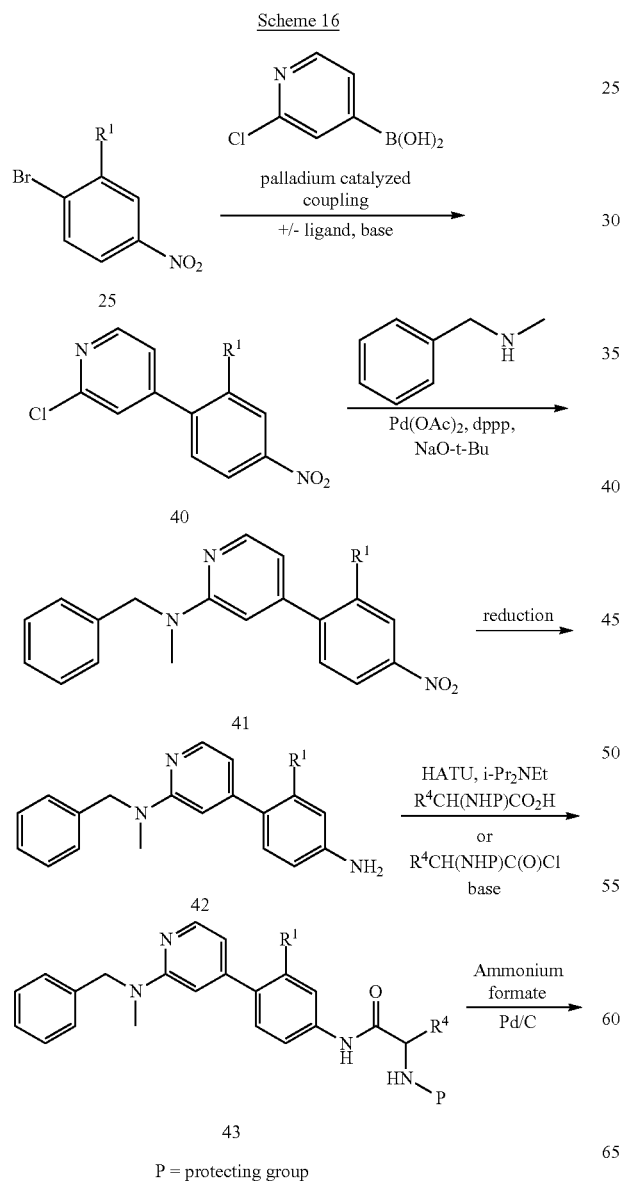

Scheme 16

P = protecting group

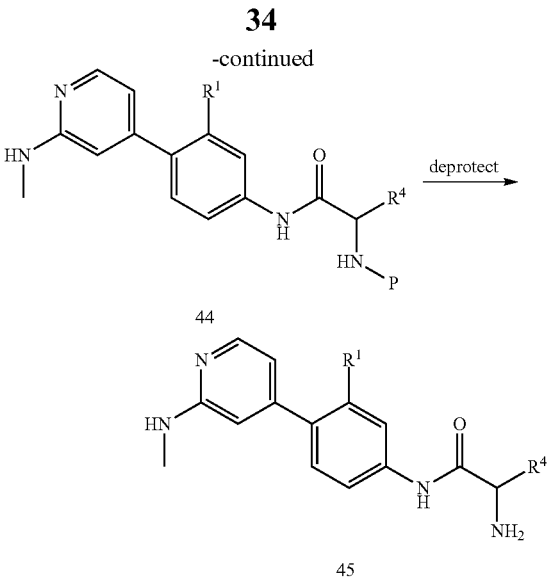

In the case of compounds of formula 46 wherein $R^5$ is alkyl, the amine can be alkylated by the method shown in Scheme 17. Compounds of formula 35 can be prepared by the route described in Schemes 1 and 2. Alkylation is carried out by treatment of 35 with an aldyhyde in the presence of a base such as N,N-diisopropylethylamine or triethylamine in a solvent such as methanol or ethanol at temperatures ranging from 20° C. to 100° C. Subsequent addition of a suitable reducing agent such as sodium borohydride, sodium triacetoxyborohydride, or sodium cyanoborohydride furnishes compounds of formula 46 wherein $R^5$=alkyl.

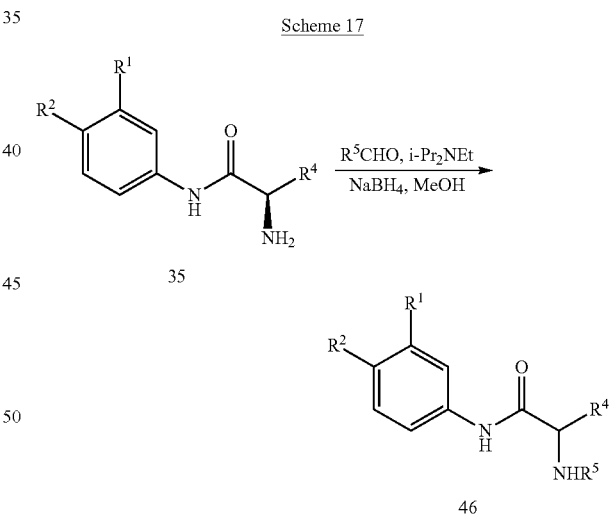

Scheme 17

In the case of compounds of formula 47 wherein $R^5$ is a sulfonamide, the sulfonamide can be formed by the method shown in Scheme 18. Compounds of formula 35 can be prepared by the route described in Schemes 1 and 2. The reaction can be carried out by treatment of 35 with a sulfonyl chloride in the presence of a base such as N,N-diisopropylethylamine or triethylamine in a solvent such as dichloromethane, dichloroethane, THF, or toluene at temperatures ranging from 20° C. to 100° C. The reaction can be carried out in the presence or absence of substance used to promote the reaction such as DMAP to furnish compounds of formula 47 wherein $R^5=SO_2R^7$.

Scheme 18

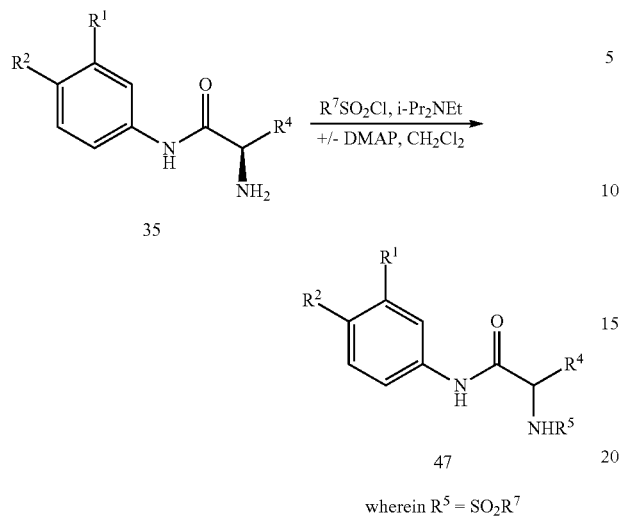

wherein $R^5 = SO_2R^7$

Compounds of formula (I) wherein $R^1$=OMe, $R^2$=oxazol-5-yl, and Z=F can be prepared according to the methods shown in Scheme 19. Alkylation of the phenol is carried out by treating compounds of formula 48 with a base such as, but not limited to, potassium carbonate, sodium carbonate, sodium hydroxide, or sodium hydride and an electrophile such as methyl iodide in the presence of a polar solvent such as DMF, THF, or DME at temperatures ranging from 0° C. to 150° C. to furnish compounds of formula 49. The bromide at $R^1$ of 49 is replaced with a vinyl group by using a palladium catalyzed coupling reaction, including reaction conditions familiar to those skilled in the art such as a Suzuki reaction, Stille reaction, or Negishi reaction. Reaction conditions include reaction of 49 with 2,4,6-trivinyl-1,3,5,2,4,6-trioxatriborinane pyridine complex in the presence of a base such as sodium carbonate, potassium carbonate, or cesium carbonate and a catalyst such as $Pd(PPh_3)_4$, $Pd_2(dba)_3$, or $PdCl_2(PPh_3)_2$ in a solvent such as toluene, dichloroethane, THF, DMF, methanol, ethanol, water or a combination thereof at temperatures ranging from 20° C. to 150° C. to form compound 50. Oxidation of the olefin in 50 using osmium tetroxide and sodium periodate in the presence of 2,6-lutidine or using ozone furnishes compounds of formula 51. Treatment of 51 with TosMIC in the presence of a base such as potassium carbonate in a solvent such as methanol affords compound 52. Reduction of the nitro group in 52 is accomplished using standard conditions such as, but not limited to, $H_2$ and Pd/C, zinc with ammonium chloride, or tin chloride in an appropriate solvent such as methanol or ethanol at temperatures ranging from 0° C. to 100° C. to give compounds of formula 53. Compounds of formula 53, are coupled with a carboxylic acid using standard peptide coupling reagents such as HATU, BOP, EDC, or TBTU in the presence of a base such as N,N-diisopropylethylamine and a solvent such as THF at temperatures ranging from 20° C. to 80° C. to form compounds of formula 54. Alternatively, compounds of formula 53 can be coupled with an acid chloride. The protecting group is then removed as described in Scheme 2 to provide compounds of formula 55.

Scheme 19

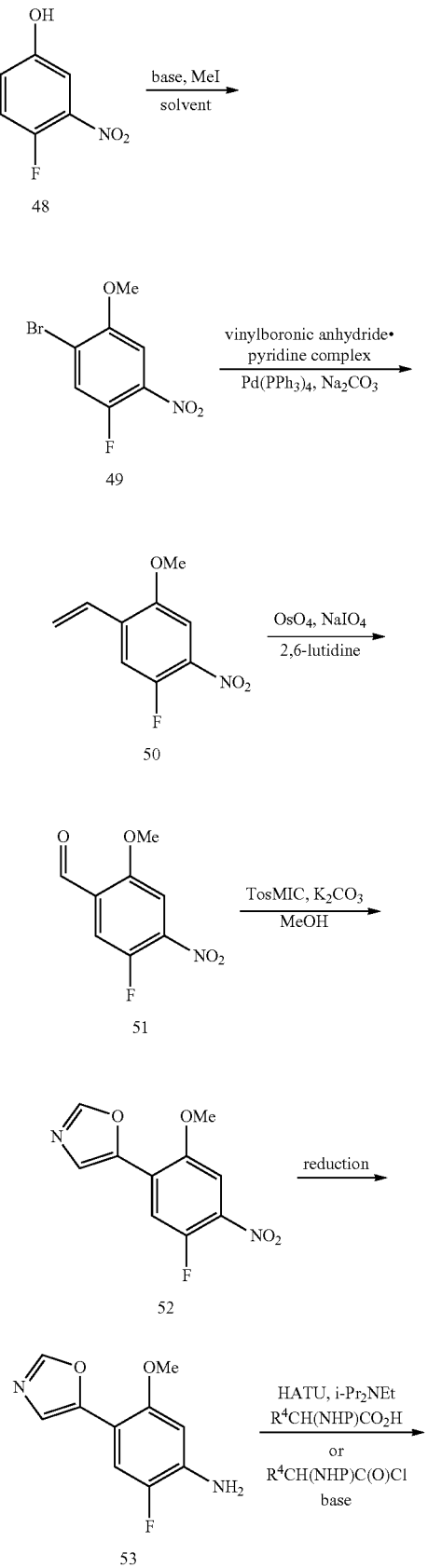

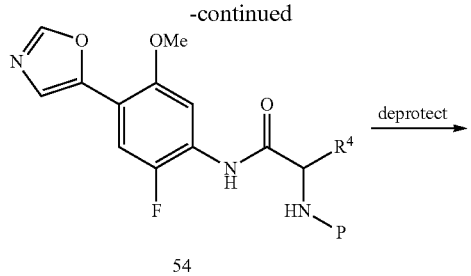

54

P = protecting group

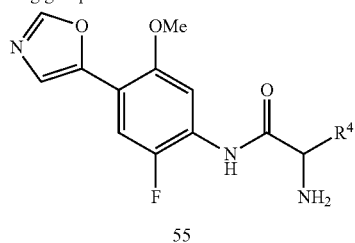

55

Compounds of formula (I) wherein $R^1$=OMe, $R^2$=oxazol-5-yl, and Z=CN can be prepared according to the methods shown in Scheme 20. Compounds of formula 56 (prepared as described by Dyke, H. J. et al., PCT Int. Appl. (2003), WO2003053958 A1 20030703) are coupled with a carboxylic acid in the presence of phosphorous oxychloride and pyridine at temperatures ranging from −10° C. to 50° C. to form compounds of formula 57. Compounds of formula 57 are then treated with CuCN and KI in a solvent such as NMP at 160° C. to afford compounds of formula 58. The protecting group is then removed as described in Scheme 2 to provide compounds of formula 59.

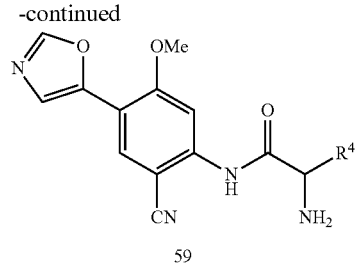

59

Compounds of formula (I) wherein Z=2H-tetrazol-5-yl can be prepared according to the methods shown in Scheme 21. Compounds of formula 60 (prepared as described by Buchmann, et al, PCT Int. Appl., 2010009845) are coupled with a carboxylic acid in the presence of phosphorous oxychloride and pyridine at temperatures ranging from −10° C. to 50° C. to form compounds of formula 61. Compounds of formula 62 are formed by heating 61 at 100° C. in a solvent such as DMF in the presence of sodium azide and ammonium chloride. Compounds of formula 63 are formed using either the three-step procedure described in Scheme 19 for the conversion of 49 to 52 when $R^2$=oxazol-5-yl or the procedure for the conversion of 33 to 34 (Scheme 10) when $R^2$=a variety of other heterocycles. The protecting group is then removed as described in Scheme 2 to provide compounds of formula 64.

Scheme 20

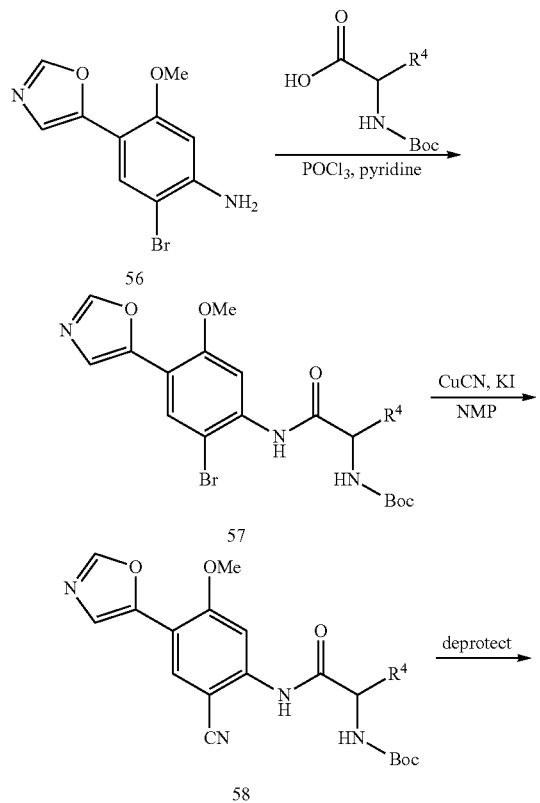

Scheme 21

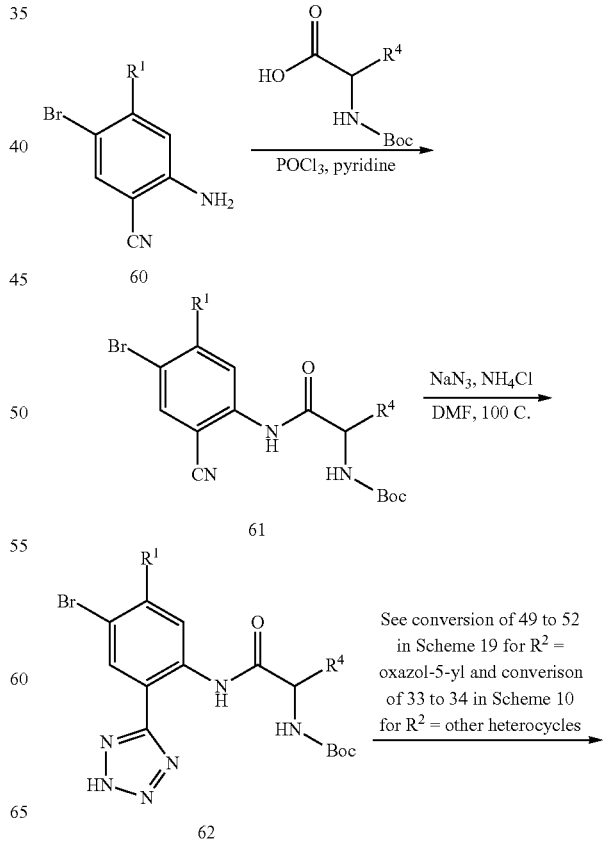

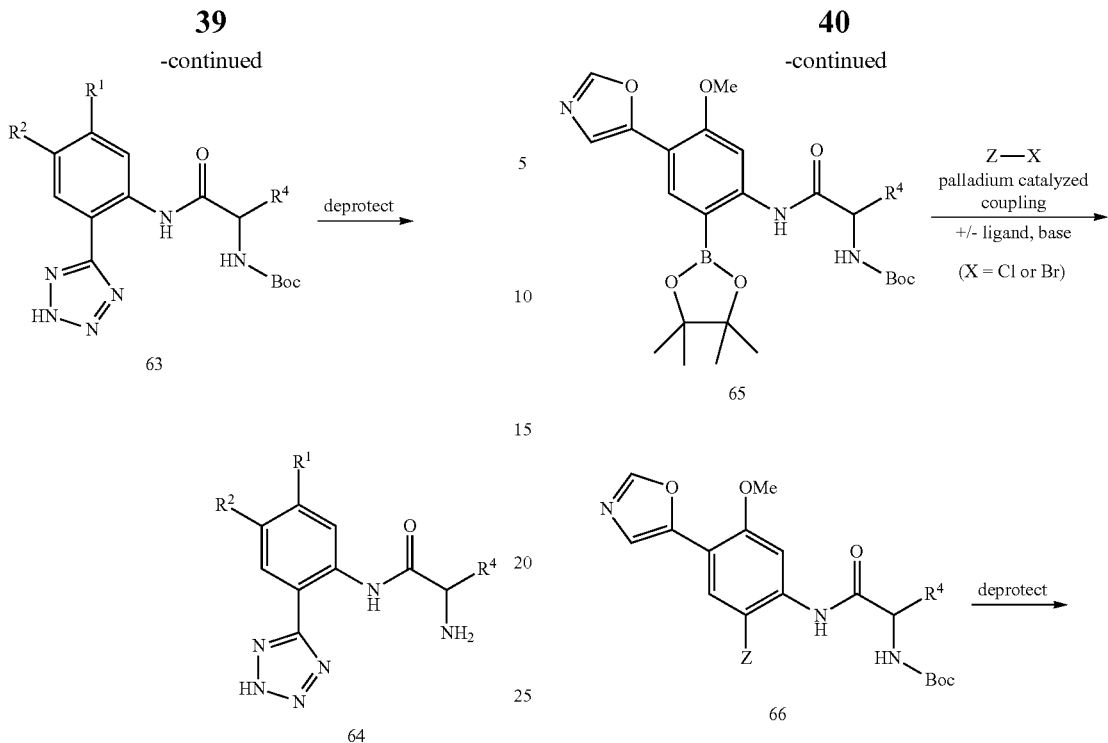

Compounds of formula (I) wherein $R^1$=OMe, $R^2$=oxazol-5-yl, and Z=aryl or heteroaryl can be prepared according to the methods shown in Scheme 22. Compounds of formula 57 (prepared as described in Scheme 20) are converted to the corresponding boronate ester (65) by treatment of 57 with bis(pinacolato)diboron in the presence of a palladium catalyst such as $PdCl_2$(dppf) and a base such as potassium acetate or potassium phosphate in a solvent such as dioxane, THF, or toluene at temperatures ranging from 20° C. to 150° C. Coupling of compounds of formula 65 with aryl and heteroaryl halides in the presence of a palladium catalyst such as $Pd(PPh_3)_4$ or $Pd(OAc)_2$ and a base such as sodium carbonate, cesium carbonate, potassium carbonate, or potassium phosphate in the presence or absence of a ligand such as SPhos or XPhos and in a solvent such as DME, DMF, toluene, THF, dioxane, methanol, ethanol, butanol or water or a combination thereof at temperatures ranging from 20° C. to 150° C. furnishes compounds of formula 66. The coupling reaction is carried out by heating the reaction mixture using standard laboratory methods or by heating the reaction mixture in a microwave. The protecting group is then removed as described in Scheme 2 to provide compounds of formula 67.

Scheme 22

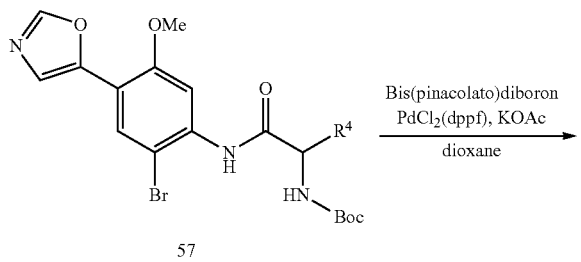

Compounds of formula (I) wherein $R^1$=OMe, $R^2$=oxazol-5-yl, and Z=oxazol-5-yl can be prepared according to the methods shown in Scheme 23. The aniline nitrogen of compound 56 (prepared as described by Dyke, H. J. et al., PCT Int. Appl. (2003), WO2003053958 A1 20030703) is protected to furnish 68. An appropriate protecting group may be chosen as described in *Protective Groups in Organic Synthesis* (Greene, Wuts; 3$^{rd}$ ed., 1999, John Wiley & Sons, Inc.). The preferred protecting group is the p-methoxybenzyl group. Reaction of 56 with a base such as sodium hydride and 1-(chloromethyl)-4-methoxybenzene in a solvent such as DMF or THF results in the formation of compound 68. Compounds of formula 69 are formed using the three-step procedure described in Scheme 19 for the conversion of 49 to 52. The protecting groups in compound 69 are removed by treating the substrate with an appropriate reagent as described in *Protective Groups in Organic Synthesis* (Greene, Wuts; 3$^{rd}$ ed., 1999, John Wiley & Sons, Inc.), preferably TFA, to provide compounds of formula 70. Compounds of formula 70 are coupled with a carboxylic acid in the presence of phosphorous oxychloride and pyridine at temperatures ranging from −10° C. to 50° C. to form compounds of formula 71. The protecting group is then removed as described in Scheme 2 to provide compounds of formula 72.

Scheme 23

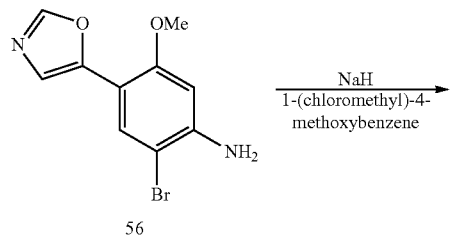

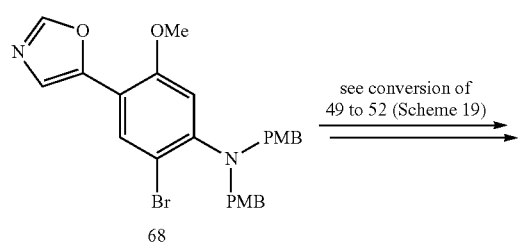

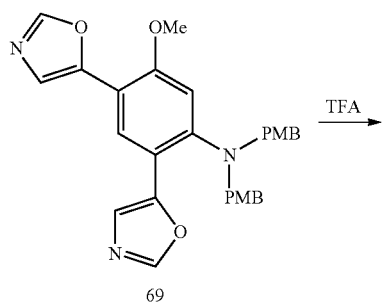

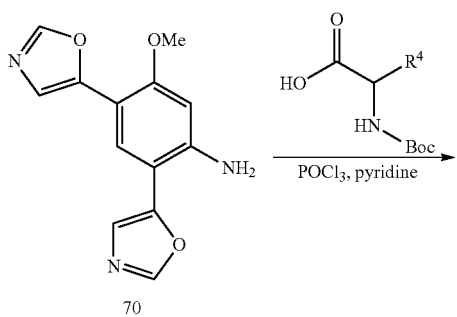

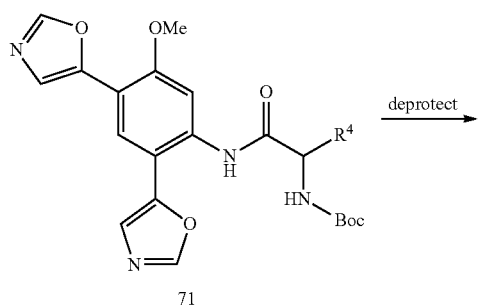

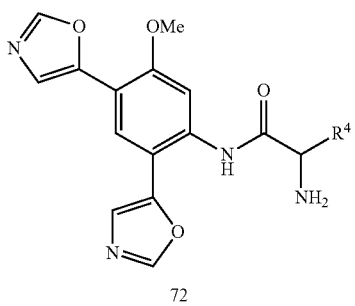

Compounds of formula (I) wherein $R^1$=F, $R^2$=oxazol-5-yl, and Z=OMe can be prepared by the methods shown in Scheme 24. The carboxylic acid in 73 may be reduced with a reducing agent such as DIBAL or lithium aluminum hydride in a solvent such as THF. Subsequent oxidation of the resultant alcohol with oxidizing agents or conditions such as Swern oxidation, TPAP, manganese dioxide, Dess-Martin periodinane or chromium trioxide may be used to furnish compound 74. Treatment of 74 with TosMIC in the presence of a base such as potassium carbonate in a solvent such as methanol affords 5-phenyloxazoles 75. Displacement of the fluoro ortho to the nitro group can be carried out by heating compound 75 in the presence of a base such as potassium carbonate in methanol at temperatures ranging from 50° C. to 120° C. Reduction of the nitro group in 76 is accomplished using standard conditions such as, but not limited to, $H_2$ and Pd/C, zinc with ammonium chloride, or tin chloride in an appropriate solvent such as methanol or ethanol at temperatures ranging from 0° C. to 100° C. to give compounds of formula 77. Compounds of formula 77, are coupled with a carboxylic acid using standard peptide coupling reagents such as HATU, BOP, EDC, or TBTU in the presence of a base such as N,N-diisopropylethylamine and a solvent such as THF at temperatures ranging from 20° C. to 80° C. to form compounds of formula 78. Alternatively, compounds of formula 77 can be coupled with an acid chloride. The protecting group is then removed as described in Scheme 2 to provide compounds of formula 79.

Scheme 24

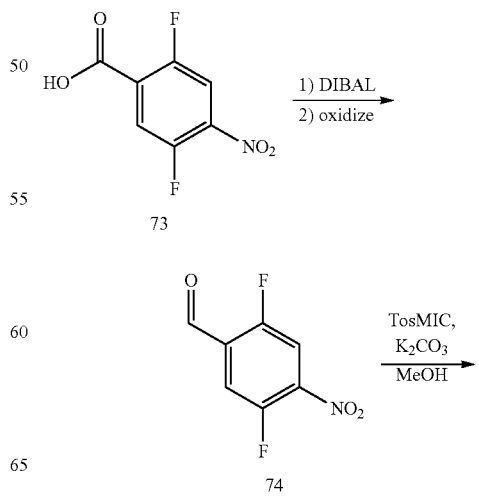

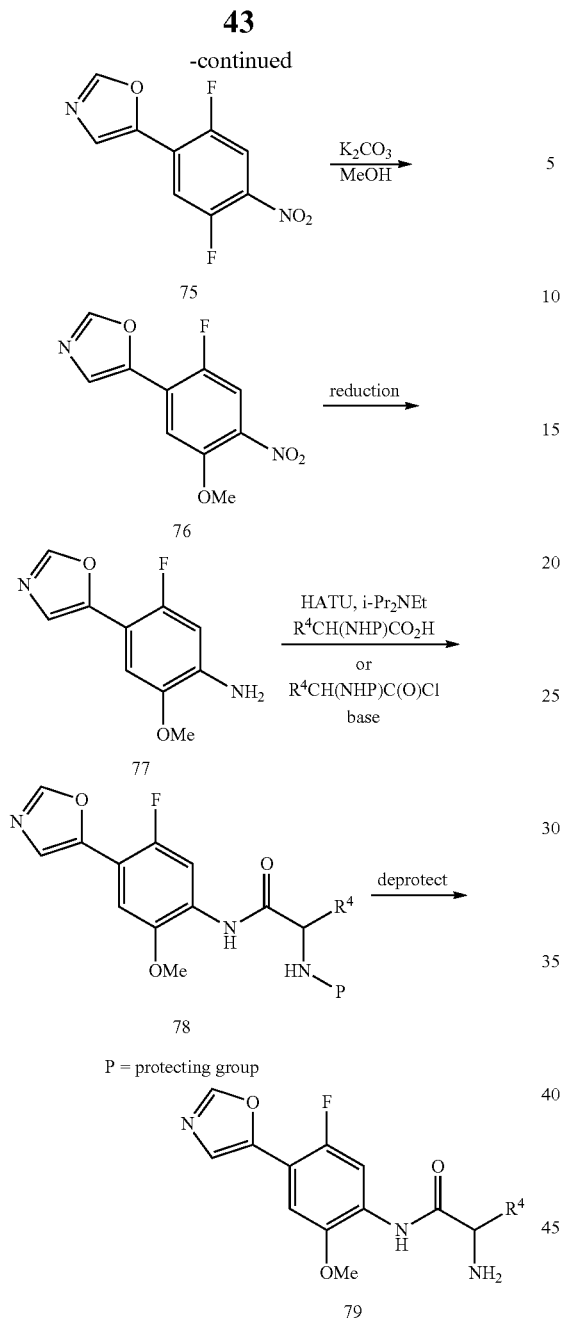

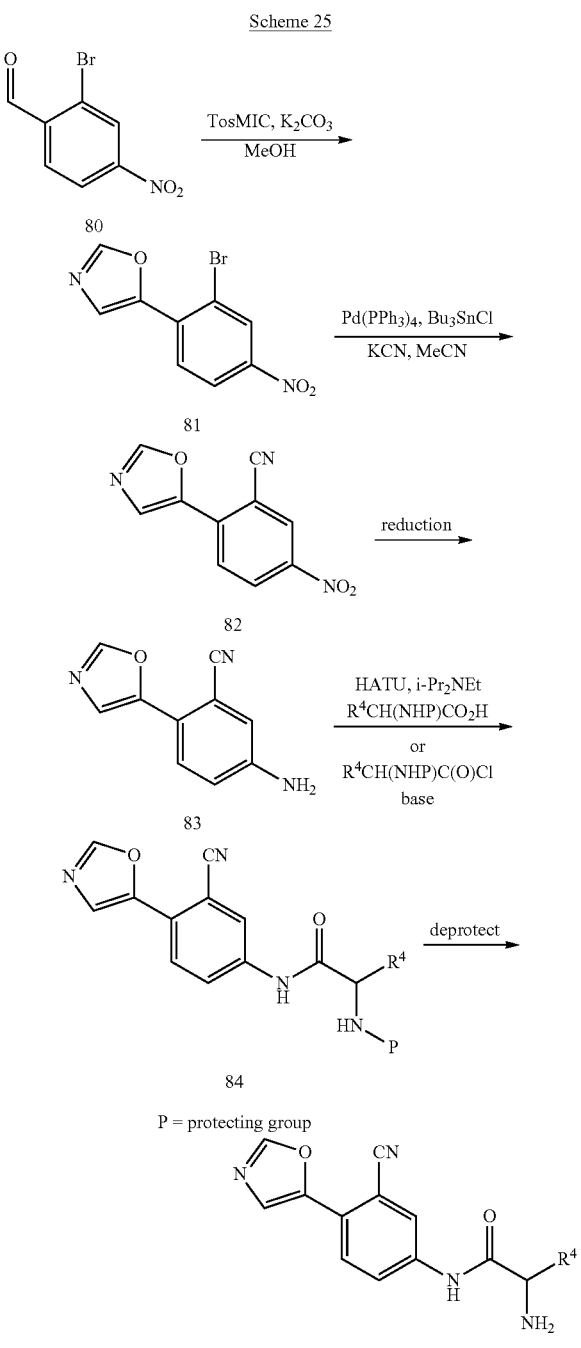

ane and aqueous KF in the presence of catalytic palladium acetate in a solvent such as THF under a $H_2$ atmosphere. Compounds of formula 83 are coupled with a carboxylic acid using standard peptide coupling reagents such as HATU, BOP, EDC, or TBTU in the presence of a base such as N,N-diisopropylethylamine and a solvent such as THF at temperatures ranging from 20° C. to 80° C. to form compounds of formula 84. Alternatively, compounds of formula 83 can be coupled with an acid chloride. The protecting group is then removed as described in Scheme 2 to provide compounds of formula 85.

Compounds of formula (I) wherein $R^1$=CN and $R^2$=oxazol-5-yl can be prepared by the methods shown in Scheme 25. Compound 81 was synthesized from compound 80 (prepared in two steps as described by Iwanowicz, Edwin J. et al. *Bioorg. Med. Chem. Lett.* 2003, 13, 2059) by treatment of 80 with TosMIC in the presence of a base such as potassium carbonate in a solvent such as methanol. Heating compound 81 with potassium cyanide and tributyltin chloride in the presence of catalytic tetrakis(triphenylphosphine)palladium(0) at temperatures ranging from 70° C. to 120° C. in a solvent such as acetonitrile, THF, or dioxane provides compounds of formula 82. Reduction of the nitro group in 82 may be carried out using standard conditions such as, but not limited to, $H_2$ and Pd/C, zinc with ammonium chloride, or tin chloride in an appropriate solvent such as methanol or ethanol at temperatures ranging from 0° C. to 100° C. to give compounds of formula 83. Alternatively, reduction of the nitro group in 82 can be carried out by treatment of 82 with polymethylhydrosilox- Compounds of formula (I) wherein $R^1$=OMe, $R^2$=oxazol-5-yl, and Z=ethyl can be prepared by the methods shown in Scheme 25. Compound 87 was synthesized from compound 86 (Pham et al. *J. Med. Chem.* 2007, 50, 3561) by bromination with a suitable brominating agent, such as bromine or NBS, in a solvent such as acetic acid. The ester in 87 may be reduced with a reducing agent such as DIBAL or lithium aluminum hydride in a solvent such as THF. Subsequent oxidation of the resultant alcohol with oxidizing agents or conditions such as Swern oxidation, TPAP, manganese dioxide, Dess-Martin periodinane or chromium trioxide may be used to furnish compound 88. Treatment of compounds of formula 88 with TosMIC in the presence of a base such as potassium carbonate in a solvent such as methanol affords compounds of formula 89. The bromide in 89 can be replaced with a vinyl group by using a palladium catalyzed coupling reaction, including reaction conditions familiar to those skilled in the art such as a Suzuki reaction, Stille reaction, or Negishi reaction. Reaction conditions include reaction of 89 with 2,4,6-trivinyl-1,3,5,2,4,6-trioxatriborinane pyridine complex in the presence of a base such as sodium carbonate, potassium carbonate, or cesium carbonate and a catalyst such as Pd(PPh$_3$)$_4$, Pd$_2$(dba)$_3$, or PdCl$_2$(PPh$_3$)$_2$ in a solvent such as toluene, dichloroethane, THF, DMF, methanol, ethanol, water or a combination thereof at temperatures ranging from 20° C. to 150° C. to form compound 90. Reduction of the olefin in 90 can be carried out using standard conditions such as, but not limited to, H$_2$ and Pd/C to give compounds of formula 91. Hydrolysis of the acetamide in 91 can be carried out by heating 91 in the presence of a hydroxide, such as potassium hydroxide of sodium hydroxide in a solvent or combination of solvents, such as methanol or ethanol and water at temperatures ranging from 50° C. to 150° C. to furnish compounds of formula 92. Compounds of formula 92 are coupled with a carboxylic acid using standard peptide coupling reagents such as HATU, BOP, EDC, or TBTU in the presence of a base such as N,N-diisopropylethylamine and a solvent such as THF at temperatures ranging from 20° C. to 80° C. to form compounds of formula 93. Alternatively, compounds of formula 92 can be coupled with an acid chloride. The protecting group is then removed as described in Scheme 2 to provide compounds of formula 94.

Scheme 26

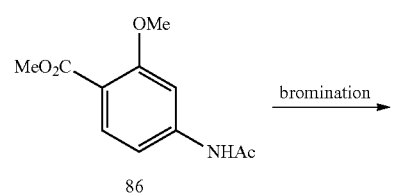

86

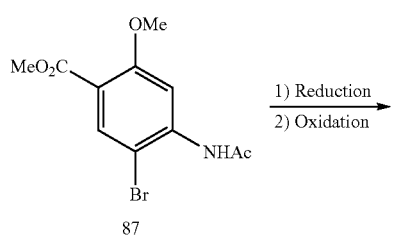

87

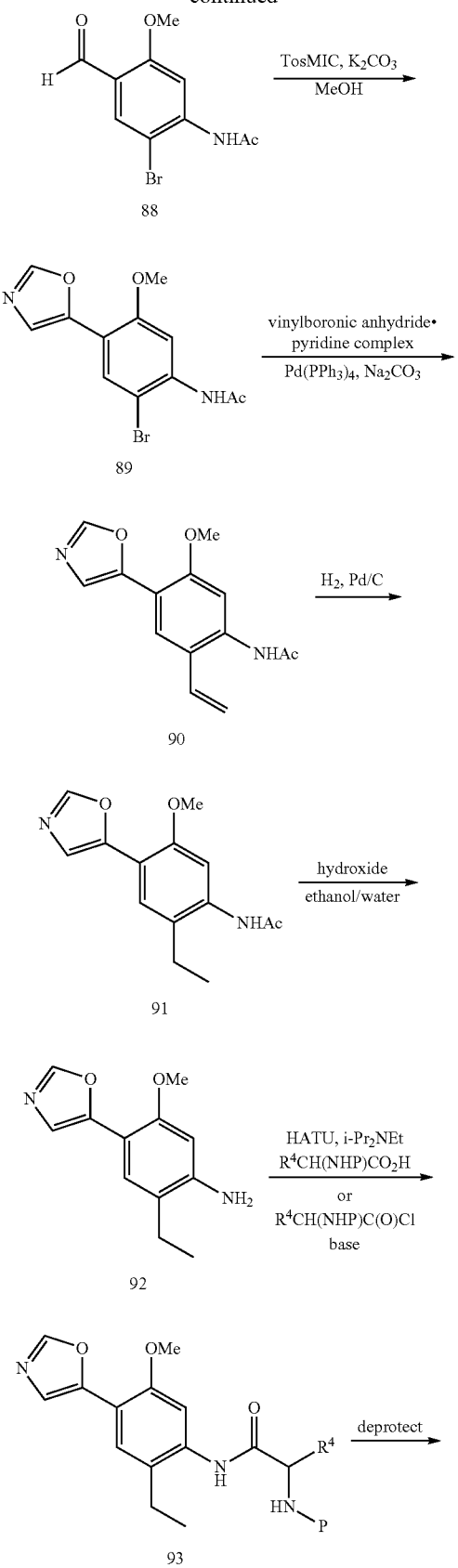

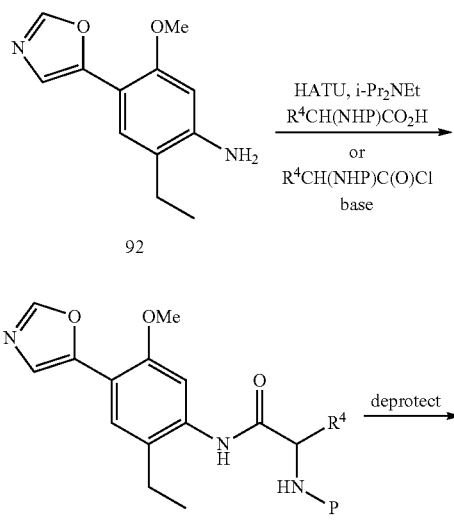

P = protecting group

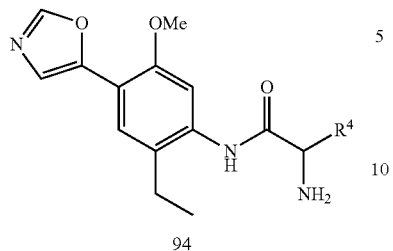

Compounds of formula (I) wherein R²=pyridyl, and Z=aryl or heteroaryl can be prepared by the methods shown in Scheme 27. Coupling of compounds of formula 95 with pyridylboronic acid in the presence of a palladium catalyst such as Pd(PPh₃)₄ or Pd(OAc)₂ and a base such as sodium carbonate, cesium carbonate, potassium carbonate, or potassium phosphate in the presence or absence of a ligand such as SPhos or XPhos and in a solvent such as DME, DMF, toluene, THF, dioxane, methanol, ethanol, butanol or water or a combination thereof at temperatures ranging from 20° C. to 150° C. furnishes compounds of formula 96. The coupling reaction is carried out by heating the reaction mixture using standard laboratory methods or by heating the reaction mixture in a microwave. Compound 97 was synthesized from compound 96 by bromination with a suitable brominating agent, such as bromine or NBS, in a solvent such as acetic acid. Hydrolysis of the acetamide in 97 can be carried out by heating 97 in the presence of a hydroxide, such as potassium hydroxide or sodium hydroxide in a solvent or combination of solvents, such as methanol or ethanol and water at temperatures ranging from 50° C. to 150° C. to furnish compounds of formula 98. Compounds of formula 98 are coupled with a carboxylic acid in the presence of phosphorous oxychloride and pyridine at temperatures ranging from −10° C. to 50° C. to form compounds of formula 99. Coupling of compounds of formula 99 with an aryl or heteroaryl boronic acid or ester (100) in the presence of a palladium catalyst such as Pd(PPh₃)₄ or Pd(OAc)₂ and a base such as sodium carbonate, cesium carbonate, potassium carbonate, or potassium phosphate in the presence or absence of a ligand such as SPhos or XPhos and in a solvent such as DME, DMF, toluene, THF, dioxane, methanol, ethanol, butanol or water or a combination thereof at temperatures ranging from 20° C. to 150° C. furnishes compounds of formula 101. The coupling reaction is carried out by heating the reaction mixture using standard laboratory methods or by heating the reaction mixture in a microwave. The protecting group is then removed using a suitable reagent, such as TFA or HCl, to provide compounds of formula 102.

Scheme 27

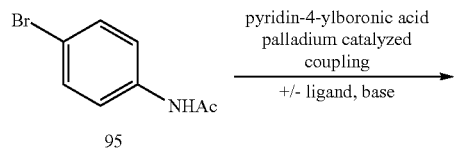

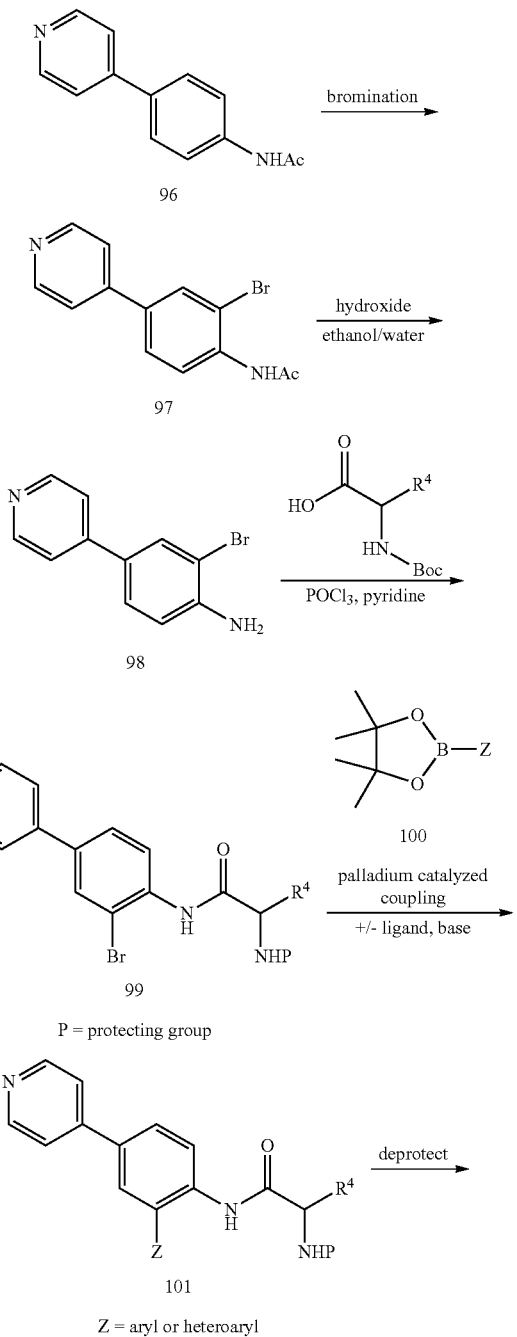

Various analogs synthesized using Schemes 1-27 are listed in Table 1.

TABLE 1

(I)

| Example | R¹ | R² | R³ | Z | Y | X | (M + H)⁺ |
|---|---|---|---|---|---|---|---|
| 1 | OMe | oxazole | H | C(O)CH(NH₂)CH₂CH(CH₃)₂ (S) | H | H | 304.3 |
| 2 | OMe | oxazole | H | C(O)-pyrrolidine (NH) | H | H | 288.2 |
| 3 | OMe | oxazole | H | C(O)CH(NH₂)-cyclopentyl (S) | H | H | 316.3 |
| 4 | OMe | oxazole | H | C(O)CH(NH₂)CH(CH₃)₂ (S) | H | H | 290.2 |
| 5 | OMe | oxazole | H | C(O)CH(NH₂)CH₂CH(CH₃)₂ (R) | H | H | 304.3 |
| 6 | OMe | oxazole | H | C(O)CH(NH₂)CH₂-cyclobutyl (S) | H | H | 316.3 |
| 7 | OMe | oxazole | H | C(O)CH(NH₂)CH₂CH(CH₃)₂ | H | H | 304.2 |
| 8 | OMe | oxazole | H | C(O)CH(NH₂)CH₂CH₂CH(CH₃)₂ | H | H | 318.2 |
| 9 | OMe | oxazole | H | C(O)CH(NH₂)CH₂-cyclopropyl (S) | H | H | 302.3 |

TABLE 1-continued (I)

| Example | R¹ | R² | R³ | Z | Y | X | (M + H)⁺ |
|---|---|---|---|---|---|---|---|
| 10 | OMe | oxazol-5-yl | Et | leucinyl | H | H | 332.4 |
| 11 | CF₃ | oxazol-5-yl | H | leucinyl | H | H | 342.3 |
| 12 | Br | oxazol-5-yl | H | leucinyl | H | H | 352.3 |
| 13 | Me | oxazol-5-yl | H | leucinyl | H | H | 288.3 |
| 14 | Et | oxazol-5-yl | H | leucinyl | H | H | 302.4 |
| 15 | thiophen-3-yl | oxazol-5-yl | H | leucinyl | H | H | 356.2 |
| 16 | OH | oxazol-5-yl | H | leucinyl | H | H | 290.3 |
| 17 | OEt | oxazol-5-yl | H | leucinyl | H | H | 318.3 |
| 18 | OCHF₂ | oxazol-5-yl | H | leucinyl | H | H | 340.3 |

TABLE 1-continued (I)

| Example | R¹ | R² | R³ | Z | Y | X | (M + H)⁺ |
|---|---|---|---|---|---|---|---|
| 19 | OMe | 2H-triazol-4-yl | H | Leu (C(O)CH(NH₂)CH₂CH(CH₃)₂) | H | H | 304.3 |
| 20 | OMe | pyridin-4-yl | H | Leu | H | H | 314.4 |
| 21 | OMe | thiazol-5-yl | H | Leu | H | H | 320.1 |
| 22 | OMe | pyridazin-4-yl | H | Leu | H | H | 315.3 |
| 23 | OMe | 1,3,4-thiadiazol-2-yl | H | Leu | H | H | 321.3 |
| 24 | OMe | 1H-pyrazol-4-yl | H | Leu | H | H | 303.2 |
| 25 | OMe | imidazol-1-yl | H | Leu | H | H | 303.2 |
| 26 | OMe | 1,2,4-triazol-1-yl | H | Leu | H | H | 304.2 |
| 27 | OMe | oxazol-5-yl | H | Leu | H | Cl | 338.2 |

TABLE 1-continued
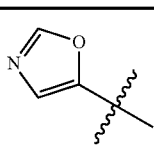
(I)
| Example | R¹ | R² | R³ | Z | Y | X | (M + H)⁺ |
|---|---|---|---|---|---|---|---|
| 28 | OMe | 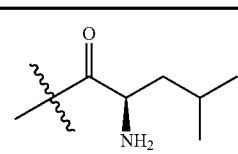 | H | 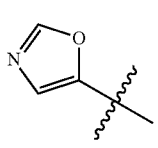 | Cl | H | 338.2 |
| 29 | OMe | 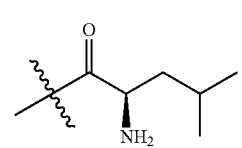 | H | 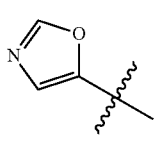 | Cl | Cl | 372.1 |
| 30 | OMe | 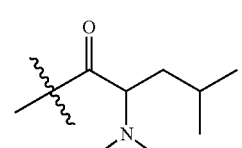 | H | 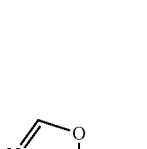 | H | H | 373.4 |
| 31 | OMe | 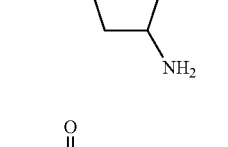 | H | 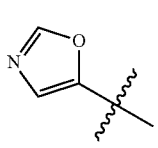 | H | H | 401.4 |
| 32 | OMe | 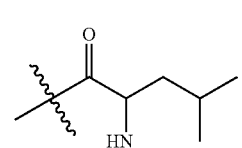 | H | 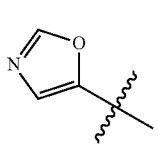 | H | H | 359.3 |
| 33 | OMe | 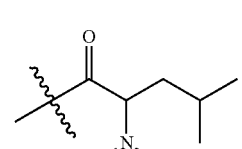 | H |  | H | H | 387.3 |

TABLE 1-continued (I)

| Example | R¹ | R² | R³ | Z | Y | X | (M + H)⁺ |
|---|---|---|---|---|---|---|---|
| 34 | OMe | oxazol-5-yl | H | C(O)CH(OH)CH₂CH(CH₃)₂ | H | H | 305.1 |
| 35 | OMe | oxazol-5-yl | H | C(O)CH(CH₂NH₂)CH₂CH(CH₃)₂ | H | H | 318.3 |
| 36 | OMe | oxazol-5-yl | H | C(O)-(3-isopropylpyrrolidin-2-yl) | H | H | 330.2 |
| 37 | OMe | oxazol-5-yl | H | C(O)-(3-isopropylpyrrolidin-2-yl) | H | H | 330.2 |
| 38 | OMe | oxazol-5-yl | H | C(O)-(3-isopropylpyrrolidin-2-yl) | H | H | 330.2 |
| 39 | OMe | oxazol-5-yl | H | C(O)-(3-isopropylpyrrolidin-2-yl) | H | H | 330.2 |
| 40 | F | oxazol-5-yl | H | C(O)CH(NH₂)CH₂CH(CH₃)₂ | H | H | 292.2 |
| 41 | OCHF₂ | 1H-pyrazol-4-yl | H | C(O)CH(NH₂)CH₂CH(CH₃)₂ | H | H | 339.1 |

TABLE 1-continued (I)

| Example | R¹ | R² | R³ | Z | Y | X | (M + H)⁺ |
|---|---|---|---|---|---|---|---|
| 42 | NMe₂ | oxazol-5-yl | H | leucinyl C(O)CH(NH₂)CH₂CH(CH₃)₂ | H | H | 317.1 |
| 43 | OMe | 6-chloropyridazin-3-yl | H | leucinyl | H | H | 348.1 |
| 44 | H | 3-methoxypyridin-4-yl | H | leucinyl | H | H | 314.1 |
| 45 | OMe | 2-aminopyridin-4-yl | H | leucinyl | H | H | 329.2 |
| 46 | OMe | imidazo[1,2-b]pyridazin-3-yl | H | leucinyl | H | H | 354.2 |
| 47 | OMe | 6-chloroimidazo[1,2-b]pyridazin-3-yl | H | leucinyl | H | H | 388.2 |
| 48 | OMe | 2-(methylamino)pyridin-4-yl | H | leucinyl | H | H | 343.2 |
| 49 | OMe | 6-(methylamino)imidazo[1,2-b]pyridazin-3-yl | H | leucinyl | H | H | 383.3 |

TABLE 1-continued (I)

| Example | R¹ | R² | R³ | Z | Y | X | (M + H)⁺ |
|---|---|---|---|---|---|---|---|
| 50 | OMe | oxazole | H | C(=O)CH(NH₂)CH₂CH₃ | H | H | 276.1 |
| 51 | OMe | oxazole | H | C(=O)CH(NH₂)CH₂CH₂CH₃ | H | H | 290.1 |
| 52 | OMe | oxazole | H | C(=O)CH(NH₂)CH₂CH₂CH₂CH₃ | H | H | 304.2 |
| 53 | OMe | oxazole | H | C(=O)CH(NH₂)CH₂CH₂CH₂CH₃ (epimer) | H | H | 304.2 |
| 54 | OMe | oxazole | H | C(=O)CH(NH₂)CH₂CH₂SCH₃ | H | H | 322.1 |
| 55 | OMe | oxazole | H | C(=O)CH(NH₂)CH(CH₃)CH₂CH₃ | H | H | 304.2 |
| 56 | OMe | oxazole | H | C(=O)CH(NH₂)CH₂-cyclohexyl | H | H | 344.2 |
| 57 | OMe | oxazole | H | C(=O)-(imidazolidin-2-one-4-yl) | H | H | 303.1 |
| 58 | OMe | oxazole | H | C(=O)-C(NHCH₃)(cyclopropyl) | H | H | 288.1 |

TABLE 1-continued
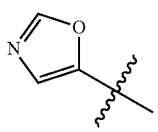 [SMILES: *c1cnco1]
(I)
| Example | R¹ | R² | R³ | Z | Y | X | (M + H)⁺ |
|---|---|---|---|---|---|---|---|
| 59 | OMe | 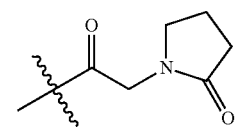 | H | 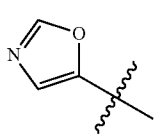 [SMILES: *c1cnco1] | H | H | 316.1 |
| 60 | OMe | 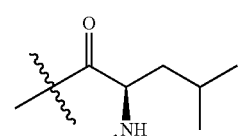 | H | 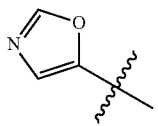 | H | H | 428.1 |
| 61 | OMe | 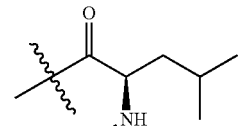 | H | 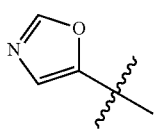 [SMILES: *c1cnco1] | H | H | 397.1 |
| 62 | OMe | 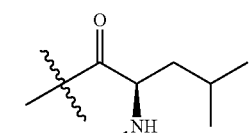 | H | 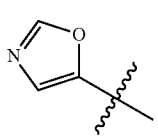 [SMILES: *c1cnco1] | H | H | 410.1 |
| 63 | OMe | 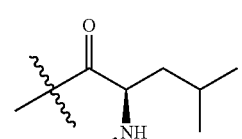 [SMILES: *C(=O)[C@H](O)CC(C)C] | H | | H | H | 408.1 |

TABLE 1-continued (I)

| Example | R¹ | R² | R³ | Z | Y | X | (M + H)⁺ |
|---|---|---|---|---|---|---|---|
| 64 | OMe | oxazole | H | leucine carbonyl with NH-CH₂-(1-methylpyrazol-4-yl) | H | H | 398.1 |
| 65 | OMe | oxazole | H | leucine carbonyl with NH-CH₂-(thiophen-3-yl) | H | H | 400.2 |
| 66 | OMe | oxazole | H | leucine carbonyl with NH-CH₂-(3-methylthiophen-2-yl) | H | H | 414.2 |
| 67 | OMe | oxazole | H | leucine carbonyl with NH-CH₂-(1,2,3-thiadiazol-4-yl) | H | H | 402.2 |
| 68 | OMe | oxazole | H | leucine carbonyl with NH-SO₂-Me | H | H | 382.1 |

TABLE 1-continued
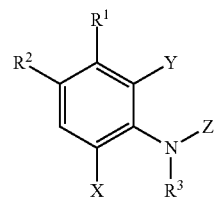
| Example | R¹ | R² | R³ | Z | Y | X | (M + H)⁺ |
|---|---|---|---|---|---|---|---|
| 69 | OMe | oxazol-5-yl | H | N-ethylsulfonyl-leucyl | H | H | 396.1 |
| 70 | OMe | oxazol-5-yl | H | N-propylsulfonyl-leucyl | H | H | 410.1 |
| 71 | OMe | oxazol-5-yl | H | N-phenylsulfonyl-leucyl | H | H | 444.1 |
| 72 | OMe | oxazol-5-yl | H | N-benzylsulfonyl-leucyl | H | H | 458.1 |
| 73 | OMe | oxazol-5-yl | H | piperidine-2-carbonyl | H | H | 302.2 |

TABLE 1-continued (I)

| Example | R¹ | R² | R³ | Z | Y | X | (M + H)⁺ |
|---|---|---|---|---|---|---|---|
| 74 | OMe | oxazole | H | C(O)CH(NH₂)CH₂C(CH₃)₃ | H | H | 317.3 |
| 75 | OMe | oxazole | H | C(O)CH(NH₂)CH₂OH | H | H | 278.2 |
| 76 | OMe | oxazole | H | C(O)CH(NH₂)CH₂CH₂CF₃ | H | H | |
| 77 | OMe | oxazole | H | C(O)CH(NH₂)CH(OH)CH₃ | H | H | |
| 78 | OMe | oxazole | H | 4-methoxyprolinoyl | H | H | 318.2 |
| 79 | OMe | oxazole | H | C(O)CH(NH₂)CH₂CH(CH₃)₂ | H | H | 304.2 |
| 80 | OMe | oxazole | H | N-isobutyryl-piperidine-2-carbonyl | H | H | 370 (M⁻) |
| 81 | OMe | oxazole | H | N-isopropyl-prolinoyl | H | H | |

TABLE 1-continued
(I)
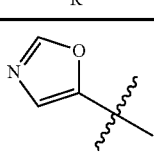
| Example | R¹ | R² | R³ | Z | Y | X | (M + H)⁺ |
|---|---|---|---|---|---|---|---|
| 82 | OMe | 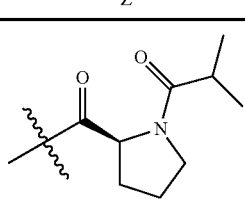 | H | 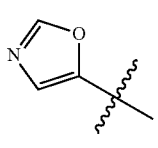 | H | H | 358.2 |
| 83 | OMe | 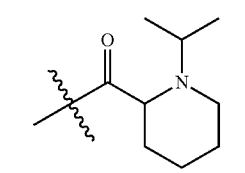 [SMILES: *C(=O)C1CCCCN1C(C)C] | H | 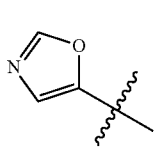 | H | H | 344.2 |
| 84 | OMe | 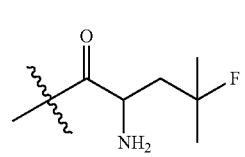 [SMILES: *C(=O)C(N)CC(C)(C)F] | H | 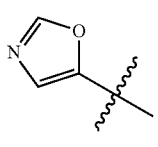 | H | H | 322.2 |
| 85 | OMe | 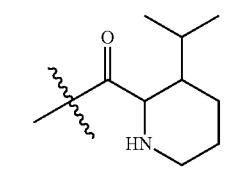 [SMILES: *C(=O)C1NCCCC1C(C)C] | H | 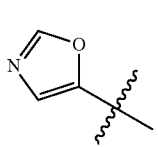 [SMILES: *c1cnco1] | H | H | 344.2 |
| 86 | OMe | 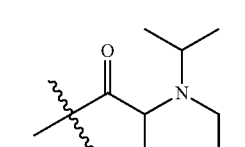 | H | 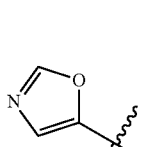 | H | H | 345.2 |
| 87 | OMe | 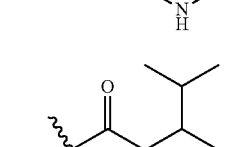 | H | 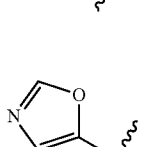 | H | H | 344.2 |
| 88 | OMe | 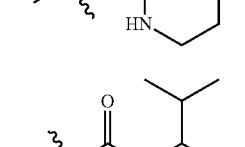 | H | 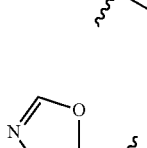 | H | H | 344.2 |
| 89 | OMe | 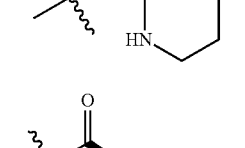 | H | | H | H | 306.0 |

TABLE 1-continued (I)

| Example | R¹ | R² | R³ | Z | Y | X | (M + H)⁺ |
|---|---|---|---|---|---|---|---|
| 90 | OMe | oxazole | H | prolinyl-F carbonyl | H | H | 306.0 |
| 91 | OMe | oxazole | H | 3-(trifluoromethyl)piperidine-2-carbonyl | H | H | 370.0 |
| 92 | OMe | oxazole | H | 3-(trifluoromethyl)piperidine-2-carbonyl | H | H | 370.0 |
| 93 | OMe | oxazole | H | 2-amino-2-(2-methylcyclohexyl)acetyl | H | H | 344.2 |
| 94 | OMe | oxazole | H | (S)-2-amino-3-cyclobutylpropanoyl | H | F | 334.2 |
| 95 | OMe | oxazole | H | (S)-2-amino-3-cyclopropylpropanoyl | H | F | 320.2 |
| 96 | OMe | oxazole | H | (S)-2-amino-3-methylbutanoyl | H | F | 308.2 |
| 97 | OMe | oxazole | H | (S)-2-amino-4,4-dimethylpentanoyl | H | F | 336.2 |

TABLE 1-continued (I)

| Example | R¹ | R² | R³ | Z | Y | X | (M + H)⁺ |
|---|---|---|---|---|---|---|---|
| 98 | OMe | oxazol-5-yl | H | (S)-2-amino-4-methylpentanoyl | H | F | 322.2 |
| 99 | OMe | oxazol-5-yl | H | (R)-2-amino-4-methylpentanoyl | H | F | 322.2 |
| 100 | OMe | oxazol-5-yl | H | (S)-2-amino-2-cyclopentylacetyl | H | F | 334.2 |
| 101 | OMe | oxazol-5-yl | H | (S)-2-amino-4-methylpentanoyl | H | CN | 329.2 |
| 102 | OMe | oxazol-5-yl | H | (S)-2-amino-4-methylpentanoyl | H | 2H-tetrazol-5-yl | 372.2 |
| 103 | OMe | oxazol-5-yl | H | (S)-2-amino-4-methylpentanoyl | H | 1,3,4-thiadiazol-2-yl | 387.5 |
| 104 | OMe | oxazol-5-yl | H | (S)-2-amino-4-methylpentanoyl | H | oxazol-5-yl | 371.0 |
| 105 | F | oxazol-5-yl | H | (S)-2-amino-4-methylpentanoyl | H | F | 310.2 |
| 106 | OCF3 | oxazol-5-yl | H | (S)-2-amino-4-methylpentanoyl | H | H | 357.3 |

TABLE 1-continued
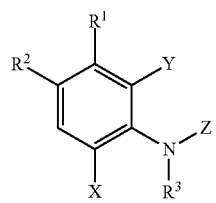
(I)
| Example | R¹ | R² | R³ | Z | Y | X | (M + H)⁺ |
|---|---|---|---|---|---|---|---|
| 107 | F | oxazol-5-yl | H | leucinyl C(O)CH(NH₂)CH₂CH(CH₃)₂ | H | OMe | 322.2 |
| 108 | CN | oxazol-5-yl | H | leucinyl | H | H | 298.3 |
| 109 | OMe | 1H-imidazol-5-yl | H | leucinyl | H | H | 303.2 |
| 110 | OMe | oxazol-5-yl | H | leucinyl | H | Et | 332.2 |
| 111 | H | pyridin-4-yl | H | leucinyl | H | CF₃ | 350.2 |
| 112 | H | pyridin-4-yl | H | leucinyl | H | 1H-pyrazol-4-yl | 350.2 |
| 113 | H | pyridin-4-yl | H | leucinyl | H | thiophen-3-yl | 366.2 |
| 114 | H | pyridin-4-yl | H | leucinyl | H | CN | 309.2 |

TABLE 1-continued (I)

| Example | R¹ | R² | R³ | Z | Y | X | (M + H)⁺ |
|---------|-----|-----|-----|-----|-----|-----|----------|
| 115 | H | 4-pyridyl | H | (S)-leucinyl C(O) | H | tetrazol-5-yl | 352.2 |
| 116 | H | 4-pyridyl | H | (S)-leucinyl C(O) | H | H | 284.2 |
| 117 | OMe | 4-pyrimidinyl | H | (S)-leucinyl C(O) | H | H | 315.2 |
| 118 | H | 2-acetamido-pyridin-4-yl | H | (S)-leucinyl C(O) | H | H | 341.2 |
| 119 | H | 4-pyridyl | H | 3-isopropyl-piperidin-2-yl C(O) | H | H | 324.0 |
| 120 | H | 4-pyridyl | H | 3-trifluoromethyl-piperidin-2-yl C(O) | H | H | 350.2 |
| 121 | H | 4-pyridyl | H | α-amino-(2-methylcyclohexyl)acetyl | H | H | 324.2 |
| 122 | H | 4-pyridyl | H | α-amino-(2-trifluoromethylcyclohexyl)acetyl | H | H | 378.2 |

DESCRIPTION OF THE SPECIFIC EMBODIMENTS

In the following examples, proton NMR spectra were recorded on either a Bruker 400 or 500 MHz NMR spectrometer. Chemical shifts are reported in δ values relative to tetramethylsilane. Liquid chromatography (LC)/mass spectra were run on a Shimadzu LC coupled to a Waters Micromass ZQ. HPLC retention times were obtained using at least one of the following methods:

Method A:
Waters analytical C18 Sunfire column (4.6×150 mm, 3.5 μm); mobile phase: A=$H_2O$ with 0.1% TFA, B=acetonitrile with 0.1% TFA; 1-15 min, 10% B→95% B; 15-18 min, 95% B; flow rate=1 mL/min; λ=254 nm; run time=18 min.

Method B:
Waters analytical Phenyl Xbridge column (4.6×150 mm, 3.5 μm), mobile phase: A=$H_2O$ with 0.1% TFA, B=acetonitrile with 0.1% TFA, 1-15 min, 10% B→95% B; 15-18 min, 95% B; flow rate=1 mL/min; λ=254 nm; run time=18 min.

Method C:
Phenomenex Gemini C18 column (4.6×150 mm, 3.5 μm); mobile phase: A=10% MeOH/90% $H_2O$ with 0.1% TFA, B=90% MeOH/10% $H_2O$ with 0.1% TFA; 1-12 min, 0% B→100% B; 12-15 min, 100% B; flow rate=1 mL/min; λ=254 nm; run time=15 min.

Method D:
Phenomenex LUNA Phenyl-Hex column (4.6×150 mm, 3.5 μm), mobile phase: A=10% MeOH/90% $H_2O$ with 0.1% TFA, B=90% MeOH/10% $H_2O$ with 0.1% TFA, 1-12 min, 0% B→100% B; 12-15 min, 100% B; flow rate=1 mL/min; λ=254 nm; run time=15 min.

Method E:
Supelco Ascentis Express C18 analytical column (4.6×50 mm, 2.7 μm); mobile phase: A=5% acetonitrile/95% $H_2O$ with 10 mM $NH_4OAc$ B=95% acetonitrile/5% $H_2O$ with 10 mM $NH_4OAc$; 1-8 min, 0% B→100% B; 9-10 min, 100% B; flow rate=2 mL/min; λ=220 nm; run time=10 min.

Method F:
Waters analytical C18 Acquity column (2.0×50 mm, 1.7 μm); mobile phase: A=5% methanol/95% $H_2O$ with 10 mM $NH_4OAc$, B=95 methanol/5% $H_2O$ with 10 mM $NH_4OAc$; 1-4 min, 0% B→100% B; 4-5 min, 100% B; flow rate=0.5 mL/min; λ=220 nm; run time=5 min.

Method G:
Supelco Ascentis Express C18 analytical column (4.6×50 mm, 2.7 μm); mobile phase: A=5% acetonitrile/95% $H_2O$ with 10 mM $NH_4OAc$, B=95% acetonitrile/5% $H_2O$ with 10 mM $NH_4OAc$; 1-8 min, 0% B→100% B; 9-10 min, 100% B; flow rate=2 mL/min; λ=220 nm; run time=10 min.

Method H:
Supelco Ascentis Express C18 analytical column (4.6×50 mm, 2.7 μm); mobile phase: A=5% acetonitrile/95% $H_2O$ with 10 mM $NH_4OAc$, B=95% acetonitrile/5% water with 10 mM $NH_4Ac$; 1-8 min, 0% B→100% B; 9-10 min, 100% B; flow rate=2 mL/min; λ=220 nm; run time=10 min.

Method I:
Waters analytical Xbridge column (2.1×50 mm, 1.7 μm); mobile phase: A=5% acetonitrile/95% $H_2O$ with 10 mM $NH_4OAc$, B=95% acetonitrile/5% $H_2O$ with 10 mM $NH_4OAc$; 1-4 min, 0% B→100% B; 4-5 min, 100% B; flow rate=0.83 mL/min; λ=220 nm; run time=5 min.

Method J:
Waters analytical C18 Sunfire column (4.6×150 mm, 3.5 μm); mobile phase: Buffer: 0.05% TFA in $H_2O$ pH=2.5 adjusted with ammonia A=buffer and acetonitrile (95:5), B=acetonitrile and buffer (95:5); 0-15 min, 0% B→50% B; 15-18 min, 50% B→100% B; 18-23 min, 100% B; flow rate=1 mL/min; λ=254 nm and 220 nm; run time=28 min.

Method K:
Waters analytical phenyl xbridge column (4.6×150 mm, 3.5 μm), mobile phase: Buffer: 0.05% TFA in $H_2O$ pH=2.5 adjusted with ammonia A=buffer and acetonitrile (95:5), B=acetonitrile and buffer (95:5); 0-15 min, 0% B→50% B; 15-18 min, 50% B→100% B; 18-23 min, 100% B; flow rate=1 mL/min; λ=254 nm and 220 nm; run time=28 min.

Method L:
Waters analytical C18 Sunfire column (4.6×150 mm, 3.5 μm); mobile phase: Buffer: 0.05% TFA in $H_2O$ pH=2.5 adjusted with ammonia A=buffer and acetonitrile (95:5), B=acetonitrile and buffer (95:5); 0-12 min, 10% B→100% B; 12-15 min, 100% B; flow rate=1 mL/min; λ=254 nm and 220 nm; run time=17 min.

Method M:
Waters analytical phenyl xbridge column (4.6×150 mm, 3.5 μm), mobile phase: Buffer: 0.05% TFA in $H_2O$ pH=2.5 adjusted with ammonia A=buffer and acetonitrile (95:5), B=acetonitrile and buffer (95:5); 0-12 min, 10% B→100% B; 12-15 min, B→100% B; flow rate=1 mL/min; k=254 nm and 220 nm; run time=17 min.

Method N:
Waters analytical phenyl xbridge column (4.6×150 mm, 3.5 μm), mobile phase: A=10 m M $NH_4HCO_3$ in $H_2O$ pH=9.5 adjusted with ammonia, B=methanol; 0-12 min, 10% B→100% B; 12-20 min, B→100% B; flow rate=1 mL/min; λ=254 nm and 220 nm; run time=23 min.

Method O:
Waters analytical C18 Sunfire column (4.6×150 mm, 3.5 μm); mobile phase: Buffer: 0.05% TFA in $H_2O$ pH=2.5 adjusted with ammonia A=buffer and acetonitrile (95:5), B=acetonitrile and buffer (95:5); 0-25 min, 10% B→100% B; 25-30 min, 100% B; flow rate=1 mL/min; λ=254 nm and 220 nm; run time=32 min.

LC-MS methods:

LC/MS Method A:
Column: PUROSPHER@star RP-18 (4×55 mm), 3 λm; Buffer: 20 mM $NH_4OAC$ IN WATER; Mphase A: Buffer+ACN (90+10); Mphase B: Buffer+MeCN (10+90); Flow: 2.5 ml/min)

LC/MS Method B:
Column: ZORBAX SB C18 (4.6×50 mm), 5 λm; Positive mode Mphase A: 10% MeOH—90% $H_2O$—0.1% TFA; Mphase B: 90% MeOH—10% $H_2O$—0.1% TFA; Flow: 5 ml/min)

LC/MS Method C:
Column—Ascentis Express C8 (5×2.1 mm), 2.7 μm; Mphase A: 2% MeCN—98% $H_2O$—10 mM $NH_4COOH$; Mphase B: 98% ACN—2% $H_2O$—10 mM $NH_4COOH$; Flow: 1/min)

LC/MS Method D:
Column—ACQUITY UPLC BEH C18 (2.1×50 mm), 1.7 μm; Mphase A:0.1% TFA in water; Mphase B: 1% TFA in ACN; Flow: 1/min)

LC/MS Method E:
Column—ACQUITY UPLC BEH C18 (2.1×50 mm), 1.7 μm; Mphase A: 5 mM $NH_4OAc$:ACN (95:5); Mphase B: 5 mM $NH_4OAc$: ACN (5:95); Flow: 1/min)

LC/MS Method F:
Column—Ascentis Express C18 (4.6×50 mm), 2.7 μm; Mphase A: 5% MeCN—95% $H_2O$—10 mM $NH_4OAC$; Mphase B: 95% ACN—5% H2O—10 mM $NH_4OAC$; Flow: 4 mL/min)

LC/MS Method G:
Column—X Bridge Phe (4.6×30 mm), 3.5 μm; Mphase A: 2% MeCN—98% $H_2O$—10 mM $NH_4COOH$; Mphase B: 98% ACN—2% $H_2O$—10 mM $NH_4COOH$; Flow: 1.8 mL/min)

LC/MS Method H:
Column—Ascentis Express C18 (5×2.1 mm), 2.7 μm; Mphase A: 2% MeCN—98% $H_2O$—10 mM $NH_4COOH$; Mphase B: 98% ACN—2% $H_2O$—10 mM $NH_4COOH$; Flow: 1/min)

Chiral HPLC methods:

Method A1:
CHIRALCEL OJH (250×4.6) mm 5 micron; Mob. phase: 0.2% DEA in n-hexane: ethanol (80:20); λ=254 nm and 220 nm Method A2:
CHIRALCEL OJH (250×4.6) mm 5 micron; Mob. phase: 0.2% DEA in n-hexane: ethanol (50:50); λ=254 nm and 220 nm Method A3:
CHIRALCEL OJH (250×4.6) mm 5 micron; Mob. phase: 0.2% DEA in n-hexane: ethanol (70:30); λ=254 nm and 220 nm Method A4:
CHIRALCEL OJH (250×4.6) mm 5 micron; Mob. phase: 0.2% DEA in n-hexane:ethanol (90:10); λ=254 nm and 220 nm Method B1:
CHIRALPAK AD-H (250×4.6) mm 5 micron; Mob. Phase: 0.2% DEA in n-hexane: ethanol (70:30); λ=254 nm and 220 nm Method B2:
CHIRALPAK AD-H (250×4.6) mm 5 micron; Mob. Phase: 0.2% DEA in n-hexane: ethanol (85:15); λ=254 nm and 220 nm Method B3:
CHIRALPAK AD-H (250×4.6) mm 5 micron; Mob. Phase: 0.2% DEA in n-hexane: ethanol (80:20); λ=254 nm and 220 nm Method B4:
CHIRALPAK AD-H (250×4.6) mm 5 micron; Mob. Phase: 0.1% TFA in n-hexane: ethanol (70:30); λ=254 nm and 220 nm Method B5:
CHIRALPAK AD-H (250×4.6) mm 5 micron; Mob. Phase: 0.2% DEA in n-hexane: IPA (80:20); λ=254 nm and 220 nm Method C1:
CHIRALPAK—ASH (250×4.6) mm 5 micron; Mob. Phase: 0.2% DEA in n-hexane: ethanol (90:10); λ=254 nm and 220 nm Method C2:
CHIRALPAK—ASH (250×4.6) mm 5 micron; Mob. Phase: 0.2% DEA in n-hexane: ethanol (85:15); λ=254 nm and 220 nm Method C3:
CHIRALPAK—ASH (250×4.6) mm 5 micron; Mob. Phase: 0.2% DEA in n-hexane: ethanol (70:30); λ=254 nm and 220 nm Method D1:
CHIRALPAK AD-H (250×4.6) mm 5 micron; Mob. Phase: n-hexane:ethanol (85:15); λ=254 nm and 220 nm Method E1:
CHIRALPAK IC (250×4.6) mm 5 micron; Mob. Phase: DCM: ethanol (70:30); λ=254 nm and 220 nm Method E2:
CHIRALPAK IC (250×4.6) mm 5 micron; Mob. Phase: 0.2% DEA in n-hexane: ethanol (90:10); λ=254 nm and 220 nm Method E3:
CHIRALPAK IC (250×4.6) mm 5 micron; Mob. Phase: 0.2% DEA in n-hexane: ethanol (80:20); λ=254 nm and 220 nm Method E4:
CHIRALPAK IC (250×4.6) mm 5 micron; Mob. Phase: 0.1% TFA in n-hexane: ethanol (40:60); λ=254 nm and 220 nm Method E5:
CHIRALPAK IC (250×4.6) mm 5 micron; Mob. Phase: hexane:ethanol (70:30); λ=254 nm and 220 nm Method F1:
CHIRALPAK IA (250×4.6) mm 5 micron; Mob. Phase: n-hexane:ethanol (90:10); λ=254 nm and 220 nm Method F2:
CHIRALPAK IA (250×4.6) mm 5 micron; Mob. Phase: 0.05% TFA in $H_2O$: acetonitrile (80:20); λ=254 nm and 220 nm Method F3:
CHIRALPAK IA (250×4.6) mm 5 micron; Mob. Phase: 0.1% TFA in hexane: ethanol (50:50); λ=254 nm and 220 nm Method G1:
ZORBAX SILICA (250×4.6) mm 5 micron; Mob. Phase: n-hexane:ethanol (60:40); λ=254 nm and 220 nm Method H1:
CHIRALPAK IA (250×4.6) mm 5 micron; Mob. Phase: 0.2% DEA in n-hexane: ethanol (70:30); λ=254 nm and 220 nm Method I1:
CHIRALPAK IC (250×4.6) mm 5 micron; Mob. Phase Buffer: 0.05% TFA in $H_2O$ pH=2.5, A=buffer and acetonitrile (95:5)-80%, B=acetonitrile and buffer (95:5)-20%; κ=254 nm and 220 nm Method I2:
CHIRALPAK IC (250×4.6) mm 5 micron; Mob. Phase: 0.05% TFA in $H_2O$: acetonitrile (90:10); λ=254 nm and 220 nm Method I3:
CHIRALPAK IC (250×4.6) mm 5 micron; Mob. Phase: 0.05% TFA in $H_2O$: acetonitrile (85:15); λ=254 nm and 220 nm Method I4:
CHIRALPAK IC (250×4.6) mm 5 micron; Mob. Phase: 0.05% TFA in $H_2O$: acetonitrile (80:20); λ=254 nm and 220 nm Method I5:
CHIRALPAK IC (250×4.6) mm 5 micron; Mob. Phase: 0.05% TFA in $H_2O$: acetonitrile (50:50); λ=254 nm and 220 nm Method J1:
CHIRALCEL ODH (250×4.6) mm 5 micron; Mob. phase: 0.2% DEA in n-hexane: ethanol (30:70); λ=254 nm and 220 nm

Example 1

(R)-2-Amino-N-(3-methoxy-4-(oxazol-5-yl)phenyl)-4-methylpentanamide

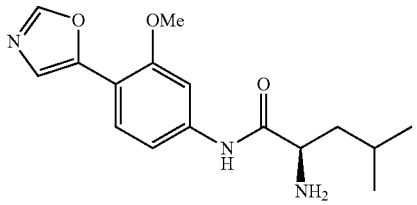 [SMILES: COc1cc(NC(=O)[C@H](N)CC(C)C)ccc1-c1cnco1]

Part A. 5-(2-Methoxy-4-nitrophenyl)oxazole

To a solution of 2-methoxy-4-nitrobenzaldehyde (700 mg, 3.86 mmol) and TosMIC (754 mg, 3.86 mmol) in MeOH (7 mL) was added potassium carbonate (561 mg, 4.06 mmol). The reaction mixture was heated at reflux for 3 h. The reaction mixture was cooled to room temperature and was transferred to a reparatory funnel containing saturated aqueous NaHCO$_3$ solution (25 mL). The aqueous layer was extracted with ethyl acetate (3×50 mL). The combined organic layers were washed with brine (25 mL), dried over MgSO$_4$, filtered and concentrated. The residue was purified by column chromatography on silica gel (30%→40% ethyl acetate in hexanes) to afford 5-(2-methoxy-4-nitrophenyl)oxazole (732 mg, 86% yield) as a yellow solid: $^1$H NMR (400 MHz, CDCl$_3$) δ 7.98 (s, 1H), 7.93 (d, J=1.8 Hz, 1H), 7.92 (s, 1H), 7.84 (d, J=1.8 Hz, 1H), 7.75 (s, 1H), 4.08 (s, 3H); LC/MS (ESI) m/e 221.3 [(M+H)$^+$, calcd for C$_{10}$H$_9$N$_2$O$_4$ 221.1].

Part B. 3-Methoxy-4-(oxazol-5-yl)aniline 5-(2-Methoxy-4-nitrophenyl)oxazole (700 mg, 3.18 mmol) was dissolved in EtOH (30 mL) and CHCl$_3$ (15 mL) in a Parr bottle. 10% palladium on carbon (677 mg, 0.318 mmol, Degussa type) was added and the mixture was placed on the Parr shaker under H$_2$ at 40 psi for 1.5 h. The catalyst was removed by filtration through a pad of diatomaceous earth (Celite®) and the filtrate was concentrated. The product was crystallized from ethyl acetate/ethanol to afford 3-methoxy-4-(oxazol-5-yl)aniline (496 mg, 2.61 mmol, 82% yield) as a gray solid: $^1$H NMR (400 MHz, DMSO-d$_6$) δ 8.34 (s, 1H), 7.55 (d, J=8.3 Hz, 1H), 7.37 (s, 1H), 6.70 (s, 1H), 6.63 (d, J=8.1 Hz, 1H), 3.89 (s, 3H); LC/MS (ESI) m/e 191.3 [(M+H)$^+$, calcd for C$_{10}$H$_{11}$N$_2$O$_2$ 191.1].

Part C. (R)-tert-Butyl 1-(3-methoxy-4-(oxazol-5-yl)phenylamino)-4-methyl-1-oxopentan-2-ylcarbamate To a mixture of 3-methoxy-4-(oxazol-5-yl)aniline (70 mg, 0.368 mmol), (R)-2-(tert-butoxycarbonylamino)-4-methylpentanoic acid (128 mg, 0.552 mmol) and N,N-diisopropylethylamine (0.257 mL, 1.472 mmol) in CH$_2$Cl$_2$ (2 mL) was added HATU (210 mg, 0.552 mmol). The reaction mixture was stirred at room temperature for 18 h. The reaction mixture was transferred to a separatory funnel containing saturated aqueous NaHCO$_3$ solution (5 mL). The aqueous layer was extracted with ethyl acetate (3×10 mL). The combined organic layers were washed with brine (5 mL), dried over MgSO$_4$, filtered and concentrated. The residue was purified by column chromatography on silica gel (40%→70% ethyl acetate in hexanes) to afford (R)-tert-butyl 1-(3-methoxy-4-(oxazol-5-yl)phenylamino)-4-methyl-1-oxopentan-2-ylcarbamate (102 mg, 69% yield) as a colorless solid: $^1$H NMR (400 MHz, DMSO-d$_6$) δ 10.15 (s, 1H), 8.38 (s, 1H), 7.63 (d, J=8.6 Hz, 1H), 7.52 (d, J=1.8 Hz, 1H), 7.44 (s, 1H), 7.36 (dd, J=8.4, 1.9 Hz, 1H), 7.08 (d, J=7.8 Hz, 1H), 4.09-4.17 (m, 1H), 3.91 (s, 3H), 1.59-1.72 (m, 1H), 1.48-1.59 (m, 1H), 1.44 (dd, J=8.4, 5.2 Hz, 1H), 1.38 (s, 9H), 0.90 (dd, J=6.5, 2.3 Hz, 6H); LC/MS (ESI) m/e 404.3 [(M+H)$^+$, calcd for C$_{21}$H$_{30}$N$_3$O$_5$ 404.2].

Part D. (R)-2-Amino-N-(3-methoxy-4-(oxazol-5-yl)phenyl)-4-methylpentanamide

To a suspension of (R)-tert-butyl 1-(3-methoxy-4-(oxazol-5-yl)phenylamino)-4-methyl-1-oxopentan-2-ylcarbamate (92 mg, 0.228 mmol) in CH$_2$Cl$_2$ (1.5 mL) at 0° C. was added TFA (0.50 mL, 6.49 mmol). The cooling bath was removed and the mixture was stirred at room temperature under N$_2$ for 1.5 h. The reaction mixture was concentrated and the product was purified by reverse phase HPLC (acetonitrile/water containing 0.1% TFA). The organic solvent was removed on the rotovapor and the free base was formed by washing with saturated aqueous K$_2$CO$_3$ (5 mL). The aqueous layer was extracted with ethyl acetate (4×10 ml). The combined organic layers were washed with brine (5 mL), dried over MgSO$_4$, filtered, and concentrated. The residue was taken up in acetonitrile/water and was frozen and placed on the lyophilizer to afford (R)-2-amino-N-(3-methoxy-(oxazol-5-yl)phenyl)-4-methylpentanamide (49 mg, 71% yield) as a colorless amorphous solid: $^1$H NMR (400 MHz, DMSO-d$_6$) δ 8.37 (s, 1H), 7.63 (d, J=8.6 Hz, 1H), 7.59 (d, J=1.8 Hz, 1H), 7.44 (s, 1H), 7.39 (dd, J=8.4, 1.9 Hz, 1H), 3.91 (s, 3H), 3.34-3.37 (m, 1H), 1.71-1.82 (m, 1H), 1.49 (ddd, J=13.5, 8.2, 5.5 Hz, 1H), 1.30-1.39 (m, 1H), 0.92 (d, J=6.8 Hz, 3H), 0.89 (d, J=6.5 Hz, 3H); LC/MS (ESI) m/e 304.3 [(M+H)$^+$, calcd for C$_{16}$H$_{22}$N$_3$O$_3$ 304.2]. HPLC (method A): t$_R$=8.01 min; HPLC (method B): t$_R$=8.03 min.

Example 2

(R)—N-(3-Methoxy-4-(oxazol-5-yl)phenyl)pyrrolidine-2-carboxamide

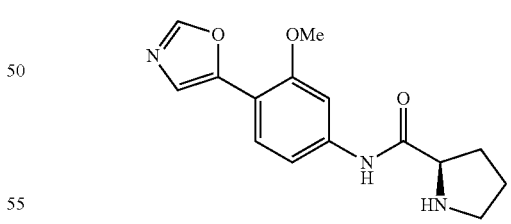

Prepared in a similar fashion as described in Example 1 using (R)-pyrrolidine-2-carboxylic acid in Part C to give (R)—N-(3-methoxy-4-(oxazol-5-yl)phenyl)pyrrolidine-2-carboxamide (80 mg), which was isolated as a TFA salt: $^1$H NMR (400 MHz, CD$_3$OD) δ 8.17 (s, 1H) 7.69 (d, J=8.6 Hz, 1H) 7.55 (d, J=1.5 Hz, 1H) 7.44 (s, 1H) 7.21 (dd, J=8.6, 1.8 Hz, 1H) 4.21 (dd, J=8.6, 6.3 Hz, 1H) 3.94 (s, 3H) 3.20-3.37 (m, 2H) 2.37-2.49 (m, 1H) 1.95-2.11 (m, 3H); LC/MS (ESI) m/e 288.2 [(M+H)$^{30}$, calcd for C$_{15}$H$_{18}$N$_3$O$_3$ 288.1]. HPLC (method A): t$_R$=7.21 min; HPLC (method B): t$_R$=7.15 min.

Example 3

(R)-2-Amino-2-cyclopentyl-N-(3-methoxy-4-(oxazol-5-yl)phenyl)acetamide

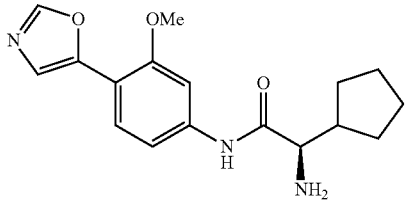 [SMILES: COc1cc(NC(=O)[C@H](N)C2CCCC2)ccc1-c1cnco1]

Prepared in a similar fashion as described in Example 1 using (R)-2-amino-2-cyclopentylacetic acid in Part C to give (R)-2-amino-2-cyclopentyl-N-(3-methoxy-4-(oxazol-5-yl)phenyl)acetamide (40 mg) as a colorless amorphous solid: $^1$H NMR (400 MHz, DMSO-$d_6$) δ 8.38 (s, 1H), 7.62 (d, J=8.56 Hz, 1H), 7.59 (d, J=1.76 Hz, 1H), 7.44 (s, 1H), 7.36 (dd, J=8.44, 1.89 Hz, 1H), 3.91 (s, 3H), 3.19 (d, J=7.30 Hz, 1H), 2.03-2.13 (m, 1H), 1.44-1.69 (m, 6H), 1.32-1.44 (m, 2H); LC/MS (ESI) m/e 316.3 [(M+H)$^+$, calcd for $C_{17}H_{22}N_3O_3$ 316.2]. HPLC (method A): $t_R$=9.91 min; HPLC (method B): $t_R$=10.76 min.

Example 4

(R)-2-Amino-N-(3-methoxy-4-(oxazol-5-yl)phenyl)-3-methylbutanamide

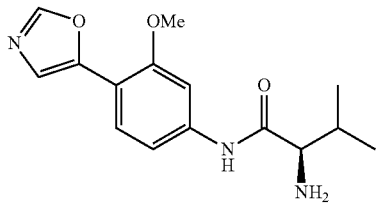 [SMILES: COc1cc(NC(=O)[C@H](N)C(C)C)ccc1-c1cnco1]

Prepared in a similar fashion as described in Example 1 using (R)-2-amino-3-methylbutanoic acid in Part C to give (R)-2-amino-N-(3-methoxy-4-(oxazol-5-yl)phenyl)-3-methylbutanamide (39 mg) as a colorless amorphous solid: $^1$H NMR (400 MHz, DMSO-$d_6$) δ 8.38 (s, 1H), 7.63 (d, J=8.6 Hz, 1H), 7.59 (d, J=1.8 Hz, 1H), 7.44 (s, 1H), 7.38 (dd, J=8.4, 1.9 Hz, 1H), 3.91 (s, 3H), 3.17 (d, J=5.5 Hz, 1H), 1.92-2.01 (m, 1H), 0.94 (d, J=6.8 Hz, 3H), 0.87 (d, J=6.8 Hz, 3H); LC/MS (ESI) m/e 290.2 ((M+H)$^+$, calcd for $C_{15}H_{20}N_3O_3$ 290.2). HPLC (method A): $t_R$=7.57 min; HPLC (method B): $t_R$=7.48 min.

Example 5

(S)-2-Amino-N-(3-methoxy-4-(oxazol-5-yl)phenyl)-4-methylpentanamide

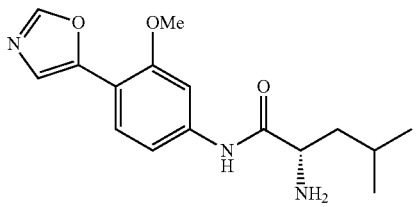

Prepared in a similar fashion as described in Example 1 using (S)-2-amino-4-methylpentanoic acid in Part C to give (S)-2-amino-N-(3-methoxy-4-(oxazol-5-yl)phenyl)-4-methylpentanamide (51 mg) as a colorless amorphous solid: $^1$H NMR (400 MHz, DMSO-$d_6$) δ 8.38 (s, 1H), 7.63 (d, J=8.3 Hz, 1H), 7.59 (d, J=1.5 Hz, 1H), 7.44 (s, 1H), 7.38 (dd, J=8.6, 1.5 Hz, 1H), 3.91 (s, 3H), 3.35-3.38 (m, 1H), 1.76 (ddd, J=13.8, 6.8, 6.5 Hz, 1H), 1.49 (ddd, J=13.5, 8.2, 5.5 Hz, 1H), 1.34 (ddd, J=13.7, 8.5, 5.8 Hz, 1H), 0.92 (d, J=6.8 Hz, 3H), 0.89 (d, J=6.5 Hz, 3H); LC/MS (ESI) m/e 304.3 [(M+H)$^+$, calcd for $C_{16}H_{22}N_3O_3$ 304.2]. HPLC (method A): $t_R$=8.02 min; HPLC (method B): $t_R$=8.02 min.

Example 6

(R)-2-Amino-3-cyclobutyl-N-(3-methoxy-4-(oxazol-5-yl)phenyl)propanamide

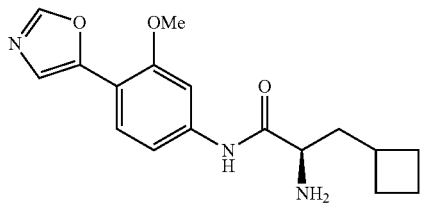 [SMILES: COc1cc(NC(=O)[C@H](N)CC2CCC2)ccc1-c1cnco1]

Prepared in a similar fashion as described in Example 1 using (R)-2-amino-3-cyclobutylpropanoic acid in Part C to give (R)-2-amino-3-cyclobutyl-N-(3-methoxy-4-(oxazol-5-yl)phenyl)propanamide (45 mg) as a colorless amorphous solid: $^1$H NMR (400 MHz, DMSO-$d_6$) δ 8.38 (s, 1H), 7.63 (d, J=8.3 Hz, 1H), 7.58 (d, J=1.8 Hz, 1H), 7.44 (s, 1H), 7.38 (dd, J=8.3, 1.8 Hz, 1H), 3.91 (s, 3H), 3.27 (dd, J=7.4, 5.9 Hz, 1H), 2.39-2.48 (m, 1H), 1.93-2.08 (m, 2H), 1.70-1.85 (m, 3H), 1.55-1.67 (m, 3H); LC/MS (ESI) m/e 316.3 [(M+H)$^+$, calcd for $C_{17}H_{22}N_3O_3$ 316.2]. HPLC (method A): $t_R$=8.24 min; HPLC (method B): $t_R$=8.28 min.

Example 7

2-Amino-N-(3-methoxy-4-(oxazol-5-yl)phenyl)-4-methylpentanamide

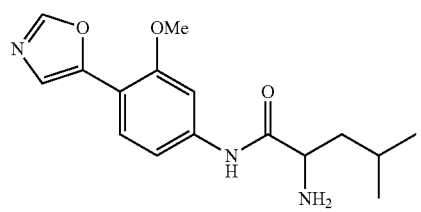 [SMILES: COc1cc(NC(=O)C(N)CC(C)C)ccc1-c1cnco1]

Prepared in a similar fashion as described in Example 1 using 2-amino-4-methylpentanoic acid in Part C to give 2-amino-N-(3-methoxy-4-(oxazol-5-yl)phenyl)-4-methylpentanamide (28 mg) as a colorless amorphous solid: $^1$H NMR (400 MHz, DMSO-$d_6$) δ 8.40 (s, 1H) 7.68 (d, J=8.3 Hz, 1H) 7.51 (d, J=1.8 Hz, 1H) 7.48 (s, 1H) 7.39 (dd, J=8.6, 1.8 Hz, 1H) 3.93 (s, 3H) 3.83 (t, J=7.1 Hz, 1H) 1.57-1.75 (m, 3H) 0.94 (d, J=6.3 Hz, 3H) 0.933 (d, J=6.0 Hz, 3H); LC/MS (ESI) m/e 304.2 [(M+H)$^+$, calcd for $C_{16}H_{22}N_3O_3$ 304.2]. HPLC (method A): $t_R$=8.14 min; HPLC (method B): $t_R$=8.20 min.

Example 8

2-Amino-N-(3-methoxy-4-(oxazol-5-yl)phenyl)-5-methylhexanamide

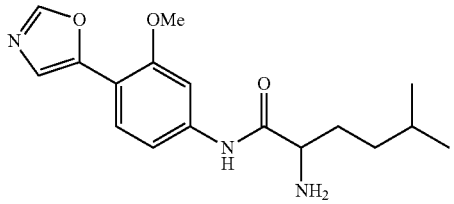 [SMILES: COc1cc(NC(=O)C(N)CCC(C)C)ccc1-c1cnco1]

Part A. (9H-Fluoren-9-yl)methyl 1-(3-methoxy-4-(oxazol-5-yl)phenylamino)-5-methyl-1-oxohexan-2-ylcarbamate To a mixture of 3-methoxy-4-(oxazol-5-yl)aniline (prepared as described in Example 1 Parts A and B) (80 mg, 0.421 mmol), 2-(((9H-fluoren-9-yl)methoxy)carbonylamino)-5-methylhexanoic acid (309 mg, 0.841 mmol), and N,N-diisopropylethylamine (0.294 mL, 1.682 mmol) in $CH_2Cl_2$ (2 mL) was added HATU (320 mg, 0.841 mmol). The reaction mixture was stirred at room temperature overnight. The mixture was transferred to a reparatory funnel containing saturated aqueous $NaHCO_3$ solution (5 mL). The aqueous layer was extracted with ethyl acetate (3×10 mL). The combined organic layers were washed with brine (5 mL), dried over $MgSO_4$, filtered, and concentrated. The residue was purified by column chromatography on silica gel (20%→60% ethyl acetate in hexanes) to afford (9H-fluoren-9-yl)methyl 1-(3-methoxy-4-(oxazol-5-yl)phenylamino)-5-methyl-1-oxohexan-2-ylcarbamate (140 mg, 62% yield) as a colorless solid: $^1$H NMR (400 MHz, DMSO-$d_6$) δ 10.24 (s, 1H) 8.38 (s, 1H) 7.89 (d, J=7.6 Hz, 2H) 7.75 (dd, J=7.3, 3.0 Hz, 2H) 7.71 (d, J=8.1 Hz, 1H) 7.64 (d, J=8.3 Hz, 1H) 7.56 (d, J=1.8 Hz, 1H) 7.45 (s, 1H) 7.38-7.44 (m, 2H) 7.29-7.36 (m, 3H) 4.19-4.35 (m, 3H) 4.07-4.15 (m, 1H) 3.91 (s, 3H) 1.50-1.75 (m, 3H) 1.25-1.36 (m, 1H) 1.14-1.25 (m, 1H) 0.87 (d, J=6.5 Hz, 6H).

Part B. 2-Amino-N-(3-methoxy-4-(oxazol-5-yl)phenyl)-5-methylhexanamide

To a solution of (9H-fluoren-9-yl)methyl 1-(3-methoxy-4-(oxazol-5-yl)phenylamino)-5-methyl-1-oxohexan-2-ylcarbamate (105 mg, 0.195 mmol) in $CH_2Cl_2$ (2 mL) at room temperature was added piperidine (0.20 mL, 2.02 mmol). The mixture was stirred at room temperature for 1.25 h. The mixture was concentrated and the product was purified by reverse phase HPLC (MeCN/$H_2O$ containing 0.1% TFA). The organic solvent was removed on the rotovapor and the free base was formed by the addition of saturated aqueous $K_2CO_3$ solution (5 mL). The aqueous layer was extracted with ethyl acetate (4×10 ml). The combined organic layers were washed with brine (5 mL), dried over $MgSO_4$, filtered, and concentrated. The residue was taken up in acetonitrile/water and was frozen and placed on the lyophilizer to afford 2-amino-N-(3-methoxy-4-(oxazol-5-yl)phenyl)-5-methylhexanamide (37 mg, 60% yield) as a colorless amorphous solid: $^1$H NMR (400 MHz, DMSO-$d_6$) δ 8.38 (s, 1H), 7.63 (d, J=8.6 Hz, 1H), 7.60 (d, J=2.0 Hz, 1H), 7.44 (s, 1H), 7.38 (dd, J=8.6, 2.0 Hz, 1H), 3.91 (s, 3H), 3.28 (dd, J=7.6, 5.5 Hz, 1H), 1.61-1.72 (m, 1H), 1.39-1.56 (m, 2H), 1.25-1.35 (m, 1H), 1.20 (td, J=12.3, 6.2 Hz, 1H), 0.865 (d, J=6.5 Hz, 3H), 0.86 (d, J=6.5 Hz, 3H); LC/MS (ESI) m/e 318.2 [(M+H)$^+$, calcd for $C_{17}H_{24}N_3O_3$ 318.2]. HPLC (method A): $t_R$=8.69 min; HPLC (method B): $t_R$=8.75 min.

Example 9

(R)-2-Amino-3-cyclopropyl-N-(3-methoxy-4-(oxazol-5-yl)phenyl)propanamide

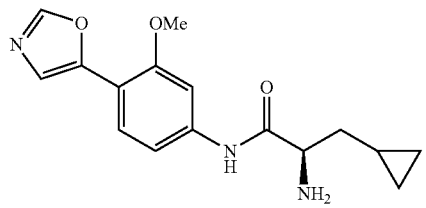 [SMILES: COc1cc(NC(=O)[C@H](N)CC2CC2)ccc1-c1cnco1]

Prepared in a similar fashion as described in Example 1 using (R)-2-amino-3-cyclopropylpropanoic acid in Part C to give (R)-2-amino-3-cyclopropyl-N-(3-methoxy-4-(oxazol-5-yl)phenyl)propanamide (145 mg) as a colorless amorphous solid: $^1$H NMR (400 MHz, DMSO-$d_6$) δ 8.38 (s, 1H), 7.63 (d, J=8.31 Hz, 1H), 7.59 (d, J=1.76 Hz, 1H), 7.44 (s, 1H), 7.39 (dd, J=8.44, 1.89 Hz, 1H), 3.91 (s, 3H), 3.42 (dd, J=7.18, 5.92 Hz, 1H), 1.49-1.58 (m, 1H), 1.38-1.48 (m, 1H), 0.77-0.86 (m, 1H), 0.37-0.46 (m, 2H), 0.01-0.11 (m, 2H); LC/MS (ESI) m/e 302.3 [(M+H)$^+$, calcd for $C_{16}H_{20}N_3O_3$ 302.2]. HPLC (method A): $t_R$=8.89 min; HPLC (method B): $t_R$=10.64 min.

Example 10

(R)-2-Amino-N-ethyl-N-(3-methoxy-4-(oxazol-5-yl)phenyl)-4-methylpentanamide

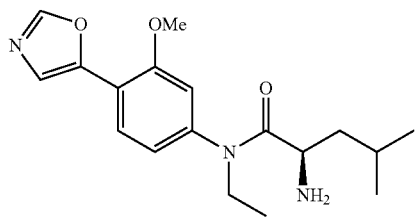 [SMILES: CCN(C(=O)[C@H](N)CC(C)C)c1ccc(-c2cnco2)c(OC)c1]

Part A. (R)-tert-Butyl 1-(ethyl(3-methoxy-4-(oxazol-5-yl)phenyl)amino)-4-methyl-1-oxopentan-2-ylcarbamate To a mixture of (R)-tert-butyl 1-(3-methoxy-4-(oxazol-5-yl)phenylamino)-4-methyl-1-oxopentan-2-ylcarbamate (100 mg, 0.248 mmol), prepared as described in Example 1 Parts A-C, and barium hydroxide (255 mg, 1.49 mmol) in DMF (3 mL) and water (1 mL) was added iodoethane (0.72 mL, 8.92 mmol). The suspension was stirred at room temperature for 12 h. The reaction mixture was transferred to a separatory funnel containing ether (50 mL). The organic layer was washed with water (20 mL), brine (20 mL), dried over $Na_2SO_4$, filtered, and concentrated to afford to afford (R)-tert-butyl 1-(ethyl(3-methoxy-4-(oxazol-5-yl)phenyl)amino)-4-methyl-1-oxopentan-2-ylcarbamate (100 mg, 93% yield) as a yellow oil which was used directly in the next step. LC/MS (ESI) m/e 432.3 [(M+H)+, calcd for $C_{23}H_{34}N_3O_5$ 432.2].

Part B. (R)-2-Amino-N-ethyl-N-(3-methoxy-4-(oxazol-5-yl)phenyl)-4-methylpentanamide To a solution of (R)-tert-butyl 1-(ethyl(3-methoxy-4-(oxazol-5-yl)phenyl)amino)-3-methyl-1-oxobutan-2-ylcarbamate (100 mg, 0.240 mmol) in $CH_2Cl_2$ (1 mL) at 0° C. was added TFA (0.277 mL, 3.59 mmol). The reaction was stirred at room temperature for 2 hours. The mixture was concentrated and purified by column chromatography on silica gel (10% 2 M $NH_3$ in MeOH in $CH_2Cl_2$) to furnish (R)-2-amino-N-ethyl-N-(3-methoxy-4-(oxazol-5-yl)phenyl)-4-methylpentanamide (55 mg, 50% yield) as a TFA salt: $^1$H NMR (400 MHz, $CDCl_3$) δ 8.42 (br s, 3H), 8.05 (br s, 1H), 7.87 (d, J=8.31 Hz, 1H), 7.66 (br s, 1H), 7.12 (br s, 1H), 7.00 (br s, 1H), 4.02-4.13 (m, 2H), 4.01 (s, 3H), 3.54 (dd, J=13.35, 6.80 Hz, 1H), 1.59-1.77 (m, 2H), 1.42-1.54 (m, 1H), 1.13 (t, J=7.05 Hz, 3H), 0.76 (d, J=6.04 Hz, 3H), 0.47 (d, J=6.30 Hz, 3H); LC/MS (ESI) m/e 332.4 [(M+H)+, calcd for $C_{18}H_{26}N_3O_3$ 332.2]. HPLC (method A): $t_R$=8.58 min; HPLC (method B): $t_R$=8.39 min.

Example 11

(R)-2-Amino-4-methyl-N-(4-(oxazol-5-yl)-3-(trifluoromethyl)phenyl)pentanamide

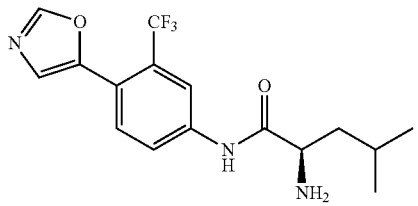

Prepared in a similar fashion as described in Example 1 using 4-nitro-2-trifluoromethylbenzaldehyde as the starting material in Part A to give (R)-2-amino-4-methyl-N-(4-(oxazol-5-yl)-3-(trifluoromethyl)phenyl)pentanamide (15 mg) as a TFA salt: $^1$H NMR (400 MHz, $CDCl_3$) δ 9.90 (br s, 1H), 7.99 (s, 1H), 7.96 (s, 1H), 7.66-7.78 (m, 2H), 7.40 (s, 1H), 3.53 (dd, J=9.95, 3.65 Hz, 1H), 1.75-1.89 (m, 2H), 1.34-1.50 (m, 1H), 0.98 (d, J=6.3 Hz, 3H) 0.96 (d, J=6.3 Hz, 3H); LC/MS (ESI) m/e 342.3 [(M+H)+, calcd for $C_{16}H_{19}F_3N_3O_2$ 342.1]. HPLC (method A): $t_R$=8.95 min; HPLC (method B): $t_R$=9.16 min.

Example 12

(R)-2-Amino-N-(3-bromo-4-(oxazol-5-yl)phenyl)-4-methylpentanamide

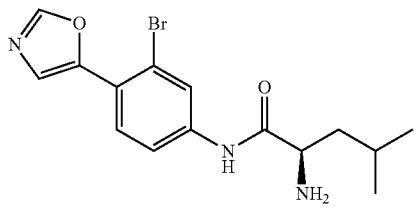 [SMILES: CC(C)C[C@@H](N)C(=O)Nc1ccc(-c2cnco2)c(Br)c1]

Part A. 2-Bromo-4-nitrobenzaldehyde

2-Bromo-1-methyl-4-nitrobenzene (15.0 g, 69.4 mmol) was dissolved in acetic acid (112 mL) and acetic anhydride (105 mL, 1,113 mmol). The mixture was placed in an ice-water bath and concentrated sulfuric acid (15 mL, 281 mmol) was added slowly. Chromium(VI) oxide (34.7 g, 347 mmol) was then added in portions while maintaining the temperature of the reaction mixture between 5-10° C. The reaction mixture was stirred in an ice-bath for 1.5 h. The internal temperature hovered between 5-10° C. It was necessary to monitor the reaction temperature due to a delayed exotherm. At one point it was necessary to place the reaction mixture in an ice-acetone bath for a period of time to keep the temperature from exceeding 10° C. The contents of the flask were then poured into a 2 liter Erlenmeyer flask containing some ice. Cold water was then added to bring the total volume to 1500 mL. The solid was collected on a Buchner funnel. The solid was washed with cold water until it was nearly colorless. The solid was suspended in cold 2% aqueous $Na_2CO_3$ solution (100 mL) and was thoroughly stirred. The solid was collected on a filter and was washed with cold water and partially dried on the Buchner funnel to give 8.3 grams of the diacetate intermediate.

A mixture of 8.3 g of crude diacetate intermediate, ethanol (16 mL), water (16 mL), and conc. $H_2SO_4$ (2.4 mL) was heated at reflux for 1 h. The mixture was cooled to room temperature and the mixture was transferred to a separatory funnel containing saturated aqueous $K_2CO_3$ (50 mL) solution. A fluffy solid formed. It was subsequently determined that this solid was not the product. The aqueous layer was extracted with ethyl acetate (4×50 mL). The combined organic layers were washed with brine (25 mL), dried over $MgSO_4$, filtered, and concentrated. The solid was purified by column chromatography on silica gel (5%→15% ethyl acetate in hexanes) to afford 2-bromo-4-nitrobenzaldehyde (1.41 g, 9% yield) as a colorless fluffy solid: $^1$H NMR (400 MHz, $CDCl_3$) δ 10.41 (s, 1H), 8.51 (d, J=2.0 Hz, 1H), 8.25 (dd, J=8.4, 2.1 Hz, 1H), 8.06 (d, J=8.6 Hz, 1H).

Part B. 5-(2-Bromo-4-nitrophenyl)oxazole

To a solution of 2-bromo-4-nitrobenzaldehyde (700 mg, 3.04 mmol) and TosMIC (594 mg, 3.04 mmol) in MeOH (7 mL) was added potassium carbonate (442 mg, 3.20 mmol). The reaction mixture was heated at reflux for 3 h. The reaction mixture was cooled to room temperature and was transferred to a separatory funnel containing saturated aqueous $NaHCO_3$ solution (25 mL). The aqueous layer was extracted with ethyl acetate (3×50 mL). The combined organic layers were washed with brine (25 mL), dried over $MgSO_4$, filtered, and concentrated. The residue was purified by column chromatography on silica gel (30%→40% ethyl acetate in hexanes) to afford 5-(2-bromo-4-nitrophenyl)oxazole (701 mg, 86% yield) as a yellow solid: $^1$H NMR (400 MHz, $CDCl_3$) δ 8.56 (d, J=2.3 Hz, 1H), 8.25 (dd, J=8.8, 2.3 Hz, 1H), 8.13 (s, 1H), 8.05 (s, 1H), 7.97 (d, J=8.8 Hz, 1H); LC/MS (ESI) m/e 269.1 [(M+H)+, calcd for $C_9H_6N_2O_3Br$ 269.0].

Part C. 3-Bromo-4-(oxazol-5-yl)aniline 5-(2-Bromo-4-nitrophenyl)oxazole (120 mg, 0.446 mmol), tin(II) chloride dihydrate (0.371 mL, 4.46 mmol), and EtOH (4 mL) were combined and heated at 75° C. for 1 h. The reaction mixture was cooled to room temperature and was concentrated. The residue was dissolved in ethyl acetate and was slowly poured into an Erlenmeyer flask containing saturated aqueous NaHCO$_3$ solution. The mixture was then filtered through a pad of diatomaceous earth (Celite®) to remove the solids (rinsed with ethyl acetate). The filtrate was poured into a separatory funnel containing saturated aqueous NaHCO$_3$ solution (50 mL). The aqueous layer was extracted with ethyl acetate (3×25 mL). The combined organic layers were washed with brine (25 mL), dried over MgSO$_4$, filtered and concentrated. The residue was purified by column chromatography on silica gel (30%→50% ethyl acetate in hexanes) to afford 3-bromo-4-(oxazol-5-yl)aniline (67 mg, 63% yield) as a yellow solid: $^1$H NMR (400 MHz, DMSO-d$_6$) δ 8.37 (s, 1H), 7.45 (s, 1H), 7.37 (d, J=8.6 Hz, 1H), 6.92 (d, J=2.3 Hz, 1H), 6.64 (dd, J=8.6, 2.3 Hz, 1H), 5.78 (s, 2H); LC/MS (ESI) m/e 239.1 [(M+H)$^+$, calcd for C$_9$H$_8$N$_2$OBr 239.0].

Part D. (R)-tert-Butyl 1-(3-bromo-4-(oxazol-5-yl) phenylamino)-4-methyl-1-oxopentan-2-ylcarbamate To a mixture of 3-bromo-4-(oxazol-5-yl)aniline (55 mg, 0.230 mmol), (R)-2-(tert-butoxycarbonylamino)-4-methylpentanoic acid (106 mg, 0.460 mmol) and N,N-diisopropylethylamine (0.161 mL, 0.920 mmol) in CH$_2$Cl$_2$ (1.5 mL) was added HATU (175 mg, 0.460 mmol). The reaction mixture was stirred at room temperature for 18 h. A significant amount of starting material still remained. Additional (R)-2-(tert-butoxycarbonylamino)-4-methylpentanoic acid (106 mg, 0.460 mmol) and HATU (175 mg, 0.460 mmol) was added and the reaction mixture was heated at 40° C. for 3 h. The reaction mixture was cooled to room temperature and was transferred to a separatory funnel containing saturated aqueous NaHCO$_3$ solution (10 mL). The aqueous layer was extracted with ethyl acetate (3×10 mL). The combined organic layers were washed with brine (10 mL), dried over MgSO$_4$, filtered, and concentrated. The residue was purified by column chromatography on silica gel (20%→40% ethyl acetate in hexanes) to afford (R)-tert-butyl 1-(3-bromo-4-(oxazol-5-yl)phenylamino)-4-methyl-1-oxopentan-2-ylcarbamate (135 mg) as a colorless oil. (The product was somewhat impure, but was carried on to the next step as is.) LC/MS (ESI) m/e 452.2 [(M+H)$^+$, calcd for C$_{20}$H$_{27}$N$_3$O$_4$Br 452.1].

Part E. (R)-2-Amino-N-(3-bromo-4-(oxazol-5-yl) phenyl)-4-methylpentanamide

To a suspension of (R)-tert-butyl 1-(3-bromo-4-(oxazol-5-yl)phenylamino)-4-methyl-1-oxopentan-2-ylcarbamate (106 mg, 0.234 mmol) in CH$_2$Cl$_2$ (2 mL) at 0° C. was added TFA (0.50 mL, 6.49 mmol). The cooling bath was removed and the mixture was stirred at room temperature under N$_2$ for 1.5 h. The reaction mixture was concentrated and the product was purified by reverse phase HPLC (MeCN/H$_2$O containing 0.1% TFA). The organic solvent was removed on the rotovapor and the aqueous mixture was transferred to a reparatory funnel containing saturated aqueous K$_2$CO$_3$ (5 mL). The aqueous layer was extracted with ethyl acetate (4×10 ml). The combined organic layers were washed with brine (5 mL), dried over MgSO$_4$, filtered, and concentrated. The residue was taken up in acetonitrile/water and was frozen and placed on the lyophilizer to afford (R)-2-amino-N-(3-bromo-4-(oxazol-5-yl)phenyl)-4-methylpentanamide (27 mg, 31% yield) as a colorless amorphous solid: $^1$H NMR (400 MHz, DMSO-d$_6$) δ 8.52 (s, 1H), 8.22 (d, J=1.5 Hz, 1H), 7.70-7.77 (m, 3H), 3.38 (dd, J=8.6, 5.5 Hz, 1H), 1.70-1.80 (m, 1H), 1.44-1.54 (m, 1H), 1.31-1.42 (m, 1H), 0.91 (d, J=6.5 Hz, 3H), 0.89 (d, J=6.5 Hz, 3H); LC/MS (ESI) m/e 352.3 [(M+H)$^+$, calcd for C$_{15}$H$_{19}$N$_3$O$_2$Br 352.1]. HPLC (method A): t$_R$=8.51 min; HPLC (method B): t$_R$=8.45 min.

Example 13

(R)-2-Amino-4-methyl-N-(3-methyl-4-(oxazol-5-yl) phenyl)pentanamide

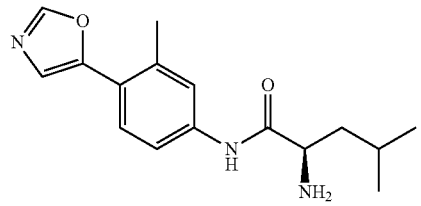 [SMILES: Cc1cc(NC(=O)[C@H](N)CC(C)C)ccc1-c1cnco1]

Part A. (R)-tert-Butyl 4-methyl-1-(3-methyl-4-(oxazol-5-yl)phenylamino)-1-oxopentan-2-ylcarbamate (R)-tert-Butyl 1-(3-bromo-4-(oxazol-5-yl)phenylamino)-4-methyl-1-oxopentan-2-ylcarbamate (100 mg, 0.221 mmol), prepared as described in Example 12 Parts A-D, methylboronic acid (26.5 mg, 0.442 mmol), sodium carbonate (2 M, aq) (0.221 mL, 0.442 mmol), toluene (1.5 mL), and MeOH (0.300 mL) were combined in a conical vial. N$_2$ was bubbled into the reaction mixture for 5 min. Pd(PPh$_3$)$_4$ (25.5 mg, 0.022 mmol) was then added to the mixture and it was heated at 90° C. for 4 h. The reaction mixture was transferred to a separatory funnel containing saturated aqueous NaHCO$_3$ solution (5 mL). The aqueous layer was extracted with ethyl acetate (3×10 mL). The combined organic layers were washed with brine (5 mL), dried over MgSO$_4$, filtered and concentrated. The residue was purified by column chromatography on silica gel (30%→50% ethyl acetate in hexanes) to afford (R)-tert-butyl 4-methyl-1-(3-methyl-4-(oxazol-5-yl)phenylamino)-1-oxopentan-2-ylcarbamate (48 mg, 56% yield) as a colorless solid: $^1$H NMR (400 MHz, DMSO-d$_6$) δ 10.06 (s, 1H), 8.44 (s, 1H), 7.60 (s, 1H), 7.59 (br s, 1H), 7.40 (s, 1H), 7.06 (d, J=7.8 Hz, 1H), 4.07-4.18 (m, 1H), 2.41 (s, 3H), 1.58-1.72 (m, 1H), 1.48-1.57 (m, 1H), 1.44 (dd, J=8.6, 5.0 Hz, 1H), 1.38 (s, 9H), 0.90 (d, J=3.5 Hz, 3H), 0.89 (d, J=3.5 Hz, 3H); LC/MS (ESI) m/e 288.3 [(M+H—C$_5$H$_8$O$_2$)$^+$, calcd for C$_{16}$H$_{22}$N$_3$O$_2$ 288.2].

Part B. (R)-2-Amino-4-methyl-N-(3-methyl-4-(oxazol-5-yl)phenyl)pentanamide

To a suspension of (R)-tert-butyl 4-methyl-1-(3-methyl-4-(oxazol-5-yl)phenylamino)-1-oxopentan-2-ylcarbamate (58 mg, 0.150 mmol) in CH$_2$Cl$_2$ (2 mL) at 0° C. was added TFA (0.50 mL, 6.49 mmol). The cooling bath was removed and the mixture was stirred at room temperature under N$_2$ for 1.5 h. The reaction mixture was concentrated and the product was purified by reverse phase HPLC (MeCN/H$_2$O containing 0.1% TFA). The organic solvent and most of the water was removed on the rotovapor and the remaining aqueous mixture was transferred to a separatory funnel containing saturated aqueous K$_2$CO$_3$ (4 mL). The aqueous layer was extracted with ethyl acetate (5×10 ml). The combined organic layers were washed with brine (5 mL), dried over MgSO$_4$, filtered, and concentrated. The residue was taken up in acetonitrile/water and was frozen and placed on the lyophilizer to afford (R)-2-amino-4-methyl-N-(3-methyl-4-(oxazol-5-yl)phenyl)pentanamide (43 mg, 95% yield) as a colorless amorphous solid: $^1$H NMR (400 MHz, DMSO-$d_6$) δ 8.44 (s, 1H), 7.60-7.64 (m, 3H), 7.40 (s, 1H), 3.38 (dd, J=8.4, 5.7 Hz, 1H), 2.41 (s, 3H), 1.70-1.79 (m, 1H), 1.49 (ddd, J=13.4, 8.0, 5.5 Hz, 1H), 1.31-1.40 (m, 1H), 0.91 (d, J=6.5 Hz, 3H), 0.89 (d, J=6.8 Hz, 3H); LC/MS (ESI) m/e 288.3 [(M+H)$^+$, calcd for $C_{16}H_{22}N_3O_2$ 288.2]. HPLC (method A): $t_R$=7.80 min; HPLC (method B): $t_R$=7.97 min.

Example 14

(R)-2-Amino-N-(3-ethyl-4-(oxazol-5-yl)phenyl)-4-methylpentanamide

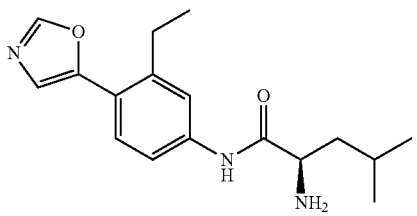

Part A. 4-Nitro-2-vinylbenzaldehyde

To a solution of 2-bromo-4-nitrobenzaldehyde (500 mg, 2.174 mmol), prepared as described in Example 12 Part A, in anhydrous toluene (15 mL) was added 2,4,6-trivinyl-1,3,5,2,4,6-trioxatriborinane-pyridine complex (785 mg, 3.26 mmol) and sodium carbonate (2 M aq.) (3.26 mL, 6.52 mmol). The solution was degassed with $N_2$ for 3 min. Pd(PPh$_3$)$_4$ (251 mg, 0.217 mmol) was subsequently added to the reaction mixture, and the mixture was heated at 100° C. under $N_2$ for 6.5 h. The reaction mixture was cooled to room temperature and was transferred to a reparatory funnel containing saturated aqueous NaHCO$_3$ solution (5 mL). The aqueous layer was extracted with ethyl acetate (3×10 mL). The combined organic layers were washed with brine (5 mL), dried over MgSO$_4$, filtered and concentrated. The residue was purified by column chromatography on silica gel (5%→20% ethyl acetate in hexanes) to afford 4-nitro-2-vinylbenzaldehyde (237 mg, 62% yield) as a yellow amorphous oil. The product contained some impurities. The product was carried forward directly to the next step.

Part B. 5-(4-Nitro-2-vinylphenyl)oxazole

To a solution of 4-nitro-2-vinylbenzaldehyde (235 mg, 1.33 mmol) and TosMIC (259 mg, 1.33 mmol) in MeOH (5 mL) was added potassium carbonate (192 mg, 1.40 mmol). The reaction mixture was heated at reflux for 2 h. The reaction mixture was cooled to room temperature and was transferred to a separatory funnel containing saturated aqueous NaHCO$_3$ solution (50 mL). The aqueous layer was extracted with ethyl acetate (3×75 mL). The combined organic layers were washed with brine (50 mL), dried over MgSO$_4$, filtered, and concentrated. The residue was purified by column chromatography on silica gel (10→40% ethyl acetate in hexanes) to afford 5-(4-nitro-2-vinylphenyl)oxazole (46 mg, 0.213 mmol, 16% yield) as a yellow solid: $^1$H NMR (400 MHz, CDCl$_3$) δ 8.42 (d, J=2.3 Hz, 1H), 8.22 (dd, J=8.7, 2.4 Hz, 1H), 8.07 (s, 1H), 7.86 (d, J=8.8 Hz, 1H), 7.45 (s, 1H), 7.05 (dd, J=17.4, 11.1 Hz, 1H), 5.91 (d, J=17.4 Hz, 1H), 5.62 (d, J=11.1 Hz, 1H); LC/MS (ESI) m/e 217.2 [(M+H)$^+$, calcd for $C_{11}H_9N_2O_3$ 217.06].

Part C. 3-Ethyl-4-(oxazol-5-yl)aniline

To a solution of 5-(4-nitro-2-vinylphenyl)oxazole (45 mg, 0.208 mmol) in ethanol (20 mL) was added palladium on carbon (10%, Degussa type) (44.3 mg, 0.021 mmol). The mixture was placed under $H_2$ on a Parr shaker at 40 psi for 2 h. The catalyst was then removed by filtration through a pad of diatomaceous earth (Celite®) and the filtrate was concentrated to give 3-ethyl-4-(oxazol-5-yl)aniline (45 mg) as a light brown solid. The crude product was used directly in the next step. $^1$H NMR (400 MHz, MeOD) δ 8.38 (s, 1H), 7.80 (d, J=8.3 Hz, 1H), 7.45 (s, 1H), 7.39 (d, J=2.3 Hz, 1H), 7.34 (dd, J=8.3, 2.5 Hz, 1H), 2.88 (q, J=7.6 Hz, 2H), 1.26 (t, J=7.6 Hz, 3H); LC/MS (ESI) m/e 189.2 [(M+H)$^+$, calcd for $C_{11}H_{13}N_2O$ 189.1].

Part D. (R)-2-Amino-N-(3-ethyl-4-(oxazol-5-yl)phenyl)-4-methylpentanamide

Prepared from 3-ethyl-4-(oxazol-5-yl)aniline as described in Example 12 Parts D-E to give (R)-2-amino-N-(3-ethyl-4-(oxazol-5-yl)phenyl)-4-methylpentanamide (24 mg, 71% yield) as an off-white amorphous solid: $^1$H NMR (400 MHz, DMSO-$d_6$) δ 8.44 (s, 1H), 7.61-7.69 (m, 2H), 7.55 (d, J=8.3 Hz, 1H), 7.37 (s, 1H), 3.37 (dd, J=8.7, 5.7 Hz, 1H), 2.73 (q, J=7.6 Hz, 2H), 1.70-1.82 (m, 1 H), 1.49 (ddd, J=13.5, 8.2, 5.5 Hz, 1H), 1.30-1.41 (m, 1H), 1.17 (t, J=7.4 Hz, 3H), 0.92 (d, J=6.5 Hz, 3H), 0.89 (d, J=6.5 Hz, 3H); LC/MS (ESI) m/e 302.4 [(M+H)$^+$, calcd for $C_{17}H_{24}N_3O_2$ 302.2]. HPLC (method A): $t_R$=8.46 min; HPLC (method B): $t_R$=8.54 min.

Example 15

(R)-2-Amino-4-methyl-N-(4-(oxazol-5-yl)-3-(thiophen-3-yl)phenyl)pentanamide

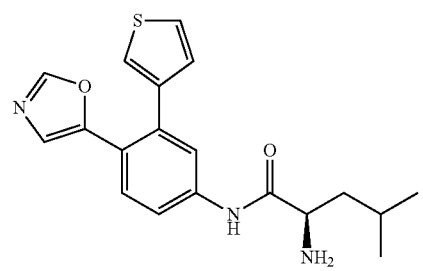 [SMILES: CC(C)C[C@@H](N)C(=O)Nc1ccc(-c2cnco2)c(-c2ccsc2)c1]

Prepared in a similar fashion as described in Example 13 using thiophen-3-ylboronic acid in Part A to give (R)-2-amino-4-methyl-N-(4-(oxazol-5-yl)-3-(thiophen-3-yl)phenyl)pentanamide (15 mg) as a TFA salt: $^1$H NMR (400 MHz, DMSO-$d_6$) δ 10.75 (s, 1H), 8.34 (s, 1H), 8.27 (br s, 3H), 7.73-7.78 (m, 1H), 7.69-7.73 (m, 1H), 7.67 (d, J=2.0 Hz, 1H), 7.65 (dd, J=4.9, 2.9 Hz, 1H), 7.50 (dd, J=3.0, 1.3 Hz, 1H), 6.96 (dd, J=5.0, 1.3 Hz, 1H), 6.41 (s, 1H), 3.94 (br s, 1H), 1.64-1.73 (m, 3H), 0.94 (d, J=3.8 Hz, 6H); LC/MS (ESI) m/e 356.2 [(M+H)$^+$, calcd for $C_{19}H_{22}N_3O_2S$ 356.1]. HPLC (method A): $t_R$=8.84 min; HPLC (method B): $t_R$=9.18 min.

Example 16

(R)-2-Amino-N-(3-hydroxy-4-(oxazol-5-yl)phenyl)-4-methylpentanamide

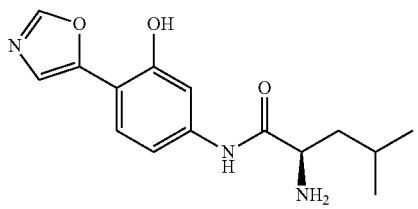

To a solution of (R)-2-amino-N-(3-methoxy-4-(oxazol-5-yl)phenyl)-4-methylpentanamide (20 mg, 0.066 mmol), prepared as described in Example 1, in CH$_2$Cl$_2$ (1 mL) in a pressure vessel, was added BBr$_3$ (1M in CH$_2$Cl$_2$) (0.025 mL, 0.264 mmol). The vessel was heated to 80° C. for 12 hours. The mixture was transferred to a separatory funnel containing saturated aqueous NaHCO$_3$ solution (5 mL). The aqueous layer was extracted with ethyl acetate (3×5 mL). The combined organic layers were concentrated and the residue was purified by reverse phase HPLC (MeCN/H$_2$O containing 0.1% TFA) to afford (R)-2-amino-N-(3-hydroxy-4-(oxazol-5-yl)phenyl)-4-methylpentanamide (5 mg, 19% yield) as a TFA salt: $^1$H NMR (400 MHz, DMSO-d$_6$) δ 10.62 (s, 1H), 10.54 (s, 1H), 8.37 (s, 1H), 8.24 (br s, 3H), 7.60 (d, J=8.56 Hz, 1H), 7.44-7.48 (m, 2H), 7.13 (dd, J=8.56, 2.01 Hz 1H), 3.87-3.95 (m, 1H), 1.61-1.71 (m, 3H), 0.83-0.97 (m, 6H); LC/MS (ESI) m/e 290.3 [(M+H)$^+$, calcd for C$_{15}$H$_{20}$N$_3$O$_3$ 290.2]. HPLC (method A): t$_R$=7.74 min; HPLC (method B): t$_R$=7.48 min.

Example 17

(R)-2-Amino-N-(3-ethoxy-4-(oxazol-5-yl)phenyl)-4-methylpentanamide

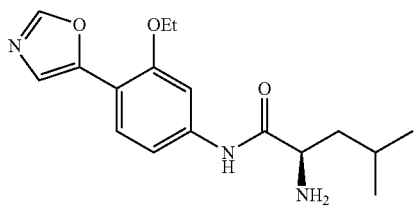

Part A. 5-Nitro-2-(oxazol-5-yl)phenol

To a solution of 5-(2-methoxy-4-nitrophenyl)oxazole (250 mg, 1.135 mmol), prepared as described in Example 1 Part A, in CH$_2$Cl$_2$ (5 mL) in a pressure vessel was added BBr$_3$ (1 M in CH$_2$Cl$_2$) (0.429 mL, 4.54 mmol). The vessel was heated to 80° C. for 12 hours. The mixture was transferred to a separatory funnel containing saturated aqueous NaHCO$_3$ solution. The aqueous layer was extracted with ethyl acetate (3×25 mL). The combined organic layers were concentrated and the residue was purified by column chromatography on silica gel (40→70% ethyl acetate in hexanes) to afford 5-nitro-2-(oxazol-5-yl)phenol (120 mg, 51% yield) as a gray solid: LC/MS (ESI) m/e 207.2 [(M+H)$^+$, calcd for C$_9$H$_7$N$_2$O$_4$ 207.0].

Part B. 5-(2-Ethoxy-4-nitrophenyl)oxazole

A mixture of 5-nitro-2-(oxazol-5-yl)phenol (110 mg, 0.534 mmol) and K$_2$CO$_3$ (81 mg, 0.587 mmol) in DMF (3 mL) was stirred at room temperature for 30 minutes. To this mixture, was added iodoethane (0.047 mL, 0.587 mmol) and the mixture was then stirred at room temperature for 14 hours. The mixture was transferred to a separatory funnel containing saturated aqueous NH$_4$Cl. The aqueous layer was extracted with ethyl acetate (3×10 mL). The combined organic layers were concentrated and the residue was purified by column chromatography on silica gel (10→30% ethyl acetate in hexanes) to afford 5-(2-ethoxy-4-nitrophenyl)oxazole (120 mg, 96% yield) as a yellow solid: LC/MS (ESI) m/e 235.2 [(M+H)$^+$, calcd for C$_{11}$H$_{11}$N$_2$O$_4$ 235.1].

Part C. (R)-2-Amino-N-(3-ethoxy-4-(oxazol-5-yl)phenyl)-4-methylpentanamide

The title compound was prepared from 5-(2-ethoxy-4-nitrophenyl)oxazole in a similar fashion as described in Example 1 Parts B-D. The product was purified by column chromatography on silica gel (10% 2 M NH$_3$ in MeOH in CH$_2$Cl$_2$) to give (R)-2-amino-N-(3-ethoxy-4-(oxazol-5-yl)phenyl)-4-methylpentanamide (72 mg) as a TFA salt: $^1$H NMR (400 MHz, DMSO-d$_6$) δ 10.74 (s, 1H), 8.41 (s, 1H), 8.29 (br s, 3H), 7.70 (d, J=8.56 Hz, 1H), 7.43-7.50 (m, 2H), 7.36 (dd, J=8.56, 1.76 Hz, 1H), 4.16 (q, J=6.97 Hz, 2H), 3.90-4.00 (m, 1H), 1.66-1.76 (m, 3H), 1.48 (t, J=6.92 Hz, 3H), 0.92 (d, J=4.78 Hz, 6H); LC/MS (ESI) m/e 318.3 [(M+H)$^+$, calcd for C$_{17}$H$_{24}$N$_3$O$_3$ 318.2]. HPLC (method A): t$_R$=8.44 min; HPLC (method B): t$_R$=8.52 min.

Example 18

(R)-2-Amino-N-(3-(difluoromethoxy)-4-(oxazol-5-yl)phenyl)-4-methylpentanamide

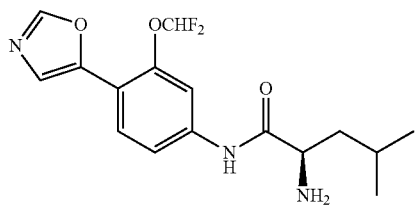 [SMILES: CC(C)C[C@@H](N)C(=O)Nc1ccc(-c2cnco2)c(OC(F)F)c1]

Part A. 5-(2-(Difluoromethoxy)-4-nitrophenyl)oxazole

To a solution of 5-nitro-2-(oxazol-5-yl)phenol (1.4 g, 6.79 mmol), prepared as described in Example 17 Part A, in DMF (15 mL) at room temperature was added potassium carbonate (3.28 g, 23.77 mmol). The resulting suspension was stirred for 20 min and was then treated with methyl 2-chloro-2,2-difluoroacetate (1.79 mL, 16.98 mmol). The reaction mixture was heated to 90° C. for 2 h. The reaction mixture was transferred to a flask containing 100 mL water resulting in formation of a precipitate which was collected by filtration. The solid was collected and dried under vacuum to afford 5-(2-(difluoromethoxy)-4-nitrophenyl)oxazole (1.40 g, 80% yield) as a yellow solid. The solid was used as is without further purification. LC/MS (ESI) m/e 257.0 [(M+H)$^+$, calcd for $C_{10}H_7N_2O_4F_2$ 257.0].

Part B. (R)-2-Amino-N-(3-(difluoromethoxy)-4-(oxazol-5-yl)phenyl)-4-methylpentanamide The title compound was prepared from 5-(2-(difluoromethoxy)-4-nitrophenyl)oxazole in a similar fashion as described in Example 1 Parts B-D. The product was purified by reverse phase HPLC (acetonitrile/water containing 0.1% TFA). The organic solvent was removed on the rotovapor and the free base was formed by washing with saturated aqueous $K_2CO_3$ (5 mL) solution. The aqueous layer was extracted with ethyl acetate (4×10 ml). The combined organic layers were washed with brine (5 mL), dried over $MgSO_4$, filtered, and concentrated. The residue was taken up in ether (20 mL) and was cooled to 0° C. To this solution was added 2 M HCl in ether (8 mL) resulting in the formation of a colorless precipitate. The precipitate was collected on a Buchner funnel and was dried under vacuum to afford (R)-2-amino-N-(3-(difluoromethoxy)-4-(oxazol-5-yl)phenyl)-4-methylpentanamide (400 mg) as the HCl salt: $^1$H NMR (400 MHz, CD$_3$OD) δ 8.44 (br s, 1H), 7.85 (s, 1H), 7.83 (s, 1H), 7.56 (d, J=7.8 Hz, 2H), 6.99 (t, J=73.0 Hz, 1H), 4.06 (t, J=6.3 Hz, 1H), 1.73-1.83 (m, 3H), 1.03 (d, J=5.3 Hz, 6H); LC/MS (ESI) m/e 340.3 [(M+H)$^+$, calcd for $C_{16}H_{20}N_3O_3F_2$ 340.4]. HPLC (method A): $t_R$=8.72 min; HPLC (method B): $t_R$=8.58 min.

Example 19

(R)-2-Amino-N-(3-methoxy-4-(2H-1,2,3-triazol-4-yl)phenyl)-4-methylpentanamide

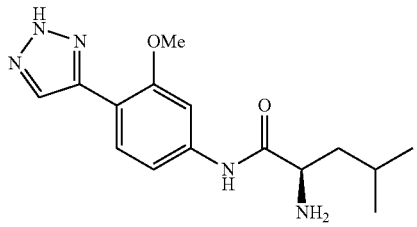 [SMILES: COc1cc(NC(=O)[C@H](N)CC(C)C)ccc1-c1cn[nH]n1]

Part A.
((2-Methoxy-4-nitrophenyl)ethynyl)trimethylsilane

1-Bromo-2-methoxy-4-nitrobenzene (3.00 g, 12.93 mmol), ethynyltrimethylsilane (1.270 g, 12.93 mmol), triethylamine (5.41 mL, 38.8 mmol) and $CH_2Cl_2$ (60 mL) were combined and $N_2$ was bubbled into the reaction mixture for 5 min. Copper (I) iodide (0.172 g, 0.905 mmol) and Pd(PPh$_3$)$_2$Cl$_2$ (0.908 g, 1.293 mmol) were then added and the mixture was heated at reflux for 16 h. The mixture was cooled to room temperature and was transferred to a separatory funnel containing saturated aqueous NaHCO$_3$ solution (50 mL). The aqueous layer was extracted with ethyl acetate (3×50 mL). The combined organic layers were washed with brine (50 mL), dried over MgSO$_4$, filtered and concentrated. The residue was purified by column chromatography on silica gel (5%→10% ethyl acetate in hexanes) to afford ((2-methoxy-4-nitrophenyl)ethynyl)trimethylsilane (2.75 g, 85% yield) as a pale yellow solid: $^1$H NMR (400 MHz, CDCl$_3$) δ 7.77 (dd, J=8.3, 2.3 Hz, 1H), 7.68-7.73 (m, 1H), 7.53 (d, J=8.6 Hz, 1H), 3.95 (s, 3H), 0.25-0.28 (m, 9H); LC/MS (ESI) m/e 249.43 [M$^+$, calcd for $C_{12}H_{15}NO_3Si$ 249.08].

Part B. 1-Ethynyl-2-methoxy-4-nitrobenzene

A solution of ((2-methoxy-4-nitrophenyl)ethynyl)trimethylsilane (2.65 g, 10.63 mmol) in THF (70 mL) was treated with tetrabutylammonium fluoride (15.94 mL, 15.94 mmol). The mixture was stirred at room temperature for 1 h. The reaction mixture was transferred to a separatory funnel containing saturated aqueous NaHCO$_3$ solution (50 mL). The aqueous layer was extracted with ether (3×100 mL). The combined organic layers were washed with brine (50 mL), dried over MgSO$_4$, filtered and concentrated. The residue was purified by column chromatography on silica gel (5%→10% ethyl acetate in hexanes) to afford 1-ethynyl-2-methoxy-4-nitrobenzene (1.04 g, 55% yield) as a pale yellow solid: $^1$H NMR (400 MHz, CDCl$_3$) δ 7.80 (dd, J=8.4, 2.1 Hz, 1H), 7.73 (d, J=2.0 Hz, 1H), 7.58 (d, J=8.3 Hz, 1H), 3.99 (s, 3H), 3.53 (s, 1H).

Part C.
4-(2-Methoxy-4-nitrophenyl)-2H-1,2,3-triazole

A mixture of 1-ethynyl-2-methoxy-4-nitrobenzene (200 mg, 1.129 mmol) and azidotrimethylsilane (3.00 mL, 22.60 mmol) in a pressure tube was heated at 125° C. for 16 h. The reaction mixture was cooled to 0° C. and was diluted with hexane (3 mL). The solid was collected on a Buchner funnel to afford 4-(2-methoxy-4-nitrophenyl)-2H-1,2,3-triazole (100 mg). The filtrate was concentrated and taken up in cold ether/hexane (1:1) and the solid was collected on a Buchner funnel to afford additional 4-(2-methoxy-4-nitrophenyl)-2H-1,2,3-triazole (26 mg). In total 126 mg (51% yield) was isolated as a yellow solid: $^1$H NMR (300 MHz, DMSO-d$_6$) δ 15.05 (br s, 1H), 8.32 (s, 1H), 8.27 (d, J=8.8 Hz, 1H), 7.87-7.98 (m, 2H), 4.08 (s, 3H); LC/MS (ESI) m/e 221.26 [(M+H)$^+$, calcd for $C_9H_9N_4O_3$ 221.07].

Part D. (R)-2-Amino-N-(3-methoxy-4-(2H-1,2,3-triazol-4-yl)phenyl)-4-methylpentanamide The title compound was prepared from 4-(2-methoxy-4-nitrophenyl)-2H-1,2,3-triazole in a similar fashion as described in Example 1 Parts B-D, except that the HATU mediated amide forming reaction was carried out at 40° C. The product was purified by reverse phase HPLC (5% MeCN/95% water→20% MeCN/80% water with 0.1% TFA). The organic solvent and most of the water was removed on the rotovapor. The residue was taken up in acetonitrile/water and was frozen and placed on the lyophilizer to afford (R)-2-amino-N-(3-methoxy-4-(2H-1,2,3-triazol-4-yl)phenyl)-4-methylpentanamide (76 mg) as a TFA salt: $^1$H NMR (400 MHz, DMSO-d$_6$) δ 10.68 (s, 1H), 8.28 (br s, 3H), 8.16 (br s, 1H), 7.97 (d, J=8.3 Hz, 1H), 7.47 (d, J=2.0 Hz, 1H), 7.34 (dd, J=8.4, 1.9 Hz, 1H), 3.95 (d, J=5.3 Hz, 1H), 3.91 (s, 3H), 1.63-1.75 (m, 3H), 0.95 (d, J=4.3 Hz, 6H); LC/MS (ESI) m/e 304.3 [(M+H)$^+$, calcd for $C_{15}H_{22}N_5O_2$ 304.2]. HPLC (method A): $t_R$=7.44 min; HPLC (method B): $t_R$=7.18 min.

Example 20

(R)-2-Amino-N-(3-methoxy-4-(pyridin-4-yl)phenyl)-4-methylpentanamide

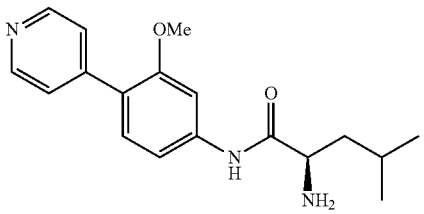 [SMILES: COc1cc(NC(=O)[C@H](N)CC(C)C)ccc1-c1ccncc1]

Part A. (R)-tert-Butyl 1-(4-bromo-3-methoxyphenylamino)-4-methyl-1-oxopentan-2-ylcarbamate To a mixture of 4-bromo-3-methoxyaniline (1.00 g, 4.95 mmol) and (R)-2-(tert-butoxycarbonylamino)-4-methylpentanoic acid (1.72 g, 7.42 mmol) in $CH_2Cl_2$ (20 mL) at room temperature was added N,N-diisopropylethylamine (4.32 mL, 24.75 mmol) and HATU (2.82 g, 7.42 mmol). The reaction mixture was stirred at room temperature for 12 hours. The reaction mixture was transferred to a separatory funnel containing saturated aqueous $NaHCO_3$ solution. The aqueous layer was extracted with $CH_2Cl_2$ (3×50 mL). The combined organic layers were washed with brine and concentrated and the residue was purified by column chromatography on silica gel (30→40% ethyl acetate in hexanes) to afford (R)-tert-butyl 1-(4-bromo-3-methoxyphenylamino)-4-methyl-1-oxopentan-2-ylcarbamate (2.00 g, 97% yield) as a yellow solid: $^1$H NMR (400 MHz, DMSO-$d_6$) δ 7.46-7.43 (m, 1H), 7.19 (dd, J=8.8, 2.3 Hz, 1H), 7.06 (d, J=7.8 Hz, 1H), 4.15-4.06 (m, 1H), 3.81 (s, 3H), 1.70-1.59 (m, 1H), 1.58-1.47 (m, 1H), 1.46-1.39 (m, 1H), 1.38 (s, 7H), 0.89 (dd, J=6.5, 2.8 Hz, 5H); LC/MS (ESI) m/e 315.2 [(M−Boc+H)$^+$, calcd for $C_{13}H_{20}BrN_2O_2$ 315.1].

Part B. (R)-tert-Butyl 1-(3-methoxy-4-(pyridin-4-yl)phenylamino)-4-methyl-1-oxopentan-2-ylcarbamate To a mixture of (R)-tert-butyl 1-(4-bromo-3-methoxyphenylamino)-4-methyl-1-oxopentan-2-ylcarbamate (200 mg, 0.482 mmol), pyridin-4-ylboronic acid (65.1 mg, 0.530 mmol), and $Na_2CO_3$ (153 mg, 1.445 mmol) dissolved in water (10 mL) in toluene (30 mL) and ethanol (7.50 mL) was added Pd(PPh$_3$)$_4$ (27.8 mg, 0.024 mmol). The reaction was heated at reflux for 12 hours. The mixture was transferred to a separatory funnel containing water. The aqueous layer was extracted with ethyl acetate (3×25 mL). The combined organic layers were concentrated and the residue was purified by column chromatography on silica gel (10→50% ethyl acetate in hexanes) to afford (R)-tert-butyl 1-(3-methoxy-4-(pyridin-4-yl)phenylamino)-4-methyl-1-oxopentan-2-ylcarbamate (151 mg, 76% yield) as a yellow solid: LC/MS (ESI) m/e 414.3 [(M+H)$^+$, calcd for $C_{23}H_{32}N_3O_4$ 414.2].

Part C. (R)-2-Amino-N-(3-methoxy-4-(pyridin-4-yl)phenyl)-4-methylpentanamide To a solution of (R)-tert-butyl 1-(3-methoxy-4-(pyridin-4-yl)phenylamino)-4-methyl-1-oxopentan-2-ylcarbamate (150 mg, 0.363 mmol) in $CH_2Cl_2$ (1 mL) at 0° C., was added TFA (1 mL, 12.98 mmol). The reaction mixture was stirred at room temperature for 2 h. The mixture was concentrated in vacuo and purified by reverse phase HPLC (acetonitrile/water containing 0.1% TFA). The organic solvent was removed on the rotovapor and the mixture was frozen and placed on the lyophilizer. The resultant solid was transferred to reparatory funnel containing saturated aqueous $NaHCO_3$ solution and the aqueous layer was extracted with ethyl acetate (3×10 mL). The combined organic layers were washed with water, brine, dried over $Na_2SO_4$, filtered, and concentrated to afford (R)-2-amino-N-(3-methoxy-4-(pyridin-4-yl)phenyl)-4-methylpentanamide (71 mg, 63% yield) as a colorless gel: $^1$H NMR (400 MHz, DMSO-$d_6$) δ 8.55 (d, J=6.0 Hz, 2H), 7.56 (d, J=1.5 Hz, 1H), 7.51 (dd, J=4.5, 1.5 Hz, 2H), 7.32-7.42 (m, 2H), 3.79 (s, 3H), 3.34-3.38 (m, 1H), 1.73-1.82 (m, 1H), 1.49 (ddd, J=13.4, 8.1, 5.4 Hz, 1H), 1.30-1.40 (m, 1H), 0.92 (d, J=6.5 Hz, 3H), 0.90 (d, J=6.5 Hz, 3H); LC/MS (ESI) m/e 314.4 [(M+H)$^+$, calcd for $C_{18}H_{24}N_3O_2$ 314.2]. HPLC (method A): $t_R$=6.18 min; HPLC (method B): $t_R$=6.09 min.

Example 21

(R)-2-Amino-N-(3-methoxy-4-(thiazol-5-yl)phenyl)-4-methylpentanamide

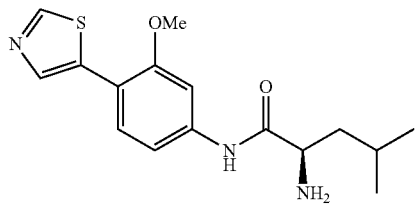

Part A. (R)-tert-Butyl 1-(3-methoxy-4-(4,4,5,5-tetramethyl-1,3,2-dioxaborolan-2-yl)phenylamino)-4-methyl-1-oxopentan-2-ylcarbamate (R)-tert-Butyl 1-(4-bromo-3-methoxyphenylamino)-4-methyl-1-oxopentan-2-ylcarbamate (300 mg, 0.722 mmol), prepared as described in Example 20 Part A, 4,4,4',4',5,5,5',5'-octamethyl-2,2'-bi(1,3,2-dioxaborolane) (275 mg, 1.083 mmol), potassium acetate (213 mg, 2.167 mmol), and dioxane (4 mL) were combined and dichloro[1,1'-bis(diphenylphosphino)ferrocene]palladium(II) dichloromethane adduct (59.4 mg, 0.072 mmol) was added to the suspension. The reaction mixture was placed under nitrogen and was heated at 80° C. overnight. The mixture was cooled to room temperature and was filtered through a pad of diatomaceous earth (Celite®). The filtrate was transferred to a separatory funnel containing saturated aqueous $NaHCO_3$ solution (10 mL). The aqueous layer was extracted with ethyl acetate (3×10 mL). The combined organic layers were washed with brine (10 mL), dried over $MgSO_4$, filtered, and concentrated. The residue was purified by column chromatography on silica gel (20%→35% ethyl acetate in hexanes) to afford (R)-tert-butyl 1-(3-methoxy-4-(4,4,5,5-tetramethyl-1,3,2-dioxaborolan-2-yl)phenylamino)-4-methyl-1-oxopentan-2-ylcarbamate (95 mg, 28% yield) as a colorless amorphous solid: $^1$H NMR (500 MHz, DMSO-$d_6$) δ 7.49 (d, J=7.9 Hz, 1H), 7.30 (d, J=1.5 Hz, 1H), 7.21 (dd, J=6.3, 2.0 Hz, 1H), 4.12 (br s, 1H), 3.72 (s, 3H), 1.65 (br s, 1H), 1.49-1.57 (m, 1H), 1.40-1.46 (m, 1H), 1.39 (s, 9H), 1.26 (s, 6H), 1.18 (s, 6H), 0.90 (d, J=6.7 Hz, 3H), 0.90 (d, J=6.1 Hz, 3H).

Part B. (R)-tert-Butyl 1-(3-methoxy-4-(thiazol-5-yl) phenylamino)-4-methyl-1-oxopentan-2-ylcarbamate 5-Bromothiazole (23.50 mg, 0.143 mmol), (R)-tert-butyl 1-(3-methoxy-4-(4,4,5,5-tetramethyl-1,3,2-dioxaborolan-2-yl)phenylamino)-4-methyl-1-oxopentan-2-ylcarbamate (53 mg, 0.115 mmol), potassium phosphate (97 mg, 0.458 mmol), and dioxane were combined in a conical vial. Nitrogen was bubbled through the reaction mixture for several min. Dichloro[1,1'-bis(diphenylphosphino)ferrocene]palladium(II) dichloromethane adduct (9.43 mg, 0.011 mmol) was added and the reaction mixture was heated at 100° C. for 4 h. The reaction mixture was cooled to room temperature and was transferred to a separatory funnel containing saturated aqueous NaHCO$_3$ solution (2 mL). The aqueous layer was extracted with ethyl acetate (3×5 mL). The combined organic layers were washed with brine (2 mL), dried over MgSO$_4$, filtered and concentrated. The residue was purified by column chromatography on silica gel (20%→60% ethyl acetate in hexanes) to afford (R)-tert-butyl 1-(3-methoxy-4-(thiazol-5-yl)phenylamino)-4-methyl-1-oxopentan-2-ylcarbamate (31 mg, 65% yield) as a colorless amorphous solid: $^1$H NMR (400 MHz, DMSO-d$_6$) δ 10.15 (s, 1H), 9.02 (s, 1H), 8.31 (s, 1H), 7.71 (d, J=8.6 Hz, 1H), 7.53 (d, J=2.0 Hz, 1H), 7.31 (dd, J=8.4, 1.9 Hz, 1H), 7.08 (d, J=8.1 Hz, 1H), 4.09-4.17 (m, 1H), 3.89 (s, 3H), 1.61-1.72 (m, 1H), 1.48-1.59 (m, 1H), 1.42-1.47 (m, 1H), 1.38 (s, 9H), 0.90 (d, J=6.3 Hz, 3H), 0.90 (d, J=6.5 Hz, 3H); LC/MS (ESI) m/e 420.2 [(M+H)$^+$, calcd for C$_{21}$H$_{30}$N$_3$O$_4$S 420.2].

Part C. (R)-2-Amino-N-(3-methoxy-4-(thiazol-5-yl) phenyl)-4-methylpentanamide

To a suspension of (R)-tert-butyl 1-(3-methoxy-4-(thiazol-5-yl)phenylamino)-4-methyl-1-oxopentan-2-ylcarbamate (40 mg, 0.095 mmol) in CH$_2$Cl$_2$ (1.5 mL) at 0° C. was added TFA (0.50 mL, 6.49 mmol). The cooling bath was removed and the mixture was stirred at room temperature under N$_2$ for 1.5 h. The reaction mixture was concentrated and the product was purified by reverse phase HPLC (MeCN/H$_2$O containing 0.1% TFA). The organic solvent was removed on the rotovapor and the aqueous mixture was transferred to a reparatory funnel containing saturated aqueous K$_2$CO$_3$ (5 mL). The aqueous layer was extracted with ethyl acetate (4×10 mL). The combined organic layers were washed with brine (5 mL), dried over MgSO$_4$, filtered and concentrated. The residue was taken up in acetonitrile/water and was frozen and placed on the lyophilizer to afford (R)-2-amino-N-(3-methoxy-4-(thiazol-5-yl)phenyl)-4-methylpentanamide (23 mg, 74% yield) as a colorless amorphous solid: $^1$H NMR (400 MHz, DMSO-d$_6$) δ 9.01 (s, 1H), 8.31 (s, 1H), 7.71 (d, J=8.6 Hz, 1H), 7.60 (d, J=2.0 Hz, 1H), 7.34 (dd, J=8.6, 2.0 Hz, 1H), 3.89 (s, 3H), 3.36 (dd, J=8.8, 5.5 Hz, 1H), 1.70-1.83 (m, 1H), 1.49 (ddd, J=13.5, 8.2, 5.5 Hz, 1H), 1.30-1.39 (m, 1H), 0.92 (d, J=6.5 Hz, 3H), 0.89 (d, J=6.5 Hz, 3H); LC/MS (ESI) m/e 320.1 [(M+H)$^+$, calcd for C$_{16}$H$_{22}$N$_3$O$_2$S 320.1]. HPLC (method A): t$_R$=7.64 min; HPLC (method B): t$_R$=7.78 min.

Example 22

(R)-2-Amino-N-(3-methoxy-4-(pyridazin-4-yl)phenyl)-4-methylpentanamide

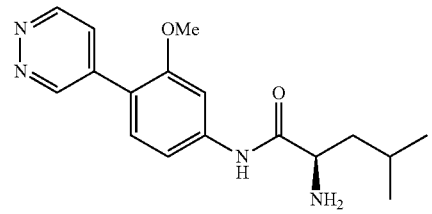 [SMILES: COc1cc(NC(=O)[C@H](N)CC(C)C)ccc1-c1ccnnc1]

Part A. 2-(2-Methoxy-4-nitrophenyl)-4,4,5,5-tetramethyl-1,3,2-dioxaborolane

1-Bromo-2-methoxy-4-nitrobenzene (4.00 g, 17.24 mmol), 4,4,4',4',5,5,5',5'-octamethyl-2,2'-bi(1,3,2-dioxaborolane) (6.57 g, 25.9 mmol), potassium acetate (5.08 g, 51.7 mmol) and dioxane (100 mL) were combined. (1,1'-bis(diphenylphosphino)ferrocene)-dichloropalladium(II) dichloromethane complex (1.418 g, 1.724 mmol) was added and the reaction mixture was heated at 80° C. for 16 h. The mixture was cooled to room temperature and was filtered through a pad of diatomaceous earth (Celite®). The filtrate was transferred to a separatory funnel containing saturated aqueous NaHCO$_3$ solution (100 mL). The aqueous layer was extracted with ethyl acetate (3×100 mL). The combined organic layers were washed with brine (50 mL), dried over MgSO$_4$, filtered, and concentrated. The residue was purified by column chromatography on silica gel (30%→70% ethyl acetate in hexanes) to afford 2-(2-methoxy-4-nitrophenyl)-4,4,5,5-tetramethyl-1,3,2-dioxaborolane (3.35 g, 70% yield) as a light brown solid: $^1$H NMR (400 MHz, CDCl$_3$) δ 7.81 (d, J=1.0 Hz, 2H), 7.69 (s, 1H), 3.95 (s, 3H), 1.39 (s, 12H).

Part B. 4-(2-Methoxy-4-nitrophenyl)pyridazine 2-(2-methoxy-4-nitrophenyl)-4,4,5,5-tetramethyl-1,3,2-dioxaborolane (750 mg, 2.69 mmol), 4-bromopyridazine (427 mg, 2.69 mmol), cesium carbonate (1751 mg, 5.37 mmol), copper(I) chloride (266 mg, 2.69 mmol) and DMF (18 mL) were combined. N$_2$ was bubbled into the reaction mixture for 5 min. Dppf (149 mg, 0.269 mmol) and Pd(OAc)$_2$ (30.2 mg, 0.134 mmol) were then added and the reaction mixture was stirred at 100° C. for 16 h. The mixture was cooled to room temperature, and was filtered through a pad of diatomaceous earth (Celite®) with ethyl acetate rinsing. The filtrate was transferred to a separatory funnel containing saturated aqueous NaHCO$_3$ solution (25 mL). The aqueous layer was extracted with ethyl acetate (3×50 mL). The combined organic layers were washed with brine (25 mL), dried over MgSO$_4$, filtered, and concentrated. The residue was purified by column chromatography on silica gel (1%→7% MeOH in CH$_2$Cl$_2$) to afford 4-(2-methoxy-4-nitrophenyl)pyridazine (169 mg, 27% yield) as a light brown solid: $^1$H NMR (400 MHz, CDCl$_3$) δ 9.42 (dd, J=2.3, 1.3 Hz, 1H), 9.31 (dd, J=5.4, 1.1 Hz, 1H), 8.02 (dd, J=8.3, 2.0 Hz, 1H), 7.92 (d, J=2.3 Hz, 1H), 7.68 (dd, J=5.4, 2.4 Hz, 1H), 7.56 (d, J=8.3 Hz, 1H), 4.01 (s, 3H); LC/MS (ESI) m/e 232.1 [(M+H)$^+$, calcd for C$_{11}$H$_{10}$N$_3$O$_3$ 232.1].

Part C. 3-Methoxy-4-(pyridazin-4-yl)aniline

To a solution of 4-(2-methoxy-4-nitrophenyl)pyridazine (160 mg, 0.692 mmol) in ethanol (20 mL) was added palladium on carbon (10%, Degussa type) (147 mg, 0.069 mmol). The mixture was placed under H$_2$ on a Parr shaker at 40 psi for 2 h. The catalyst was then removed by filtration through a pad of diatomaceous earth (Celite®) and the filtrate was concentrated to give 3-methoxy-4-(pyridazin-4-yl)aniline (139 mg, 100% yield) as a light brown solid which was used directly in the next step: $^1$H NMR (400 MHz, DMSO-d$_6$) δ 9.64 (d, J=2.0 Hz, 1H), 9.28 (d, J=6.0 Hz, 1H), 8.33 (dd, J=6.0, 2.5 Hz, 1H), 7.66 (d, J=8.8 Hz, 1H), 6.59 (d, J=1.8 Hz, 1H), 6.54 (dd, J=8.7, 1.9 Hz, 1H), 3.87 (s, 3H); LC/MS (ESI) m/e 202.2 [(M+H)$^+$, calcd for C$_{11}$H$_{12}$N$_2$O 202.1].

Part D. (R)-tert-Butyl 1-(3-methoxy-4-(pyridazin-4-yl)phenylamino)-4-methyl-1-oxopentan-2-ylcarbamate To a mixture of 3-methoxy-4-(pyridazin-4-yl)aniline (142 mg, 0.706 mmol), (R)-2-(tert-butoxycarbonylamino)-4-methylpentanoic acid (490 mg, 2.117 mmol) and N,N-diisopropylethylamine (0.616 mL, 3.53 mmol) in DMF (4 mL) was added HATU (805 mg, 2.117 mmol). The reaction mixture was stirred at room temperature for 5 min and then at 40° C. for 16 h. The reaction mixture was transferred to a reparatory funnel containing ethyl acetate (20 mL). The organic layer was washed with water (2×10 mL), brine (10 mL), dried over MgSO$_4$, filtered, and concentrated. The residue was purified by column chromatography on silica gel (1%→7% MeOH in CH$_2$Cl$_2$) to afford (R)-tert-butyl 1-(3-methoxy-4-(pyridazin-4-yl)phenylamino)-4-methyl-1-oxopentan-2-ylcarbamate (292 mg, 100% yield) as a red-brown solid: LC/MS (ESI) m/e 415.3 [(M+H)$^+$, calcd for C$_{22}$H$_{31}$N$_4$O$_4$ 415.2].

Part E. (R)-2-Amino-N-(3-methoxy-4-(pyridazin-4-yl)phenyl)-4-methylpentanamide To a suspension of (R)-tert-butyl 1-(3-methoxy-4-(pyridazin-4-yl)phenylamino)-4-methyl-1-oxopentan-2-ylcarbamate (290 mg, 0.700 mmol) in CH$_2$Cl$_2$ (3 mL) at 0° C. was added TFA (1.0 mL, 12.98 mmol). The cooling bath was removed and the mixture was stirred at room temperature under N$_2$ for 1.5 h. The reaction mixture was concentrated and the product was purified by reverse phase HPLC (MeCN/H$_2$O containing 0.1% TFA). The solvent was removed on the rotovapor and the residue was transferred to separatory funnel containing saturated aqueous K$_2$CO$_3$ solution. The aqueous layer was extracted with CH$_2$Cl$_2$ (5×10 mL). The combined organic layers were washed with brine (5 mL), dried over MgSO$_4$, filtered, and concentrated. The residue was taken up in water/acetonitrile containing 0.1% TFA and was frozen and placed on the lyophilizer to give (R)-2-amino-N-(3-methoxy-4-(pyridazin-4-yl)phenyl)-4-methylpentanamide (40 mg, 18% yield) as a colorless amorphous solid: $^1$H NMR (500 MHz, DMSO-d$_6$) δ 9.42 (br s, 1H), 9.20 (d, J=5.5 Hz, 1H), 7.78-7.85 (m, 1H), 7.61 (s, 1H), 7.52 (d, J=8.5 Hz, 1H), 7.44 (d, J=8.5 Hz, 1H), 3.84 (s, 3H), 3.36-3.45 (m, 1H), 1.72-1.83 (m, 1H), 1.47-1.57 (m, 1H), 1.31-1.44 (m, 1H), 0.81-1.00 (m, 6H); LC/MS (ESI) m/e 315.3 [(M+H)$^+$, calcd for C$_{17}$H$_{23}$N$_4$O$_2$ 315.2]. HPLC (method A): t$_R$=6.81 min; HPLC (method B): t$_R$=6.41 min.

Example 23

(R)-2-Amino-N-(3-methoxy-4-(1,3,4-thiadiazol-2-yl)phenyl)-4-methylpentanamide

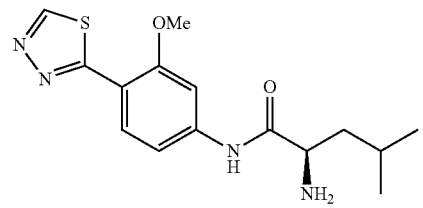 [SMILES: COc1cc(NC(=O)[C@H](N)CC(C)C)ccc1-c1nncs1]

Prepared in a similar fashion as described in Example 22 except that the following conditions were used in Part B: 2-(2-methoxy-4-nitrophenyl)-4,4,5,5-tetramethyl-1,3,2-dioxaborolane (700 mg, 2.508 mmol), 2-bromo-1,3,4-thiadiazole (414 mg, 2.508 mmol), cesium carbonate (1634 mg, 5.02 mmol), and DMF (12 mL) were combined. N$_2$ was bubbled into the reaction mixture for 2 min. (1,1'-Bis(diphenylphosphino)ferrocene)-dichloropalladium(II) dichloromethane complex (206 mg, 0.251 mmol) was then added and the reaction mixture was stirred at 100° C. for 16 h. The mixture was cooled to room temperature, and was filtered through a pad of diatomaceous earth (Celite®) with ethyl acetate rinsing. The filtrate was transferred to a separatory funnel containing saturated aqueous NaHCO$_3$ solution (15 mL). The aqueous layer was extracted with ethyl acetate (3×15 mL). The combined organic layers were washed with brine (10 mL), dried over MgSO$_4$, filtered, and concentrated. The residue was purified by column chromatography on silica gel (1%→3% MeOH in CH$_2$Cl$_2$) to afford 2-(2-methoxy-4-nitrophenyl)-1,3,4-thiadiazole (42 mg, 7% yield) as a light brown solid: LC/MS (ESI) m/e 238.2 ((M+H)$^+$, calcd for C$_9$H$_8$N$_3$O$_3$S 238.0).

After completing parts C-E, (R)-2-amino-N-(3-methoxy-4-(1,3,4-thiadiazol-2-yl)phenyl)-4-methylpentanamide (20 mg) was isolated as a colorless amorphous solid: $^1$H NMR (500 MHz, DMSO-d$_6$) δ 9.59 (s, 1H, major), 9.57 (s, 1H, minor), 8.28 (d, J=8.5 Hz, 1H, major), 8.25 (d, J=8.9 Hz, 1H, minor), 7.77 (d, J=1.8 Hz, 1H, major), 7.67 (s, 1H, minor), 7.46 (dd, J=8.9, 1.8 Hz, 1H, major), 7.26 (d, J=9.2 Hz, 1H, minor), 4.00 (s, 3H, major), 3.99 (s, 3H, minor), 3.38 (br s, 1H), 1.75-1.82 (m, 1H, major) 1.72 (dt, J=13.4, 6.7 Hz, 1H, minor) 1.47-1.55 (m, 1H, major and minor) 1.32-1.40 (m, 1H, major) 0.93 (d, J=6.7 Hz, 3H, major) 0.91 (d, J=6.4 Hz, 3H, major) 0.89 (d, J=6.7 Hz, 3H, minor); LC/MS (ESI) m/e 321.3 [(M+H)$^+$, calcd for C$_{15}$H$_{21}$N$_4$O$_2$S 321.1]. HPLC (method A): t$_R$=7.85 min; HPLC (method B): t$_R$=7.99 min.

Example 24

(R)-2-Amino-N-(3-methoxy-4-(1H-pyrazol-4-yl)phenyl)-4-methylpentanamide

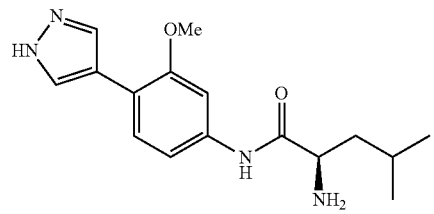 [SMILES: COc1cc(NC(=O)[C@H](N)CC(C)C)ccc1-c1cn[nH]c1]

Prepared in a similar fashion as described in Example 20 using 1H-pyrazol-4-ylboronic acid in Part B to give (R)-2-amino-N-(3-methoxy-4-(1H-pyrazol-4-yl)phenyl)-4-methylpentanamide (18 mg) as a TFA salt: $^1$H NMR (500 MHz, CD$_3$OD) δ 8.09 (br s, 2H), 7.58 (d, J=8.2 Hz, 1H), 7.50 (d, J=2.1 Hz, 1H), 7.19 (dd, J=8.2, 1.8 Hz, 1H), 4.00-4.05 (m, 1H), 3.94 (s, 3H), 1.75-1.86 (m, 3H), 1.08 (d, J=2.4 Hz, 3H), 1.06 (d, J=2.4 Hz, 3H); LC/MS (ESI) m/e 303.2 [(M+H)$^+$, calcd for C$_{16}$H$_{23}$N$_4$O$_2$ 303.2]. HPLC (method A): t$_R$=7.01 min; HPLC (method B): t$_R$=7.01 min.

Example 25

(R)—N-(4-(1H-Imidazol-1-yl)-3-methoxyphenyl)-2-amino-4-methylpentanamide

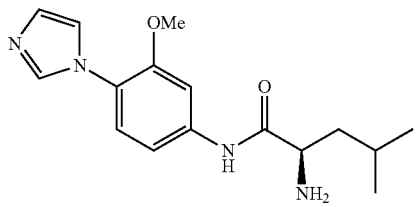 [SMILES: COc1cc(NC(=O)[C@H](N)CC(C)C)ccc1-n1ccnc1]

Part A. 1-(2-Methoxy-4-nitrophenyl)-1H-imidazole

Copper(I) iodide (24.62 mg, 0.129 mmol) and L-histidine (40.1 mg, 0.259 mmol) in DMSO (8 mL) were stirred at 100° C. for 30 min. To this mixture, 1-bromo-2-methoxy-4-nitrobenzene (300 mg, 1.293 mmol), 1H-imidazole (106 mg, 1.552 mmol) and K$_2$CO$_3$ (357 mg, 2.59 mmol) were added. The reaction mixture was stirred at 100° C. for 48 h. The mixture was transferred to a reparatory funnel containing saturated NaHCO$_3$ solution. The aqueous layer was extracted with ethyl acetate (3×). The combined organic layers were concentrated and the residue was purified by column chromatography on silica gel (10% MeOH in CH$_2$Cl$_2$) to afford 1-(2-methoxy-4-nitrophenyl)-1H-imidazole (300 mg, 97% yield) as a yellow solid: LC/MS (ESI) m/e 220.1 [(M+H)$^+$, calcd for C$_{10}$H$_{10}$N$_3$O$_3$ 220.1].

Part B. (R)—N-(4-(1H-Imidazol-1-yl)-3-methoxyphenyl)-2-amino-4-methylpentanamide (R)—N-(4-(1H-Imidazol-1-yl)-3-methoxyphenyl)-2-amino-4-methylpentanamide was prepared from 1-(2-methoxy-4-nitrophenyl)-1H-imidazole in a similar fashion as described in Example 1 Parts B-D. The product was purified by reverse phase HPLC (acetonitrile/water containing 0.1% TFA). The organic solvent was removed on the rotovapor and the aqueous mixture was frozen and placed on the lyophilizer to afford (R)—N-(4-(1H-imidazol-1-yl)-3-methoxyphenyl)-2-amino-4-methylpentanamide (70 mg) as a TFA salt: $^1$H NMR (400 MHz, CD$_3$OD) δ 9.21 (br s, 1H), 7.80 (br s, 1H), 7.74 (d, J=1.8 Hz, 1H), 7.69 (br s, 1H), 7.52 (d, J=8.8 Hz, 1H), 7.38 (dd, J=8.6, 1.8 Hz, 1H), 4.06 (t, J=6.9 Hz, 1H), 3.90 (s, 3H), 1.70-1.87 (m, 3H), 1.02 (d, J=6.3 Hz, 6H); LC/MS (ESI) m/e 303.2 [(M+H)$^+$, calcd for C$_{16}$H$_{23}$N$_4$O$_2$ 303.2]. HPLC (method A): t$_R$=5.63 min; HPLC (method B): t$_R$=5.75 min.

Example 26

(R)-2-Amino-N-(3-methoxy-4-(1H-1,2,4-triazol-1-yl)phenyl)-4-methylpentanamide

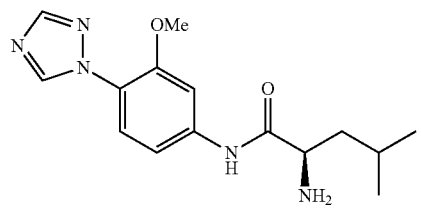 [SMILES: COc1cc(NC(=O)[C@H](N)CC(C)C)ccc1-n1cncn1]

Prepared in a similar fashion as described in Example 25 using 1H-1,2,4-triazole in Part A to give (R)-2-amino-N-(3-methoxy-4-(1H-1,2,4-triazol-1-yl)phenyl)-4-methylpentanamide (60 mg) as a TFA salt: $^1$H NMR (400 MHz, CD$_3$OD) δ 8.85 (s, 1H), 8.11 (s, 1H), 7.70 (br s, 1H), 7.63 (d, J=8.6 Hz, 1H), 7.30 (d, J=8.6 Hz, 1H), 3.95-4.11 (m, 1H), 3.91 (s, 3H), 1.64-1.89 (m, 3H), 1.02 (d, J=3.8 Hz, 6H); LC/MS (ESI) m/e 304.2 [(M+H)$^+$, calcd for C$_{15}$H$_{22}$N$_5$O$_2$ 304.2]. HPLC (method A): t$_R$=7.23 min; HPLC (method B): t$_R$=7.17 min.

Example 27

(R)-2-Amino-N-(2-chloro-5-methoxy-4-(oxazol-5-yl)phenyl)-4-methylpentanamide

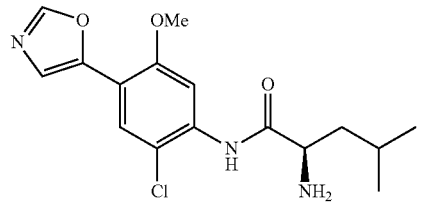 [SMILES: COc1cc(NC(=O)[C@H](N)CC(C)C)c(Cl)cc1-c1cnco1]

Part A. (R)-tert-Butyl 1-(2-chloro-5-methoxy-4-(oxazol-5-yl)phenylamino)-4-methyl-1-oxopentan-2-ylcarbamate, (R)-tert-Butyl 1-(2-chloro-3-methoxy-4-(oxazol-5-yl)phenylamino)-4-methyl-1-oxopentan-2-ylcarbamate, and (R)-tert-Butyl 1-(2,6-dichloro-3-methoxy-4-(oxazol-5-yl)phenylamino)-4-methyl-1-oxopentan-2-ylcarbamate A mixture of (R)-tert-butyl 1-(3-methoxy-4-(oxazol-5-yl)phenylamino)-4-methyl-1-oxopentan-2-ylcarbamate (330 mg, 0.818 mmol), prepared as described in Example 1 Parts A-C, and N-chlorosuccinimide (115 mg, 0.859 mmol) in DMF (5 mL) was stirred at room temperature for 12 h. LC/MS showed three products formed. The mixture was transferred to a reparatory funnel containing brine. The aqueous layer was extracted with ethyl acetate (3×). The combined organic layers were concentrated and the residue was purified by reverse phase HPLC (water/acetonitrile with 0.1% TFA) to afford the following three products:

(R)-tert-Butyl 1-(2-chloro-5-methoxy-4-(oxazol-5-yl)phenylamino)-4-methyl-1-oxopentan-2-ylcarbamate (45 mg, 13% yield) as a colorless solid: $^1$H NMR (400 MHz, DMSO-d$_6$) δ 9.37 (s, 1H), 8.45 (s, 1H), 7.86 (s, 1H), 7.72 (s, 1H), 7.56 (s, 1H), 7.38 (d, J=7.8 Hz, 1H), 4.15-4.25 (m, 1H), 3.93 (s, 3H), 1.69 (br s, 1H), 1.52-1.62 (m, 2H), 1.41 (s, 9H), 0.92 (d, J=6.8 Hz, 3H), 0.89 (d, J=6.5 Hz, 3H); LC/MS (ESI) m/e 438.4 [(M+H)$^+$, calcd for $C_{21}H_{29}N_3O_5Cl$ 438.2].

(R)-tert-Butyl 1-(2-chloro-3-methoxy-4-(oxazol-5-yl) phenylamino)-4-methyl-1-oxopentan-2-ylcarbamate (25 mg, 7% yield) as a colorless solid: $^1$H NMR (400 MHz, DMSO-d$_6$) δ 10.23 (s, 1H), 8.52 (s, 1H), 7.52 (d, J=1.5 Hz, 1H), 7.32-7.42 (m, 2H), 7.10 (d, J=7.6 Hz, 1H), 4.10-4.18 (m, 1H), 3.80 (s, 3H), 1.62-1.73 (m, 1H), 1.50-1.60 (m, 1H), 1.42-1.48 (m, 1H), 1.38 (s, 9H), 0.91 (d, J=2.5 Hz, 3H), 0.89 (d, J=2.3 Hz, 3H); LC/MS (ESI) m/e 438.2 [(M+H)$^+$, calcd for $C_{21}H_{29}N_3O_5Cl$ 438.2].

(R)-tert-Butyl 1-(2,6-dichloro-3-methoxy-4-(oxazol-5-yl) phenylamino)-4-methyl-1-oxopentan-2-ylcarbamate (45 mg, 12% yield) as a colorless solid: $^1$H NMR (400 MHz, CD$_3$OD) δ 8.21 (s, 1H), 8.04 (s, 1H), 7.51 (s, 1H), 4.25 (dd, J=9.7, 3.7 Hz, 1H), 3.85 (s, 3H), 1.59-1.80 (m, 3H), 1.46 (s, 9H), 0.98 (d, J=6.3 Hz, 3H), 0.96 (d, J=6.3 Hz, 3H); LC/MS (ESI) m/e 472.3 [(M+H)$^+$, calcd for $C_{21}H_{28}N_3O_5Cl_2$ 472.1].

Part B. (R)-2-Amino-N-(2-chloro-5-methoxy-4-(oxazol-5-yl)phenyl)-4-methylpentanamide (R)-tert-Butyl 1-(2-chloro-5-methoxy-4-(oxazol-5-yl) phenylamino)-4-methyl-1-oxopentan-2-ylcarbamate (40 mg, 0.085 mmol) was dissolved in CH$_2$Cl$_2$ (1 mL) and cooled to 0° C. To this solution, TFA (0.065 mL, 0.847 mmol) was added. The reaction mixture was stirred at room temperature for 12 h. The solvent was evaporated and the residue was purified by reverse phase HPLC (acetonitrile/water with 0.1% TFA) to afford (R)-2-amino-N-(2-chloro-5-methoxy-4-(oxazol-5-yl)phenyl)-4-methylpentanamide (25 mg, 61% yield) as a TFA salt: $^1$H NMR (400 MHz, CD$_3$OD) δ 8.19 (s, 1H), 8.16 (s, 1H), 7.71 (s, 1H), 7.47 (s, 1H), 3.95 (s, 3H), 3.52 (dd, J=9.6, 4.5 Hz, 1H), 1.80-1.89 (m, 1H), 1.65-1.75 (m, 1H), 1.40-1.51 (m, 1H), 0.98 (t, J=6.9 Hz, 6H); LC/MS (ESI) m/e 338.2 [(M+H)$^+$, calcd for $C_{16}H_{21}N_3O_3Cl$ 338.1]. HPLC (method A): $t_R$=8.78 min; HPLC (method B): $t_R$=8.67 min.

Example 28

(R)-2-Amino-N-(2-chloro-3-methoxy-4-(oxazol-5-yl)phenyl)-4-methylpentanamide

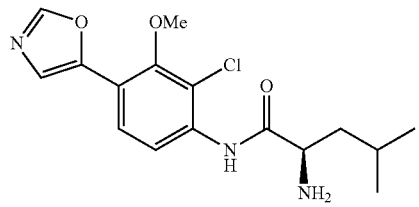 [SMILES: COc1c(-c2cnco2)ccc(NC(=O)[C@H](N)CC(C)C)c1Cl]

Prepared from (R)-tert-butyl 1-(2-chloro-3-methoxy-4-(oxazol-5-yl)phenylamino)-4-methyl-1-oxopentan-2-ylcarbamate from Example 27 Part A in a similar fashion as described in Example 27 Part B to give (R)-2-amino-N-(2-chloro-3-methoxy-4-(oxazol-5-yl)phenyl)-4-methylpentanamide (25 mg) as a TFA salt: $^1$H NMR (400 MHz, CD$_3$OD) δ 8.18 (s, 1H), 7.60 (d, J=1.8 Hz, 1H), 7.38 (d, J=8.3 Hz, 1H), 7.21 (dd, J=8.4, 1.9 Hz, 1H), 3.84 (s, 3H), 3.44-3.54 (m, 1H), 1.75 (dddd, J=13.2, 7.1, 6.8, 6.7 Hz, 1H), 1.57-1.68 (m, 1H), 1.41-1.53 (m, 1H), 0.97 (t, J=7.1 Hz, 6H); LC/MS (ESI) m/e 338.2 [(M+H)$^+$, calcd for $C_{16}H_{21}N_3O_3Cl$ 338.1]. HPLC (method A): $t_R$=8.60 min; HPLC (method B): $t_R$=8.89 min.

Example 29

(R)-2-Amino-N-(2,6-dichloro-3-methoxy-4-(oxazol-5-yl)phenyl)-4-methylpentanamide

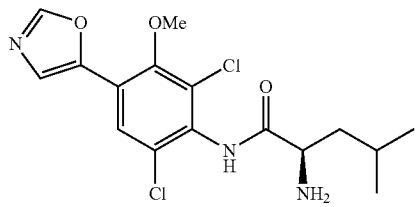 [SMILES: COc1c(-c2cnco2)cc(Cl)c(NC(=O)[C@H](N)CC(C)C)c1Cl]

Prepared from (R)-tert-butyl 1-(2,6-dichloro-3-methoxy-4-(oxazol-5-yl)phenylamino)-4-methyl-1-oxopentan-2-ylcarbamate from Example 27 Part A in a similar fashion as described in Example 27 Part B to give (R)-2-amino-N-(2,6-dichloro-3-methoxy-4-(oxazol-5-yl)phenyl)-4-methylpentanamide (25 mg) as a TFA salt: $^1$H NMR (400 MHz, DMSO-d$_6$) δ 10.37 (br s, 1H), 8.61 (s, 1H), 8.31 (br s, 3H), 7.66 (s, 1H), 7.55 (s, 1H), 4.17 (br s, 1H), 3.82 (s, 3H), 1.66-1.82 (m, 3H), 0.97 (t, J=6.5 Hz, 6H); LC/MS (ESI) m/e 372.1 [(M+H)$^+$, calcd for $C_{16}H_{20}N_3O_3Cl_2$ 372.1]. HPLC (method A): $t_R$=9.33 min; HPLC (method B): $t_R$=9.40 min.

Example 30

2-(3-Aminopyrrolidin-1-yl)-N-(3-methoxy-4-(oxazol-5-yl)phenyl)-4-methylpentanamide

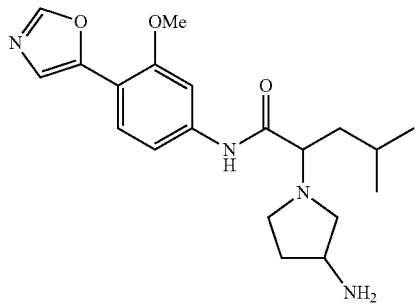 [SMILES: COc1cc(NC(=O)C(CC(C)C)N2CCC(N)C2)ccc1-c1cnco1]

Part A. 2-Bromo-N-(3-methoxy-4-(oxazol-5-yl)phenyl)-4-methylpentanamide

To a mixture of 3-methoxy-4-(oxazol-5-yl)aniline (250 mg, 1.314 mmol) and DL-α-bromoisocaproic acid (385 mg, 1.972 mmol) in dichloromethane (5 mL) at room temperature was added HATU (750 mg, 1.972 mmol) and N,N-diisopropylethylamine (0.758 mL, 4.34 mmol). The reaction mixture was stirred at room temperature for 12 hours. The reaction mixture was transferred to a separatory funnel containing saturated aqueous NaHCO$_3$ solution. The aqueous layer was extracted with dichloromethane (3×). The combined organic layers were separated, concentrated and the residue was purified by column chromatography on silica gel (40→50% ethyl acetate in hexanes) to afford 2-bromo-N-(3-methoxy-4-(oxazol-5-yl)phenyl)-4-methylpentanamide (430 mg, 89% yield) as a colorless solid: LC/MS (ESI) m/e 367.6 [(M+H)+, calcd for C$_{16}$H$_{20}$N$_2$O$_3$Br 367.0].

Part B. tert-Butyl 1-(1-(3-methoxy-4-(oxazol-5-yl) phenylamino)-4-methyl-1-oxopentan-2-yl)pyrrolidin-3-ylcarbamate A mixture of 2-bromo-N-(3-methoxy-4-(oxazol-5-yl)phenyl)-4-methylpentanamide (80 mg, 0.218 mmol), tert-butyl pyrrolidin-3-ylcarbamate (60.9 mg, 0.327 mmol), and N,N-diisopropylethylamine (0.054 mL, 0.327 mmol) in acetonitrile (3 mL) was heated at reflux for 12 h. The mixture was diluted with ether and transferred to a separatory funnel containing water. The aqueous layer was extracted with ether (3×). The combined organic layers were concentrated and the residue was purified by column chromatography on silica gel (40→80% ethyl acetate in hexanes) to afford tert-butyl 1-(1-(3-methoxy-4-(oxazol-5-yl)phenylamino)-4-methyl-1-oxopentan-2-yl)pyrrolidin-3-ylcarbamate (40 mg, 39% yield) as a yellow solid: LC/MS (ESI) m/e 473.3 [(M+H)+, calcd for C$_{25}$H$_{37}$N$_4$O$_5$ 473.3].

Part C. 2-(3-Aminopyrrolidin-1-yl)-N-(3-methoxy-4-(oxazol-5-yl)phenyl)-4-methylpentanamide tert-Butyl 1-(1-(3-methoxy-4-(oxazol-5-yl)phenylamino)-4-methyl-1-oxopentan-2-yl)pyrrolidin-3-ylcarbamate (40 mg, 0.085 mmol) was dissolved in CH$_2$Cl$_2$ (1 mL) and cooled to 0° C. To this solution was added TFA (0.065 mL, 0.846 mmol). The reaction mixture was stirred at room temperature for 12 h. The solvent was evaporated and the residue was purified by column chromatography on silica gel (10% 2 M NH$_3$ in methanol in methylene chloride) to afford 2-(3-aminopyrrolidin-1-yl)-N-(3-methoxy-4-(oxazol-5-yl)phenyl)-4-methylpentanamide (31 mg, 60% yield) as a TFA salt: $^1$H NMR (400 MHz, CD$_3$OD) δ 8.18 (s, 1H), 7.70 (dd, J=8.6, 2.0 Hz, 1H), 7.60 (dd, J=3.7, 1.9 Hz, 1H), 7.45 (s, 1H), 7.25 (ddd, J=8.4, 3.4, 2.0 Hz, 1H), 3.96 (d, J=1.5 Hz, 3H), 3.69-3.77 (m, 1H), 3.23-3.28 (m, 1H), 3.14 (ddd, J=8.7, 4.5, 4.4 Hz, 0.5H), 2.93-3.01 (m, 1H), 2.84 (d, J=3.5 Hz, 1H), 2.76 (dd, J=10.3, 5.8 Hz, 0.5H), 2.59-2.67 (m, 0.5H), 2.46-2.54 (m, 0.5H), 2.22-2.34 (m, J=13.4, 8.9, 8.9, 4.5 Hz, 1H), 1.72-1.84 (m, 2H), 1.53-1.68 (m, 2H), 0.99 (d, J=6.0 Hz, 3H), 0.95 (d, J=6.3 Hz, 3H); LC/MS (ESI) m/e 373.4 [(M+H)+, calcd for C$_{20}$H$_{29}$N$_4$O$_3$ 373.2]. HPLC (method A): t$_R$=10.32 min; HPLC (method B): t$_R$=11.32 min.

Example 31

2-(trans-4-Aminocyclohexylamino)-N-(3-methoxy-4-(oxazol-5-yl)phenyl)-4-methylpentanamide

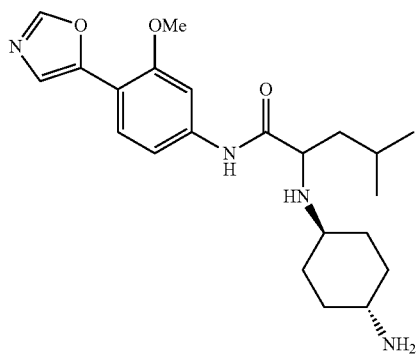 [SMILES: COc1cc(NC(=O)C(CC(C)C)N[C@H]2CC[C@H](N)CC2)ccc1-c1cnco1]

Prepared in a similar fashion as described in Example 30 using tert-butyl 4-aminocyclohexylcarbamate in Part B to give 2-(trans-4-aminocyclohexylamino)-N-(3-methoxy-4-(oxazol-5-yl)phenyl)-4-methylpentanamide (23 mg) as a TFA salt: $^1$H NMR (400 MHz, CD$_3$OD) δ 8.18 (s, 1H), 7.68-7.73 (m, 1H), 7.63 (d, J=2.0 Hz, 1H), 7.43-7.47 (m, 1H), 7.20 (dd, J=8.3, 2.0 Hz, 1H), 3.97 (s, 3H), 3.40 (t, J=7.1 Hz, 1H), 2.71 (ddd, J=10.6, 6.9, 3.9 Hz, 1H), 2.32-2.44 (m, 1H), 2.07 (br s, 1H), 1.80-1.95 (m, 3H), 1.72 (dt, J=13.4, 6.8 Hz, 1H), 1.41-1.59 (m, 2H), 1.13-1.30 (m, 4H), 0.97 (d, J=6.5 Hz, 3H), 0.94 (d, J=6.5 Hz, 3H); LC/MS (ESI) m/e 401.4 [(M+H)+, calcd for C$_{22}$H$_{33}$N$_4$O$_3$ 401.3]. HPLC (method A): t$_R$=11.78 min; HPLC (method B): t$_R$=12.29 min.

Example 32

2-(Azetidin-3-ylamino)-N-(3-methoxy-4-(oxazol-5-yl)phenyl)-4-methylpentanamide

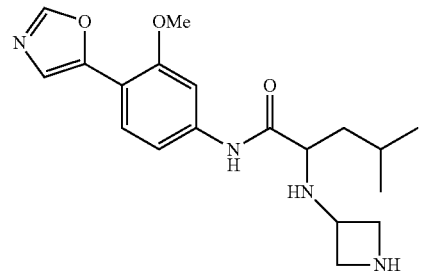 [SMILES: COc1cc(NC(=O)C(CC(C)C)NC2CNC2)ccc1-c1cnco1]

Prepared in a similar fashion as described in Example 30 using tert-butyl 3-aminoazetidine-1-carboxylate in Part B to give 2-(azetidin-3-ylamino)-N-(3-methoxy-4-(oxazol-5-yl)phenyl)-4-methylpentanamide (23 mg) as a TFA salt: $^1$H NMR (400 MHz, CD$_3$OD) δ 8.17 (s, 1H), 7.69 (d, J=8.6 Hz, 1H), 7.56 (d, J=1.8 Hz, 1H), 7.44 (s, 1H), 7.26 (dd, J=8.6, 2.0 Hz, 1H), 4.13-4.22 (m, 1H), 4.04-4.11 (m, 1H), 3.95 (s, 3H), 3.92-4.00 (m, 3H), 3.41 (t, J=7.2 Hz, 1H), 1.76 (ddd, J=13.5, 6.7, 6.5 Hz, 1H), 1.47-1.64 (m, 2H), 0.96 (d, J=6.5 Hz, 3H), 0.94 (d, J=6.5 Hz, 3H); LC/MS (ESI) m/e 359.3 [(M+H)+, calcd for C$_{19}$H$_{27}$N$_4$O$_3$ 359.2]. HPLC (method A): t$_R$=12.81 min; HPLC (method B): t$_R$=11.27 min.

Example 33

2-(4-Aminopiperidin-1-yl)-N-(3-methoxy-4-(oxazol-5-yl)phenyl)-4-methylpentanamide

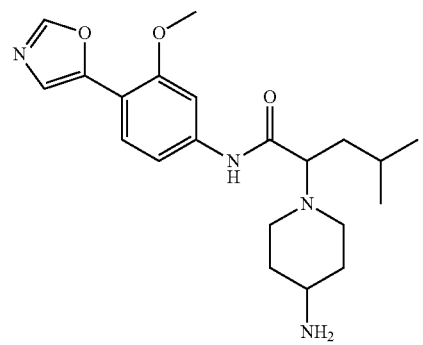 [SMILES: COc1cc(NC(=O)C(CC(C)C)N2CCC(N)CC2)ccc1-c1cnco1]

Prepared as described in Example 30 using tert-butyl 1-(1-(3-methoxy-4-(oxazol-5-yl)phenylamino)-4-methyl-1-oxopentan-2-yl)piperidin-4-ylcarbamate in Part B to give 2-(4-aminopiperidin-1-yl)-N-(3-methoxy-4-(oxazol-5-yl)phenyl)-4-methylpentanamide (40 mg) as a TFA salt: $^1$H NMR (400 MHz, CD$_3$OD) δ 8.17 (s, 1H), 7.69 (d, J=8.31 Hz, 1H), 7.61 (d, J=2.01 Hz, 1H), 7.43 (s, 1H), 7.21 (dd, J=8.56, 2.01 Hz, 1H), 3.96 (s, 3H), 3.34-3.41 (m, 1H), 3.29 (dt, J=3.34, 1.73 Hz, 1H), 2.94-3.17 (m, 3H), 2.33-2.58 (m, 2H), 1.98 (dd, J=5.04, 2.27 Hz, 1H), 1.51-1.75 (m, 5H), 0.83-1.05 (m, 6H); LC/MS (ESI) m/e 387.3 [(M+H)$^+$, calcd for C$_{21}$H$_{31}$N$_4$O$_3$ 387.2]. HPLC (method A): t$_R$=9.59 min; HPLC (method B): t$_R$=9.85 min.

Example 34

(R)-2-Hydroxy-N-(3-methoxy-4-(oxazol-5-yl)phenyl)-4-methylpentanamide

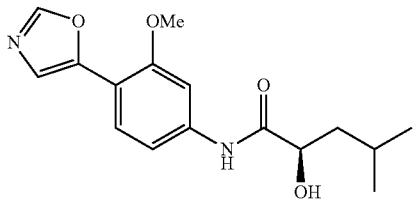 [SMILES: COc1cc(NC(=O)[C@H](O)CC(C)C)ccc1-c1cnco1]

Prepared in a similar fashion as described in Example 1 Parts A-C using (R)-2-hydroxy-4-methylpentanoic acid in Part C to give (R)-2-hydroxy-N-(3-methoxy-4-(oxazol-5-yl)phenyl)-4-methylpentanamide (50 mg) as a yellow solid: $^1$H NMR (400 MHz, DMSO-d$_6$) δ 9.85 (s, 1H), 8.38 (s, 1H), 7.66 (d, J=1.8 Hz, 1H), 7.58-7.64 (m, J=8.6 Hz, 1H), 7.52 (dd, J=8.6, 1.8 Hz, 1H), 7.44 (s, 1H), 4.05 (t, J=6.8 Hz, 1H), 3.90 (s, 3H), 1.82 (dt, J=13.5, 6.7 Hz, 1H), 1.51 (t, J=6.8 Hz, 2H), 0.92 (d, J=6.5 Hz, 6H); LC/MS (ESI) m/e 305.1 [(M+H)$^+$, calcd for C$_{16}$H$_{21}$N$_2$O$_4$ 305.1]. HPLC (method A): t$_R$=11.96 min; HPLC (method B): t$_R$=10.66 min.

Example 35

2-(Aminomethyl)-N-(3-methoxy-4-(oxazol-5-yl)phenyl)-4-methylpentanamide

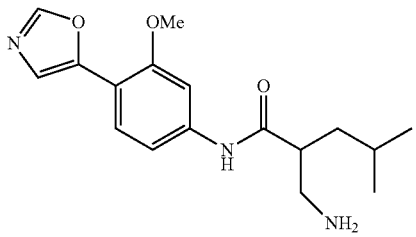 [SMILES: COc1cc(NC(=O)C(CN)CC(C)C)ccc1-c1cnco1]

Part A. Benzyl 2-(3-methoxy-4-(oxazol-5-yl)phenylcarbamoyl)-4-methylpentylcarbamate Prepared in a similar fashion as described in Example 1 Parts A-C using 2-((benzyloxycarbonylamino)methyl)-4-methylpentanoic acid in Part C to give benzyl 2-(3-methoxy-4-(oxazol-5-yl)phenylcarbamoyl)-4-methylpentylcarbamate (200 mg) as a yellow solid: LC/MS (ESI) m/e 452.4 [(M+H)$^+$, calcd for C$_{25}$H$_{30}$N$_3$O$_5$ 452.2].

Part B. 2-(Aminomethyl)-N-(3-methoxy-4-(oxazol-5-yl)phenyl)-4-methylpentanamide

A mixture of benzyl 2-(3-methoxy-4-(oxazol-5-yl)phenylcarbamoyl)-4-methylpentylcarbamate (200 mg, 0.443 mmol), 10% Pd/C (236 mg, 0.221 mmol), and ammonium hydroxide (1 mL, 25.7 mmol) in MeOH (20 mL) was stirred under an H$_2$ atm for 12 h. The catalyst was removed by filtration through a pad of diatomaceous earth (Celite®). The filtrate was concentrated and the residue was purified by column chromatography on silica gel (10% 2 M NH$_3$ in methanol in CH$_2$Cl$_2$) to afford 2-(aminomethyl)-N-(3-methoxy-4-(oxazol-5-yl)phenyl)-4-methylpentanamide (65 mg, 44% yield) as a red solid: $^1$H NMR (400 MHz, CD$_3$OD) 8.16 (s, 1H), 7.66 (d, J=8.3 Hz, 1H), 7.61 (d, J=2.0 Hz, 1H), 7.39-7.43 (m, 1H), 7.19 (dd, J=8.4, 1.9 Hz, 1H), 3.94 (s, 3H), 2.86-2.94 (m, 1H), 2.75 (d, J=11.8 Hz, 1H), 2.54-2.66 (m, 1H), 1.54-1.69 (m, 2H), 1.25-1.35 (m, 1H), 0.96 (d, J=6.3 Hz, 3H), 0.92 (d, J=6.3 Hz, 3H); LC/MS (ESI) m/e 318.3 [(M+H)$^+$, calcd for C$_{17}$H$_{24}$N$_3$O$_3$ 318.2]. HPLC (method A): t$_R$=11.85 min; HPLC (method B): t$_R$=12.85 min.

Example 36

3-Isopropyl-N-(3-methoxy-4-(oxazol-5-yl)phenyl)pyrrolidine-2-carboxamide

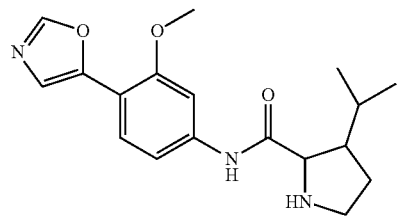 [SMILES: COc1cc(NC(=O)C2NCCC2C(C)C)ccc1-c1cnco1]

Part A. 1-(tert-Butoxycarbonyl)-3-isopropylpyrrolidine-2-carboxylic acid

3-Isopropylpyrrolidine-2-carboxylic acid (200 mg, 1.272 mmol), prepared using a procedure described by Chung et al., J. Org. Chem. 1990, 55, 270-275, was suspended in THF/H$_2$O (2:1, 6 mL). A solution of 10% aqueous sodium hydroxide (0.6 mL, 1.590 mmol) was added. To the resultant biphasic mixture was added Boc$_2$O (0.354 mL, 1.527 mmol) in THF/H$_2$O (2:1, 6 mL). The reaction was stirred at room temperature overnight. The THF was removed by evaporation under reduced pressure. The residual aqueous solution was adjusted to pH 2 by the addition of 10% aq KHSO$_4$. The acidic solution was extracted with ethyl acetate (2×20 mL). The combined organic extracts were washed with H$_2$O (30 mL) and brine (30 mL), dried (Na$_2$SO$_4$), filtered, and concentrated to afford 1-(tert-butoxycarbonyl)-3-isopropylpyrrolidine-2-carboxylic acid (230 mg, 70% yield) as an off-white solid: LC/MS (ESI) m/e 256.2 [(M−H)$^−$, calcd for C$_{13}$H$_{22}$NO$_4$ 256.2].

Part B. tert-Butyl 3-isopropyl-2-(3-methoxy-4-(oxazol-5-yl)phenylcarbamoyl)pyrrolidine-1-carboxylate To a mixture of 3-methoxy-4-(oxazol-5-yl)aniline (0.15 g, 0.789 mmol), prepared as described in Example 1 Parts A and B, and 1-(tert-butoxycarbonyl)-3-isopropylpyrrolidine-2-carboxylic acid (0.244 g, 0.946 mmol) in dichloromethane (5 mL) was added N,N-diisopropylethylamine (0.689 mL, 3.94 mmol) and HATU (0.360 g, 0.946 mmol). The reaction mixture was stirred at room temperature for 12 hours. The reaction mixture was transferred to a separatory funnel containing saturated aqueous $NaHCO_3$ solution. The aqueous layer was extracted with dichloromethane (3×30 mL). The combined organic layers were concentrated and the residue was purified by column chromatography on silica gel (40→50% ethyl acetate in hexanes) to afford tert-butyl 3-isopropyl-2-(3-methoxy-4-(oxazol-5-yl)phenylcarbamoyl)pyrrolidine-1-carboxylate (120 mg, 35% yield) as a yellow solid: LC/MS (ESI) m/e 430.2 [(M+H)$^+$, calcd for $C_{23}H_{32}N_3O_5$ 430.2].

This mixture of the two pairs of enantiomers was separated by chiral chromatography (ChiralCel OD-H column, 30×250 mm, 5 μm, 10% methanol with 0.1% diethylamine/90% $CO_2$, 120 bar, 35° C., 70 mL/min, λ=285 nm) to give four compounds designated as A, B, C, and D:

Compound A (peak 1, $t_R$=9.8 min): 30 mg, $[\alpha]^{22}_D$=15.8° (c 1.52, MeOH); $^1$H NMR (400 MHz, CDCl$_3$) δ 9.67 (br. s., 1H), 7.82 (br. s., 1H), 7.52 (d, J=6.5 Hz, 1H), 7.37 (d, J=6.0 Hz, 2H), 7.05 (d, J=6.3 Hz, 1H), 4.23 (br. s., 1H), 3.87 (br. s., 3H), 3.62 (br. s., 1H), 3.51-3.39 (m, 1H), 2.50 (br. s., 1H), 2.07 (br. s., 1H), 1.74 (dd, J=12.3, 7.0 Hz, 2H), 1.51 (br. s., 9H), 1.00 (d, J=6.5 Hz, 3H), 0.96 (d, J=6.5 Hz, 3H); LC/MS (ESI) m/e 430.2 [(M+H)$^+$, calcd for $C_{23}H_{32}N_3O_5$ 430.2].

Compound B (peak 2, $t_R$=11.4 min): 24 mg, $[\alpha]^{22}_D$=−13.9° (c 1.19, MeOH); $^1$H NMR (400 MHz, CDCl$_3$) δ 9.56 (br. s., 1H), 7.81 (s, 1H), 7.39 (d, J=8.5 Hz, 1H), 7.31 (s, 1H), 7.19 (s, 1H), 6.89 (dd, J=8.5, 1.5 Hz, 1H), 4.59 (d, J=7.3 Hz, 1H), 3.78 (t, J=9.8 Hz, 1H), 3.69 (s, 3H), 3.39 (td, J=10.6, 6.4 Hz, 1H), 2.21 (t, J=10.0 Hz, 1H), 2.09-1.95 (m, 2H), 1.78-1.69 (m, 1H), 1.51 (s, 9H), 1.12 (d, J=6.5 Hz, 3H), 0.93 (d, J=6.8 Hz, 3H); LC/MS (ESI) m/e 430.2 [(M+H)$^+$, calcd for $C_{23}H_{32}N_3O_5$ 430.2].

Compound C (peak 3, $t_R$=16.0 min): 31 mg, $[\alpha]^{22}_D$=−14.9° (c 1.53, MeOH); $^1$H NMR (400 MHz, CDCl$_3$) δ 9.67 (br. s., 1H), 7.84 (br. s., 1H), 7.56 (d, J=5.8 Hz, 1H), 7.42 (d, J=6.5 Hz, 2H), 7.05 (d, J=6.0 Hz, 1H), 4.25 (br. s., 1H), 3.89 (br. s., 3H), 3.62 (br. s., 1H), 3.48-3.38 (m, 1H), 2.53 (br. s., 1H), 2.07 (br. s., 1H), 1.75 (dd, J=12.4, 6.7 Hz, 2H), 1.51 (br. s., 9H), 1.00 (d, J=6.5 Hz, 3H), 0.97 (d, J=6.8 Hz, 4H); LC/MS (ESI) m/e 430.2 [(M+H)$^+$, calcd for $C_{23}H_{32}N_3O_5$ 430.2].

Compound D (peak 4, $t_R$=29.6 min): 17 mg, $[\alpha]^{22}_D$=−21.7° (c 0.87, MeOH); $^1$H NMR (400 MHz, CDCl$_3$) δ 9.57 (s, 1H), 7.81 (s, 1H), 7.40 (d, J=8.3 Hz, 1H), 7.32 (s, 1H), 7.22 (s, 1H), 6.91 (dd, J=8.5, 1.8 Hz, 1H), 4.59 (d, J=7.3 Hz, 1H), 3.78 (t, J=9.7 Hz, 1H), 3.70 (s, 3H), 3.39 (td, J=10.6, 6.4 Hz, 1H), 2.20 (t, J=10.2 Hz, 1H), 2.08-1.95 (m, 2H), 1.78-1.69 (m, 1H), 1.51 (s, 7H), 1.12 (d, J=6.5 Hz, 3H), 0.93 (d, J=6.5 Hz, 3H); LC/MS (ESI) m/e 430.2 [(M+H)$^+$, calcd for $C_{23}H_{32}N_3O_5$ 430.2].

Part C. 3-Isopropyl-N-(3-methoxy-4-(oxazol-5-yl)phenyl)pyrrolidine-2-carboxamide To a solution of Compound A from Part B (30 mg, 0.070 mmol) in dichloromethane (1 mL) was added TFA (0.108 mL, 1.397 mmol). The mixture was heated to 40° C. for 5 hours. The mixture was concentrated and the residue was purified by reverse phase HPLC (acetonitrile:water containing 0.1% TFA) to afford 3-isopropyl-N-(3-methoxy-4-(oxazol-5-yl)phenyl)pyrrolidine-2-carboxamide (15 mg, 49% yield) as a TFA salt: $[\alpha]^{22}_D$=−25.2° (c 0.12, MeOH); $^1$H NMR (400 MHz, DMSO-d$_6$) δ 10.85 (s, 1H), 8.43 (s, 1H), 7.72 (d, J=8.5 Hz, 1H), 7.57 (d, J=1.8 Hz, 1H), 7.51 (s, 1H), 7.37 (dd, J=8.5, 2.0 Hz, 1H), 4.13 (br. s., 1H), 3.98 (d, J=5.0 Hz, 1H), 3.95 (s, 3H), 3.38 (br. s., 1H), 3.27 (d, J=6.3 Hz, 1H), 2.29 (quin, J=7.8 Hz, 1H), 2.14-2.06 (m, 1H), 1.84 (sxt, J=6.6 Hz, 1H), 1.78-1.65 (m, 1H), 0.97 (d, J=6.8 Hz, 3H), 0.95 (d, J=6.8 Hz, 3H); LC/MS (ESI) m/e 330.2 [(M+H)$^+$, calcd for $C_{18}H_{24}N_3O_3$ 330.2]. HPLC (method A): $t_R$=8.33 min; HPLC (method B): $t_R$=8.41 min.

Example 37

3-Isopropyl-N-(3-methoxy-4-(oxazol-5-yl)phenyl)pyrrolidine-2-carboxamide

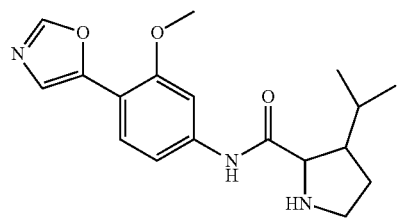 [SMILES: COc1cc(NC(=O)C2NCCC2C(C)C)ccc1-c1cnco1]

To a solution of Compound B from Example 36 Part B (23 mg, 0.054 mmol) in dichloromethane (1 mL) was added TFA (0.083 mL, 1.071 mmol). The reaction was stirred at room temperature for 4 hours. The mixture was concentrated and the residue was purified by reverse phase HPLC (acetonitrile:water containing 0.1% TFA) to give 3-isopropyl-N-(3-methoxy-4-(oxazol-5-yl)phenyl)pyrrolidine-2-carboxamide (7 mg, 30% yield) as a TFA salt: $[\alpha]^{22}_D$=−35.7° (c 0.08, MeOH); $^1$H NMR (400 MHz, DMSO-d$_6$) δ 10.85 (s, 1H), 8.43 (s, 1H), 7.72 (d, J=8.5 Hz, 1H), 7.56 (d, J=2.0 Hz, 1H), 7.51 (s, 1H), 7.32 (dd, J=8.5, 2.0 Hz, 1H), 4.35 (d, J=6.0 Hz, 1H), 3.94 (s, 4H), 3.76 (br. s., 1H), 3.51 (d, J=11.5 Hz, 1H), 3.26 (br. s., 1H), 2.25-2.16 (m, 1H), 2.13-2.05 (m, 1H), 2.03-1.88 (m, 1H), 1.62-1.53 (m, 1H), 1.04 (d, J=6.5 Hz, 3H), 0.90 (d, J=6.5 Hz, 3H); LC/MS (ESI) m/e 330.2 [(M+H)$^+$, calcd for $C_{18}H_{24}N_3O_3$ 330.2]. HPLC (method A): $t_R$=8.17 min; HPLC (method B): $t_R$=8.49 min.

Example 38

3-Isopropyl-N-(3-methoxy-4-(oxazol-5-yl)phenyl)pyrrolidine-2-carboxamide

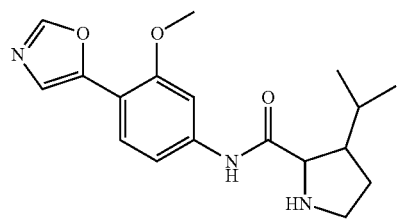 [SMILES: COc1cc(NC(=O)C2NCCC2C(C)C)ccc1-c1cnco1]

To a solution of Compound C from Example 36 Part B (30 mg, 0.070 mmol) in dichloromethane (1 mL) was added TFA (0.108 mL, 1.397 mmol). The reaction was stirred at room temperature for 12 hours. The mixture was concentrated and the residue was purified by reverse phase HPLC (acetonitrile:water containing 0.1% TFA) to afford 3-isopropyl-N-(3-methoxy-4-(oxazol-5-yl)phenyl)pyrrolidine-2-carboxamide (18 mg, 58% yield) as a TFA salt: [α]$^{22}_D$=20.7° (c 0.15, MeOH); $^1$H NMR (400 MHz, DMSO-d$_6$) δ 10.83 (s, 1H), 8.43 (s, 1H), 7.72 (d, J=8.5 Hz, 1H), 7.57 (d, J=1.8 Hz, 1H), 7.51 (s, 1H), 737 (dd, J=8.5, 1.8 Hz, 1H), 3.98 (br. s., 1H), 3.95 (s, 3H), 3.38 (br. s., 1H), 3.27 (d, J=6.3 Hz, 1H), 2.32-2.25 (m, 1H), 2.10 (dd, J=12.4, 4.1 Hz, 1H), 1.88-1.79 (m, 1H), 1.77-1.67 (m, 1H), 0.95 (d, J=6.8 Hz, 3H), 0.97 (d, J=6.8 Hz, 3H); LC/MS (ESI) m/e 330.1 [(M+H)$^+$, calcd for C$_{18}$H$_{24}$N$_3$O$_3$ 330.2]. HPLC (method A): t$_R$=8.39 min; HPLC (method B): t$_R$=8.46 min.

Example 39

3-Isopropyl-N-(3-methoxy-4-(oxazol-5-yl)phenyl)pyrrolidine-2-carboxamide

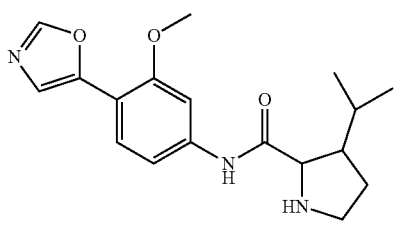 [SMILES: COc1cc(NC(=O)C2NCCC2C(C)C)ccc1-c1cnco1]

To a solution of Compound D from Example 36 Part B (17 mg, 0.040 mmol) in dichloromethane (1 mL) was added TFA (0.061 mL, 0.792 mmol). The reaction mixture was heated to 50° C. for 12 h. The mixture was concentrated and the residue was purified by reverse phase HPLC (acetonitrile:water containing 0.1% TFA) to afford 3-isopropyl-N-(3-methoxy-4-(oxazol-5-yl)phenyl)pyrrolidine-2-carboxamide (10 mg, 57% yield) as a TFA salt: [α]$^{22}_D$=34.9° (c 0.17, MeOH); $^1$H NMR (400 MHz, CD$_3$OD-d$_4$) δ 8.24 (s, 1H), 7.77 (d, J=8.5 Hz, 1H), 7.62 (d, J=1.8 Hz, 1H), 7.52 (s, 1H), 7.25 (dd, J=8.5, 2.0 Hz, 1H), 4.40 (d, J=7.8 Hz, 1H), 4.00 (s, 3H), 3.71-3.63 (m, 1H), 3.44-3.34 (m, 1H), 2.41-2.28 (m, 1H), 2.27-2.18 (m, 1H), 2.16-2.10 (m, 1H), 1.74 (dt, J=8.7, 6.6 Hz, 1H), 1.12 (d, J=6.5 Hz, 3H), 0.99 (d, J=6.8 Hz, 3H); LC/MS (ESI) m/e 330.1 [(M+H)$^+$, calcd for C$_{18}$H$_{24}$N$_3$O$_3$ 330.2]. HPLC (method A): t$_R$=8.13 min; HPLC (method B): t$_R$=8.18 min.

Example 40

(R)-2-Amino-N-(3-fluoro-4-(oxazol-5-yl)phenyl)-4-methylpentanamide

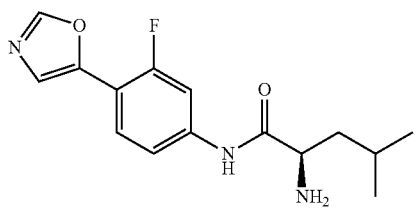

Prepared in a similar fashion as described in Example 1 using 2-fluoro-4-nitrobenzaldehyde in Part A to give (R)-2-amino-N-(3-fluoro-4-(oxazol-5-yl)phenyl)-4-methylpentanamide (170 mg) as a TFA salt: $^1$H NMR (400 MHz, DMSO-d$_6$) δ 10.96 (br s, 1H), 8.54 (s, 1H), 8.30 (br s, 3H), 7.76-7.84 (m, 2H), 7.47-7.53 (m, 2H), 3.96 (t, J=6.2 Hz, 1H), 1.64-1.72 (m, 3H), 0.93 (d, J=5.5 Hz, 6H); LC/MS (ESI) m/e 292.2 [(M+H)$^+$, calcd for C$_{15}$H$_{19}$N$_3$O$_2$F 292.2]. HPLC (method A): t$_R$=8.02 min; HPLC (method B): t$_R$=7.94 min.

Example 41

2-Amino-N-(3-(difluoromethoxy)-4-(1H-pyrazol-4-yl)phenyl)-4-methylpentanamide

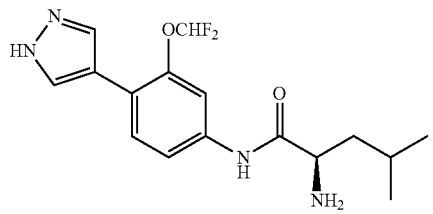 [SMILES: CC(C)C[C@@H](N)C(=O)Nc1ccc(-c2cn[nH]c2)c(OC(F)F)c1]

Part A.
1-Benzyl-4-(2-methoxy-4-nitrophenyl)-1H-pyrazole

To a mixture of 1-bromo-2-methoxy-4-nitrobenzene (1 g, 4.31 mmol) and 1-benzyl-4-(4,4,5,5-tetramethyl-1,3,2-dioxaborolan-2-yl)-1H-pyrazole (1.592 g, 5.60 mmol) in THF (20 mL) was added sodium carbonate (2M in H$_2$O) (6.46 mL, 12.93 mmol). N$_2$ was bubbled through the reaction mixture for 2 min. Bis(triphenylphosphine)palladium(II) chloride (0.151 g, 0.215 mmol) was then added and the reaction mixture was heated at 70° C. for 2 h. The reaction mixture was cooled to room temperature and was transferred to a separatory funnel containing saturated aqueous NaHCO$_3$ solution (10 mL). The aqueous layer was extracted with ethyl acetate (3×25 mL). The combined organic layers were washed with brine (10 mL), dried over MgSO$_4$, filtered, and concentrated. The residue was purified by column chromatography on silica gel (30%→70% ethyl acetate in hexanes; 40 g column) to afford 1-benzyl-4-(2-methoxy-4-nitrophenyl)-1H-pyrazole (900 mg, 68% yield) as a yellow solid: LC/MS (ESI) m/e 310.1 [(M+H)$^+$, calcd for C$_{17}$H$_{16}$N$_3$O$_3$ 310.1].

Part B. 2-(1-Benzyl-1H-pyrazol-4-yl)-5-nitrophenol

A mixture of 1-benzyl-4-(2-methoxy-4-nitrophenyl)-1H-pyrazole (500 mg, 1.616 mmol) and BBr$_3$ (1M in dichloromethane) (8.08 mL, 8.08 mmol) in dichloromethane (4 mL) was heated to reflux for 4 h. The mixture was poured onto ice resulting in formation of a precipitate. The precipitate was loaded onto a silica gel column and eluted with 10% MeOH in dichloromethane to afford 2-(1-benzyl-1H-pyrazol-4-yl)-5-nitrophenol (170 mg, 36% yield) as a yellow solid: LC/MS (ESI) m/e 294.1 [(M−H$^−$), calcd for C$_{16}$H$_{12}$N$_3$O$_3$ 294.1].

Part C. 1-Benzyl-4-(2-(difluoromethoxy)-4-nitrophenyl)-1H-pyrazole

To a solution of 2-(1-benzyl-1H-pyrazol-4-yl)-5-nitrophenol (170 mg, 0.576 mmol) in DMF (15 mL) at room temperature was added potassium carbonate (278 mg, 2.015 mmol). The resulting suspension was stirred for 20 min and then was treated with methyl 2-chloro-2,2-difluoroacetate (0.152 mL, 1.439 mmol). The reaction mixture was heated to 90° C. for 2 h. The reaction mixture was transferred to a separatory funnel containing saturated aqueous NaHCO$_3$ solution (20 mL). The aqueous layer was extracted with ethyl acetate (3×20 mL). The combined organic layers were washed with brine (25 mL), dried over MgSO$_4$, filtered, and concentrated. The residue was purified by column chromatography on silica gel (5%→20% ethyl acetate in hexanes; 25 g column) to afford 1-benzyl-4-(2-(difluoromethoxy)-4-nitrophenyl)-1H-pyrazole (90 mg, 45% yield) as a yellow solid: $^1$H NMR (400 MHz, CDCl$_3$) δ 8.12 (dd, J=8.8, 2.3 Hz, 1H), 8.06 (d, J=2.0 Hz, 1H), 7.99 (d, J=14.6 Hz, 2H), 7.74 (d, J=8.6 Hz, 1H), 7.44-7.36 (m, 3H), 7.33-7.29 (m, 2H), 6.81-6.42 (m, 1H), 5.40 (s, 2H); LC/MS (ESI) m/e 346.1 [(M+H)$^+$, calcd for C$_{17}$H$_{14}$N$_3$O$_3$F$_2$ 346.1].

Part D. 4-(1-Benzyl-1H-pyrazol-4-yl)-3-(difluoromethoxy)aniline

To a solution of 1-benzyl-4-(2-(difluoromethoxy)-4-nitrophenyl)-1H-pyrazole (80 mg, 0.232 mmol) in ethanol (5 mL) was added ammonium chloride (149 mg, 2.78 mmol) and zinc powder (212 mg, 3.24 mmol). The reaction mixture was heated at 70° C. for 12 h. The reaction mixture was cooled to room temperature and was filtered through a pad of diatomaceous earth (Celite®). The filtrate was transferred to a reparatory funnel containing saturated aqueous NaHCO$_3$ solution (10 mL). The aqueous layer was extracted with ethyl acetate (3×15 mL). The combined organic layers were washed with brine (10 mL), dried over MgSO$_4$, filtered, and concentrated. The residue was purified by column chromatography on silica gel (20%→50% ethyl acetate in hexanes; 25 g column) to afford 4-(1-benzyl-1H-pyrazol-4-yl)-3-(difluoromethoxy)aniline (70 mg, 0.222 mmol, 96% yield) as a yellow solid: $^1$H NMR (400 MHz, CD$_3$OD) δ 7.90 (s, 1H), 7.80 (s, 1H), 7.37-7.21 (m, 6H), 6.56 (dd, J=8.4, 2.1 Hz, 1H), 6.52 (s, 1H), 6.87-6.48 (m, 1H), 5.36 (s, 2H); LC/MS (ESI) m/e 316.14 ((M+H)$^+$, calcd for C$_{17}$H$_{16}$N$_3$OF$_2$ 316.13).

Part E. (R)-tert-Butyl 1-(4-(1-benzyl-1H-pyrazol-4-yl)-3-(difluoromethoxy)phenylamino)-4-methyl-1-oxopentan-2-ylcarbamate To a mixture of 4-(1-benzyl-1H-pyrazol-4-yl)-3-(difluoromethoxy)aniline (70 mg, 0.222 mmol) and (R)-2-(tert-butoxycarbonylamino)-4-methylpentanoic acid (103 mg, 0.444 mmol) in dichloromethane (3 mL) was added N,N-diisopropylethylamine (0.388 mL, 2.220 mmol) and O-benzotriazol-1-yl-N,N,N,N-tetramethyluronium tetrafluoroborate (TBTU) (143 mg, 0.444 mmol). The reaction mixture was stirred at room temperature for 12 hours. The reaction mixture was transferred to a separatory funnel containing saturated aqueous NaHCO$_3$ solution (25 mL). The aqueous layer was extracted with ethyl acetate (3×25 mL). The combined organic layers were washed with brine (25 mL), dried over MgSO$_4$, filtered, and concentrated. The residue was purified by column chromatography on silica gel (50%→70% ethyl acetate in hexanes; 25 g column) to afford (R)-tert-butyl 1-(4-(1-benzyl-1H-pyrazol-4-yl)-3-(difluoromethoxy)phenylamino)-4-methyl-1-oxopentan-2-ylcarbamate (40 mg, 34% yield) as a yellow solid: $^1$H NMR (400 MHz, CD$_3$OD) δ 8.04 (s, 1H), 7.88 (s, 1H), 7.62 (s, 1H), 7.58 (d, J=8.6 Hz, 1H), 7.38 (dd, J=8.3, 1.8 Hz, 1H), 7.35-7.21 (m, 5H), 6.79 (t, J=73.8 Hz, 1H), 5.35 (s, 2H), 3.99 (d, J=7.6 Hz, 1H), 1.80 (br. s., 1H), 1.58 (br. s., 1H), 1.43 (s, 9H), 1.25-1.15 (m, 1H), 0.99-0.86 (m, 6H); LC/MS (ESI) m/e 529.2 [(M+H)$^+$, calcd for C$_{28}$H$_{35}$N$_4$O$_4$F$_2$ 529.3]

Part F. 2-Amino-N-(3-(difluoromethoxy)-4-(1H-pyrazol-4-yl)phenyl)-4-methylpentanamide A mixture of (R)-tert-butyl 1-(4-(1-benzyl-1H-pyrazol-4-yl)-3-(difluoromethoxy)phenylamino)-4-methyl-1-oxopentan-2-ylcarbamate (40 mg, 0.076 mmol), ammonium formate (23.86 mg, 0.378 mmol) and Pd/C (32.2 mg, 0.030 mmol) in ethanol (10 mL) was heated at reflux for 4 hours. The solvent was concentrated in vacuo and the residue was suspended in dichloromethane (2 mL). To this mixture was added TFA (0.058 mL, 0.757 mmol) and the resultant mixture was stirred for 2 h at room temperature. The mixture was purified by reverse phase HPLC (acetonitrile:water containing 0.1% TFA) to afford 2-amino-N-(3-(difluoromethoxy)-4-(1H-pyrazol-4-yl)phenyl)-4-methylpentanamide (8 mg, 19% yield) as a TFA salt: $^1$H NMR (400 MHz, CD$_3$OD-d$_4$) δ 8.00 (br. s., 2H), 7.62-7.70 (m, 2H), 7.42 (dd, J=8.6, 2.0 Hz, 1H), 6.81 (t, J=76.3 Hz, 1H), 3.80 (d, J=6.0 Hz, 1H), 1.96-2.12 (m, 1H), 1.59-1.67 (m, 1H), 1.22-1.29 (m, 1H), 1.08 (d, J=7.1 Hz, 3H), 0.99 (t, J=7.4 Hz, 3H); LC/MS (ESI) m/e 339.1 [(M+H)$^+$, calcd for C$_{16}$H$_{21}$F$_2$N$_4$O$_2$ 339.2]. HPLC (method A): t$_R$=7.70 min; HPLC (method B): t$_R$=7.77 min.

Example 42

2-Amino-N-(3-(dimethylamino)-4-(oxazol-5-yl)phenyl)-4-methylpentanamide

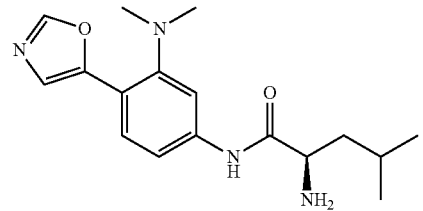 [SMILES: CC(C)C[C@@H](N)C(=O)Nc1ccc(-c2cnco2)c(N(C)C)c1]

Part A. (2-Amino-4-nitrophenyl)methanol

To a solution of 2-amino-4-nitrobenzoic acid (1.00 g, 5.49 mmol) in THF (20 mL) at room temperature was added BH$_3$-THF (21.96 mL, 21.96 mmol) dropwise via an addition funnel. The reaction mixture was stirred at room temperature for 12 h. The reaction was then cooled in an ice bath and quenched by slow addition of methanol (100 mL). The mixture was concentrated and the residue was transferred to a separatory funnel containing saturated aqueous NaHCO$_3$ solution (50 mL). The aqueous layer was extracted with ether (3×75 mL). The combined organic layers were washed with brine (50 mL), dried over MgSO$_4$, filtered, and concentrated. The residue was suspended in water, filtered and dried to afford (2-amino-4-nitrophenyl)methanol (650 mg, 70% yield) as an orange solid: $^1$H NMR (400 MHz, DMSO-d$_6$) δ 7.46 (d, J=2.0 Hz, 1H), 7.38-7.35 (m, 2H), 5.57 (s, 2H), 5.34 (t, J=5.4 Hz, 1H), 4.43 (d, J=5.5 Hz, 2H).

Part B. 2-Amino-4-nitrobenzaldehyde

A mixture of (2-amino-4-nitrophenyl)methanol (650 mg, 3.87 mmol) and manganese dioxide (1680 mg, 19.33 mmol)

in THF (5 mL) and dichloromethane (25 mL) was stirred at room temperature for 2 h. The mixture was filtered and the filtrate was concentrated. The residue was purified by column chromatography on silica gel (40%→50% ethyl acetate in hexanes; 25 g column) to afford 2-amino-4-nitrobenzaldehyde (550 mg, 86% yield) as an orange solid: $^1$H NMR (400 MHz, DMSO-$d_6$) δ 9.99 (s, 1H), 7.85 (d, J=8.6 Hz, 1H), 7.63 (d, J=2.3 Hz, 1H), 7.55 (br. s., 2H), 7.35 (dd, J=8.6, 2.3 Hz, 1H).

Part C. 5-Nitro-2-(oxazol-5-yl)aniline

To a solution of 2-amino-4-nitrobenzaldehyde (550 mg, 3.31 mmol) and TosMIC (970 mg, 4.97 mmol) in methanol (20 mL) was added $K_2CO_3$ (480 mg, 3.48 mmol). The reaction mixture was heated at reflux for 1.5 h. The reaction mixture was cooled to room temperature and was transferred to a separatory funnel containing saturated aqueous $NaHCO_3$ solution (80 mL). The aqueous layer was extracted with ethyl acetate (3×25). The combined organic layers were washed with brine (60 mL), dried over $Na_2SO_4$, filtered and concentrated. The residue was suspended in hexanes and the solid was collected by filtration to afford 5-nitro-2-(oxazol-5-yl)aniline (600 mg, 88% yield) as a tan solid: $^1$H NMR (500 MHz, DMSO-$d_6$) δ 8.55 (s, 1H), 7.76 (s, 1H), 7.74 (d, J=2.4 Hz, 1H), 7.69 (d, J=8.5 Hz, 1H), 7.48 (dd, J=8.9, 2.4 Hz, 1H), 6.02 (s, 2H); LC/MS (ESI) m/e 205.9 [(M+H)$^+$, calcd for $C_9H_8N_3O_3$ 206.1].

Part D. N,N-Dimethyl-5-nitro-2-(oxazol-5-yl)aniline

To a solution of 5-nitro-2-(oxazol-5-yl)aniline (100 mg, 0.487 mmol) in THF (2 mL) at 0° C. was added sodium hydride (48.7 mg, 1.219 mmol). After stirring for 30 min, iodomethane (0.076 mL, 1.219 mmol) was added. The reaction mixture was stirred at room temperature for 12 h. The reaction mixture was transferred to a separatory funnel containing saturated aqueous $NaHCO_3$ solution (20 mL). The aqueous layer was extracted with ethyl acetate (2×10 mL). The combined organic layers were concentrated to afford a red residue. The residue was purified by column chromatography on silica gel (60%→70% ethyl acetate in hexanes; 25 g column) to afford N,N-dimethyl-5-nitro-2-(oxazol-5-yl)aniline (50 mg, 44% yield) as a yellow solid: $^1$H NMR (500 MHz, CD$_3$OD) δ 8.37 (s, 1H), 8.08 (d, J=2.1 Hz, 1H), 8.00-7.98 (m, 2H), 7.88 (s, 1H), 2.80 (s, 6H); LC/MS (ESI) m/e 234.0 [(M+H)$^+$, calcd for $C_{11}H_{12}N_3O_3$ 234.1].

Part E. (R)-tert-Butyl 1-(3-(dimethylamino)-4-(oxazol-5-yl)phenylamino)-4-methyl-1-oxopentan-2-ylcarbamate A mixture of N,N-dimethyl-5-nitro-2-(oxazol-5-yl)aniline (50 mg, 0.214 mmol) and Pd/C (45.6 mg, 0.043 mmol) in ethanol (10 mL) and chloroform (5 mL) was placed under hydrogen in a Parr shaker for 2 h. The mixture was filtered through diatomaceous earth (Celite®) and the filtrate was concentrated in vacuo to afford the $N^1,N^1$-dimethyl-6-(oxazol-5-yl)benzene-1,3-diamine as a red oil: LC/MS (ESI) m/e 204.0 [(M+H)$^+$, calcd for $C_{11}H_{14}N_3O$ 204.1].

This oil was taken up in dichloromethane (5 mL) followed by the addition of (R)-2-(tert-butoxycarbonylamino)-4-methylpentanoic acid (99 mg, 0.429 mmol), HATU (163 mg, 0.429 mmol) and N,N-diisopropylethylamine (0.187 mL, 1.072 mmol). The mixture was stirred at room temperature for 12 h. The reaction mixture was transferred to a reparatory funnel containing saturated aqueous $NaHCO_3$ solution (25 mL). The aqueous layer was extracted with methylene chloride (3×25 mL). The combined organic layers were washed with brine (25 mL), dried over $MgSO_4$, filtered, and concentrated. The residue was purified by column chromatography on silica gel (60%→80% ethyl acetate in hexanes; 25 g column) to afford (R)-tert-butyl 1-(3-(dimethylamino)-4-(oxazol-5-yl)phenylamino)-4-methyl-1-oxopentan-2-ylcarbamate (50 mg, 56% yield) as a yellow solid: $^1$H NMR (500 MHz, DMSO-$d_6$) δ 10.12 (s, 1H), 8.38 (s, 1H), 7.60 (d, J=8.5 Hz, 1H), 7.54 (s, 1H), 7.51 (s, 1H), 7.46 (d, J=8.5 Hz, 1H), 6.95 (t, J=8.1 Hz, 1H), 3.95 (t, J=8.2 Hz, 1H), 2.63 (s, 6H), 1.80-1.71 (m, J=16.5, 7.3 Hz, 1H), 1.54-1.45 (m, J=10.7 Hz, 1H), 1.39 (br. s., 9H), 1.18 (td, J=13.4, 6.6 Hz, 1H), 0.89-0.80 (m, 6H); LC/MS (ESI) m/e 417.1 [(M+H)$^+$, calcd for $C_{22}H_{33}N_4O_4$ 417.3].

Part F. (R)-2-Amino-N-(3-(dimethylamino)-4-(oxazol-5-yl)phenyl)-4-methylpentanamide (R)-tert-Butyl 1-(3-(dimethylamino)-4-(oxazol-5-yl)phenylamino)-4-methyl-1-oxopentan-2-ylcarbamate (50 mg, 0.120 mmol) was dissolved in dichloromethane (1 mL) and cooled to 0° C. To this solution was added TFA (0.092 mL, 1.200 mmol). The reaction mixture was stirred at room temperature for 12 hours. The solvent was evaporated and the residue was purified by reverse phase HPLC (acetonitrile:water containing 0.1% TFA) to afford (R)-2-amino-N-(3-(dimethylamino)-4-(oxazol-5-yl)phenyl)-4-methylpentanamide (3 mg, 8% yield) as a TFA salt: $^1$H NMR (400 MHz, DMSO-$d_6$) δ 7.44 (s, 1H), 6.94 (d, J=8.5 Hz, 1H), 6.97-6.92 (m, 1H), 6.83 (d, J=2.0 Hz, 1H), 6.81 (s, 1H), 6.61 (dd, J=8.5, 2.3 Hz, 1H), 3.05 (d, J=5.8 Hz, 1H), 1.93 (s, 6H), 1.27 (dtd, J=9.8, 6.6, 3.4 Hz, 1H), 0.89 (ddd, J=13.7, 7.5, 3.6 Hz, 1H), 0.51 (ddd, J=13.7, 9.6, 7.3 Hz, 1H), 0.33 (d, J=7.0 Hz, 3H), 0.23 (t, J=7.4 Hz, 3H); LC/MS (ESI) m/e 317.1 [(M+H)$^+$, calcd for $C_{17}H_{25}N_4O_2$ 317.2]. HPLC (method A): $t_R$=6.58 min; HPLC (method B): $t_R$=6.38 Min.

Example 43

(R)-2-Amino-N-(4-(2-chloropyridin-4-yl)-3-methoxyphenyl)-4-methylpentanamide

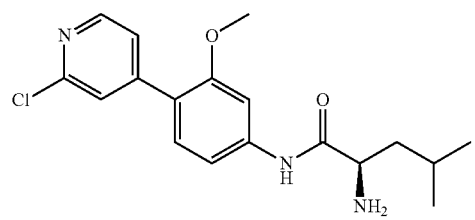 [SMILES: COc1cc(NC(=O)[C@H](N)CC(C)C)ccc1-c1ccnc(Cl)c1]

Prepared in a similar fashion as described in Example 20 using 2-chloropyridin-4-ylboronic acid in Part B to give (R)-2-amino-N-(4-(2-chloropyridin-4-yl)-3-methoxyphenyl)-4-methylpentanamide (60 mg) as a TFA salt: $^1$H NMR (400 MHz, DMSO-$d_6$) δ 10.80 (s, 1H), 8.41 (d, J=5.3 Hz, 1H), 8.31 (br s, 3H), 7.63 (s, 1H), 7.56 (dd, J=5.3, 1.5 Hz, 1H), 7.45-7.52 (m, 2H), 7.36-7.42 (m, 1H), 3.97 (d, J=5.0 Hz, 1H), 3.82 (s, 3H), 1.64-1.72 (m, 3H), 0.94 (d, J=5.5 Hz, 6H); LC/MS (ESI) m/e 348.1 [(M+H)$^+$, calcd for $C_{18}H_{23}N_3O_2Cl$ 348.15]. HPLC (method A): $t_R$=9.16 min; HPLC (method B): $t_R$=9.38 min.

Example 44

(R)-2-Amino-N-(4-(3-methoxypyridin-4-yl)phenyl)-4-methylpentanamide

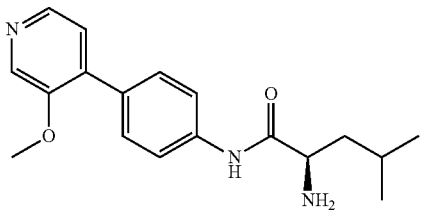 [SMILES: COc1cnccc1-c1ccc(NC(=O)[C@H](N)CC(C)C)cc1]

Prepared in a similar fashion as described in Example 20 using (R)-tert-butyl(1-((4-bromophenyl)amino)-4-methyl-1-oxopentan-2-yl)carbamate and 3-methoxypyridin-4-ylboronic acid in Part B to give (R)-2-amino-N-(4-(3-methoxypyridin-4-yl)phenyl)-4-methylpentanamide (27 mg) as a TFA salt: $^1$H NMR (400 MHz, DMSO-$d_6$) δ 10.77 (s, 1H), 8.57 (s, 1H), 8.41 (d, J=5.3 Hz, 1H), 8.32 (br s, 3H), 7.75 (d, J=8.8 Hz, 2H), 7.69 (d, J=8.8 Hz, 2H), 7.59 (d, J=5.0 Hz, 1H), 3.98-4.02 (m, 1H), 3.96 (s, 3H), 1.65-1.76 (m, 3H), 0.90-1.02 (m, 6H); LC/MS (ESI) m/e 314.1 [(M+H)$^+$, calcd for $C_{18}H_{24}N_3O_2$ 314.2]. HPLC (method A): $t_R$=6.14 min; HPLC (method B): $t_R$=6.12 min.

Example 45

2-Amino-N-(4-(2-aminopyridin-4-yl)-3-methoxyphenyl)-4-methylpentanamide

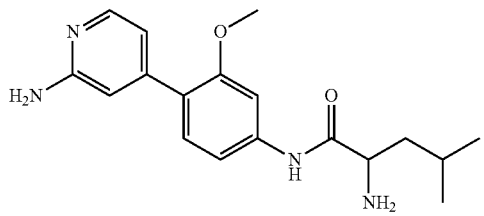 [SMILES: COc1cc(NC(=O)C(N)CC(C)C)ccc1-c1ccnc(N)c1]

Part A. 4-(2-methoxy-4-nitrophenyl)pyridin-2-amine

To a mixture of 4-chloropyridin-2-amine (100 mg, 0.778 mmol), $K_3PO_4$ (413 mg, 1.945 mmol), palladium(II)acetate (17.46 mg, 0.078 mmol), and 2-dicyclohexylphosphino-2',6'-dimethoxy-1,1'-biphenyl (63.9 mg, 0.156 mmol) under nitrogen in a vial was added 2-(2-methoxy-4-nitrophenyl)-4,4,5,5-tetramethyl-1,3,2-dioxaborolane (239 mg, 0.856 mmol), prepared as described in Example 26 Part A, in n-butanol (2 mL). The reaction mixture was heated at 100° C. for 4.5 h. The mixture was cooled to room temperature and was filtered through a pad of diatomaceous earth (Celite®) with methanol rinsing and the filtrate was concentrated. The residue was purified by column chromatography on silica gel (1%→4% methanol in dichloromethane; 12 g column) to afford 4-(2-methoxy-4-nitrophenyl)pyridin-2-amine (120 mg, 63% yield) as a pale yellow solid: $^1$H NMR (400 MHz, DMSO-$d_6$) δ 7.97 (dd, J=5.3, 0.8 Hz, 1H), 7.92 (dd, J=8.3, 2.3 Hz, 1H), 7.89 (d, J=2.3 Hz, 1H), 7.57 (d, J=8.5 Hz, 1H), 6.61 (dd, J=5.3, 1.5 Hz, 1H), 6.58 (dd, J=1.3, 0.8 Hz, 1H), 6.04 (s, 2H), 3.93 (s, 3H); LC/MS (ESI) m/e 246.1 [(M+H)$^+$, calcd for $C_{12}H_{12}N_3O_3$ 246.1].

Part B. 4-(4-amino-2-methoxyphenyl)pyridin-2-amine

A mixture of 4-(2-methoxy-4-nitrophenyl)pyridin-2-amine (110 mg, 0.449 mmol) and tin chloride dihydrate (595 mg, 3.14 mmol) in ethanol (10 mL) was heated to 70° C. for 20 min. To this mixture was added ammonium hydroxide solution (10 mL) and the reaction mixture was stirred at room temperature for 2 h. The reaction mixture was taken in a separatory funnel containing brine (20 mL). The aqueous layer was extracted with ethyl acetate (2×20 mL). The organic layer was separated and concentrated to afford 4-(4-amino-2-methoxyphenyl)pyridin-2-amine (90 mg, 93% yield) as red oil: $^1$H NMR (400 MHz, DMSO-$d_6$) δ 7.65-7.92 (m, 1H), 6.91-7.08 (m, 1H), 6.46-6.63 (m, 2H), 6.13-6.37 (m, 2H), 5.68 (s, 2H), 5.25-5.44 (m, 2H), 3.70 (s, 3H); LC/MS (ESI) m/e 216.1 [(M+H)$^+$, calcd for $C_{12}H_{14}N_3O$ 216.1].

Part C. (R)-2-Amino-N-(4-(2-aminopyridin-4-yl)-3-methoxyphenyl)-4-methylpentanamide Prepared from 4-(4-amino-2-methoxyphenyl)pyridin-2-amine (130 mg, 0.303 mmol) in a similar fashion as described in Example 22 Parts D-E to give the to give (R)-2-amino-N-(4-(2-aminopyridin-4-yl)-3-methoxyphenyl)-4-methylpentanamide (90 mg) as a TFA salt: $^1$H NMR (400 MHz, DMSO-$d_6$) δ 10.87 (s, 1H), 8.32 (br s, 2H), 8.00 (br s, 2H), 7.95 (d, J=6.78 Hz, 1H), 7.48-7.55 (m, 2H), 7.39-7.47 (m, 1H), 7.16 (d, J=1.3 Hz, 1H), 7.03 (dd, J=6.8, 1.8 Hz, 1H), 4.00 (d, J=9.3 Hz, 1H), 3.85 (s, 3H), 1.70 (d, J=5.8 Hz, 3H), 0.96 (d, J=5.8 Hz, 6H); LC/MS (ESI) m/e 329.2 [(M+H)$^+$, calcd for $C_{18}H_{25}N_4O_2$ 329.2]. HPLC (method A): $t_R$=6.50 min; HPLC (method B): $t_R$=7.95 min.

Example 46

(R)-2-amino-N-(4-(imidazo[1,2-b]pyridazin-3-yl)-3-methoxyphenyl)-4-methylpentanamide

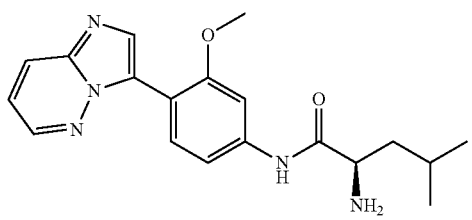 [SMILES: COc1cc(NC(=O)[C@H](N)CC(C)C)ccc1-c1cnc2cccnn12]

Part A. 3-Bromo-6-chloroimidazo[1,2-b]pyridazine

To a mixture of 6-chloroimidazo[1,2-b]pyridazine.HCl (600 mg, 3.16 mmol) (Vaccaro W. et al. United States Patent Appl. US 2008/0045536 A1, 2008) in acetonitrile (15 mL) was added NBS (590 mg, 3.32 mmol). The mixture was stirred at room temperature for 2 h. The reaction mixture was concentrated to afford a yellow solid which was suspended in water (30 mL). The precipitate was collected by filtration and dried under vacuum to afford 3-bromo-6-chloroimidazo[1,2-b]pyridazine (600 mg, 82% yield) as a yellow solid: $^1$H NMR (400 MHz, DMSO-$d_6$) δ 8.28 (d, J=9.6 Hz, 1H), 8.00 (s, 1H), 7.46 (d, J=9.6 Hz, 1H); LC/MS (ESI) m/e 233.98 [(M+H)$^+$, calcd for $C_6H_4N_3BrCl$ 233.48].

Part B. 6-Chloro-3-(2-methoxy-4-nitrophenyl)imidazo[1,2-b]pyridazine

A mixture of 3-bromo-6-chloroimidazo[1,2-b]pyridazine (200 mg, 0.860 mmol), 2-(2-methoxy-4-nitrophenyl)-4,4,5,5-tetramethyl-1,3,2-dioxaborolane (264 mg, 0.946 mmol), prepared according to the procedure described in Example 22 Part A, and sodium carbonate (2 M in $H_2O$) (1.291 mL, 2.58 mmol) in acetonitrile (10 mL) was degassed followed by the addition of $PdCl_2(dppf).CH_2Cl_2$ adduct (70.3 mg, 0.086 mmol). The mixture was heated to 150° C. in a microwave for 60 minutes. The mixture was filtered through a pad of diatomaceous earth (Celite®) and was concentrated. The residue was purified by reverse phase HPLC (acetonitrile/water with 0.1% TFA) to afford 6-chloro-3-(2-methoxy-4-nitrophenyl)imidazo[1,2-b]pyridazine (50 mg, 19% yield) as a yellow solid: LC/MS (ESI) m/e 305.0 [(M+H)$^+$, calcd for $C_{13}H_{10}N_4O_3Cl$ 305.0].

Part C. (R)-2-Amino-N-(4-(imidazo[1,2-b]pyridazin-3-yl)-3-methoxyphenyl)-4-methylpentanamide The title compound was prepared from 6-chloro-3-(2-methoxy-4-nitrophenyl)imidazo[1,2-b]pyridazine in a similar fashion as described in Example 22 Parts C-E. The product was purified by reverse phase HPLC (acetonitrile/water containing 0.1% TFA) to give (R)-2-amino-N-(4-(imidazo[1,2-b]pyridazin-3-yl)-3-methoxyphenyl)-4-methylpentanamide (7 mg) as a TFA salt: $^1$H NMR (500 MHz, $CD_3OD$) δ 8.74 (d, J=4.6 Hz, 1H), 8.30 (d, J=9.5 Hz, 1H), 8.23 (s, 1H) 7.97 (d, J=8.5 Hz, 1H), 7.67 (d, J=1.8 Hz, 1H), 7.59 (dd, J=9.3, 4.4 Hz, 1H), 7.34 (dd, J=8.4, 2.0 Hz, 1H), 3.90 (s, 3H), 2.05-2.14 (m, 1H), 1.71 (ddd, J=13.6, 7.5, 3.4 Hz, 1H), 1.27-1.42 (m, 2H), 1.15 (d, J=7.0 Hz, 3H), 1.01-1.07 (m, 3H); LC/MS (ESI) m/e 354.2 [(M+H)$^+$, calcd for $C_{19}H_{24}N_5O_2$ 354.2]. HPLC (method A): $t_R$=6.16 min; HPLC (method B): $t_R$=6.29 min.

Example 47

(R)-2-Amino-N-(4-(6-chloroimidazo[1,2-b]pyridazin-3-yl)-3-methoxyphenyl)-4-methylpentanamide

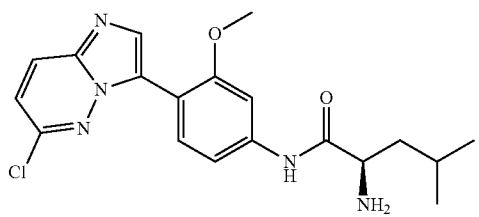 [SMILES: COc1cc(NC(=O)[C@H](N)CC(C)C)ccc1-c1cnc2ccc(Cl)nn12]

Part A. 4-(6-Chloroimidazo[1,2-b]pyridazin-3-yl)-3-methoxyaniline

A mixture of 6-chloro-3-(2-methoxy-4-nitrophenyl)imidazo[1,2-b]pyridazine (25 mg, 0.082 mmol), prepared as described in Example 46 Parts A-B, and $SnCl_2.2H_2O$ (93 mg, 0.410 mmol) in ethyl acetate (5 mL) and ethanol (2.5 mL) was heated to 70° C. for 3 hours. The mixture was transferred to a flask containing saturated aqueous $NaHCO_3$ solution (20 mL) and the mixture was filtered through a pad of diatomaceous earth (Celite®). The filtrated was transferred to a separatory funnel containing saturated aqueous $NaHCO_3$ solution (10 mL). The aqueous layer was extracted with ethyl acetate (3×20 mL). The combined organic layers were washed with brine (15 mL), dried over $MgSO_4$, filtered, and concentrated. The residue was purified by reverse phase HPLC (water/acetonitrile with 0.1% TFA) to afford 4-(6-chloroimidazo[1,2-b]pyridazin-3-yl)-3-methoxyaniline (10 mg, 44% yield) as a yellow gel: $^1$H NMR (400 MHz, $CDCl_3$) δ 8.81 (d, J=9.6 Hz, 1H), 8.12 (s, 1H), 7.71 (d, J=8.3 Hz, 1H), 7.43 (d, J=9.3 Hz, 1H), 6.46 (dd, J=8.3, 2.3 Hz, 1H), 6.38 (d, J=2.3 Hz, 1H), 3.85 (s, 3H); LC/MS (ESI) m/e 275.05 [(M+H)$^+$, calcd for $C_{13}H_{12}N_4OCl$ 275.07].

Part B. (R)-2-Amino-N-(4-(6-chloroimidazo[1,2-b]pyridazin-3-yl)-3-methoxyphenyl)-4-methylpentanamide (R)-2-Amino-N-(4-(6-chloroimidazo[1,2-b]pyridazin-3-yl)-3-methoxyphenyl)-4-methylpentanamide was prepared from 4-(6-chloroimidazo[1,2-b]pyridazin-3-yl)-3-methoxyaniline in a similar fashion as described in Example 22 Parts D-E. The product was purified by reverse phase HPLC (acetonitrile/water containing 0.1% TFA) to give (R)-2-amino-N-(4-(6-chloroimidazo[1,2-b]pyridazin-3-yl)-3-methoxyphenyl)-4-methylpentanamide (7 mg) as a TFA salt: $^1$H NMR (400 MHz, $CD_3OD$) δ 8.11 (d, J=9.6 Hz, 1H), 8.06 (br s, 1H), 7.86 (d, J=8.6 Hz, 1H), 7.63 (d, J=2.0 Hz, 1H), 7.38 (d, J=9.6 Hz, 1H), 7.28 (dd, J=8.3, 2.0 Hz, 1H), 3.87 (s, 3H), 2.01-2.09 (m, 1H), 1.61-1.71 (m, 1H), 1.21-1.37 (m, 2H), 1.12 (d, J=6.8 Hz, 3H), 1.01 (t, J=7.4 Hz, 3H); LC/MS (ESI) m/e 388.2 [(M+H)$^+$, calcd for $C_{19}H_{23}N_5O_2C$; 388.2]. HPLC (method A): $t_R$=7.36 min; HPLC (method B): $t_R$=7.55 min.

Example 48

2-Amino-N-(3-methoxy-4-(2-(methylamino)pyridin-4-yl)phenyl)-4-methylpentanamide

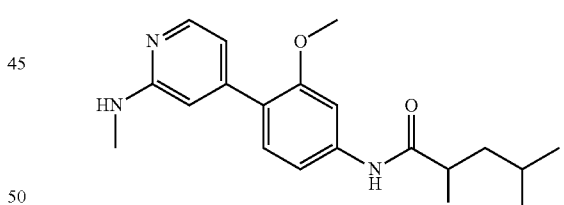

Part A.
2-Chloro-4-(2-methoxy-4-nitrophenyl)pyridine

To a mixture of 1-bromo-2-methoxy-4-nitrobenzene (1.00 g, 4.31 mmol) and 2-chloropyridin-4-ylboronic acid (1.02 g, 6.46 mmol) in THF (20 mL) was added sodium carbonate (2M in $H_2O$) (6.46 mL, 12.93 mmol) and bis(triphenylphosphine)palladium(II) chloride (0.151 g, 0.215 mmol) was added. $N_2$ was bubbled for 2 min. The reaction mixture was heated in at 70° C. for 2 h. The mixture was transferred to a separatory funnel containing saturated aqueous $NaHCO_3$ solution (25 mL). The aqueous layer was extracted with ethyl acetate (3×20 mL). The combined organic layers were washed with brine (20 mL), dried over $MgSO_4$, filtered, and concentrated. The residue was purified by column chromatography on silica gel (20%→50% ethyl acetate in hexanes; 40 g column) to afford 2-chloro-4-(2-methoxy-4-nitrophenyl)pyridine (320 mg, 28% yield) as a colorless solid: $^1$H NMR (400 MHz, DMSO-d$_6$) δ 8.51 (d, J=5.5 Hz, 1H), 7.96-7.92 (m, 2H), 7.74-7.70 (m, 2H), 7.61 (dd, J=5.0, 1.5 Hz, 1H), 3.95 (s, 3H); LC/MS (ESI) m/e 265.0 [(M+H)$^+$, calcd for C$_{12}$H$_{10}$N$_2$O$_3$Cl 265.0].

Part B. N-Benzyl-4-(2-methoxy-4-nitrophenyl)-N-methylpyridin-2-amine

A mixture of 2-chloro-4-(2-methoxy-4-nitrophenyl)pyridine (320 mg, 1.209 mmol), N-benzylmethylamine (0.187 mL, 1.451 mmol) and sodium t-butoxide (256 mg, 2.66 mmol) in toluene (10 mL) was placed in a round bottom flask. N$_2$ gas was bubbled for 2 minutes. Palladium(II) acetate (27.1 mg, 0.121 mmol) and 1,3-bis(diphenylphosphino)propane (100 mg, 0.242 mmol) were added. The dark red mixture was heated at reflux for 14 h. The reaction mixture was transferred to a separatory funnel containing saturated aqueous NaHCO$_3$ solution (25 mL). The aqueous layer was extracted with ethyl ether (3×25 mL). The combined organic layers were washed with brine (25 mL), dried over MgSO$_4$, filtered, and concentrated. The residue was purified by column chromatography on silica gel (30% ethyl acetate in hexanes; 25 g column) to afford a mixture of the desired product and the starting material. This mixture was then purified by reverse phase HPLC (acetonitrile:water containing 0.1% TFA) to afford N-benzyl-4-(2-methoxy-4-nitrophenyl)-N-methylpyridin-2-amine (150 mg, 35% yield) as a yellow solid: $^1$H NMR (400 MHz, DMSO-d$_6$) δ 8.16-8.13 (m, 1H), 7.90 (dd, J=8.3, 2.3 Hz, 1H), 7.86 (d, J=2.0 Hz, 1H), 7.62 (d, J=8.3 Hz, 1H), 7.35-7.29 (m, 2H), 7.27-7.20 (m, 3H), 6.74-6.70 (m, 2H), 4.82 (s, 2H), 3.86 (s, 3H), 3.07 (s, 3H); LC/MS (ESI) m/e 350.1 [(M+H)$^+$, calcd for C$_{20}$H$_{20}$N$_3$O$_3$ 350.1].

Part C. 4-(4-Amino-2-methoxyphenyl)-N-benzyl-N-methylpyridin-2-amine

A mixture of N-benzyl-4-(2-methoxy-4-nitrophenyl)-N-methylpyridin-2-amine (150 mg, 0.429 mmol) and tin(II) chloride dihydrate (484 mg, 2.147 mmol) in ethyl acetate (10 mL) and ethanol (5.00 mL) was heated to 70° C. for 3 hours. The mixture was poured in a flask containing saturated aqueous NaHCO$_3$ solution (20 mL). The mixture was filtered through diatomaceous earth (Celite®). The filtrate was transferred to a separatory funnel containing saturated aqueous NaHCO$_3$ solution (15 mL). The aqueous layer was extracted with ethyl acetate (3×20 mL). The combined organic layers were washed with brine (20 mL), dried over MgSO$_4$, filtered, and concentrated to afford 4-(4-amino-2-methoxyphenyl)-N-benzyl-N-methylpyridin-2-amine (70 mg, 51% yield) as a green oil: $^1$H NMR (400 MHz, CDCl$_3$) δ 8.19 (dd, J=5.3, 0.5 Hz, 1H), 7.39-7.23 (m, 5H), 7.16 (d, J=8.1 Hz, 1H), 6.77 (dd, J=5.2, 1.4 Hz, 1H), 6.72 (s, 1H), 6.35 (dd, J=8.1, 2.0 Hz, 1H), 6.31 (d, J=2.0 Hz, 1H), 4.84 (s, 2H), 3.82 (s, 2H), 3.74 (s, 3H), 3.12 (s, 3H) LC/MS (ESI) m/e 320.2 [(M+H)$^+$, calcd for C$_{20}$H$_{22}$N$_3$O 320.2].

Part D. (R)-tert-Butyl 1-(4-(2-(benzyl(methyl)amino)pyridin-4-yl)-3-methoxyphenylamino)-4-methyl-1-oxopentan-2-ylcarbamate To a mixture of 4-(4-amino-2-methoxyphenyl)-N-benzyl-N-methylpyridin-2-amine (75 mg, 0.235 mmol) and (R)-2-(tert-butoxycarbonylamino)-4-methylpentanoic acid (109 mg, 0.470 mmol) in dichloromethane (3 mL) was added N,N-diisopropylethylamine (0.205 mL, 1.174 mmol) and O-benzotriazol-1-yl-N,N,N,N-tetramethyluronium tetrafluoroborate (TBTU) (151 mg, 0.470 mmol). The reaction mixture was stirred at room temperature for 12 hours. The reaction mixture was transferred to a separatory funnel containing saturated aqueous NaHCO$_3$ solution (25 mL). The aqueous layer was extracted with ethyl acetate (3×25 mL). The combined organic layers were washed with brine (25 mL), dried over MgSO$_4$, filtered, and concentrated. The residue was purified by column chromatography on silica gel (50%→70% ethyl acetate in hexanes; 25 g column) to afford (R)-tert-butyl 1-(4-(2-(benzyl(methyl)amino)pyridin-4-yl)-3-methoxyphenylamino)-4-methyl-1-oxopentan-2-ylcarbamate (110 mg, 88% yield) as a yellow solid: $^1$H NMR (400 MHz, CDCl$_3$) δ 9.19 (br. s., 1H), 8.13 (d, J=5.3 Hz, 1H), 8.01 (s, 1H), 7.33-7.29 (m, 1H), 7.28-7.25 (m, 2H), 7.24-7.19 (m, 3H), 7.09 (d, J=9.3 Hz, 1H), 7.06-7.01 (m, 1H), 6.64 (d, J=4.8 Hz, 1H), 6.56 (br. s., 1H), 4.73 (s, 2H), 4.20 (t, J=7.3 Hz, 1H), 3.65 (s, 3H), 3.00 (s, 3H), 1.90 (br. s., 1H), 1.64 (br. s., 1H), 1.45 (s, 9H), 1.30-1.21 (m, 1H), 1.01 (d, J=6.8 Hz, 3H), 0.95-0.89 (m, 3H); LC/MS (ESI) m/e 533.3 [(M+H)$^+$, calcd for C$_{31}$H$_{41}$N$_4$O$_4$ 533.3].

Part E. (R)-tert-Butyl 1-(3-methoxy-4-(2-(methylamino)pyridin-4-yl)phenylamino)-4-methyl-1-oxopentan-2-ylcarbamate A mixture of (R)-tert-butyl 1-(4-(2-(benzyl(methyl)amino)pyridin-4-yl)-3-methoxyphenylamino)-4-methyl-1-oxopentan-2-ylcarbamate (110 mg, 0.207 mmol), ammonium formate (65.1 mg, 1.033 mmol) and Pd/C (88 mg, 0.083 mmol) in ethanol (10 mL) was heated at reflux for 2 h. The mixture was filtered through diatomaceous earth) (Celite®) and the filtrate was concentrated. The residue was purified by column chromatography on silica gel (5% methanol in dichloromethane; 25 g column) to afford (R)-tert-butyl 1-(3-methoxy-4-(2-(methylamino)pyridin-4-yl)phenylamino)-4-methyl-1-oxopentan-2-ylcarbamate (60 mg, 66% yield) as a colorless solid: LC/MS (ESI) m/e 443.2 [(M+H)$^+$, calcd for C$_{24}$H$_{35}$N$_4$O$_4$ 443.3].

Part F. 2-(4-Aminopiperidin-1-yl)-N-(3-methoxy-4-(oxazol-5-yl)phenyl)-4-methylpentanamide (R)-tert-butyl 1-(3-methoxy-4-(2-(methylamino)pyridin-4-yl)phenylamino)-4-methyl-1-oxopentan-2-ylcarbamate (60 mg, 0.136 mmol) was dissolved in dichloromethane (1 mL) and cooled to 0° C. To this solution was added TFA (0.104 mL, 1.356 mmol). The reaction mixture was stirred at room temperature for 12 hours. The solvent was evaporated and the residue was purified by reverse phase HPLC (acetonitrile:water containing 0.1% TFA) to afford 2-(4-aminopiperidin-1-yl)-N-(3-methoxy-4-(oxazol-5-yl)phenyl)-4-methylpentanamide (25 mg, 40% yield) as a TFA salt: $^1$H NMR (400 MHz, CD$_3$OD-d$_4$) δ 7.77 (d, J=6.8 Hz, 1H), 7.60 (d, J=1.8 Hz, 1H), 7.47 (d, J=8.6 Hz, 1H), 7.31 (dd, J=8.4, 1.9 Hz, 1H), 7.18 (s, 1H), 7.09 (dd, J=6.9, 1.6 Hz, 1H), 3.87-3.90 (m, 1H), 3.87 (s, 3H), 3.03 (s, 3H), 2.03 (ddd, J=9.7, 6.5, 3.4 Hz, 1H), 1.58-1.71 (m, 1H), 1.19-1.32 (m, 1H), 1.09 (d, J=7.1 Hz, 3H), 0.99 (t, J=7.4 Hz, 3H); LC/MS (ESI) m/e 343.2 [(M+H)$^+$, calcd for C$_{19}$H$_{27}$N$_4$O$_2$ 343.2]. HPLC (method A): t$_R$=6.62 min; HPLC (method B): t$_R$=6.79 min.

Example 49

(R)-2-Amino-N-(3-(methoxy)-4-(6-(methylamino)imidazo[1,2-b]pyridazin-3-yl)phenyl)-4-methylpentanamide

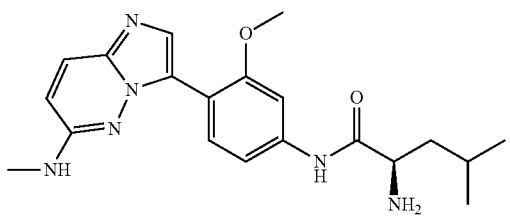 [SMILES: CNc1ccc2ncc(-c3ccc(NC(=O)[C@H](N)CC(C)C)cc3OC)n2n1]

Part A. N-Benzyl-3-chloro-N-methylimidazo[1,2-b]pyridazin-6-amine

A mixture of 3-bromo-6-chloroimidazo[1,2-b]pyridazine (100 mg, 0.430 mmol), prepared according to the procedure described in Example 46 Part A, and N-benzylmethylamine (0.56 mL, 4.30 mmol) in NMP (1 mL) was heated in a sealed tube at 150° C. for 2 h. The reaction mixture was cooled to room temperature and was transferred to a separatory funnel containing saturated aqueous $NaHCO_3$ solution (50 mL). The aqueous layer was extracted with ethyl acetate (3×25 mL). The combined organic layers were washed with brine (25 mL), dried over $MgSO_4$, filtered, and concentrated. The residue was purified by column chromatography on silica gel (30%→35% ethyl acetate in hexanes; 25 g column) to afford N-benzyl-3-bromo-N-methylimidazo[1,2-b]pyridazin-6-amine (120 mg, 88% yield) as a yellow solid: $^1$H NMR (400 MHz, DMSO-$d_6$) δ 7.84 (d, J=10.1 Hz, 1H), 7.57 (s, 1H), 7.51-7.47 (m, 1H), 7.46-7.38 (m, 2H), 7.35-7.29 (m, 2H), 7.28-7.23 (m, 1H), 7.11 (d, J=10.1 Hz, 1H), 4.80 (s, 2H), 3.15 (s, 3H); LC/MS (ESI) m/e 317.0 [(M+H)$^+$, calcd for $C_{14}H_{14}N_4Br$ 317.0].

Part B. N-Benzyl-3-(2-methoxy-4-nitrophenyl)-N-methylimidazo[1,2-b]pyridazin-6-amine A mixture of N-benzyl-3-bromo-N-methylimidazo[1,2-b]pyridazin-6-amine (120 mg, 0.378 mmol), 2-(2-methoxy-4-nitrophenyl)-4,4,5,5-tetramethyl-1,3,2-dioxaborolane (116 mg, 0.416 mmol), prepared according to the procedure described in Example 22 Part A, and sodium carbonate (2M in $H_2O$) (0.567 mL, 1.135 mmol) in THF (5 mL) was degassed. Bis(triphenylphosphene)palladium(II) chloride (13.28 mg, 0.019 mmol) was added and the mixture was heated to 70° C. in a microwave for 2 h. The reaction mixture was transferred to a separatory funnel containing saturated aqueous $NaHCO_3$ solution (25 mL). The aqueous layer was extracted with ethyl acetate (3×25 mL). The combined organic layers were washed with brine (25 mL), dried over $MgSO_4$, filtered, and concentrated. The residue was purified by reverse phase HPLC (acetonitrile:water containing 0.1% TFA) to afford N-benzyl-3-(2-methoxy-4-nitrophenyl)-N-methylimidazo[1,2-b]pyridazin-6-amine (100 mg, 68% yield) as a yellow solid: LC/MS (ESI) m/e 390.1 [(M+H)$^+$, calcd for $C_{21}H_{20}N_5O_3$ 390.2].

Part C. (R)-2-Amino-N-(3-(methoxy)-4-(6-(methylamino)imidazo[1,2-b]pyridazin-3-yl)phenyl)-4-methylpentanamide The title compound was prepared from N-benzyl-3-(2-methoxy-4-nitrophenyl)-N-methylimidazo[1,2-b]pyridazin-6-amine in a similar fashion as described in Example 22 Parts C-F. The product was purified by reverse phase HPLC (acetonitrile/water containing 0.1% TFA) to give (R)-2-amino-N-(3-(difluoromethoxy)-4-(6-(methylamino)imidazo[1,2-b]pyridazin-3-yl)phenyl)-4-methylpentanamide (15 mg) as a TFA salt: $^1$H NMR (400 MHz, DMSO-$d_6$) δ 10.67 (s, 1H), 8.26 (br. s., 3H), 8.12 (d, J=8.6 Hz, 1H), 8.02 (s, 1H), 7.91 (d, J=9.8 Hz, 1H), 7.47 (d, J=1.8 Hz, 1H), 7.45 (d, J=2.0 Hz, 1H), 7.40 (dd, J=8.6, 2.0 Hz, 1H), 6.99 (d, J=9.6 Hz, 1H), 3.85 (s, 3H), 2.78 (d, J=4.5 Hz, 3H), 1.96 (d, J=5.8 Hz, 1H), 1.52-1.61 (m, 1H), 1.11-1.29 (m, 2H), 0.96-1.03 (m, 3H), 0.85-0.94 (m, 3H); LC/MS (ESI) m/e 383.3 [(M+H)$^+$, calcd for $C_{20}H_{27}N_6O_2$ 383.2]. HPLC (method C): $t_R$=11.00 min; HPLC (method D): $t_R$=10.90 min.

Example 50

(R)-2-Amino-N-(3-methoxy-4-(oxazol-5-yl)phenyl)butanamide

To a mixture of 3-methoxy-4-(oxazol-5-yl)aniline (50 mg, 0.263 mmol), prepared as described in Example 1 Parts A-B, (R)-2-((tert-butoxycarbonyl)amino)butanoic acid (133 mg, 0.657 mmol), and N,N-diisopropylethylamine (0.230 mL, 1.314 mmol) in THF (1.5 mL) was added 1-propanephosphonic acid cyclic anhydride (0.469 mL, 0.789 mmol). The reaction mixture was stirred at room temperature for 16 h. The mixture was concentrated. The residue was taken up in dichloromethane (1 mL) and TFA (0.75 mL) was added. The reaction mixture was heated at 50° C. for 2 h. The mixture was then concentrated under vacuum. The product was purified by reverse phase HPLC (methanol/water containing 20 mM ammonium acetate; Waters 19×100 mm, 5 µm, C18 column) to give (R)-2-amino-N-(3-methoxy-4-(oxazol-5-yl)phenyl)butanamide (36 mg): LC/MS (ESI) m/e 276.1 [(M+H)$^+$, calcd for $C_{14}H_{18}N_3O_3$ 276.1]. HPLC (method E): $t_R$=2.44 min.

Example 51

(S)-2-Amino-N-(3-methoxy-4-(oxazol-5-yl)phenyl)pentanamide

Prepared in a similar fashion as described in Example 50 using (S)-2-((tert-butoxycarbonyl)amino)pentanoic acid to give (S)-2-amino-N-(3-methoxy-4-(oxazol-5-yl)phenyl)

pentanamide (36 mg): LC/MS (ESI) m/e 290.1 [(M+H)+, calcd for $C_{15}H_{20}N_3O_3$ 290.2]. HPLC (method E): $t_R$=2.47 min.

Example 52

(R)-2-Amino-N-(3-methoxy-4-(oxazol-5-yl)phenyl) hexanamide

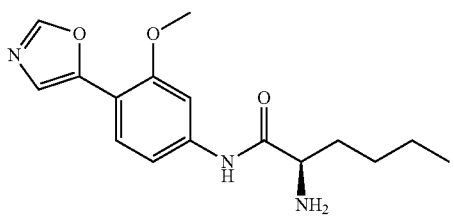 [SMILES: CCCC[C@@H](N)C(=O)Nc1ccc(-c2cnco2)c(OC)c1]

Prepared in a similar fashion as described in Example 50 using (R)-2-((tert-butoxycarbonyl)amino)hexanoic acid to give (R)-2-amino-N-(3-methoxy-4-(oxazol-5-yl)phenyl) hexanamide (42 mg): LC/MS (ESI) m/e 304.2 [(M+H)+, calcd for $C_{16}H_{22}N_3O_3$ 304.2]. HPLC (method E): $t_R$=2.91 min.

Example 53

(S)-2-Amino-N-(3-methoxy-4-(oxazol-5-yl)phenyl) hexanamide

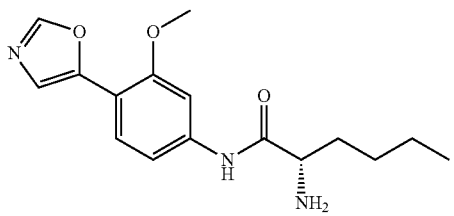 [SMILES: CCCC[C@H](N)C(=O)Nc1ccc(-c2cnco2)c(OC)c1]

Prepared in a similar fashion as described in Example 50 using (S)-2-((tert-butoxycarbonyl)amino)hexanoic acid to give (S)-2-amino-N-(3-methoxy-4-(oxazol-5-yl)phenyl) hexanamide (53 mg): LC/MS (ESI) m/e 304.2 [(M+H)+, calcd for $C_{16}H_{22}N_3O_3$ 304.2]. HPLC (method E): $t_R$=2.94 min.

Example 54

(R)-2-Amino-N-(3-methoxy-4-(oxazol-5-yl)phenyl)-4-(methylthio)butanamide

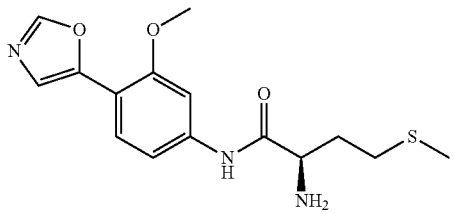 [SMILES: COc1cc(NC(=O)[C@H](N)CCSC)ccc1-c1cnco1]

Prepared in a similar fashion as described in Example 50 using (R)-2-((tert-butoxycarbonyl)amino)-4-(methylthio) butanoic acid to give (R)-2-amino-N-(3-methoxy-4-(oxazol-5-yl)phenyl)-4-(methylthio)butanamide (50 mg): LC/MS (ESI) m/e 322.1 [(M+H)+, calcd for $C_{15}H_{20}N_3O_3S$ 322.1]. HPLC (method E): $t_R$=2.56 min.

Example 55

(2R,3R)-2-Amino-N-(3-methoxy-4-(oxazol-5-yl) phenyl)-3-methylpentanamide

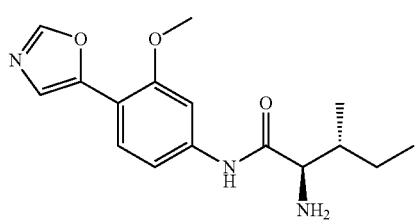 [SMILES: CC[C@@H](C)[C@@H](N)C(=O)Nc1ccc(-c2cnco2)c(OC)c1]

Prepared in a similar fashion as described in Example 50 using (2R,3R)-2-((tert-butoxycarbonyl)amino)-3-methylpentanoic acid to give (2R,3R)-2-amino-N-(3-methoxy-4-(oxazol-5-yl)phenyl)-3-methylpentanamide (39 mg): LC/MS (ESI) m/e 304.2 [(M+H)+, calcd for $C_{16}H_{22}N_3O_3$ 304.2]. HPLC (method E): $t_R$=2.83 min.

Example 56

(R)-2-Amino-3-cyclohexyl-N-(3-methoxy-4-(oxazol-5-yl)phenyl)propanamide

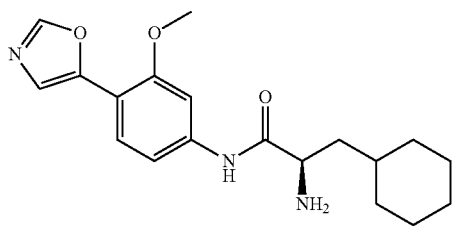 [SMILES: COc1cc(NC(=O)[C@H](N)CC2CCCCC2)ccc1-c1cnco1]

Prepared in a similar fashion as described in Example 50 using (R)-2-((tert-butoxycarbonyl)amino)-3-cyclohexylpropanoic acid to give (R)-2-amino-3-cyclohexyl-N-(3-methoxy-4-(oxazol-5-yl)phenyl)propanamide (63 mg): LC/MS (ESI) m/e 344.2 [(M+H)+, calcd for $C_{19}H_{26}N_3O_3$ 344.2]. HPLC (method E): $t_R$=3.56 min.

Example 57

N-(3-Methoxy-4-(oxazol-5-yl)phenyl)-2-oxoimidazolidine-4-carboxamide

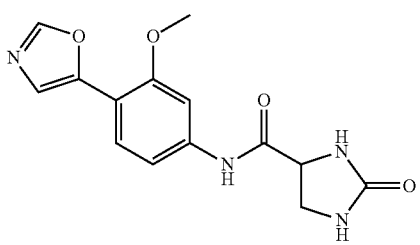 [SMILES: COc1cc(NC(=O)C2CNC(=O)N2)ccc1-c1cnco1]

2-Oxoimidazolidine-4-carboxylic acid (85 mg, 0.657 mmol), N,N-diisopropylethylamine (0.230 mL, 1.314 mmol), and HATU (255 mg, 0.670 mmol) were dissolved in DMF (0.8 mL) and stirred for 5 min at room temperature. To this mixture was added a premixed solution of 3-methoxy-4-(oxazol-5-yl)aniline (50 mg, 0.263 mmol), prepared as described in Example 1 Parts A-B, and N,N-diisopropylethylamine (0.230 mL, 1.314 mmol) in DMF (0.6 mL). The reaction mixture was stirred at room temperature for 16 h. The mixture was concentrated under vacuum. The product was purified by reverse phase HPLC (methanol/water containing 20 mM ammonium hydroxide; Waters Xbridge 30×100 mm, 5 μm, C18 column) to give N-(3-methoxy-4-(oxazol-5-yl)phenyl)-2-oxoimidazolidine-4-carboxamide (30 mg): LC/MS (ESI) m/e 303.1 [(M+H)+, calcd for $C_{14}H_{15}N_4O_4$ 303.1]. HPLC (method F): $t_R$=1.93 min.

Example 58

N-(3-Methoxy-4-(oxazol-5-yl)phenyl)-1-(methylamino)cyclopropanecarboxamide

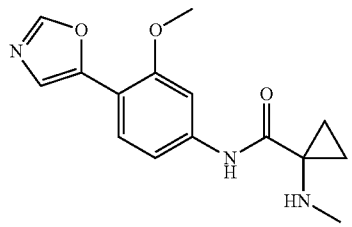 [SMILES: CNC1(C(=O)Nc2ccc(-c3cnco3)c(OC)c2)CC1]

A solution of 1-(Methylamino)cyclopropanecarboxylic acid (76 mg, 0.657 mmol) and HATU (255 mg, 0.670 mmol) in DMF (0.75 mL) was treated with N,N-diisopropylethylamine (0.230 mL, 1.314 mmol) and the mixture was stirred for 5 min at room temperature. To this mixture was added a premixed solution of 3-methoxy-4-(oxazol-5-yl)aniline (50 mg, 0.263 mmol), prepared as described in Example 1 Parts A-B, and N,N-diisopropylethylamine (0.230 mL, 1.314 mmol) in DMF (0.6 mL). The reaction mixture was stirred at room temperature for 16 h. The mixture was concentrated under vacuum. The product was purified by reverse phase HPLC (methanol/water containing 20 mM ammonium acetate; Waters Xbridge 19×100 mm, 5 μm, C18 column) to give N-(3-methoxy-4-(oxazol-5-yl)phenyl)-1-(methylamino)cyclopropanecarboxamide (2 mg): LC/MS (ESI) m/e 288.1 [(M+H)+, calcd for $C_{16}H_{18}N_3O_3$ 288.1]. HPLC (method G): $t_R$=3.02 min.

Example 59

N-(3-Methoxy-4-(oxazol-5-yl)phenyl)-2-(2-oxopyrrolidin-1-yl)acetamide

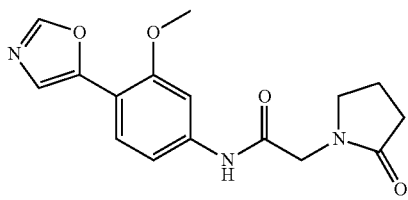 [SMILES: COc1cc(NC(=O)CN2CCCC2=O)ccc1-c1cnco1]

Prepared in a similar fashion as described in Example 58 using 2-(2-oxopyrrolidin-1-yl)acetic acid. The product was purified by reverse phase HPLC (acetonitrile/water containing 20 mM ammonium acetate; Waters Xbridge 19×200 mm, 5 μm, C18 column) to give N-(3-methoxy-4-(oxazol-5-yl)phenyl)-2-(2-oxopyrrolidin-1-yl)acetamide (62 mg): LC/MS (ESI) m/e 316.1 [(M+H)+, calcd for $C_{16}H_{18}N_3O_4$ 316.1]. HPLC (method G): $t_R$=2.43 min.

Example 60

(R)-2-((4-Chlorobenzyl)amino)-N-(3-methoxy-4-(oxazol-5-yl)phenyl)-4-methylpentanamide

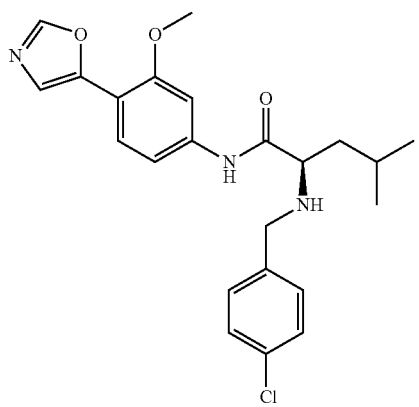 [SMILES: COc1cc(NC(=O)[C@@H](CC(C)C)NCc2ccc(Cl)cc2)ccc1-c1cnco1]

To a solution of (R)-2-amino-N-(3-methoxy-4-(oxazol-5-yl)phenyl)-4-methylpentanamide (41.6 mg, 0.122 mmol), prepared as described in Example 1, in methanol (1.0 mL) was added 4-chlorobenzaldehyde (25.3 mg, 0.180 mmol) and N,N-diisopropylethylamine (0.086 mL, 0.490 mmol). The reaction mixture was stirred for 16 h at room temperature. To the reaction mixture was added sodium borohydride (23 mg, 0.612 mmol). The reaction mixture was heated at 50° C. for 36 h. The reaction was then quenched by the addition of water (50 μL) and the mixture was concentrated. The product was purified by reverse phase HPLC (acetonitrile/water containing 20 mM ammonium acetate; Waters Xbridge 19×150 mm, 5 μm, C18 column) to give (R)-2-((4-chlorobenzyl)amino)-N-(3-methoxy-4-(oxazol-5-yl)phenyl)-4-methylpentanamide (2 mg): LC/MS (ESI) m/e 428.1 [(M+H)+, calcd for $C_{23}H_{27}ClN_3O_3$ 428.2]. HPLC (method H): $t_R$=5.69 min.

Example 61

(R)—N-(3-Methoxy-4-(oxazol-5-yl)phenyl)-4-methyl-2-(((1-methyl-1H-pyrrol-2-yl)methyl)amino)pentanamide

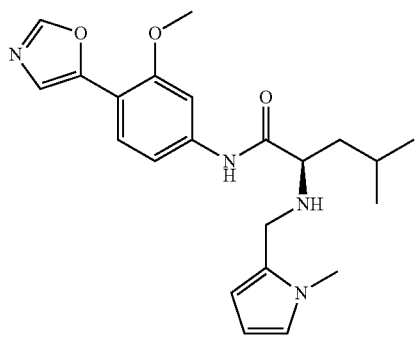 [SMILES: COc1cc(NC(=O)[C@@H](CC(C)C)NCc2cccn2C)ccc1-c1cnco1]

Prepared in a similar fashion as described in Example 60 using 1-methyl-1H-pyrrole-2-carbaldehyde to give (R)—N-(3-methoxy-4-(oxazol-5-yl)phenyl)-4-methyl-2-(((1-methyl-1H-pyrrol-2-yl)methyl)amino)pentanamide (20 mg): LC/MS (ESI) m/e 397.1 [(M+H)$^+$, calcd for $C_{22}H_{29}N_4O_3$ 397.2]. HPLC (method H): $t_R$=4.92 min.

Example 62

(R)-2-((2-Chlorobenzyl)amino)-N-(3-methoxy-4-(oxazol-5-yl)phenyl)-4-methylpentanamide

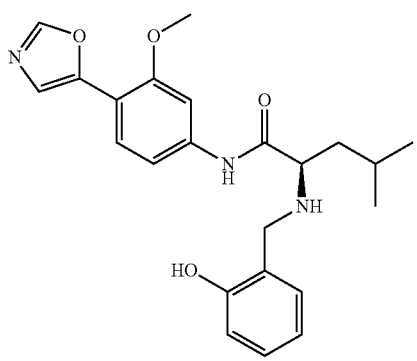 [SMILES: COc1cc(NC(=O)[C@@H](CC(C)C)NCc2ccccc2O)ccc1-c1cnco1]

Prepared in a similar fashion as described in Example 60 using 2-hydroxybenzaldehyde to give (R)-2-((2-chlorobenzyl)amino)-N-(3-methoxy-4-(oxazol-5-yl)phenyl)-4-methylpentanamide (13 mg): LC/MS (ESI) m/e 410.1 [(M+H)$^+$, calcd for $C_{23}H_{28}N_3O_4$ 410.2]. HPLC (method H): $t_R$=4.92 min.

Example 63

(R)—N-(3-Methoxy-4-(oxazol-5-yl)phenyl)-4-methyl-2-((4-methylbenzyl)amino)pentanamide

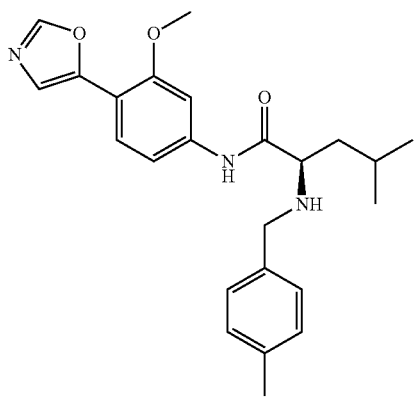 [SMILES: COc1cc(NC(=O)[C@@H](CC(C)C)NCc2ccc(C)cc2)ccc1-c1cnco1]

Prepared in a similar fashion as described in Example 60 using 4-methylbenzaldehyde to give (R)—N-(3-methoxy-4-(oxazol-5-yl)phenyl)-4-methyl-2-((4-methylbenzyl)amino)pentanamide (12 mg): LC/MS (ESI) m/e 408.1 [(M+H)$^+$, calcd for $C_{24}H_{30}N_3O_3$ 408.2]. HPLC (method H): $t_R$=5.74 min.

Example 64

(R)—N-(3-Methoxy-4-(oxazol-5-yl)phenyl)-4-methyl-2-(((1-methyl-1H-pyrazol-4-yl)methyl)amino)pentanamide

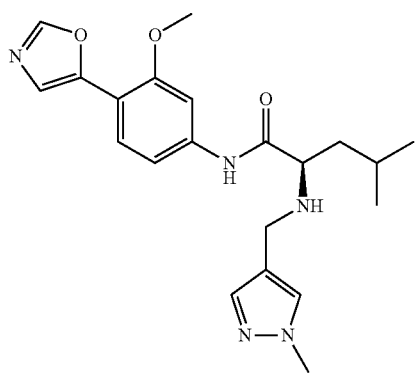 [SMILES: COc1cc(NC(=O)[C@@H](CC(C)C)NCc2cnn(C)c2)ccc1-c1cnco1]

Prepared in a similar fashion as described in Example 60 using 1-methyl-1H-pyrazole-4-carbaldehyde to give (R)—N-(3-methoxy-4-(oxazol-5-yl)phenyl)-4-methyl-2-(((1-methyl-1H-pyrazol-4-yl)methyl)amino)pentanamide (4 mg): LC/MS (ESI) m/e 398.1 [(M+H)$^+$, calcd for $C_{21}H_{28}N_5O_3$ 398.2]. HPLC (method H): $t_R$=1.77 min.

Example 65

(R)—N-(3-Methoxy-4-(oxazol-5-yl)phenyl)-4-methyl-2-((thiophen-3-ylmethyl)amino)pentanamide

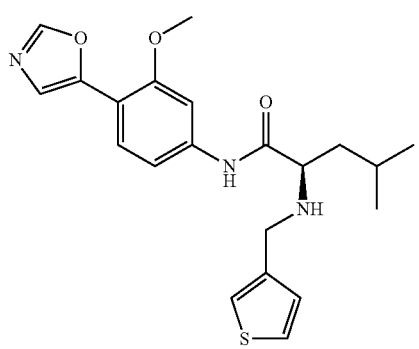 [SMILES: COc1cc(NC(=O)[C@@H](CC(C)C)NCc2ccsc2)ccc1-c1cnco1]

Prepared in a similar fashion as described in Example 60 using thiophene-3-carbaldehyde to give (R)—N-(3-methoxy-4-(oxazol-5-yl)phenyl)-4-methyl-2-((thiophen-3-ylmethyl)amino)pentanamide (2.5 mg): LC/MS (ESI) m/e 400.2 [(M+H)$^+$, calcd for $C_{21}H_{26}N_3O_3S$ 400.2]. HPLC (method H): $t_R$=2.48 min.

Example 66

(R)—N-(3-Methoxy-4-(oxazol-5-yl)phenyl)-4-methyl-2-(((3-methylthiophen-2-yl)methyl)amino)pentanamide

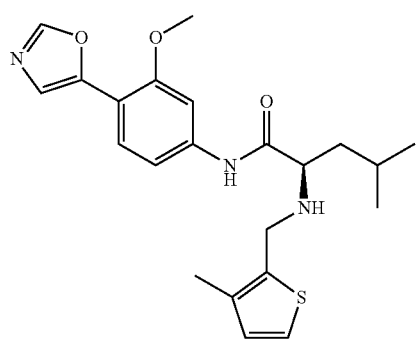 [SMILES: COc1cc(NC(=O)[C@@H](CC(C)C)NCc2sccc2C)ccc1-c1cnco1]

Prepared in a similar fashion as described in Example 60 using 3-methylthiophene-2-carbaldehyde to give (R)—N-(3-methoxy-4-(oxazol-5-yl)phenyl)-4-methyl-2-(((3-methylthiophen-2-yl)methyl)amino)pentanamide (1.1 mg): LC/MS (ESI) m/e 414.2 [(M+H)$^+$, calcd for $C_{22}H_{28}N_3O_3S$ 414.2]. HPLC (method H): $t_R$=2.72 min.

Example 67

(R)-2-(((1,2,3-Thiadiazol-4-yl)methyl)amino)-N-(3-methoxy-4-(oxazol-5-yl)phenyl)-4-methylpentanamide

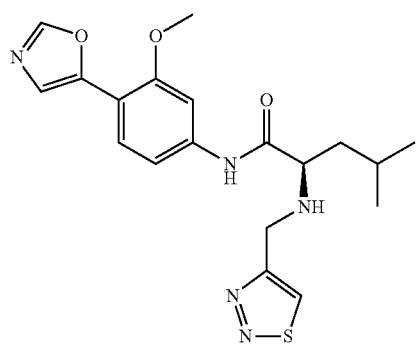 [SMILES: COc1cc(NC(=O)[C@@H](CC(C)C)NCc2csnn2)ccc1-c1cnco1]

Prepared in a similar fashion as described in Example 60 using 1,2,3-thiadiazole-4-carbaldehyde to give (R)-2-(((1,2,3-thiadiazol-4-yl)methyl)amino)-N-(3-methoxy-4-(oxazol-5-yl)phenyl)-4-methylpentanamide (1.4 mg): LC/MS (ESI) m/e 402.2 [(M+H)$^+$, calcd for $C_{19}H_{24}N_5O_3S$ 402.2]. HPLC (method H): $t_R$=2.03 min.

Example 68

(R)—N-(3-Methoxy-4-(oxazol-5-yl)phenyl)-4-methyl-2-(methylsulfonamido)pentanamide

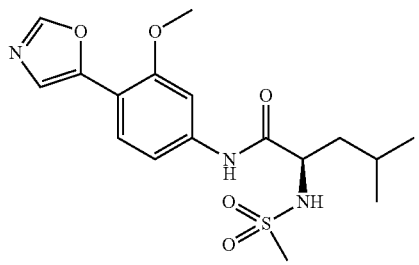 [SMILES: COc1cc(NC(=O)[C@@H](CC(C)C)NS(C)(=O)=O)ccc1-c1cnco1]

To a solution of (R)-2-amino-N-(3-methoxy-4-(oxazol-5-yl)phenyl)-4-methylpentanamide (45 mg, 0.133 mmol), prepared as described in Example 1, in dichloromethane (0.5 mL) at room temperature was added N,N-diisopropylethylamine (0.14 mL, 0.798 mmol) followed by the addition of a solution of methanesulfonyl chloride (46 mg, 0.400 mmol) in dichloromethane (0.5 mL). The reaction mixture was stirred for 16 h at room temperature. The reaction was not complete. DMAP (16 mg, 0.133 mmol) and N,N-diisopropylethylamine (0.100 mL) were added followed by additional methanesulfonyl chloride (46 mg, 0.400 mmol). The reaction mixture was stirred at room temperature for an additional 16 h. The reaction mixture was concentrated and the product was purified by reverse phase HPLC (acetonitrile/water containing 20 mM ammonium acetate; Waters Sunfire 19×150 mm, 5 µm, C18 column) to give (R)—N-(3-methoxy-4-(oxazol-5-yl)phenyl)-4-methyl-2-(methylsulfonamido)pentanamide (22 mg): LC/MS (ESI) m/e 382.1 [(M+H)$^+$, calcd for $C_{17}H_{24}N_3O_5S$ 382.1]. HPLC (method I): $t_R$=1.74 min.

Example 69

(R)-2-(Ethylsulfonamido)-N-(3-methoxy-4-(oxazol-5-yl)phenyl)-4-methylpentanamide

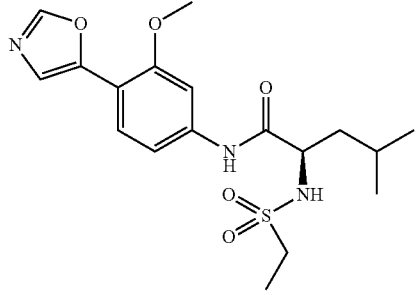 [SMILES: CCS(=O)(=O)N[C@H](CC(C)C)C(=O)Nc1ccc(-c2cnco2)c(OC)c1]

Prepared in a similar fashion as described in Example 68 using ethanesulfonyl chloride to give (R)-2-(ethylsulfonamido)-N-(3-methoxy-4-(oxazol-5-yl)phenyl)-4-methylpentanamide (7 mg): LC/MS (ESI) m/e 396.1 [(M+H)$^+$, calcd for C$_{18}$H$_{26}$N$_3$O$_5$S 396.2]. HPLC (method I): t$_R$=1.86 min.

Example 70

(R)—N-(3-Methoxy-4-(oxazol-5-yl)phenyl)-4-methyl-2-(propylsulfonamido)pentanamide

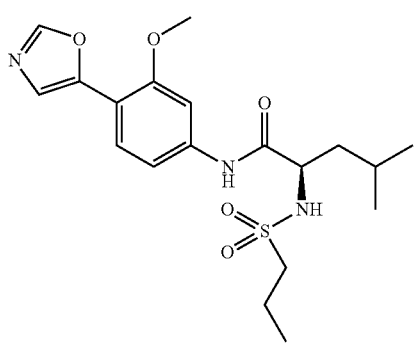 [SMILES: CCCS(=O)(=O)N[C@H](CC(C)C)C(=O)Nc1ccc(-c2cnco2)c(OC)c1]

Prepared in a similar fashion as described in Example 68 using propanesulfonyl chloride to give (R)—N-(3-methoxy-4-(oxazol-5-yl)phenyl)-4-methyl-2-(propylsulfonamido)pentanamide (15 mg): LC/MS (ESI) m/e 410.1.1 [(M+H)$^+$, calcd for C$_{19}$H$_{28}$N$_3$O$_5$S 410.2]. HPLC (method I): t$_R$=2.02 min.

Example 71

(R)—N-(3-methoxy-4-(oxazol-5-yl)phenyl)-4-methyl-2-(phenylsulfonamido)pentanamide

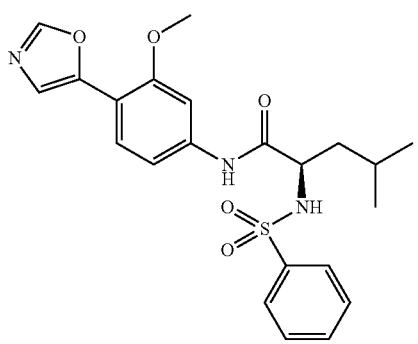 [SMILES: COc1cc(NC(=O)[C@@H](CC(C)C)NS(=O)(=O)c2ccccc2)ccc1-c1cnco1]

Prepared in a similar fashion as described in Example 68 using benzenesulfonyl chloride to give (R)—N-(3-methoxy-4-(oxazol-5-yl)phenyl)-4-methyl-2-(phenylsulfonamido)pentanamide (26 mg): LC/MS (ESI) m/e 444.1 [(M+H)$^+$, calcd for C$_{22}$H$_{26}$N$_3$O$_5$S 444.2]. HPLC (method I): t$_R$=2.14 min.

Example 72

(R)—N-(3-Methoxy-4-(oxazol-5-yl)phenyl)-4-methyl-2-(phenylmethylsulfonamido)pentanamide

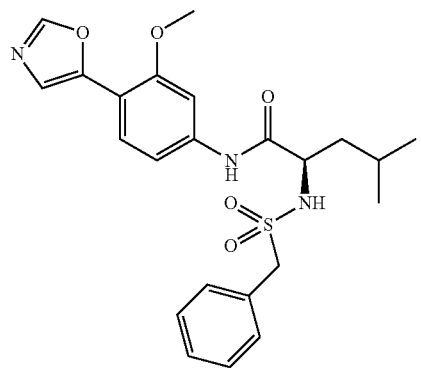 [SMILES: COc1cc(NC(=O)[C@@H](CC(C)C)NS(=O)(=O)Cc2ccccc2)ccc1-c1cnco1]

Prepared in a similar fashion as described in Example 68 using phenylmethanesulfonyl chloride to give (R)—N-(3-methoxy-4-(oxazol-5-yl)phenyl)-4-methyl-2-(phenylmethylsulfonamido)pentanamide (28 mg): LC/MS (ESI) m/e 458.1 [(M+H)$^+$, calcd for C$_{23}$H$_{28}$N$_3$O$_5$S 458.2]. HPLC (method I): t$_R$=2.23 min.

Example 73

(S)—N-(3-Methoxy-4-(oxazol-5-yl)phenyl)piperidine-2-carboxamide

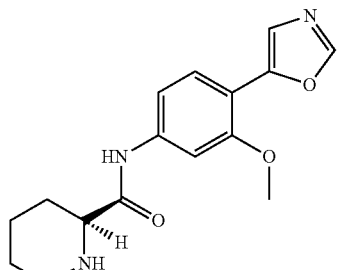

Prepared in a similar fashion as described in Example 1 using (S)-1-(tert-butoxycarbonyl)piperidine-2-carboxylic acid in Part C to give (S)—N-(3-methoxy-4-(oxazol-5-yl)phenyl)piperidine-2-carboxamide (14.6 mg, 13% yield) as an off white solid isolated as the HCl salt: $^1$H NMR (400 MHz, CD$_3$OD) δ 8.3 (s, 1H), 7.77 (d, J=8.8 Hz, 1H), 7.60 (d, J=1.6 Hz, 1H), 7.54 (s, 1H), 7.27 (dd, J=8.4, 1.6 Hz, 1H), 4.00 (s, 3H), 3.90-3.96 (m, 1H), 3.45-3.55 (m, 1H), 3.07-3.16 (m, 1H), 2.3-2.4 (m, 1H), 1.90-2.1 (m, 2H), 1.70-1.90 (m, 3H); LCMS (ESI) m/e 302.2 [(M+H)$^+$, calcd for C$_{16}$H$_{20}$N$_3$O$_3$, 302.2]; LC/MS retention time (method B): t$_R$=1.27 min; HPLC retention time (method J): t$_R$=9.27 min; HPLC retention time (method K): t$_R$=9.85 min; Chiral HPLC retention time (method E3): t$_R$=14.29 min.

Example 74

(R)-2-Amino-N-(3-methoxy-4-(oxazol-5-yl)phenyl)-4,4-dimethylpentanamide

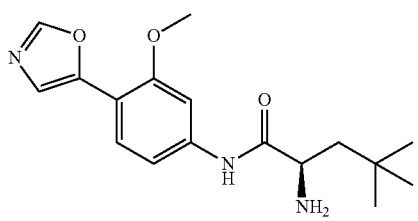 [SMILES: COc1cc(NC(=O)[C@H](N)CC(C)(C)C)ccc1-c1cnco1]

Prepared in a similar fashion as described in Example 1 using (R)-2-(tert-butoxycarbonylamino)-4,4-dimethylpentanoic acid in Part C to give (R)-2-amino-N-(3-methoxy-4-(oxazol-5-yl)phenyl)-4,4-dimethylpentanamide (80 mg, 52% yield) as yellow solid, which was isolated as the free base: $^1$H NMR (400 MHz, CD$_3$OD) δ 8.22 (s, 1H), 7.74 (d, J=8.8 Hz, 1H), 7.64 (d, J=1.6 Hz, 1H), 7.48 (s, 1H), 7.25 (dd, J=8.4, 2.0 Hz, 1H), 4.00 (s, 3H), 3.50-3.57 (m, 1H), 1.90-2.00 (m, 1H), 1.41-1.52 (m, 1H), 1.03 (s, 9H); LCMS (ESI) m/e 318.2 [(M+H)$^+$, calcd for C$_{17}$H$_{24}$N$_3$O$_3$, 318.2]; LC/MS retention time (method B): $t_R$=1.61 min; HPLC retention time (method L): $t_R$=5.90 min; HPLC retention time (method M): $t_R$=6.25 min; Chiral HPLC retention time (method I5): $t_R$=4.32 min.

Example 75

(R)-2-Amino-3-hydroxy-N-(3-methoxy-4-(oxazol-5-yl)phenyl)propanamide

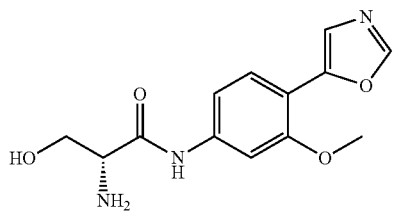 [SMILES: COc1cc(NC(=O)[C@H](N)CO)ccc1-c1cnco1]

Part A. (R)-tert-butyl(3-(benzyloxy)-1-((3-methoxy-4-(oxazol-5-yl)phenyl)amino)-1-oxopropan-2-yl)carbamate Prepared in a similar fashion as described in Example 1, Parts A-C using (R)-3-(benzyloxy)-2-(tert-butoxycarbonylamino)propanoic acid in Part C to give (R)-tert-butyl(3-(benzyloxy)-1-((3-methoxy-4-(oxazol-5-yl)phenyl)amino)-1-oxopropan-2-yl)carbamate (300 mg, 61% yield).

Part B. (R)-tert-Butyl 3-hydroxy-1-(3-methoxy-4-(oxazol-5-yl)phenylamino)-1-oxopropan-2-ylcarbamate A solution of (R)-tert-butyl 3-(benzyloxy)-1-(3-methoxy-4-(oxazol-5-yl)phenylamino)-1-oxopropan-2-ylcarbamate (250 mg, 0.53 mmol) in methanol (25 mL) was stirred for 5 min at room temperature and treated with 10% Pd/C (50 mg, 0.05 mmol). The resultant mixture was stirred under 45 psi hydrogen atmosphere for 12 h after which the mixture was filtered through a diatomaceous earth (Celite®) pad. The filtrate was concentrated under reduced pressure to afford a residue which was purified by preparative TLC (using 10% MeOH in dichloromethane) to afford (R)-tert-butyl 3-hydroxy-1-(3-methoxy-4-(oxazol-5-yl)phenylamino)-1-oxopropan-2-ylcarbamate (30 mg, 15% yield) as an off-white solid.

Part C. (R)-2-Amino-3-hydroxy-N-(3-methoxy-4-(oxazol-5-yl)phenyl)propanamide

To a solution of (R)-tert-butyl 3-hydroxy-1-(3-methoxy-4-(oxazol-5-yl)phenylamino)-1-oxopropan-2-ylcarbamate (30 mg, 0.079 mmol) in dichloromethane (2 mL) was added TFA at 0° C. and the mixture was stirred for 3 h at room temperature. Upon completion of the reaction, the volatiles were removed under reduced pressure and the residue so obtained was washed with diethyl ether (2×3 mL). The salt so obtained was dissolved in water (10 mL) and basified with saturated sodium carbonate solution (10 mL). The product was extracted with dichloromethane (5×3 mL) and the combined organic layers were dried over sodium sulfate and concentrated under reduced pressure to afford (R)-2-amino-3-hydroxy-N-(3-methoxy-4-(oxazol-5-yl)phenyl)propanamide (9.5 mg, 45% yield) as an off white solid, which was isolated as free base: $^1$H NMR (400 MHz, CD$_3$OD) δ 8.22 (s, 1H), 7.74 (d, J=8.4 Hz, 1H), 7.67 (d, J=1.6 Hz, 1H), 7.49 (s, 1H), 7.26 (dd, J=8.4, 2 Hz, 1H), 4.01 (s, 3H), 3.84 (d, J=5.2 Hz, 2H), 3.61-3.67 (m, 1H); LCMS (ESI) m/e 278.2 [(M+H)$^+$, calcd for C$_{13}$H$_{16}$N$_3$O$_4$, 278.1]; LC/MS retention time (method A): $t_R$=0.97 min; HPLC retention time (method J): $t_R$=7.09 min; HPLC retention time (method K): $t_R$=8.09 min; Chiral HPLC retention time (method 13): $t_R$=5.12 min.

Example 76

2-Amino-5,5,5-trifluoro-N-(3-methoxy-4-(oxazol-5-yl)phenyl)pentanamide

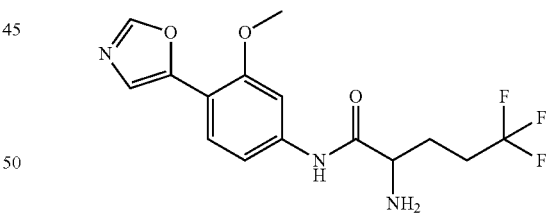

Part A. tert-Butyl 2-(diphenylmethyleneamino)-5,5,5-trifluoropentanoate

To a stirred solution of tert-butyl 2-((diphenylmethylene)amino)acetate (1 g, 3.39 mmol) in THF (20 ml) at −78° C. under a nitrogen atmosphere was added 2M LDA (2.54 ml, 5.08 mmol) dropwise for 30 min. To this mixture was then added 3,3,3-trifluoropropyl trifluoromethanesulfonate (1.083 g, 4.40 mmol). The reaction was gradually warmed to rt and was stirred for 4 h. The completion of reaction was determined by TLC using 20% ethyl acetate in hexane as mobile phase. The reaction mixture was quenched by addition of satd. aq. ammonium chloride at 0° C. The reaction mixture was then extracted with ethyl acetate (3×10 mL). The combined organic extracts were washed with water and brine, dried over sodium sulfate and concentrated under vacuum to yield an oil. The crude product was purified by silica gel column chromatography (2% ethyl acetate in hexanes) to afford tert-butyl 2-((diphenylmethylene)amino)-5,5,5-trifluoropentanoate (800 mg, 60% yield) as a yellow oil. LCMS (ESI) m/e 391.9 [(M+H)$^+$, calcd for $C_{22}H_{24}F_3NO_2$, 392.2]; LC/MS retention time (method E): $t_R$=2.49 min.

Part B. (S)-2-Amino-5,5,5-trifluoropentanoic acid (Hydrochloride salt)

The stirred solution of tert-butyl 2-((diphenylmethylene) amino)-5,5,5-trifluoropentanoate (800 mg, 2.023 mmol) in 50% aq. HCl (0.123 ml, 2.023 mmol) was heated at reflux at 100° C. for 8 h. The reaction mixture was cooled to rt and diluted with ethyl acetate (10 mL). The aqueous layer was concentrated under reduced pressure to afford 2-amino-5,5,5-trifluoropentanoic acid hydrochloride (400 mg, 78% pure by LCMS, 90% yield) as white solid. LC/MS Method=Column: Zorbax AQ (4.6×50) 3.5 µm; Mphase A: 0.1% HCOOH in Water; Mphase B: ACN; Flow: 1.0 ml/min. LCMS (ESI) m/e 171.7 [(M+H)$^+$, calcd for $C_5H_9F_3NO_2$, 172.0]; LC/MS retention time (method E): $t_R$=0.80 min.

Part C. (S)-2-(tert-Butoxycarbonylamino)-5,5,5-trifluoropentanoic acid

To a stirred solution of 2-amino-5,5,5-trifluoropentanoic acid hydrochloride (400 mg, 78% pure by LCMS) in THF (8 mL) and water (8 mL) was added $K_2CO_3$ (831 mg, 6.01 mmol) at rt and the reaction mixture was stirred for 10 min. To this mixture was added $Boc_2O$ (656 mg, 3.01 mmol). The reaction mixture was stirred for 8 h at rt. The reaction mixture was concentrated under reduced pressure. The aq. layer was washed with ethyl acetate (3×5 mL). The aq. layer was acidified with saturated citric acid solution (5 mL) and then extracted with ethyl acetate (3×8 mL). The combined organic layers were washed with water (3×5 mL) followed by brine solution (10 mL), dried over sodium sulfate and concentrated under reduced pressure to afford 2-((tert-butoxycarbonyl)amino)-5,5,5-trifluoropentanoic acid (500 mg, 1.84 mmol) as a colorless oil. The crude product was used directly in the next step. $^1$H NMR (400 MHz, CDCl$_3$) δ 5.04 (s, 1H), 4.38 (s, 1H), 2.15-2.28 (m, 2H), 1.91-1.95 (m, 2H), 1.46 (s, 9H).

Part D. 2-Amino-5,5,5-trifluoro-N-(3-methoxy-4-(oxazol-5-yl)phenyl)pentanamide

Prepared in a similar fashion as described in Example 1 using 2-(tert-butoxycarbonylamino)-5,5,5-trifluoropentanoic acid in Part C to give 2-amino-5,5,5-trifluoro-N-(3-methoxy-4-(oxazol-5-yl)phenyl)pentanamide (1.00 g, 53% yield) as an off white solid isolated as the free base: $^1$H NMR (400 MHz, DMSO d$_6$) δ 8.38 (s, 1H), 7.64 (d, J=8.8 Hz, 1H), 7.59 (d, J=2.0 Hz, 1H), 7.45 (s, 1H), 7.39 (dd, J=8.4, 1.6 Hz, 1H), 3.92 (s, 3H), 3.36-3.40 (m, 1H), 2.32-2.41 (m, 2H), 1.88-1.96 (m, 1H), 1.60-1.69 (m, 1H); LCMS (ESI) m/e 344.2 [(M+H)$^+$, calcd for $C_{15}H_{17}F_3N_3O_3$, 344.1]; LC/MS retention time (method A): $t_R$=1.49 min; HPLC retention time (method a): $t_R$=1.49 min; HPLC retention time (method M): $t_R$=6.14 min.

Example 77

(2R,3S)-2-Amino-3-hydroxy-N-(3-methoxy-4-(oxazol-5-yl)phenyl)butanamide

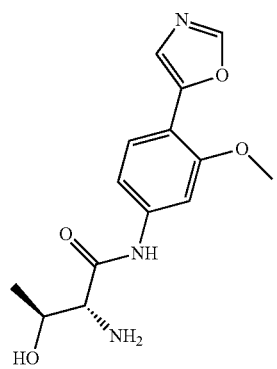 [SMILES: COc1cc(NC(=O)[C@H](N)[C@H](C)O)ccc1-c1cnco1]

Prepared in a similar fashion as described in Example 75 using (2R,3S)-3-(benzyloxy)-2-(tert-butoxycarbonylamino) butanoic acid to give (2R,3S)-2-amino-3-hydroxy-N-(3-methoxy-4-(oxazol-5-yl)phenyl)butanamide (50 mg, 51% yield) as an off white solid isolated as the free base: $^1$H NMR (400 MHz, CD$_3$OD) δ 8.21 (s, 1H), 7.74 (d, J=8.4 Hz, 1H), 7.67 (d, J=1.6 Hz, 1H), 7.49 (s, 1H), 7.25 (dd, J=8.4, 1.6 Hz, 1H), 4.10-4.15 (m, 1H), 4.01 (s, 3H), 3.30-3.32 (m, 1H), 1.28 (d, J=6.4 Hz, 3H); LCMS (ESI) m/e 290.2 [(M)$^-$, calcd for $C_{14}H_{16}N_3O_4$, 290.1]; LC/MS retention time (method G): $t_R$=1.55 min; HPLC retention time (method J): $t_R$=7.67 min; HPLC retention time (method K): $t_R$=8.54 min; Chiral HPLC retention time (method J1): $t_R$=3.71 min.

Example 78

(2R,4S)-4-Methoxy-N-(3-methoxy-4-(oxazol-5-yl)phenyl)pyrrolidine-2-carboxamide

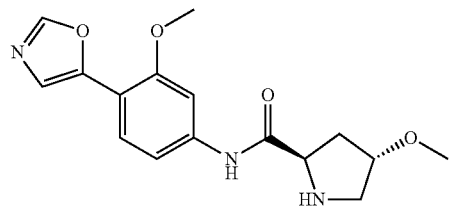 [SMILES: COc1cc(NC(=O)[C@H]2C[C@H](OC)CN2)ccc1-c1cnco1]

Prepared in a similar fashion as described in Example 1 using (4S)-1-(tert-butoxycarbonyl)-4-methoxypyrrolidine-2-carboxylic acid in Part C to give (2R,4S)-4-methoxy-N-(3-methoxy-4-(oxazol-5-yl)phenyl)pyrrolidine-2-carboxamide (15 mg, 50% yield) as an off-white sticky solid, which was isolated as the free base: $^1$H NMR (400 MHz, CD$_3$OD) δ 8.22 (s, 1H), 7.75 (d, J=8.4 Hz, 1H), 7.64 (d, J=2.0 Hz, 1H), 7.49 (s, 1H), 7.26 (dd, J=8.4, 1.6 Hz, 1H), 4.08-4.14 (m, 2H), 4.0 (s, 3H), 3.1-3.4 (m, 5H), 2.45-2.52 (m, 1H), 1.96-2.03 (m, 1H); LCMS (ESI) m/e 318.2 [(M+H)$^+$, calcd for $C_{16}H_{20}N_3O_4$, 318.1]; LC/MS retention time (method C): $t_R$=1.54 min; HPLC retention time (method J): $t_R$=8.90 min; HPLC retention time (method M): $t_R$=5.20 min; Chiral HPLC retention time (method E5): $t_R$=11.24, 14.36 min.

(HPLC predominant enantiomer at 14.36)–(Some amount of other enantiomer was seen from using commercially available amino acid.)

Example 79

(R)-3-Amino-N-(3-methoxy-4-(oxazol-5-yl)phenyl)-4-methylpentanamide

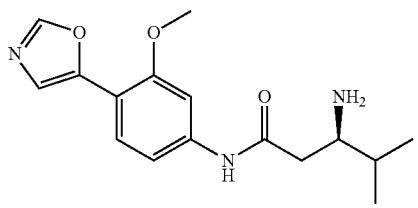 [SMILES: COc1cc(NC(=O)C[C@@H](N)C(C)C)ccc1-c1cnco1]

Prepared in a similar fashion as described in Example 1 using (R)-3-(tert-butoxycarbonylamino)-4-methylpentanoic acid in Part C give (R)-3-amino-N-(3-methoxy-4-(oxazol-5-yl)phenyl)-4-methylpentanamide (45 mg, 48% yield) in as an off-white solid which was isolated as the free base: $^1$H NMR (400 MHz, CD$_3$OD) δ 8.21 (s, 1H), 7.72 (d, J=8.4 Hz, 1H), 7.64 (d, J=2.0 Hz, 1H), 7.48 (s, 1H), 7.21 (dd, J=8.4, 2.0 Hz, 1H), 4.0 (s, 3H), 3.1-3.4 (m, 1H), 2.74-2.80 (m, 1H), 2.51-2.59 (m, 1H), 1.96 (m, 1H), 1.04-1.07 (m, 6H); LCMS (ESI) m/e 304.2 [(M+H)$^+$, calcd for C$_{16}$H$_{22}$N$_3$O$_3$, 304.2]; LC/MS retention time (method B): $t_R$=1.35 min; HPLC retention time (method J): $t_R$=9.71 min; HPLC retention time (method K): $t_R$=10.37 min; Chiral HPLC retention time (method I1): $t_R$=4.74 min.

Example 80

1-Isobutyryl-N-(3-methoxy-4-(oxazol-5-yl)phenyl)piperidine-2-carboxamide

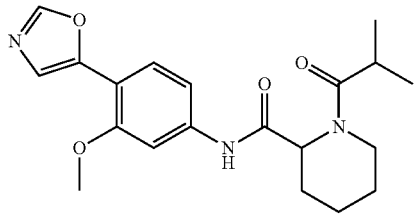 [SMILES: COc1cc(NC(=O)C2CCCCN2C(=O)C(C)C)ccc1-c1cnco1]

Part A. (S)-1-Isobutyrylpiperidine-2-carboxylic acid

To a stirred solution of (S)-piperidine-2-carboxylic acid (500 mg, 3.4 mmol) in dioxane (6 mL) and water (2 mL) was added triethylamine (0.8 mL, 10.3 mmol) followed by isobutyryl chloride (0.41 g, 4.1 mmol) and the reaction mass was stirred at room temperature for 12 h. The reaction mixture was partitioned between ethyl acetate (5 mL) and water (3 mL). Organic layer was separated, dried with sodium sulfate and concentrated under reduced pressure to afford (S)-1-isobutyrylpiperidine-2-carboxylic acid (285 mg, 42% yield). LCMS (ESI) m/e 200.2 [(M+H)$^+$, calcd for C$_{10}$H$_{18}$NO$_3$, 200.1]; LC/MS retention time (method B): $t_R$=1.09 min.

Part B. 1-Isobutyryl-N-(3-methoxy-4-(oxazol-5-yl)phenyl)piperidine-2-carboxamide Prepared in a similar fashion as described in Example 1 using 1-isobutyrylpiperidine-2-carboxylic acid in Part C to give 1-isobutyryl-N-(3-methoxy-4-(oxazol-5-yl)phenyl)piperidine-2-carboxamide (70 mg, 18% yield) as a white solid isolated as the free base: $^1$H NMR (400 MHz, CD$_3$OD) δ 8.21 (s, 1H), 7.73 (d, J=8.8 Hz, 1H), 7.60 (d, J=1.6 Hz, 1H), 7.48 (s, 1H), 7.19 (dd, J=8.8, 2.0 Hz, 1H), 5.23-5.25 (s, 1H), 4.05-4.1 (m, 1H), 4.0 (s, 3H), 3.56-3.70 (m, 1H), 3.0-3.14 (m, 1H), 2.2-2.30 (m, 1H), 1.73-1.94 (m, 3H), 1.52-1.7 (m, 2H), 1.05-1.2 (m, 6H); LCMS (ESI) m/e 370.2 [(M)$^-$, calcd for C$_{20}$H$_{24}$N$_3$O$_4$, 370.2]; LC/MS retention time (method H): $t_R$=1.79 min; HPLC retention time (method L): $t_R$=9.36 min; HPLC retention time (method M): $t_R$=8.61 min;

Example 81

(S)-1-Isopropyl-N-(3-methoxy-4-(oxazol-5-yl)phenyl)pyrrolidine-2-carboxamide

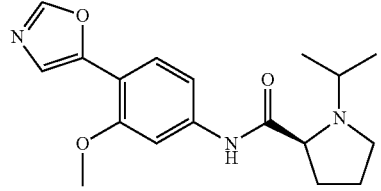 [SMILES: COc1cc(NC(=O)[C@@H]2CCCN2C(C)C)ccc1-c1cnco1]

Prepared in a similar fashion as described in Example 1 using (R)-1-isopropylpyrrolidine-2-carboxylic acid (prepared from L-proline as described by Traverse, J. F. et. al. Org. Lett. 2005, 7, 3151) in Part C to give (S)-1-isopropyl-N-(3-methoxy-4-(oxazol-5-yl)phenyl)pyrrolidine-2-carboxamide (34.6 mg, 10% yield) as an off-white solid, which was isolated as the free base: $^1$H NMR (400 MHz, CD$_3$OD) δ 8.21 (s, 1H), 7.75 (d, J=8.4 Hz, 1H), 7.66 (d, J=1.6 Hz, 1H), 7.48 (s, 1H), 7.24 (dd, J=8.4, 2.0 Hz, 1H), 4.01 (s, 3H), 3.45-3.51 (m, 1H), 3.20-3.29 (m, 1H), 2.88-3.02 (m, 1H), 2.66-2.78 (m, 1H), 2.19-2.31 (m, 1H), 1.96-2.04 (m, 1H), 1.82-1.92 (m, 2H), 1.14-1.21 (m, 6H); LCMS (ESI) m/e 330.2 [(M+H)$^+$, calcd for C$_{18}$H$_{24}$N$_3$O$_3$, 330.2]; LC/MS retention time (method A): $t_R$=1.76 min; HPLC retention time (method J): $t_R$=10.01 min; HPLC retention time (method K): $t_R$=11.09 min; Chiral HPLC retention time (method E3): $t_R$=14.04 min.

Example 82

(S)-1-Isobutyryl-N-(3-methoxy-4-(oxazol-5-yl)phenyl)pyrrolidine-2-carboxamide

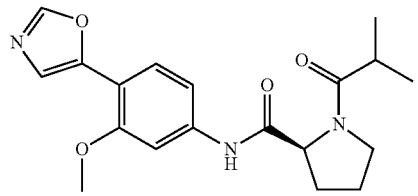 [SMILES: COc1cc(NC(=O)[C@@H]2CCCN2C(=O)C(C)C)ccc1-c1cnco1]

Part A. (S)—N-(3-methoxy-4-(oxazol-5-yl)phenyl) pyrrolidine-2-carboxamide

Prepared in a similar fashion as described in Example 1 using (S)-1-(tert-butoxycarbonyl)pyrrolidine-2-carboxylic acid in Part C to give (S)—N-(3-methoxy-4-(oxazol-5-yl) phenyl)pyrrolidine-2-carboxamide (0.12 g, quantitative) as a brown oil.

Part B. (S)-1-Isobutyryl-N-(3-methoxy-4-(oxazol-5-yl)phenyl)pyrrolidine-2-carboxamide To the solution of (S)—N-(3-methoxy-4-(oxazol-5-yl) phenyl)pyrrolidine-2-carboxamide (0.12 g, 0.3 mmol) in dichloromethane (20 mL) at 0° C. was added diisopropyl ethyl amine (0.2 mL, 1.55 mmol) and the mixture was stirred for 15 min. To this mixture was added isobutyryl chloride (36 mg, 0.34 mmol) dropwise and stirring was continued at room temperature for 12 h. Upon completion the reaction was quenched with saturated aqueous ammonium chloride and extracted with ethyl acetate (2×5 mL). The combined organic layers were dried over sodium sulfate and concentrated under reduced pressure to afford (S)-1-isobutyryl-N-(3-methoxy-4-(oxazol-5-yl)phenyl)pyrrolidine-2-carboxamide (39 mg, 41% yield) as a white solid, isolated as the free base: $^1$H NMR (400 MHz, CD$_3$OD) δ 8.21 (s, 1H), 7.71 (d, J=8.53 Hz, 1H), 7.63 (d, J=1.51 Hz, 1H), 7.47 (s, 1H), 7.19 (dd, J=8.41, 1.88 Hz, 1H), 4.52-4.56 (m, 1H), 3.99 (s, 3H), 3.71-3.79 (m, 2H), 2.83-2.90 (m, 1H), 2.05-2.32 (m, 4H), 1.13-1.18 (m, 6H); LCMS (ESI) m/e 358.2 [(M+H)$^+$, calcd for C$_{19}$H$_{24}$N$_3$O$_4$, 358.2]; LC/MS retention time (method B): t$_R$=1.62 min; HPLC retention time (method L): t$_R$=7.90 min; HPLC retention time (method M): t$_R$=7.34 min; Chiral HPLC retention time (method H1): t$_R$=11.11 min.

Example 83

1-Isopropyl-N-(3-methoxy-4-(oxazol-5-yl)phenyl) piperidine-2-carboxamide

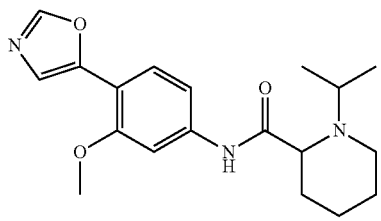 [SMILES: COc1cc(NC(=O)C2CCCCN2C(C)C)ccc1-c1cnco1]

Part A. N-(3-methoxy-4-(oxazol-5-yl)phenyl)piperidine-2-carboxamide

Prepared in a similar fashion as described in Example 1 using 1-isopropylpiperidine-2-carboxylic acid in Part C to give N-(3-methoxy-4-(oxazol-5-yl)phenyl)piperidine-2-carboxamide (80 mg, 24% yield over 2 steps) as a white solid.

Part B. 1-Isopropyl-N-(3-methoxy-4-(oxazol-5-yl) phenyl)piperidine-2-carboxamide To a stirred solution of N-(3-methoxy-4-(oxazol-5-yl) phenyl)piperidine-2-carboxamide (50 mg, 0.17 mmol) in dichloroethane (5 mL) was added triethylamine (167 mg, 1.66 mmol) followed by 2-iodopropane (84 mg, 0.49 mmol) and the resultant mixture was stirred at room temperature overnight. Upon completion of reaction the volatile organics were removed under reduced pressure and the residue was partitioned between water (4 mL) and ethyl acetate (5 mL). The organic layer was separated and washed with brine (3 mL), dried with sodium sulfate and concentrated under reduced pressure to afford crude which was purified by preparative HPLC to give 1-isopropyl-N-(3-methoxy-4-(oxazol-5-yl)phenyl)piperidine-2-carboxamide (30 mg, 53% yield) as a white solid isolated as the free base: $^1$H NMR (400 MHz, CD$_3$OD) δ 8.21 (s, 1H), 7.74 (d, J=8.4 Hz, 1H), 7.65 (d, J=2.0 Hz, 1H), 7.49 (s, 1H), 7.24 (dd, J=8.4, 1.6 Hz, 1H), 4.01 (s, 3H), 3.40-3.47 (m, 1H), 3.39-3.46 (m, 1H), 2.46-2.55 (m, 1H), 1.94-2.05 (m, 2H), 1.77-1.89 (m, 2H), 1.64-1.74 (m, 1H), 1.30-1.51 (m, 2H), 1.25 (d, J=6.78 Hz, 3H), 1.11 (d, J=6.53 Hz, 3H); LCMS (ESI) m/e 344.2 [(M+H)$^+$, calcd C$_{19}$H$_{26}$N$_3$O$_3$, 344.2]; LC/MS retention time (method A): t$_R$=1.48 min; HPLC retention time (method L): t$_R$=5.05 min; HPLC retention time (method M): t$_R$=5.77 min.

Example 84

2-Amino-4-fluoro-N-(3-methoxy-4-(oxazol-5-yl) phenyl)-4-methylpentanamide

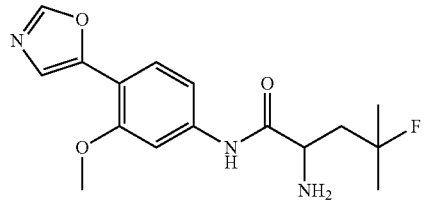 [SMILES: COc1cc(NC(=O)C(N)CC(C)(C)F)ccc1-c1cnco1]

Prepared in a similar fashion as described in Example 1 using 2-(tert-butoxycarbonylamino)-4-fluoro-4-methylpentanoic acid (prepared as described by Easton, C. J. et al. *Synlett*, 2007, 1083) in Part C to give 2-amino-4-fluoro-N-(3-methoxy-4-(oxazol-5-yl)phenyl)-4-methylpentanamide (40 mg, 63% yield) as white solid, which was isolated as the HCl salt: $^1$H NMR (400 MHz, CD$_3$OD) δ 8.30-8.40 (m, 1H), 7.78 (d, J=8.4 Hz, 1H), 7.63 (s, 1H), 7.54 (d, J=2.4 Hz, 1H), 7.29 (dd, J=8.4, 1.6 Hz, 1H), 4.27-4.34 (m, 1H), 4.01 (s, 3H), 2.29-2.39 (m, 2H), 1.49-1.63 (m, 6H); LCMS (ESI) m/e 322.2 [(M+H)$^+$, calcd C$_{16}$H$_{21}$FN$_3$O$_3$, 322.2]; LC/MS retention time (method A): t$_R$=1.37 min; HPLC retention time (method J): t$_R$=9.44 min; HPLC retention time (method K): t$_R$=9.99 min.

Example 85

3-Isopropyl-N-(3-methoxy-4-(oxazol-5-yl)phenyl) piperidine-2-carboxamide

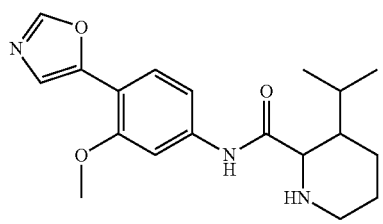

Prepared in a similar fashion as described in Example 1 using 1-(tert-butoxycarbonyl)-3-isopropylpiperidine-2-carboxylic acid (prepared as described by Subramanyam, C. et al. Tet. Lett. 1996, 37, 459) in Part C to give 3-isopropyl-N-(3-methoxy-4-(oxazol-5-yl)phenyl)piperidine-2-carboxamide (28 mg, 52% yield) as an off-white solid, which was isolated as the HCl salt: $^{1}$H NMR (400 MHz, CD$_{3}$OD) δ 10.43-10.48 (m, 1H), 8.47 (br. s., 1H), 7.79 (d, J=8.53 Hz, 1H), 7.62 (s, 2H), 7.25-7.34 (m, 1H), 4.16-4.20 (m, 1H), 4.01 (s, 3H), 3.57-3.67 (m, 1H), 3.13-3.23 (m, 1H), 2.2-2.1 (m, 1H), 2.04-2.19 (m, 2H), 1.88-1.98 (m, 2H), 0.98-1.04 (m, 6H); LCMS (ESI) m/e 344.2 [(M+H)$^{+}$, calcd C$_{19}$H$_{26}$N$_{3}$O$_{3}$, 344.2]; LC/MS retention time (method B): $t_R$=1.63 min; HPLC retention time (method L): $t_R$=5.91 min; HPLC retention time (method M): $t_R$=6.50 min.

Example 86

1-Isopropyl-N-(3-methoxy-4-(oxazol-5-yl)phenyl)piperazine-2-carboxamide

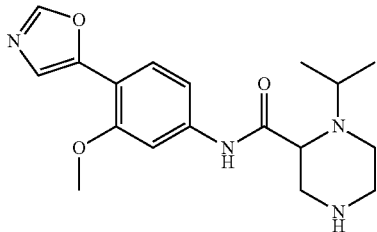

Prepared in a similar fashion as described in Example 1 using 4-(tert-butoxycarbonyl)-1-isopropylpiperazine-2-carboxylic acid in Part C to give 1-isopropyl-N-(3-methoxy-4-(oxazol-5-yl)phenyl)piperazine-2-carboxamide (66 mg, 92% yield) as a yellow solid, which was isolated as the HCl salt: $^{1}$H NMR (400 MHz, CD$_{3}$OD) δ 8.88-9.01 (m, 1H), 7.84 (d, J=8.4 Hz, 2H), 7.69 (s, 1H), 7.45 (d, J=8.0 Hz, 1H), 5.00 (d, J=10.2 Hz, 1H), 4.10-4.18 (m, 1H), 4.04 (s, 3H), 3.83-3.97 (m, 3H), 3.58-3.75 (m, 3H), 1.45-1.55 (m, 6H); LCMS (ESI) m/e 345.2 [(M+H)$^{+}$, calcd C$_{18}$H$_{25}$N$_{4}$O$_{3}$, 345.2]; LC/MS retention time (method A): $t_R$=1.19 min; HPLC retention time (method P): $t_R$=6.14 min; HPLC retention time (method M): $t_R$=5.16 min.

Example 87

3-Isopropyl-N-(3-methoxy-4-(oxazol-5-yl)phenyl)piperidine-2-carboxamide

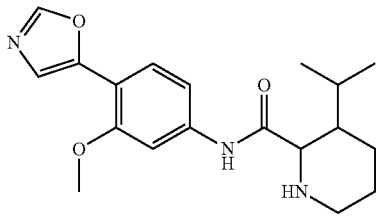

Diastereomer - 1

Prepared in a similar fashion as described in Example 1 using 1-(tert-butoxycarbonyl)-3-isopropylpiperidine-2-carboxylic acid in Part C to give 3-isopropyl-N-(3-methoxy-4-(oxazol-5-yl)phenyl)piperidine-2-carboxamide (14 mg, 4% yield) as a white solid, which was isolated as the TFA salt: $^{1}$H NMR (400 MHz, CD$_{3}$OD) δ 8.23 (s, 1H), 7.78 (d, J=8.4 Hz, 1H), 7.59 (d, J=2.0 Hz, 1H), 7.51 (s, 1 H), 7.26 (dd, J=8.4, 2.0 Hz, 1H), 4.13 (d, J=4.27 Hz, 1H), 4.01 (s, 3H), 3.59-3.66 (m, 1H), 3.13-3.21 (m, 1H), 2.12-2.20 (m, 1H), 2.03-2.09 (m, 1H), 1.88-1.98 (m, 2H), 1.74-1.82 (m, 2H), 1.02 (dd, J=9.6, 6.4 Hz, 6H); LCMS (ESI) m/e 344.2 [(M+H)$^{+}$, calcd C$_{19}$H$_{26}$N$_{3}$O$_{3}$, 344.2]; LC/MS retention time (method H): $t_R$=1.61 min; HPLC retention time (method J): $t_R$=5.97 min; HPLC retention time (method M): $t_R$=6.54 min; Chiral HPLC retention time (method B3): $t_R$=7.14 min.

Example 88

(2R,3R)-3-Isopropyl-N-(3-methoxy-4-(oxazol-5-yl)phenyl)piperidine-2-carboxamide

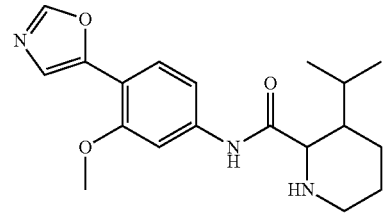 [SMILES: COc1cc(NC(=O)C2NCCCC2C(C)C)ccc1-c1cnco1]

Diastereomer - 2

Prepared in a similar fashion as described in Example 1 using 1-(tert-butoxycarbonyl)-3-isopropylpiperidine-2-carboxylic acid in Part C to give (2R,3R)-3-isopropyl-N-(3-methoxy-4-(oxazol-5-yl)phenyl)piperidine-2-carboxamide (13 mg, 4% yield) as white solid, which was isolated as the TFA salt: $^{1}$H NMR (400 MHz, CD$_{3}$OD) δ 8.23 (s, 1H), 7.78 (d, J=8.4 Hz, 1H), 7.59 (d, J=2.0 Hz, 1H), 7.51 (s, 1H), 7.26 (dd, J=8.8, 2.0 Hz, 1H), 4.14 (d, J=4.02 Hz, 1H), 4.01 (s, 3H), 3.60-3.66 (m, 1H), 3.14-3.21 (m, 1H), 2.11-2.18 (m, 1H), 2.02-2.08 (m, 1H), 1.87-1.98 (m, 2H), 1.72-1.83 (m, 2H), 1.02 (dd, J=10.0, 6. Hz, 6H); LCMS (ESI) m/e 344.2 [(M+H)$^{+}$, calcd C$_{19}$H$_{26}$N$_{3}$O$_{3}$, 344.2]; LC/MS retention time (method H): $t_R$=1.59 min; HPLC retention time (method L): $t_R$=5.97 min; HPLC retention time (method M): $t_R$=6.51 min; Chiral HPLC retention time (method B3): $t_R$=14.96 min.

Example 89

(2R,4S)-4-Fluoro-N-(3-methoxy-4-(oxazol-5-yl)phenyl)pyrrolidine-2-carboxamide

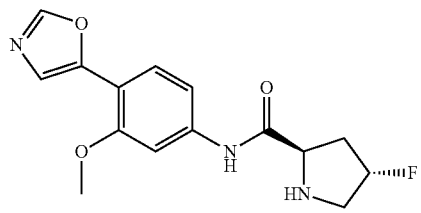 [SMILES: COc1cc(NC(=O)[C@H]2C[C@H](F)CN2)ccc1-c1cnco1]

Prepared in a similar fashion as described in Example 1 using (2R,4S)-1-(tert-butoxycarbonyl)-4-fluoropyrrolidine-2-carboxylic acid in Part C to give (2R,4S)-4-fluoro-N-(3- methoxy-4-(oxazol-5-yl)phenyl)pyrrolidine-2-carboxamide (15 mg, 36% yield) as a white solid, which was isolated as a TFA salt: $^1$H NMR (400 MHz, CD$_3$OD) δ 8.6 (s, 1H), 7.81 (d, J=8.8 Hz, 1H), 7.63-7.66 (m, 2H), 7.31 (dd, J=8.8, 2.0 Hz, 1H), 5.42-5.58 (m, 1H), 4.66-4.71 (m, 1H), 4.03 (s, 3H), 3.81-3.91 (m, 1H), 3.55-3.70 (m, 1H), 2.81-2.99 (m, 1H), 2.58-2.70 (m, 1H); LCMS (ESI) m/e 306.0 [(M+H)$^+$, calcd for C$_{15}$H$_{17}$FN$_3$O$_3$, 306.1]; LC/MS retention time (method A): t$_R$=1.27 min; HPLC retention time (method J): t$_R$=8.24 min; HPLC retention time (method K): t$_R$=8.96 min; Chiral HPLC retention time (method A3): t$_R$=13.80 min.

Example 90

(2R,4R)-4-Fluoro-N-(3-methoxy-4-(oxazol-5-yl)phenyl)pyrrolidine-2-carboxamide

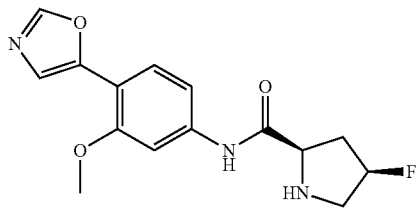 [SMILES: COc1cc(NC(=O)[C@H]2C[C@@H](F)CN2)ccc1-c1cnco1]

Prepared in a similar fashion as described in Example 1 using (2R,4R)-1-(tert-butoxycarbonyl)-4-fluoropyrrolidine-2-carboxylic acid in Part C to give (2R,4R)-4-fluoro-N-(3-methoxy-4-(oxazol-5-yl)phenyl)pyrrolidine-2-carboxamide (25 mg, 30% yield) as a white solid, which was isolated as a TFA salt: $^1$H NMR (400 MHz, CD$_3$OD) δ 8.6 (s, 1H), 7.81 (d, J=8.8 Hz, 1H), 7.62-7.67 (m, 2H), 7.31 (dd, J=8.8, 2.0 Hz, 1H), 5.42-5.58 (m, 1H), 4.66-4.72 (m, 1H), 4.03 (s, 3H), 3.81-3.92 (m, 1H), 3.55-3.70 (m, 1H), 2.82-2.99 (m, 1H), 2.58-2.70 (m, 1H); LCMS (ESI) m/e 306.0 [(M+H)$^+$, calcd for C$_{15}$H$_{17}$FN$_3$O$_3$, 306.2]; LC/MS retention time (method A): t$_R$=1.31 min; HPLC retention time (method J): t$_R$=8.78 min; HPLC retention time (method K): t$_R$=9.62 min; Chiral HPLC retention time (method B1): t$_R$=12.63 min.

Example 91

N-(3-Methoxy-4-(oxazol-5-yl)phenyl)-3-(trifluoromethyl)piperidine-2-carboxamide

Diastereomer - 1

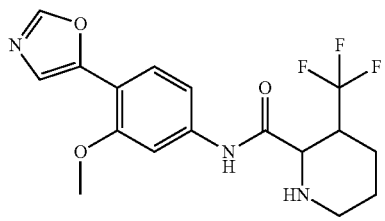

Part A. 3-(Trifluoromethyl)piperidine-2-carboxylic acid

To a stirred solution of 3-(trifluoromethyl)picolinic acid (0.5 g, 2.62 mmol) in acetic acid (4 mL) was added platinum(IV) oxide (0.25 g, 1.101 mmol) and the mixture was stirred at room temperature under a hydrogen atmosphere (60 psi) for 14 h. After the reaction was complete, the reaction mixture was filtered through a pad of diatomaceous earth)(Celite® and the filtrate was concentrated under reduced pressure to afford 3-(trifluoromethyl)piperidine-2-carboxylic acid (500 mg, 97% yield). LC/MS Method=Column: Zorbax AQ (4.6×50) 3.5 μm; Mphase A: 0.1% HCOOH in Water; Mphase B: ACN; Flow: 1.0 ml/min. LCMS (ESI) m/e 198.2, [(M+H)$^+$, calcd for C$_7$H$_{11}$F$_3$NO$_2$, 198.1]; LC/MS retention time t$_R$=0.89 min.

Part B. N-(3-Methoxy-4-(oxazol-5-yl)phenyl)-3-(trifluoromethyl)piperidine-2-carboxamide Prepared in a similar fashion as described in Example 1 using 3-(trifluoromethyl)piperidine-2-carboxylic acid in Part C to give N-(3-methoxy-4-(oxazol-5-yl)phenyl)-3-(trifluoromethyl)piperidine-2-carboxamide (8 mg, 6% yield) as a white solid isolated as the HCl salt: $^1$H NMR (400 MHz, CDCl$_3$) δ 7.88 (s, 1H), 7.70-7.72 (m, 2H), 7.51 (s, 1H), 6.98 (dd, J=8.4, 1.6 Hz, 1H), 4.00 (s, 3H), 3.81-3.85 (m, 1H), 3.18-3.29 (m, 1H), 2.96-3.04 (m, 1H), 2.64-2.72 (m, 1H), 1.99-2.07 (m, 1H), 1.70-1.83 (m, 2H), 1.40-1.46 (m, 1H); LCMS (ESI) m/e 370.0 [(M+H)$^+$, calcd for C$_{17}$H$_{19}$F$_3$N$_3$O$_3$, 370.1]; LC/MS retention time (method B): t$_R$=1.52 min; HPLC retention time (method L): t$_R$=5.38 min; HPLC retention time (method M): t$_R$=6.04 min; Chiral HPLC retention time (method G1): t$_R$=6.47 min.

Example 92

N-(3-Methoxy-4-(oxazol-5-yl)phenyl)-3-(trifluoromethyl)piperidine-2-carboxamide

Diastereomer 2

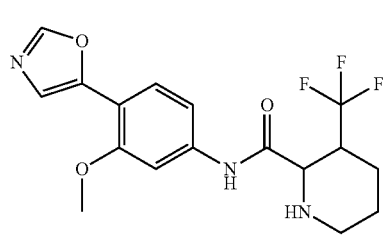

Prepared as described in Example 91 to give N-(3-methoxy-4-(oxazol-5-yl)phenyl)-3-(trifluoromethyl)piperidine-2-carboxamide (8 mg, 6% yield) as white solid, which was isolated as the HCl salt: $^1$H NMR (400 MHz, CD$_3$OD) δ 8.21 (s, 1H), 7.73 (d, J=8.4 Hz, 1H), 7.6 (d, J=2 Hz, 1H), 7.48 (s, 1H), 7.20 (dd, J=8.4, 2.0 Hz, 1H), 4.01 (s, 3H), 3.82-3.84 (m, 1H), 2.76-2.84 (m, 2H), 2.29-2.39 (m, 1H), 1.74-1.93 (m, 2H), 1.54-1.64 (m, 2H); LCMS (ESI) m/e 370.0, [(M+H)$^+$, calcd for C$_{18}$H$_{19}$F$_3$N$_2$O$_3$, 370.35]; LC/MS retention time (method A): t$_R$=1.54 min; HPLC retention time (method L): t$_R$=4.89 min; HPLC retention time (method M): t$_R$=5.67 min; Chiral HPLC retention time (method G1): t$_R$=9.44 min.

Example 93

2-Amino-N-(3-methoxy-4-(oxazol-5-yl)phenyl)-2-(2-methylcyclohexyl)acetamide

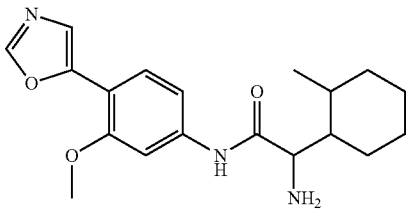 [SMILES: COc1cc(NC(=O)C(N)C2CCCCC2C)ccc1-c1cnco1]

Part A. 2-Acetamido-2-(2-methylcyclohexyl)acetic acid

To a stirred solution of 2-acetamido-2-(o-tolyl)acetic acid (80 mg, 0.386 mmol) in 2-propanol (10 mL) was added 10% rhodium on carbon (20 mg, 0.386 mmol) and the mixture was subjected to hydrogenation (80 psi) for 14 h at 60° C. After the reaction was complete, the mixture was allowed to cool room temperature and was filtered through a pad of diatomaceous earth (Celite®). The filtrate was concentrated under reduced pressure to afford 2-acetamido-2-(2-methylcyclohexyl)acetic acid (60 mg, 73% yield): LCMS (ESI) m/e 214 [(M+H)$^+$, calcd for $C_{11}H_{20}NO_3$, 214.1]; LC/MS retention time (method C): $t_R$=1.41 min

Part B. 2-((tert-Butoxycarbonyl)amino)-2-(2-methylcyclohexyl)acetic acid

To a stirred solution of 2-amino-2-(2-methylcyclohexyl)acetic acid (60 mg, 0.350 mmol) in dioxane (2 mL) and water (2 mL) was added NaHCO$_3$ (149 mg, 1.402 mmol) followed by Boc$_2$O (0.163 mL, 0.701 mmol). The reaction mixture was stirred at rt for 14 h. After completion of the reaction, the volatiles were removed under reduced pressure and the residue was acidified with saturated aq. citric acid solution to pH=4 and extracted with ethyl acetate (2×20 mL). The combined organic extracts were dried over sodium sulfate and concentrated under reduced pressure to afford 2-((tert-butoxycarbonyl)amino)-2-(2-methylcyclohexyl)acetic acid (60 mg, 0.221 mmol, 63% yield) as a colorless oil. LCMS (ESI) m/e 270.2 [(M)$^-$, calcd for $C_{14}H_{24}NO_4$, 270.2]; LC/MS retention time (method C): $t_R$=1.76 min

Part C. 2-Amino-N-(3-methoxy-4-(oxazol-5-yl)phenyl)-2-(2-methylcyclohexyl)acetamide Prepared in a similar fashion as described in Example 1 using 2-((tert-butoxycarbonyl)amino)-2-(2-methylcyclohexyl)acetic acid in Part C to give 2-amino-N-(3-methoxy-4-(oxazol-5-yl)phenyl)-2-(2-methylcyclohexyl)acetamide (12 mg, 19% yield) as an off-white solid isolated as the TFA salt: $^1$H NMR (400 MHz, CD$_3$OD) δ 8.21-8.25 (m, 1H), 7.75-7.80 (m, 1H), 7.64-7.67 (m, 1H), 7.49-7.53 (m, 1H), 7.24-7.32 (m, 1H), 4.01 (s, 3H), 3.65-3.78 (m, 1H), 1.73-2.20 (m, 4H), 1.24-1.68 (m, 6H), 1.05-1.16 (m, 3H); LCMS (ESI) m/e 344.2 [(M+H)$^+$, calcd for $C_{19}H_{26}N_3O_3$, 344.2]; LC/MS retention time (method A): $t_R$=1.58, 1.73 min (Diastereomeric mixture); HPLC retention time (method L): $t_R$=5.73, 5.80 min (Diastereomeric mixture); HPLC retention time (method M): $t_R$=6.75 min (Diastereomers unresolved).

Example 94

2-Amino-3-cyclobutyl-N-(2-fluoro-5-methoxy-4-(oxazol-5-yl)phenyl)propanamide

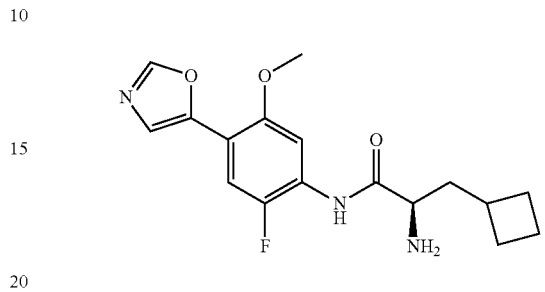

Part A. 1-Bromo-5-fluoro-2-methoxy-4-nitrobenzene

To a solution of 2-bromo-4-fluoro-5-nitrophenol (2.0 g, 8.4 mmol) and potassium carbonate (3.51 g, 25.4 mmol) in acetone (20 mL) was added methyl iodide (1.79 g, 12.6 mmol) and the reaction mixture was heated at reflux for 4 h. After the reaction was complete, the mixture was concentrated under reduced pressure and the reaction mixture was diluted with water and ethyl acetate. Combined organic extracts were dried over sodium sulfate and concentrated under reduced pressure to afford 1-bromo-5-fluoro-2-methoxy-4-nitrobenzene (1.90 g, 90% yield) as a brown solid. $^1$H NMR (400 MHz, CDCl$_3$) δ 7.56-7.54 (m, 2H), 3.97 (s, 3H).

Part B. 1-Fluoro-4-methoxy-2-nitro-5-vinylbenzene

To a solution of bromo-5-fluoro-2-methoxy-4-nitrobenzene (0.50 g, 2 mmol) in toluene (15 mL) and ethanol (5 mL) was added vinyl boronic anhydride (0.96 g, 4 mmol), sodium carbonate (0.25 g, 2.4 mmol) and tetrakis(triphenylphosphine)palladium(0) (0.1 g, 0.09 mmol) and the reaction was degassed with nitrogen for 5 min. The mixture was heated at 95° C. in a pressure tube for 12 h. The reaction mixture was cooled and was quenched with water (5 mL) and the mixture was extracted with ethyl acetate (2×8 mL). The combined organic extracts were dried with sodium sulfate and concentrated under reduced pressure to afford 1-fluoro-4-methoxy-2-nitro-5-vinylbenzene (0.33 g, 83% yield) as a yellow solid. $^1$H NMR (400 MHz, CDCl$_3$) δ 7.56-7.52 (m, 1H), 7.36-7.33 (d, J=12 Hz, 1H), 7.03-6.96 (dd, J=10.4 Hz, 1H), 5.91-5.86 (d, J=20 Hz, 1H), 5.54-5.52 (d, J=11.2 Hz, 1H).

Part C. 5-Fluoro-2-methoxy-4-nitrobenzaldehyde

To a solution of 1-fluoro-4-methoxy-2-nitro-5-vinylbenzene (0.030 g, 1.5 mmol) in 1,4-dioxane (10 mL) and water (3 mL) at 0° C. was added 2,6-lutidine (0.35 mL, 3 mmol) followed by osmium tetroxide (0.014 mL, 0.45 mmol) and sodium periodate (1.3 g, 6 mmol). After addition of the reagents, the cooling bath was removed and the reaction mass was stirred at room temperature for 14 h. After the reaction was complete, water (1 mL) was added to the reaction mixture and the mixture was extracted with ethyl acetate (2×4 mL). The combined organic extracts were washed with brine and concentrated under reduced pressure to afford the crude product, which was purified by a flash chromatography to afford 5-fluoro-2-methoxy-4-nitrobenzaldehyde (0.22 g, 85% yield) as a yellow solid. $^1$H NMR (400 MHz, CDCl$_3$) δ 10.45 (s, 1H), 7.74-7.71 (d, J=10 Hz, 1H), 7.64-7.63 (d, J=5.6 Hz, 1H), 4.02 (s, 3H).

Part D.
5-(5-Fluoro-2-methoxy-4-nitrophenyl)oxazole

5-Fluoro-2-methoxy-4-nitrobenzaldehyde (0.02 g, 0.099 mmol) was subjected to reaction with TosMIC (19.4 mg, 0.099 mmol) using potassium carbonate (13.6 mg, 0.099 mmol) in methanol (10 mL) to afford 5-(5-fluoro-2-methoxy-4-nitrophenyl)oxazole (20 mg, 85% yield) as a yellow solid as described in Example 1, Part A. $^1$H NMR (400 MHz, DMSO-d$_6$) δ 8.65 (s, 1H), 7.89 (s, 1H), 7.85-7.83 (m, 2H), 4.07 (s, 3H).

Part E. 2-Amino-3-cyclobutyl-N-(2-fluoro-5-methoxy-4-(oxazol-5-yl)phenyl)propanamide Prepared in a similar fashion as described in Example 1, Parts B-D using 2-(tert-butoxycarbonylamino)-3-cyclobutylpropanoic acid in Part C to give 2-amino-3-cyclobutyl-N-(2-fluoro-5-methoxy-4-(oxazol-5-yl)phenyl)propanamide (50 mg, 36% yield) as a pale yellow solid, which was isolated as the free base: $^1$H NMR (400 MHz, CD$_3$OD) δ 8.24 (s, 1H), 8.06 (d, J=6.4 Hz, 1H), 7.54-7.61 (m, 2H), 4.00 (s, 3H), 3.51-3.57 (m, 1H), 2.49-2.60 (m, 1H), 2.08-2.19 (m, 2H), 1.73-1.98 (m, 6H); LCMS (ESI) m/e 334.2, [(M+H)$^+$, calcd for C$_{17}$H$_{21}$FN$_3$O$_3$, 334.2]; LC/MS retention time (method B): t$_R$=1.58 min; HPLC retention time (method L): t$_R$=5.58 min; HPLC retention time (method M): t$_R$=6.37 min; Chiral HPLC retention time (method A2): t$_R$=9.07 min (HPLC predominant enantiomer)–(Small amount of other enantiomer formed from using commercial available amino acid).

Example 95

2-Amino-3-cyclopropyl-N-(2-fluoro-5-methoxy-4-(oxazol-5-yl)phenyl)propanamide

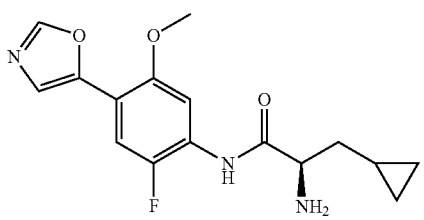 [SMILES: COc1cc(NC(=O)[C@H](N)CC2CC2)c(F)cc1-c1cnco1]

Prepared in a similar fashion as described in Example 94 using 2-(tert-butoxycarbonylamino)-3-cyclopropylpropanoic acid to give 2-amino-3-cyclopropyl-N-(2-fluoro-5-methoxy-4-(oxazol-5-yl)phenyl)propanamide (6.6 mg, 8% yield) as an off-white solid, which was isolated as the free base: $^1$H NMR (400 MHz, CD$_3$OD) δ 8.25 (s, 1H), 8.08 (d, J=6.4 Hz, 1H), 7.56 (s, 2H), 4.00 (s, 3H), 3.65-3.69 (m, 1H), 1.64-1.70 (m, 2H), 0.82-0.92 (m, 1H), 0.46-0.57 (m, 2H), 0.12-0.20 (m, 2H); LCMS (ESI) m/e 320.2 [(M+H)$^+$, calcd for C$_{16}$H$_{19}$FN$_3$O$_3$, 320.1]; LC/MS retention time (method B): t$_R$=1.45 min; HPLC retention time (method L): t$_R$=5.06 min; HPLC retention time (method M): t$_R$=5.77 min; Chiral HPLC retention time (method A3): t$_R$=10.67 min (HPLC predominant enantiomer). (Small amount of other enantiomer formed from using commercial available amino acid).

Example 96

(R)-2-Amino-N-(2-fluoro-5-methoxy-4-(oxazol-5-yl)phenyl)-3-methylbutanamide

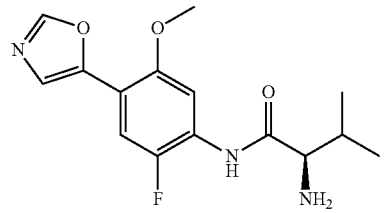 [SMILES: COc1cc(NC(=O)[C@H](N)C(C)C)c(F)cc1-c1cnco1]

Prepared in a similar fashion as described in Example 94 using (R)-2-(tert-butoxycarbonylamino)-3-methylbutanoic acid to give (R)-2-amino-N-(2-fluoro-5-methoxy-4-(oxazol-5-yl)phenyl)-3-methylbutanamide (5.4 mg, 13% yield) as a white solid, which was isolated as the free base: $^1$H NMR (400 MHz, CD$_3$OD) δ 8.25 (s, 1H), 8.08 (d, J=6.8 Hz, 1H), 7.56 (s, 2H), 4.00 (s, 3H), 3.40-3.44 (m, 1H), 2.15-2.24 (m, 1H), 1.08 (d, J=6.8 Hz, 3H), 0.98 (d, J=6.8 Hz, 3H); LCMS (ESI) m/e 308.2, [(M+H)$^+$, calcd for C$_{15}$H$_{19}$FN$_3$O$_3$, 308.1]; LC/MS retention time (method B): t$_R$=1.39 min; HPLC retention time (method J): t$_R$=9.52 min; HPLC retention time (method K): t$_R$=10.23 min; Chiral HPLC retention time (method A4): t$_R$=9.89 min.

Example 97

2-Amino-N-(2-fluoro-5-methoxy-4-(oxazol-5-yl)phenyl)-4,4-dimethylpentanamide

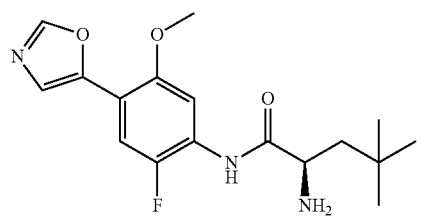 [SMILES: COc1cc(NC(=O)[C@H](N)CC(C)(C)C)c(F)cc1-c1cnco1]

Prepared in a similar fashion as described in Example 94 using 2-(tert-butoxycarbonylamino)-4,4-dimethylpentanoic acid to give 2-amino-N-(2-fluoro-5-methoxy-4-(oxazol-5-yl)phenyl)-4,4-dimethylpentanamide (50 mg, 43% yield) as a white solid, which was isolated as the free base: $^1$H NMR (400 MHz, CD$_3$OD) δ 8.25 (s, 1H), 8.09 (d, J=6.8 Hz, 1H), 7.55-7.61 (m, 2H), 4.00 (s, 3H), 3.60-3.64 (m, 1H), 1.97-2.03 (m, 1H), 1.41-1.47 (m, 1H), 1.04 (s, 9H); LCMS (ESI) m/e 336.2, [(M+H)$^+$, calcd for C$_{17}$H$_{23}$FN$_3$O$_3$, 336.2]; LC/MS retention time (method B): t$_R$=1.60 min; HPLC retention time (method L): t$_R$=5.65 min; HPLC retention time (method M): t$_R$=6.53 min; Chiral HPLC retention time (method F1): t$_R$=14.87 min.

Example 98

(R)-2-Amino-N-(2-fluoro-5-methoxy-4-(oxazol-5-yl)phenyl)-4-methylpentanamide

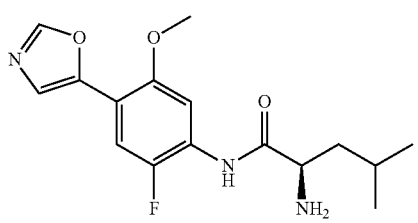 [SMILES: COc1cc(NC(=O)[C@H](N)CC(C)C)c(F)cc1-c1cnco1]

Prepared in a similar fashion as described in Example 94 using (R)-2-(tert-butoxycarbonylamino)-4-methylpentanoic acid to give (R)-2-amino-N-(2-fluoro-5-methoxy-4-(oxazol-5-yl)phenyl)-4-methylpentanamide (30 mg, 49% yield) as an off-white solid, which was isolated as the free base: $^1$H NMR (400 MHz, CD$_3$OD) δ 8.25 (s, 1H), 8.07 (d, J=6.4 Hz, 1H), 7.55-7.61 (m, 2H), 4.00 (s, 3H), 3.63-3.68 (m, 1H), 1.79-1.88 (m, 1H), 1.68-1.76 (m, 1H), 1.50-1.58 (m, 1H), 1.00-1.04 (m, 6H); LCMS (ESI) m/e 322.2 [(M+H)$^+$, calcd for C$_{16}$H$_{21}$FN$_3$O$_3$, 322.2]; LC/MS retention time (method B): t$_R$=1.53 min; HPLC retention time (method J): t$_R$=10.57 min; HPLC retention time (method K): t$_R$=11.29 min; Chiral HPLC retention time (method A3): t$_R$=7.41 min.

Example 99

(S)-2-Amino-N-(2-fluoro-5-methoxy-4-(oxazol-5-yl)phenyl)-4-methylpentanamide

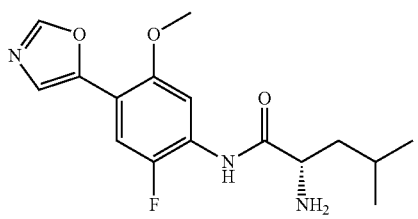 [SMILES: COc1cc(NC(=O)[C@@H](N)CC(C)C)c(F)cc1-c1cnco1]

Prepared in a similar fashion as described in Example 94 using (S)-2-(tert-butoxycarbonylamino)-4-methylpentanoic acid to give (S)-2-amino-N-(2-fluoro-5-methoxy-4-(oxazol-5-yl)phenyl)-4-methylpentanamide (11 mg, 9% yield) as a white solid, which was isolated as the free base: $^1$H NMR (400 MHz, CD$_3$OD) δ 8.25 (s, 1H), 8.08 (d, J=6.8 Hz, 1H), 7.54-7.61 (m, 2H), 4.00 (s, 3H), 3.57-3.62 (m, 1H), 1.79-1.89 (m, 1H), 1.66-1.75 (m, 1H), 1.46-1.55 (m, 1H), 1.01 (dd, J=7.65, 6.65 Hz, 6H); LCMS (ESI) m/e 322.2 [(M+H)$^+$, calcd for C$_{16}$H$_{21}$FN$_3$O$_3$, 322.2]; LC/MS retention time (method B): t$_R$=1.53 min; HPLC retention time (method L): t$_R$=5.37 min; HPLC retention time (method M): t$_R$=6.06 min; Chiral HPLC retention time (method A3): t$_R$=8.44 min.

Example 100

(R)-2-Amino-2-cyclopentyl-N-(2-fluoro-5-methoxy-4-(oxazol-5-yl)phenyl)acetamide

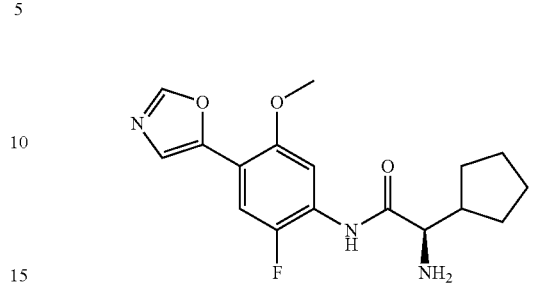

Prepared in a similar fashion as described in Example 94 using (R)-2-((tert-butoxycarbonyl)amino)-2-cyclopentylacetic acid to give (R)-2-amino-2-cyclopentyl-N-(2-fluoro-5-methoxy-4-(oxazol-5-yl)phenyl)acetamide (8 mg, 10% yield) as a white solid, which was isolated as the free base: $^1$H NMR (400 MHz, CD$_3$OD) δ 8.23-8.25 (m, 1H), 8.03 (d, J=6.4 Hz, 1H), 7.54-7.62 (m, 2H), 4.00 (s, 3H), 3.45-3.49 (m, 1H), 2.20-2.29 (m, 1H), 1.58-1.89 (m, 6H), 1.39-1.55 (m, 2H); LCMS (ESI) m/e 334.2 [(M+H)$^+$, calcd for C$_{17}$H$_{21}$FN$_3$O$_3$, 334.2]; LC/MS retention time (method C): t$_R$=1.69 min; HPLC retention time (method L): t$_R$=5.44 min; HPLC retention time (method M): t$_R$=6.46 min.

Example 101

(R)-2-Amino-N-(2-cyano-5-methoxy-4-(oxazol-5-yl)phenyl)-4-methylpentanamide

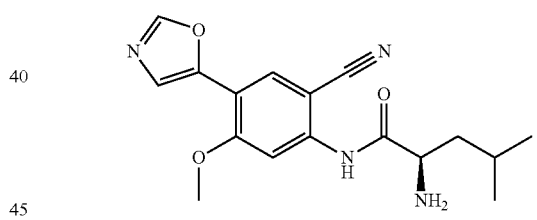

Part A. (R)-tert-Butyl(1-((2-bromo-5-methoxy-4-(oxazol-5-yl)phenyl)amino)-4-methyl-1-oxopentan-2-yl)carbamate To a stirred solution of 2-bromo-5-methoxy-4-(oxazol-5-yl)aniline (2.0 g, 7.4 mmol) (prepared as described by Dyke, H. J. et al., PCT Int. Appl. (2003), WO2003053958A1) and (R)-2-((tert-butoxycarbonyl)amino)-4-methylpentanoic acid (2.06 g, 8.92 mmol) in pyridine (20 mL) at −10° C. was added POCl$_3$ (0.85 mL, 8.8 mmol) drop wise and the reaction was stirred at this temperature for 30 min. The reaction was then stirred at room temperature for 1 hr. After the reaction was complete, the solvent was evaporated and the residue partitioned between with 1.0 N aqueous HCl and ethyl acetate. The organic layer was washed with water, dried (Na$_2$SO$_4$) and purified by silica gel column chromatography to give (R)-tert-butyl(1-((2-bromo-5-methoxy-4-(oxazol-5-yl)phenyl)amino)-4-methyl-1-oxopentan-2-yl)carbamate (2 g, 47% yield): LCMS (ESI) m/e 482.8 [(M+

H)+, calcd for $C_{21}H_{29}BrN_3O_5$, 482.1]; LC/MS retention time (method C): $t_R=1.09$ min.

Part B. (R)-tert-Butyl(1-((2-cyano-5-methoxy-4-(oxazol-5-yl)phenyl)amino)-4-methyl-1-oxopentan-2-yl)carbamate To the solution of (R)-tert-butyl(1-((2-bromo-5-methoxy-4-(oxazol-5-yl)phenyl)amino)-4-methyl-1-oxopentan-2-yl)carbamate (200 mg, 0.41 mmol) in NMP (6 mL) was added CuCN (74 mg, 0.82 mmol), and potassium iodide (6 mg, 0.04 mmol). The resultant mixture was heated at 160° C. for 5 h. The reaction mixture was cooled to room temperature and partitioned between water and ethyl acetate. The organic layer was separated, dried ($Na_2SO_4$) and concentrated under reduced pressure to afford (R)-tert-butyl(1-((2-cyano-5-methoxy-4-(oxazol-5-yl)phenyl)amino)-4-methyl-1-oxopentan-2-yl)carbamate (82 mg, 47% yield): LCMS (ESI) m/e 429.9 [(M+H)+, calcd for $C_{22}H_{29}N_4O_5$, 429.2]; LC/MS retention time (method D): $t_R=0.98$ min.

Part C. (R)-2-Amino-N-(2-cyano-5-methoxy-4-(oxazol-5-yl)phenyl)-4-methylpentanamide Prepared in a similar fashion as described in Example 1, Part D to give (R)-2-amino-N-(2-cyano-5-methoxy-4-(oxazol-5-yl)phenyl)-4-methylpentanamide (49.7 mg, 81% yield) as a white solid, which was isolated as the free base: $^1$H NMR (400 MHz, $CD_3OD$) δ 8.28 (s, 1H), 8.13 (s, 1H), 8.08 (s, 1H), 7.59 (s, 1H), 4.10 (s, 3H), 3.56-3.61 (m, 1H), 1.85-1.94 (m, 1H), 1.71-1.79 (m, 1H), 1.49-1.57 (m, 1H), 1.03 (dd, J=7.40, 6.65 Hz, 6H); LCMS (ESI) m/e 329.2 [(M+H)+, calcd for $C_{17}H_{21}N_4O_3$, 329.2]; LC/MS retention time (method A): $t_R=1.67$ min; HPLC retention time (method L): $t_R=5.25$ min; HPLC retention time (method M): $t_R=5.76$ min; Chiral HPLC retention time (method A2): $t_R=13.61$ min.

Example 102

(R)-2-Amino-N-(5-methoxy-4-(oxazol-5-yl)-2-(2H-tetrazol-5-yl)phenyl)-4-methylpentanamide

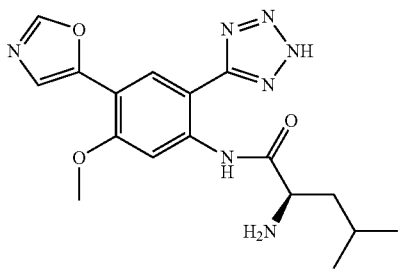 [SMILES: COc1cc(NC(=O)[C@H](N)CC(C)C)c(-c2nn[nH]n2)cc1-c1cnco1]

Part A. (R)-tert-Butyl(1-((4-bromo-2-cyano-5-methoxyphenyl)amino)-4-methyl-1-oxopentan-2-yl)carbamate To a stirred solution of 2-amino-5-bromo-4-methoxybenzonitrile (0.5 g, 2.202 mmol) (prepared as described by Buchmann, Bernd et al, PCT Int. Appl., 2010009845, 2010) and (R)-2-((tert-butoxycarbonyl)amino)-4-methylpentanoic acid (0.611 g, 2.64 mmol) in pyridine (20 mL) at −10° C. was added $POCl_3$ (0.267 mL, 2.86 mmol) dropwise and the reaction mixture was stirred at this temperature for 30 min. The reaction mixture was then stirred at room temperature for 1 h. Additional $POCl_3$ (3 mL) was then added and the reaction mixture was stirred for an additional 2 h at room temperature. After the reaction was complete, the solvent was evaporated and the residue partitioned between with 1.0 N aqueous HCl and ethyl acetate. The organic layer was washed with water, dried ($Na_2SO_4$) and purified by silica gel column chromatography to afford (R)-tert-butyl(1-((4-bromo-2-cyano-5-methoxyphenyl)amino)-4-methyl-1-oxopentan-2-yl)carbamate (700 mg, 67% yield): LCMS (ESI) m/e 440.2 [(M+H)+, calcd for $C_{19}H_{27}BrN_3O_4$, 440.1]; LC/MS retention time (method A): $t_R=2.13$ min.

Part B. (R)-tert-Butyl(1-((4-bromo-5-methoxy-2-(2H-tetrazol-5-yl)phenyl)amino)-4-methyl-1-oxopentan-2-yl)carbamate To a stirred solution of (R)-tert-butyl(1-((4-bromo-2-cyano-5-methoxyphenyl)amino)-4-methyl-1-oxopentan-2-yl)carbamate (0.7 g, 1.594 mmol) and ammonium chloride (0.93 g, 17.42 mmol) in DMF (15 mL) was added sodium azide (1.13 g, 17.42 mmol) and the reaction mixture was stirred at 100° C. for 2 h. After the disappearance of starting material, water was added and the mixture was extracted with dichloromethane (2×). The organic layer was washed with water, dried (sodium sulfate) and concentrated under reduced pressure to give (R)-tert-butyl(1-((4-bromo-5-methoxy-2-(2H-tetrazol-5-yl)phenyl)amino)-4-methyl-1-oxopentan-2-yl)carbamate (0.64 g, 70% yield) as an off-white solid: LCMS (ESI) m/e 483.2, [(M+H)+, calcd for $C_{19}H_{28}BrN_6O_4$, 483.13]; LC/MS retention time (method A): $t_R=1.55$ min.

Part C. (R)-tert-Butyl(1-((5-methoxy-2-(2H-tetrazol-5-yl)-4-vinylphenyl)amino)-4-methyl-1-oxopentan-2-yl)carbamate To a stirred solution of (R)-tert-butyl(1-((4-bromo-5-methoxy-2-(2H-tetrazol-5-yl)phenyl)amino)-4-methyl-1-oxopentan-2-yl)carbamate (0.6 g, 1.241 mmol), vinyl boronic anhydride pyridine complex (0.597 g, 2.483 mmol) and cesium carbonate (1.213 g, 3.72 mmol) in dioxane (20 mL) and water (5 mL) was added tetrakis(triphenylphosphine)palladium(0) (0.143 g, 0.124 mmol) and the reaction mixture was stirred at 95° C. for 14 h. After the reaction was complete, ethyl acetate was added and the organic layer was separated and washed with water, dried, and taken to next step without further purification. LCMS (ESI) m/e 431.5 [(M+H)+, calcd for $C_{21}H_{31}N_6O_4$, 431.2]; LC/MS retention time (method A): $t_R=1.56$ min.

Part D. (R)-tert-Butyl(1-((4-formyl-5-methoxy-2-(2H-tetrazol-5-yl)phenyl)amino)-4-methyl-1-oxopentan-2-yl)carbamate To a stirred solution of (R)-tert-butyl(1-((5-methoxy-2-(2H-tetrazol-5-yl)-4-vinylphenyl)amino)-4-methyl-1-oxopentan-2-yl)carbamate (0.85 g, 1.974 mmol) and 2,6-lutidine (0.460 mL, 3.95 mmol) in dioxane (25 mL) and water (5 mL) was added osmium tetraoxide (0.744 mL, 2.369 mmol) at 0° C. followed by the addition of sodium periodate (1.267 g, 5.92 mmol) and the reaction was stirred at room temperature for 10 h. After the disappearance of starting material, water was added and the mixture was extracted with EtOAc. The organic layer was washed with water followed by brine solution, dried ($Na_2SO_4$), concentrated, and taken to the next step without purification. LCMS (ESI) m/e 433.2 [(M+H)$^+$, calcd for $C_{20}H_{29}N_6O_5$, 433.2]; LC/MS retention time (method A): $t_R$=1.49 min.

Part E. (R)-tert-Butyl(1-((5-methoxy-4-(oxazol-5-yl)-2-(2H-tetrazol-5-yl)phenyl)amino)-4-methyl-1-oxopentan-2-yl)carbamate (R)-tert-butyl(1-((4-formyl-5-methoxy-2-(2H-tetrazol-5-yl)phenyl)amino)-4-methyl-1-oxopentan-2-yl)carbamate was subjected to reaction with TosMIC (54 mg, 0.277 mmol) using potassium carbonate (38 mg, 0.277 mmol) in methanol (20 mL) to afford (R)-tert-butyl(1-((5-methoxy-4-(oxazol-5-yl)-2-(2H-tetrazol-5-yl)phenyl)amino)-4-methyl-1-oxopentan-2-yl)carbamate (150 mg, 55% yield) as described in Example 1, Part A: LCMS (ESI) m/e 470.5 [(M)$^-$, calcd for $C_{22}H_{28}N_7O_5$, 470.2]; LC/MS retention time (method C): $t_R$=1.64 min.

Part F. (R)-2-Amino-N-(5-methoxy-4-(oxazol-5-yl)-2-(2H-tetrazol-5-yl)phenyl)-4-methylpentanamide (R)-tert-Butyl(1-((5-methoxy-4-(oxazol-5-yl)-2-(2H-tetrazol-5-yl)phenyl)amino)-4-methyl-1-oxopentan-2-yl)carbamate was subjected to Boc deprotection as described in Example 1, Part D to give (R)-2-amino-N-(5-methoxy-4-(oxazol-5-yl)-2-(2H-tetrazol-5-yl)phenyl)-4-methylpentanamide (15 mg, 27% yield) as a white solid isolated as the TFA salt: $^1$H NMR (400 MHz, DMSO d$_6$) δ 11.80 (br.s., 1H), 8.53 (s, 1H), 8.44 (s, 1H), 8.21-8.36 (m, 4H), 7.62 (s, 1H), 4.14-4.20 (m, 1H), 4.02 (s, 3H), 1.72-1.85 (m, 3H), 0.96-1.01 (m, 6H); LCMS (ESI) m/e 372.2 [(M+H)$^+$, calcd for $C_{17}H_{22}N_7O_3$, 372.2]; LC/MS retention time (method A): $t_R$=1.11 min; HPLC retention time (method J): $t_R$=10.45 min; HPLC retention time (method K): $t_R$=10.78 min.

Example 103

(R)-2-Amino-N-(5-methoxy-4-(oxazol-5-yl)-2-(1,3,4-thiadiazol-2-yl)phenyl)-4-ethylpentanamide

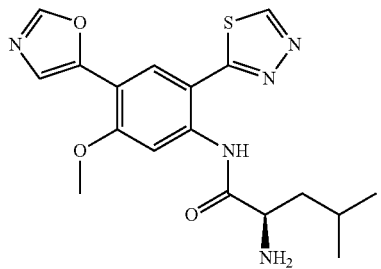 [SMILES: COc1cc(NC(=O)[C@H](N)CC(C)C)c(-c2nncs2)cc1-c1cnco1]

Part A. (R)-tert-Butyl(1-((2-bromo-5-methoxy-4-(oxazol-5-yl)phenyl)amino)-4-methyl-1-oxopentan-2-yl)carbamate To a stirred solution of 2-bromo-5-methoxy-4-(oxazol-5-yl)aniline (2 g, 7.4 mmol) (prepared as described by Dyke, H. J. et al., PCT Int. Appl. (2003), WO2003053958A1) and (R)-2-((tert-butoxycarbonyl)amino)-4-methylpentanoic acid (2.06 g, 8.92 mmol) in pyridine (20 mL) at −10° C. was added POCl$_3$ (0.85 mL, 8.8 mmol) drop wise and the reaction was stirred at this temperature for 30 min. The reaction mixture was then stirred at room temperature for 1 h. After the reaction was complete, the solvent was evaporated and the residue was partitioned between with 1.0 N aqueous HCl and ethyl acetate. The organic layer was washed with water, dried (Na$_2$SO$_4$) and purified by silica gel column chromatography to give (R)-tert-butyl(1-((2-bromo-5-methoxy-4-(oxazol-5-yl)phenyl)amino)-4-methyl-1-oxopentan-2-yl)carbamate (2 g, 47% yield). LCMS (ESI) m/e 482.8 [(M+H)$^+$, calcd for $C_{21}H_{29}BrN_3O_5$, 482.1]; LC/MS retention time (method C): $t_R$=1.09 min.

Part B. (R)-tert-Butyl(1-((5-methoxy-4-(oxazol-5-yl)-2-(4,4,5,5-tetramethyl-1,3,2-dioxaborolan-2-yl)phenyl)amino)-4-methyl-1-oxopentan-2-yl)carbamate (R)-tert-Butyl(1-((2-bromo-5-methoxy-4-(oxazol-5-yl)phenyl)amino)-4-methyl-1-oxopentan-2-yl)carbamate (430 mg, 0.891 mmol) is was taken up in 1,4-dioxane (10 mL) and treated with bis(pinacolato)diboron (679 mg, 2.67 mmol) and triethylamine (0.373 mL, 2.67 mmol). The resultant mixture was degassed for 10 min and treated with PdCl$_2$(dppf) (52.2 mg, 0.071 mmol). The resultant mixture was degassed again for 10 min and then heated to 100° C. for 12 h. The reaction mixture was cooled to room temperature and was partitioned between water and ethyl acetate. The organic layer was separated and concentrated to give the crude product, (R)-tert-butyl(1-((5-methoxy-4-(oxazol-5-yl)-2-(4,4,5,5-tetramethyl-1,3,2-dioxaborolan-2-yl)phenyl)amino)-4-methyl-1-oxopentan-2-yl)carbamate (680 mg, quantitative yield). The crude product was used in the next step without further purification. LCMS (ESI) m/e 528.2 [(M)$^-$, calcd for $C_{27}H_{39}BN_3O_7$, 528.3]; LC/MS retention time (method C): $t_R$=2.24 min.

Part C. (R)-tert-Butyl(1-((5-methoxy-4-(oxazol-5-yl)-2-(1,3,4-thiadiazol-2-yl)phenyl)amino)-4-methyl-1-oxopentan-2-yl)carbamate (R)-tert-Butyl(1-((5-methoxy-4-(oxazol-5-yl)-2-(4,4,5,5-tetramethyl-1,3,2-dioxaborolan-2-yl)phenyl)amino)-4-methyl-1-oxopentan-2-yl)carbamate (400 mg, 0.756 mmol) was taken up in 1,4-dioxane (8 mL) and water (4 mL) and treated with 2-bromo-1,3,4-thiadiazole (150 mg, 0.907 mmol), Cs$_2$CO$_3$ (738 mg, 2.267 mmol) and tetrakis(triphenylphosphine)palladium(0) (873 mg, 0.756 mmol). The resultant mixture was degassed for 5 min and heated at reflux overnight. After the reaction was complete, the mixture was partitioned between water (10 mL) and ethyl acetate (3×10 mL). The combined organic layers were washed with brine (10 mL), dried (sodium sulfate), filtered, and concentrated under reduced pressure to give crude (R)-tert-butyl(1-((5-methoxy-4-(oxazol-5-yl)-2-(1,3,4-thiadiazol-2-yl)phenyl)amino)-4-methyl-1-oxopentan-2-yl)carbamate (230 mg, 62% yield): LCMS (ESI) m/e 486.4 [(M)$^-$, calcd for $C_{23}H_{28}N_5O_5S$, 486.2]; LC/MS retention time (method C): $t_R$=2.09 min.

Part D. (R)-2-Amino-N-(5-methoxy-4-(oxazol-5-yl)-2-(1,3,4-thiadiazol-2-yl)phenyl)-4-ethylpentanamide (R)-tert-Butyl(1-((5-methoxy-4-(oxazol-5-yl)-2-(1,3,4-thiadiazol-2-yl)phenyl)amino)-4-methyl-1-oxopentan-2-yl)carbamate was subjected to Boc deprotection as described in Example 1, Part D to give (R)-2-amino-N-(5-methoxy-4-(oxazol-5-yl)-2-(1,3,4-thiadiazol-2-yl)phenyl)-4-ethylpentanamide (8 mg, 4% yield) as a yellow solid isolated as the HCl salt: $^1$H NMR (400 MHz, CD$_3$OD) δ 9.52 (s, 1H), 8.58 (s, 1H), 8.34 (s, 1H), 8.25 (s, 1H), 7.63 (s, 1H), 4.26-4.31 (m, 1H), 4.13 (s, 3H), 1.96-2.05 (m, 1H), 1.81-1.91 (m, 2H), 1.08-1.14 (m, 6H); LCMS (ESI) m/e 386.2 [(M)$^-$, calcd for C$_{18}$H$_{20}$N$_5$O$_3$S, 386.1]; LC/MS retention time (method H): t$_R$=1.69 min; HPLC retention time (method L): t$_R$=5.72 min; HPLC retention time (method M): t$_R$=6.25 min; Chiral HPLC retention time (method B1): t$_R$=14.59 min.

Example 104

(R)-2-Amino-N-(5-methoxy-2,4-bis(oxazol-5-yl) phenyl)-4-methylpentanamide

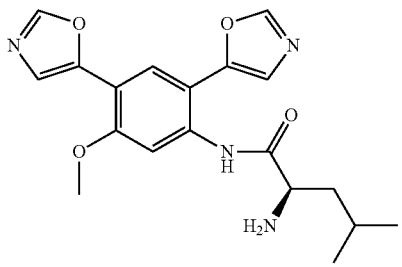 [SMILES: COc1cc(NC(=O)[C@H](N)CC(C)C)c(-c2cnco2)cc1-c1cnco1]

Part A. 2-Bromo-5-methoxy-N,N-bis(4-methoxy-benzyl)-4-(oxazol-4-yl)aniline

To a stirred solution of 2-bromo-5-methoxy-4-(oxazol-4-yl)aniline (2.0 g, 7.43 mmol) (prepared as described by Dyke, H. J. et al., PCT Int. Appl. (2003), WO2003053958A1) in DMF (40 mL) at 0° C. was added sodium hydride (0.535 g, 22.30 mmol). The reaction mixture was stirred for 10 min and 1-(chloromethyl)-4-methoxybenzene (2.44 g, 15.61 mmol) was added drop wise and the reaction was stirred at room temperature for 12 h. After the reaction was complete, it was quenched by addition of water and extracted with ethyl acetate (3×20 mL). The combined organic extracts were washed with water, dried over sodium sulfate, and concentrated under reduced pressure to afford 2-bromo-5-methoxy-N,N-bis(4-methoxybenzyl)-4-(oxazol-4-yl)aniline (1.7 g, 45% yield): LCMS (ESI) m/e 509.2 [(M+H)$^+$, calcd for C$_{26}$H$_{26}$BrN$_2$O$_4$, 509.2]; LC/MS retention time (method A): t$_R$=2.59 min.

Part B. 5-Methoxy-N,N-bis(4-methoxybenzyl)-4-(oxazol-4-yl)-2-vinylaniline

To a stirred solution of 2-bromo-5-methoxy-N,N-bis(4-methoxybenzyl)-4-(oxazol-4-yl)aniline (2 g, 3.93 mmol), 2,4,6-trivinyl-1,3,5,2,4,6-trioxatriborinane pyridine complex (1.889 g, 7.85 mmol), cesium carbonate (3.84 g, 11.78 mmol) in dioxane (35 mL) and water (7 mL) was added tetrakis(triphenylphosphine)palladium(0) (0.454 g, 0.393 mmol) and the reaction was heated to 95° C. for 10 h. After the reaction was complete, it was quenched by addition of water and extracted with ethyl acetate (2×50 mL). The combined organic extracts were washed with water, dried over sodium sulfate and concentrated under reduced pressure to afford 5-methoxy-N,N-bis(4-methoxybenzyl)-4-(oxazol-4-yl)-2-vinylaniline which was used directly in the next step without further purification: LCMS showed mono-PMB cleaved mass. LCMS (ESI) m/e 337.2 [(M+M)$^+$, calcd for C$_{20}$H$_{21}$N$_2$O$_3$, 337.1]; LC/MS retention time (method B): t$_R$=2.08 min.

Part C. 2-(Bis(4-methoxybenzyl)amino)-4-methoxy-5-(oxazol-4-yl)benzaldehyde

To a stirred solution of 5-methoxy-N,N-bis(4-methoxybenzyl)-4-(oxazol-4-yl)-2-vinylaniline (3.0 g, 6.57 mmol) and 2,6-lutidine (1.531 mL, 13.14 mmol) in dioxane (30 mL) and water (10 mL) at 0° C. was added osmium tetraoxide (3.09 mL, 9.86 mmol) followed by the addition of sodium periodate (4.22 g, 19.71 mmol). The reaction mixture was stirred at room temperature for 12 h. The reaction mixture was diluted with water and extracted with ethyl acetate (3×25 mL). The combined organic extracts were washed with water, brine, dried over sodium sulfate, and concentrated under reduced pressure to afford 2-(bis(4-methoxybenzyl)amino)-4-methoxy-5-(oxazol-4-yl)benzaldehyde, which was used directly in the next step without further purification.

Part D. 5-Methoxy-2,4-bis(oxazol-5-yl)aniline

A stirred solution of 2-(bis(4-methoxybenzyl)amino)-4-methoxy-5-(oxazol-5-yl)benzaldehyde (0.6 g, 1.309 mmol), potassium carbonate (0.181 g, 1.309 mmol) and TosMIC (0.255 g, 1.309 mmol) in methanol (20 mL) was heated to 60° C. for 2 h. The reaction mixture was concentrated under reduced pressure and partitioned between 10% aq. sodium bicarbonate solution and DCM. The combined organic extracts were dried over sodium sulfate and concentrated under reduced pressure resulting in a residue that was re-dissolved in dry DCM. To this TFA (3 mL) was added at 0° C. and the mixture was stirred at room temperature for 12 h. The reaction mixture was concentrated under reduced pressure, and the pH was adjusted to 8 by the addition of 10% aq. sodium hydroxide solution. The aqueous mixture was extracted with DCM. The combined organic extracts were dried over sodium sulfate and concentrated under reduced pressure to yield 5-methoxy-2,4-bis(oxazol-5-yl)aniline (0.4 g, 18% yield): LCMS (ESI) m/e 258.2 [(M+H)$^+$, calcd for C$_{13}$H$_{12}$N$_3$O$_3$, 258.1]; LC/MS retention time (method A): t$_R$=1.31 min.

Part E. (R)-tert-Butyl(1-((5-methoxy-2,4-bis(oxazol-5-yl)phenyl)amino)-4-methyl-1-oxopentan-2-yl) carbamate To a stirred solution of 5-methoxy-2,4-bis(oxazol-5-yl) aniline (0.15 g, 0.583 mmol) and (R)-2-((tert-butoxycarbonyl)amino)-4-methylpentanoic acid (0.202 g, 0.875 mmol) in pyridine (10 mL) was added POCl$_3$ (0.082 mL, 0.875 mmol) drop wise and the reaction mixture was stirred for 15 minutes at −10° C. The reaction mixture was added to 50 mL of 1.5 N HCl solution and extracted with ethyl acetate (2×15 mL). The organic layer was washed with water (25 mL) and brine (25 mL). The organic layer was dried over sodium sulfate and concentrated under reduced pressure to afford (R)-tert-butyl(1-((5-methoxy-2,4-bis(oxazol-5-yl)phenyl) amino)-4-methyl-1-oxopentan-2-yl)carbamate (150 mg, 5% yield): LCMS (ESI) m/e 471 [(M+H)$^+$, calcd for C$_{24}$H$_{31}$N$_4$O$_6$, 471.2]; LC/MS retention time (method A): t$_R$=1.85 min.

Part F. 2-Amino-N-(5-methoxy-2,4-di(oxazol-5-yl) phenyl)-4-methylpentanamide (R)-tert-Butyl(1-((5-methoxy-2,4-bis(oxazol-5-yl)phenyl)amino)-4-methyl-1-oxopentan-2-yl)carbamate was subjected to Boc deprotection as described in Example 1, Part D to give 2-amino-N-(5-methoxy-2,4-di(oxazol-5-yl)phenyl)-4-methylpentanamide (6.5 mg, 7% yield) as a white solid isolated as the HCl salt: $^1$H NMR (400 MHz, DMSO d$_6$) δ 8.47-8.52 (m, 2H), 8.18-8.28 (m, 3H), 7.97 (s, 1H), 7.64 (s, 1H), 7.55 (s, 1H), 7.37 (s, 1H), 4.04-4.11 (m, 1H), 3.98 (s, 3H), 1.69-1.79 (m, 3H), 0.96-1.01 (m, 6H); LCMS (ESI) m/e 371.0 [(M+H)$^+$, calcd for C$_{19}$H$_{23}$N$_4$O$_4$, 371.2]; LC/MS retention time (method A): t$_R$=1.54 min; HPLC retention time (method L): t$_R$=5.15 min; HPLC retention time (method M): t$_R$=5.83 min.

Example 105

(R)-2-Amino-N-(2,5-difluoro-4-(oxazol-5-yl)phenyl)-4-methylpentanamide

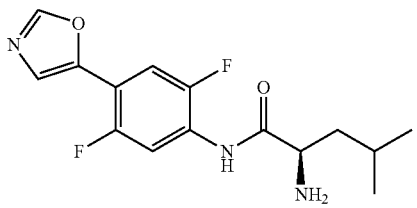 [SMILES: CC(C)C[C@@H](N)C(=O)Nc1cc(F)c(-c2cnco2)cc1F]

Part A. (2,5-Difluoro-4-nitrophenyl)methanol

To a solution of methyl 2,5-difluoro-4-nitrobenzoate (0.2 g, 0.92 mmol) in dry THF (10 mL) at −78° C. was added 25% of DIBAL-H in toluene (2.09 mL, 4 mmol) and the reaction mixture was allowed to warm up to room temperature during 1 h time period. The mixture was then quenched with 1.5 N HCl (2 mL). The mixture was extracted with ethyl acetate (2×10 mL). The combined organic extracts were dried over sodium sulfate and concentrated under reduced pressure to afford (2,5-difluoro-4-nitrophenyl) methanol (15 mg, 86% yield): (LCMS (ESI) m/e 188 [(M)$^-$, calcd for C$_7$H$_4$F$_2$NO$_3$, 188.0]; LC/MS retention time (method A): t$_R$=1.35 min.

Part B. 2,5-Difluoro-4-nitrobenzaldehyde

To the solution of (2,5-difluoro-4-nitrophenyl)methanol (2.0 g, 10.5 mmol) in dry DCM (20 mL) was added a solution of Des-Martin periodinane (4.94 g, 11.6 mmol) in DCM (10 mL) dropwise at 0° C. After the addition was complete, the reaction mixture was allowed to stir overnight at room temperature. The reaction mixture was then concentrated and reconstituted in a mixture of ethyl acetate (20 mL) and water (15 mL). Organic layer was separated and washed in sequence with a saturated solution of sodium thiosulfate (15 mL), sodium bicarbonate (15 mL), dried over sodium sulfate, and concentrated under reduced pressure to afford 2,5-difluoro-4-nitrobenzaldehyde (1.8 g, 91% yield): $^1$H NMR (400 MHz, DMSO d$_6$) δ 10.18 (s, 1H), 8.37-8.33 (m, 1H), 8.03-7.98 (m, 1H).

Part C. 5-(2,5-Difluoro-4-nitrophenyl)oxazole 5-(2,5-Difluoro-4-nitrophenyl)oxazole was synthesized as described in Example 1, Part A to give 2,5-difluoro-4-(oxazol-5-yl)aniline (2 g, 92% yield): $^1$H NMR (400 MHz, DMSO d$_6$) δ 8.75 (s, 1H), 8.37-8.33 (m, 1H), 8.04-8.0 (m, 1H), 7.91-7.90 (d, J=3.6 Hz, 1H).

Part D. 2,5-Difluoro-4-(oxazol-5-yl)aniline

To a solution of 5-(2,5-difluoro-4-nitrophenyl)oxazole (0.2 g, 0.88 mmol) in methanol (30 mL) was added palladium on carbon (10%) (60 mg) and the mixture was stirred under a hydrogen atmosphere (45 psi) at room temperature for 12 h. The reaction mixture was filtered through a pad of diatomaceous earth (Celite®) and the volatiles were removed under reduced pressure to afford 2,5-difluoro-4-(oxazol-5-yl)aniline (0.15 g, 86% yield): $^1$H NMR (400 MHz, DMSO d$_6$) δ 8.39 (s, 1H), 7.36-7.32 (m, 1H), 7.27-7.26 (d, J=3.6 Hz, 1H), 6.68-6.63 (m, 1H), 5.89 (s, 2H).

Part E. (R)-2-Amino-N-(2,5-difluoro-4-(oxazol-5-yl)phenyl)-4-methylpentanamide

Prepared in a similar fashion as described in Example 1, Parts C-D using (R)-2-(tert-butoxycarbonylamino)-4-methylpentanoic acid in Part C and 2,5-difluoro-4-(oxazol-5-yl) aniline to give (R)-2-amino-N-(2,5-difluoro-4-(oxazol-5-yl) phenyl)-4-methylpentanamide as a pale yellow solid (50 mg, 67% yield), which was isolated as a free base: $^1$H NMR (400 MHz, DMSO d$_6$) δ 8.53 (s, 1H), 8.19-8.26 (m, 1H), 7.65-7.72 (m, 1H), 7.52-7.55 (m, 1H), 4.99 (br.s, 3H), 3.39-3.43 (m, 1H), 1.73-1.82 (m, 1H), 1.48-1.57 (m, 1H), 1.30-1.39 (m, 1H), 0.86-0.91 (m, 6H); LCMS (ESI) m/e 310.2 [(M+H)$^+$, calcd for C$_{15}$H$_{18}$F$_2$N$_3$O$_2$, 310.1]; LC/MS retention time (method B): t$_R$=1.51 min; HPLC retention time (method L): t$_R$=5.25 min; HPLC retention time (method M): t$_R$=5.88 min; Chiral HPLC retention time (method C2): t$_R$=10.33 min.

Example 106

(R)-2-Amino-4-methyl-N-(4-(oxazol-5-yl)-3-(trifluoromethoxy)phenyl)pentanamide

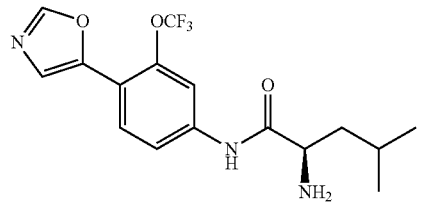

(R)-2-Amino-4-methyl-N-(4-(oxazol-5-yl)-3-(trifluoromethoxy)phenyl)pentanamide was synthesised from 4-bromo-3-(trifluoromethoxy)aniline (prepared as described by Cassayre et. al., PCT Int. Appl., 2011003684, 2011) in 5 steps (synthesis described elsewhere in the patent) namely amide formation (Example 102, Part A), vinylation (Example 102, Part C), oxidation to corresponding aldehyde (Example 102, Part D), oxazole synthesis (Example 1, Part A) followed by Boc deprotection (Example 1, Part D). (R)-2-Amino-4-methyl-N-(4-(oxazol-5-yl)-3-(trifluoromethoxy)phenyl)pentanamide (95 mg, 81% yield) was a pale yellow solid, which was isolated as the free base: $^1$H NMR (400 MHz, DMSO d$_6$) δ 8.54 (s, 1H), 8.10 (s, 1H), 7.81-7.86 (m, 1H), 7.74 (dd, J=8.8, 1.6 Hz, 1H), 7.44 (s, 1H), 3.33-3.38 (m, 1H), 1.73-1.82 (m, 1H), 1.45-1.55 (m, 1H), 1.31-1.40 (m, 1H), 0.91 (dd, J=9.41, 6.65 Hz, 6H); LCMS (ESI) m/e 356.0 [(M)⁻, calcd for $C_{16}H_{17}F_3N_3O_3$, 356.1]; LC/MS retention time (method C): $t_R$=1.75 min; HPLC retention time (method L): $t_R$=6.12 min; HPLC retention time (method M): $t_R$=6.81 min; Chiral HPLC retention time (method B3): $t_R$=5.57 min.

Example 107

(R)-2-Amino-N-(5-fluoro-2-methoxy-4-(oxazol-5-yl)phenyl)-4-methylpentanamide

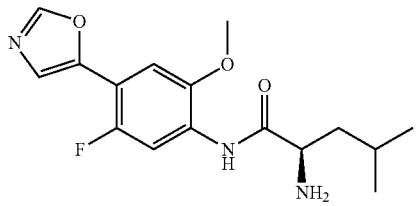 [SMILES: COc1cc(-c2cnco2)c(F)cc1NC(=O)[C@H](N)CC(C)C]

Part A. (2,5-Difluoro-4-nitrophenyl)methanol

To a solution of methyl 2,5-difluoro-4-nitrobenzoate (0.2 g, 0.92 mmol) in anhydrous THF (10 mL) was added DIBAL-H (25% in Toluene, 2.09 mL, 3.6 mmol) at −78° C. The reaction mixture was stirred for 45 min at that temperature. Additional DIBAL-H (2 eq) was added to the solution at rt and the mixture was stirred for 1 h. The reaction mixture cooled to 0° C. and was quenched with 1.5 N HCl. The mixture was extracted with ethyl acetate (2×10 mL). The combined organic layers were dried ever sodium sulfate and concentrated under reduced pressure to afford (2,5-difluoro-4-nitrophenyl)methanol (0.15 g, 86% yield): ¹H NMR (400 MHz, DMSO-$d_6$) δ 8.72 (s, 1H), 8.13 (d, J=10.4 Hz, 1H), 7.81 (d, J=3.6 Hz, 1H), 7.61 (d, J=5.6 Hz, 1H).

Part B. 2,5-Difluoro-4-nitrobenzaldehyde

To a solution of (2,5-difluoro-4-nitrophenyl)methanol (2.0 g, 10.5 mmol) in dry DCM (20 mL) was added a solution of Des-Martin periodinane (4.94 g, 11.6 mmol) in DCM (10 mL) dropwise at 0° C. The reaction was stirred at rt overnight and concentrated to near dryness. The crude mass was reconstituted in a mixture of ethyl acetate and water. The organic layer was separated and was washed with saturated aq. $Na_2S_2O_3$ and sodium bicarbonate solution. The combined organic layers were dried over sodium sulfate and concentrated under reduced pressure to afford 2,5-difluoro-4-nitrobenzaldehyde (1.8 g, 91% yield): ¹H NMR (400 MHz, DMSO-$d_6$) δ 10.18 (s, 1H), 8.35 (m, 1H), 8.00 (m, 1H).

Part C. 5-(2,5-Difluoro-4-nitrophenyl)oxazole 5-(2,5-Difluoro-4-nitrophenyl)oxazole was synthesized as described in Example 1, Part A to afford the desired product (2.0 g, 92% yield): ¹H NMR (400 MHz, DMSO-$d_6$) δ 8.75 (s, 1H), 8.34 (m, 1H), 8.03 (m, 1H), 7.90 (s, 1H).

Part D.
5-(2-Fluoro-5-methoxy-4-nitrophenyl)oxazole

To a solution of 5-(2,5-difluoro-4-nitrophenyl)oxazole (0.4 g, 1.8 mmol) in dry methanol (20 mL) was added potassium carbonate (0.74 g, 5.4 mmol). The mixture was heated at 80° C. overnight. The reaction mixture was concentrated and treated with water (20 mL) and extracted with ethyl acetate (2×15 mL). The combined organic layers were washed with brine (10 mL), dried over sodium sulfate, and concentrated under reduced pressure to afford the crude product, which was purified by column chromatography using silica gel (20% ethyl acetate in hexane) to afford 5-(2-fluoro-5-methoxy-4-nitrophenyl)oxazole (0.25 g, 60% yield): ¹H NMR (400 MHz, DMSO-$d_6$) δ 8.72 (s, 1H), 8.13 (d, J=10.4 Hz, 1H), 7.81 (d, J=3.6 Hz, 1H), 7.61 (d, J=5.6 Hz, 1H).

Part E. 5-Fluoro-2-methoxy-4-(oxazol-5-yl)aniline

To a solution of 5-(2-fluoro-5-methoxy-4-nitrophenyl)oxazole (0.25 g, 1.05 mmol) in methanol (30 mL) was added palladium on carbon (10%) (75 mg) and the mixture was stirred under a hydrogen atmosphere (45 psi) at room temperature overnight. The reaction mixture was filtered through a pad of diatomaceous earth (Celite®) and the volatiles removed under reduced pressure to afford 5-fluoro-2-methoxy-4-(oxazol-5-yl)aniline (0.14 g, 64% yield): ¹H NMR (400 MHz, DMSO-$d_6$) δ 8.36 (s, 1H), 7.21 (d, J=3.2 Hz, 1H), 7.02 (d, J=6.8 Hz, 1H), 6.53 (d, J=12.8 Hz, 1H), 5.48 (s, 2H), 3.82 (s, 3H).

Part F. (R)-2-Amino-N-(5-fluoro-2-methoxy-4-(oxazol-5-yl)phenyl)-4-methylpentanamide Prepared in a similar fashion as described in Example 1, Parts C-D using (R)-2-(tert-butoxycarbonylamino)-4-methylpentanoic acid in Part C to give (R)-2-amino-N-(5-fluoro-2-methoxy-4-(oxazol-5-yl)phenyl)-4-methylpentanamide (25 mg, 40% yield) as a pale yellow solid, which was isolated as the free base: ¹H NMR (400 MHz, $CD_3OD$) δ 8.27-8.33 (m, 2H), 7.45-7.48 (m, 1H), 7.38-7.41 (m, 1H), 4.01 (s, 3H), 3.57-3.62 (m, 1H), 1.79-1.89 (m, 1H), 1.67-1.75 (m, 1H), 1.45-1.54 (m, 1H), 0.99-1.04 (m, 6H); LCMS (ESI) m/e 322.2 [(M+H)⁺, calcd for $C_{16}H_{21}FN_3O_3$, 322.2]; LC/MS retention time (method B): $t_R$=1.56 min; HPLC retention time (method L): $t_R$=5.44 min; HPLC retention time (method K): $t_R$=6.20 min; Chiral HPLC retention time (method C2): $t_R$=14.85 min.

Example 108

(R)-2-Amino-N-(3-cyano-4-(oxazol-5-yl)phenyl)-4-methylpentanamide

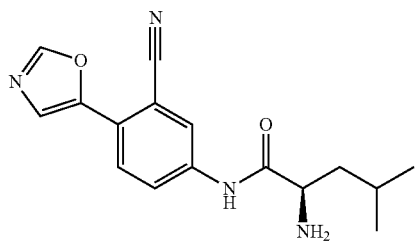 [SMILES: CC(C)C[C@@H](N)C(=O)Nc1ccc(-c2cnco2)c(C#N)c1]

Part A. 5-(2-Bromo-4-nitrophenyl)oxazole 5-(2-Bromo-4-nitrophenyl)oxazole was synthesized from 2-bromo-4-nitrobenzaldehyde (prepared in two steps as described by Iwanowicz, Edwin J. et al. *Bioorg. Med. Chem. Lett.* 2003, 13, 2059) as described in Example 1, Part A to give the desired product (1.35 g, 70% yield): $^1$H NMR (400 MHz, DMSO-d$_6$) δ 8.72 (s, 1H), 8.58 (s, 1H), 8.35 (m, 1H), 8.15 (s, 1H), 8.06 (d, J=8.8 Hz, 1H).

Part B. 5-Nitro-2-(oxazol-5-yl)benzonitrile

To a solution of 5-(2-bromo-4-nitrophenyl)oxazole (0.05 g, 0.19 mmol) in acetonitrile (5 mL) was added potassium cyanide (0.025 g, 0.38 mmol), tributyltin chloride (0.062 g, 0.19 mmol) and tetrakis(triphenylphosphine)palladium(0) (0.004 g, 0.0038 mmol) and the mixture was degassed for 10 min at room temperature followed by further degassing at 50° C. The resultant mixture was then heated at 95° C. for 12 h. The reaction mixture was then cooled to room temperature and partitioned between water (5 mL) and ethyl acetate (5 mL). The organic layer was separated and dried over sodium sulfate and concentrated under reduced pressure to afford the crude product which was purified by preparative TLC (40% ethyl acetate in hexane) to afford 5-nitro-2-(oxazol-5-yl)benzonitrile (0.02 g, 52% yield): $^1$H NMR (400 MHz, DMSO-d$_6$) δ 8.87 (s, 1H), 8.81 (s, 1H), 8.59 (m, 1H), 8.21 (d, J=8.8 Hz, 1H), 8.16 (s, 1H).

Part C. 5-Amino-2-(oxazol-5-yl)benzonitrile

To a solution of 5-nitro-2-(oxazol-5-yl)benzonitrile (0.05 g, 0.23 mmol) in dry THF (3 mL) was added palladium acetate (0.003 g, 0.012 mmol), aqueous KF solution (0.027 g in 0.5 mL water), and PMHS (0.24 mL) and the mixture was stirred under a hydrogen atmosphere at room temperature for 12 h. The reaction was quenched with water (2 mL) and extracted with ethyl acetate (5 mL). The organic layer was separated, dried with sodium sulfate and concentrated under reduced pressure to afford the crude product which was purified on a neutral alumina column to afford 5-amino-2-(oxazol-5-yl)benzonitrile (0.1 g, 83% yield): LCMS (ESI) m/e 186, [(M+H)$^+$, calcd for C$_{10}$H$_8$N$_3$O, 186]; LC/MS retention time (method B): t$_R$=1.07 min.

Part D. (R)-2-Amino-N-(3-cyano-4-(oxazol-5-yl)phenyl)-4-methylpentanamide

Prepared from 5-amino-2-(oxazol-5-yl)benzonitrile in a similar fashion as described in Example 1, Parts C-D using 2-(tert-butoxycarbonylamino)-4-methylpentanoic acid in Part C to give (R)-2-amino-N-(3-cyano-4-(oxazol-5-yl)phenyl)-4-methylpentanamide (0.04 g, 50% yield) as a white solid, isolated as the TFA salt: $^1$H NMR (400 MHz, CD$_3$OD) δ 8.39 (s, 1H), 8.28-8.30 (m, 1H), 7.95-7.97 (m, 2H), 7.86 (s, 1H), 4.05-4.09 (m, 1H), 1.76-1.88 (m, 3H), 1.06-1.09 (m, 6H); LCMS (ESI) m/e 297.2 [(M)$^-$, calcd for C$_{16}$H$_{17}$N$_4$O$_2$, 297.1]; LC/MS retention time (method A): t$_R$=1.38 min; HPLC retention time (method J): t$_R$=10.11 min; HPLC retention time (method K): t$_R$=10.52 min.

Example 109

(R)—N-(4-(1H-Imidazol-5-yl)-3-methoxyphenyl)-2-amino-4-methylpentanamide

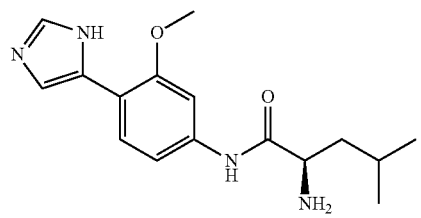 [SMILES: COc1cc(NC(=O)[C@H](N)CC(C)C)ccc1-c1cnc[nH]1]

Part A. (2-Methoxy-4-nitrophenyl)trimethylstannane

To a solution of 1-bromo-2-methoxy-4-nitrobenzene (2.0 g, 8.6 mmol) in dioxane (40 mL) was added hexamethylditin (4.23 g, 12.9 mmol). The reaction mixture was degassed for 5 min. The resultant mixture was treated with bis(triphenylphosphine)palladium(II) chloride (0.6 g, 0.86 mmol) and degassed again for 5 min. The reaction mixture was then heated at 80° C. overnight. The resultant mixture was then cooled to room temperature and partitioned between ethyl acetate (25 mL) and water (25 mL). The organic layer was separated and washed with brine (15 mL), dried with sodium sulfate, and concentrated under reduced pressure to afford the crude product, which was purified by column chromatography over neutral alumina (Pet ether:ethyl acetate as eluent) to afford (2-methoxy-4-nitrophenyl)trimethylstannane (1.9 g, 70% yield): $^1$H NMR (400 MHz, CDCl$_3$) δ 7.81-7.79 (m, 1H), 7.59 (s, 1H), 7.50-7.48 (d, J=7.6 Hz, 1H), 3.88 (s, 3H), 0.31 (s, 9H).

Part B. 5-(2-Methoxy-4-nitrophenyl)-1-trityl-1H-imidazole

To a solution of 5-bromo-1-trityl-1H-imidazole (0.25 g, 0.64 mmol) (prepared from imidazole in two steps as described by P. K. Chattise et al. *Tet. Lett.* 2008, 49, 189 and William, D. A. et. al, *J. Chem. Soc., Perkin Trans* 1, 1989, 95) in DMF (6 mL) was added (2-methoxy-4-nitrophenyl)trimethylstannane (0.24 g, 0.77 mmol), potassium carbonate (0.266 g, 1.93 mmol), and tetrabutyl ammonium bromide (0.31 g, 0.96 mmol). The resultant mixture was degassed for 5 min and treated with bis(triphenylphosphine)palladium(II) chloride (0.045 g, 0.064 mmol). The mixture was degassed again for 5 min and heated in an oil bath at 110° C. overnight. The reaction mixture was cooled, quenched with water (5 mL), and extracted with ethyl acetate (2×5 mL). The combined organic layers were dried over sodium sulfate and concentrated under reduced pressure to afford the crude product which was purified by column chromatography on neutral alumina column (hexane:ethyl acetate as eluent) to afford 5-(2-methoxy-4-nitrophenyl)-1-trityl-1H-imidazole (85 mg, 29% yield): $^1$H NMR (400 MHz, CDCl$_3$) δ 8.36 (d, J=8.8 Hz, 1H), 7.94 (d, J=2 Hz, 1H), 7.73 (s, 1H), 7.61 (s, 1H), 7.51 (s, 1H), 7.25 (m, 9H), 7.19 (m, 6H), 3.83 (s, 3H).

Part C. 4-(1H-Imidazol-5-yl)-3-methoxyaniline

To a solution of 5-(2-methoxy-4-nitrophenyl)-1-trityl-1H-imidazole (85 mg, 0.18 mmol) in methanol (10 mL) was added palladium on carbon (10%) (10 mg) and the mixture was stirred under a hydrogen atmosphere (45 psi) at room temperature for 3 h. The reaction mixture was filtered through a pad of diatomaceous earth (Celite®) and the volatiles were removed under reduced pressure to afford 4-(1H-imidazol-5-yl)-3-methoxyaniline in crude form which was taken to the next step without further purification.

Part D. (R)—N-(4-(1H-Imidazol-5-yl)-3-methoxyphenyl)-2-amino-4-methylpentanamide Prepared from 4-(1H-imidazol-5-yl)-3-methoxyaniline in a similar fashion as described in Example 1, Parts C-D using (R)-2-(tert-butoxycarbonylamino)-4-methylpentanoic acid in Part C to give (R)—N-(4-(1H-imidazol-5-yl)-3-methoxyphenyl)-2-amino-4-methylpentanamide (8 mg, 53% yield) as an off-white solid isolated as the free base: $^1$H NMR (400 MHz, CD$_3$OD) δ 7.77 (d, J=8.0 Hz, 1H), 7.70-7.71 (m, 1H), 7.58 (d, J=2.0 Hz, 1H), 7.49 (s, 1H), 7.16 (dd, J=8.4, 2.0 Hz, 1H), 3.96 (s, 3H), 3.50-3.55 (m, 1H), 1.75-1.85 (m, 1H), 1.62-1.70 (m, 1 H), 1.49-1.55 (m, 1H), 0.95-1.10 (m, 6H); LCMS (ESI) m/e 303.2 [(M+H)$^+$, calcd for C$_{16}$H$_{23}$N$_4$O$_2$, 303.2]; LC/MS retention time (method A): $t_R$=1.12 min; HPLC retention time (method N): $t_R$=10.44 min; Chiral HPLC retention time (method B2): $t_R$=20.27 min.

Example 110

(R)-2-Amino-N-(2-ethyl-5-methoxy-4-(oxazol-2-yl)phenyl)-4-methylpentanamide

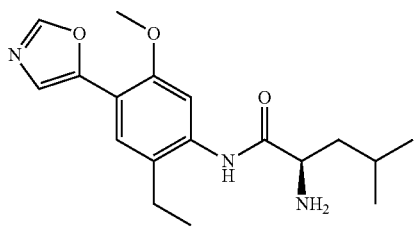 [SMILES: CCc1cc(-c2cnco2)c(OC)cc1NC(=O)[C@H](N)CC(C)C]

Part A. Methyl 4-amino-2-methoxybenzoate

To a solution of methyl 2-methoxy-4-nitrobenzoate (12.00 g, 56.86 mmol) in methanol (100 mL) at room temperature under nitrogen was added 10% palladium on carbon (4.88 g, 4.61 mmol). The resultant mixture was stirred under hydrogen (45 psi) for 12 h at room temperature. After the completion of reaction, the mixture was filtered through a diatomaceous earth (Celite®) pad and the filtrate was concentrated under reduced pressure to afford methyl 4-amino-2-methoxybenzoate (10 g, 97% yield) as a yellow solid: LCMS (ESI) m/e 182.2 [(M+H)$^+$, calcd for C$_9$H$_{12}$NO$_3$, 182.1]; LC/MS retention time (method B): $t_R$=0.87 min.

Part B. Methyl 4-acetamido-2-methoxybenzoate

To a stirred solution of methyl 4-amino-2-methoxybenzoate (10 g, 55 mmol) in dichloromethane (100 mL) was added triethylamine (15.4 mL, 110 mmol) at 0° C. and the mixture was stirred for 15 min. To this mixture, acetyl chloride (5.68 g, 71 mmol) was added drop wise and the mixture was stirred at room temperature overnight. The reaction was quenched by addition of water (75 mL). The organic layer was separated, washed with brine solution (100 mL), dried over sodium sulfate and concentrated under reduced pressure to afford methyl 4-acetamido-2-methoxybenzoate (13.0 g, 58.2 mmol, quantitative yield) as a yellow solid: LCMS (ESI) m/e 224.2 [(M+H)$^+$, calcd for C$_{11}$H$_{14}$NO$_4$, 224.1]; LC/MS retention time (method B): $t_R$=1.21 min.

Part C. Methyl 4-acetamido-5-bromo-2-methoxybenzoate

To the stirred solution of methyl 4-acetamido-2-methoxybenzoate (13.0 g, 58.2 mmol) in acetic acid (130 mL) was added bromine (4.5 mL, 58 mmol) at 0° C. and the mixture was stirred for 30 min. Upon completion of reaction, the reaction mixture was concentrated under reduced pressure and basified to pH=8 with a saturated solution of sodium bicarbonate. The product was extracted with dichloromethane (3×50 mL). The combined organic extracts were dried over sodium sulfate and concentrated under reduced pressure to afford methyl 4-acetamido-5-bromo-2-methoxybenzoate (7.0 g, 40% yield) as a yellow solid. The residue so obtained was taken to the next step without further purification. LCMS (ESI) m/e 303 [(M+H)$^+$, calcd for C$_{11}$H$_{13}$BrNO$_4$, 303.1]; LC/MS retention time (method B): $t_R$=1.51 min.: $^1$H NMR (DMSO-d$_6$, 400 MHz) δ 9.47 (s, 1H), 7.81 (s, 1H), 7.69 (s, 1H), 2.15 (s, 3H).

Part D. N-(2-Bromo-4-(hydroxymethyl)-5-methoxyphenyl)acetamide

To a solution of methyl 4-acetamido-5-bromo-2-methoxybenzoate (7.0 g, 23.3 mmol) in anhydrous THF (100 mL) at −10° C. was added a solution of 25% DIBAL-H in toluene (39.8 mL, 69 mmol). The reaction mixture was warmed to 0° C. and stirred for 2 h. Upon completion, the reaction was quenched with a saturated solution of ammonium chloride (50 mL) and extracted with ethyl acetate (3×50 mL). Combined organic layer was washed with brine (50 mL), dried over sodium sulfate and concentrated under reduced pressure to afford N-(2-bromo-4-(hydroxymethyl)-5-methoxyphenyl)acetamide (4.0 g, 63% yield) as a yellow solid: LCMS (ESI) m/e 274 [(M+H)$^+$, calcd for C$_{10}$H$_{13}$BrNO$_3$, 274]; LC/MS retention time (method B): $t_R$=0.998 min.

Part E. N-(2-Bromo-4-formyl-5-methoxyphenyl)acetamide

To a solution of N-(2-bromo-4-(hydroxymethyl)-5-methoxyphenyl)acetamide (4.0 g, 14.5 mmol) in dichloromethane (60 mL) at room temperature was added Des-Martin periodinane (6.8 g, 16 mmol) in 3 portions and the reaction mixture was allowed to stir at room temperature for 12 h. The reaction was quenched by the addition of an aqueous solution of sodium bisulfite (25 mL) and sodium bicarbonate (25 mL). The organic layer was separated and washed with water (50 mL) and brine (50 mL), dried over sodium sulfate and concentrated under reduced pressure to afford N-(2-bromo-4-formyl-5-methoxyphenyl)acetamide (2.9 g, 74% yield) as a yellow oil: $^1$H NMR (400 MHz, DMSO-d$_6$) δ 10.18 (s, 1H), 9.51 (s, 1H), 7.84 (s, 1H), 7.82 (s, 1H), 3.89 (s, 3H), 2.18 (s, 3H).

Part F. N-(2-Bromo-5-methoxy-4-(oxazol-2-yl)phenyl)acetamide

Prepared from N-(2-bromo-4-formyl-5-methoxyphenyl)acetamide (5.7 g, 21 mmol) as described in Example 1 Part A to afford N-(2-bromo-5-methoxy-4-(oxazol-2-yl)phenyl)acetamide (3.9 g, 60% yield) as a yellow solid: LCMS (ESI) m/e 311 [(M+H)+, calcd for $C_{12}H_{12}BrN_2O_3$, 311.0]; LC/MS retention time (method I): $t_R$=2.29 min. Method I: Column—Xterra C18 (3×50 mm), 2.5 micron; Mphase A: 2% MeCN—98% H2O—10 mM NH4COOH; Mphase B: 98% MeCN—2% H2O—10 mM $NH_4COOH$; Flow: 1 mL/min.

Part G. N-(5-Methoxy-4-(oxazol-2-yl)-2-vinylphenyl)acetamide

To a stirred solution of N-(2-bromo-5-methoxy-4-(oxazol-2-yl)phenyl)acetamide (2.0 g, 6.45 mmol) and vinyl boronic anhydride (3.05 g, 12.8 mmol) in toluene (20 mL) and ethanol (5 mL) was added sodium carbonate (2.7 g, 25.6 mmol) followed by the addition of $Pd(PPh_3)_4$ (0.44 g, 0.38 mmol). The reaction mixture was heated to 95° C. for 14 h. Upon completion of reaction, ethyl acetate (20 mL) and water (25 mL) were added and the organic layer was separated, washed with brine (25 mL), dried with sodium sulfate, and concentrated under reduced pressure to afford the crude product, which was purified by silica gel column chromatography (ethyl acetate/hexanes gradient) to afford N-(5-methoxy-4-(oxazol-2-yl)-2-vinylphenyl)acetamide (0.9 g, 54% yield): LCMS (ESI) m/e 259.0 [(M+H)+, calcd for $C_{14}H_{15}N_2O_3$, 259.1]; LC/MS retention time (method B): $t_R$=1.43 min.

Part H. N-(2-Ethyl-5-methoxy-4-(oxazol-2-yl)phenyl)acetamide

To a solution of N-(5-methoxy-4-(oxazol-2-yl)-2-vinylphenyl)acetamide (0.3 g, 1.16 mmol) in ethyl acetate (15 mL) at room temperature under nitrogen was added 10% palladium on carbon (123 mg, 0.12 mmol). The resultant mixture was stirred under hydrogen (1 atm) for 48 h at room temperature. After the reaction was complete the mixture was filtered through a diatomaceous earth (Celite®) pad and the filtrate was concentrated under reduced pressure to afford N-(2-ethyl-5-methoxy-4-(oxazol-2-yl)phenyl)acetamide (0.3 g, quantitative yield) as a yellow solid: LCMS (ESI) m/e 261.2 [(M+H)+, calcd for $C_{14}H_{17}N_2O_3$, 261.1]; LC/MS retention time (method B): $t_R$=1.48 min.

Part I. 2-Ethyl-5-methoxy-4-(oxazol-2-yl)aniline

To the solution of N-(2-ethyl-5-methoxy-4-(oxazol-2-yl)phenyl)acetamide (0.3 g, 1.16 mmol) in a mixture of ethanol (10 mL) and water (2 mL) was added potassium hydroxide (0.64 g, 1.16 mmol) and the mixture heated at 65° C. for 12 h. Upon completion of reaction the volatiles were removed under reduced pressure and the residue was partitioned between dichloromethane (15 mL) and water (10 mL). The organic layer was separated, dried under sodium sulfate, and concentrated under reduced pressure to afford 2-ethyl-5-methoxy-4-(oxazol-2-yl)aniline (0.18 g, 53% pure by LCMS, 38% yield) as a yellow solid: LCMS (ESI) m/e 219.2 [(M+H)+, calcd for $C_{12}H_{15}N_2O_2$, 219.1]; LC/MS retention time (method B): $t_R$=1.30 min.

Part J. (R)-tert-Butyl(1-((2-ethyl-5-methoxy-4-(oxazol-2-yl)phenyl)amino)-4-methyl-1-oxopentan-2-yl)carbamate To the solution of 2-ethyl-5-methoxy-4-(oxazol-2-yl)aniline (0.18 g, 53% pure, 0.44 mmol) and Boc-D-Leucine (0.42 g, 1.8 mmol) in dichloromethane (15 mL) at room temperature was added N,N-disopropylethylamine (0.64 mL, 3.6 mmol) and HATU (0.68 g, 1.8 mmol). The resultant mixture was stirred at room temperature under a nitrogen atmosphere for 14 h. Upon completion of the reaction, water (10 mL) was added and the aqueous layer was extracted with dichloromethane (2×15 mL). The combined organic layers were separated, dried with sodium sulfate, and concentrated under reduced pressure to afford the crude product, which was purified by preparative TLC (30% ethyl acetate: 70% hexane) to afford (R)-tert-butyl(1-((2-ethyl-5-methoxy-4-(oxazol-2-yl)phenyl)amino)-4-methyl-1-oxopentan-2-yl)carbamate (0.15 g, 0.35 mmol, 79% yield) as a pale yellow solid. LCMS (ESI) m/e 432.2 [(M+H)+, calcd for $C_{23}H_{34}N_3O_5$, 432.24]; LC/MS retention time (method B): $t_R$=2.07 min.

Part K. (R)-2-Amino-N-(2-ethyl-5-methoxy-4-(oxazol-2-yl)phenyl)-4-methylpentanamide (R)-tert-Butyl(1-((2-ethyl-5-methoxy-4-(oxazol-2-yl)phenyl)amino)-4-methyl-1-oxopentan-2-yl)carbamate (0.12 g, 0.28 mmol) was taken up in dichloromethane (10 mL) and treated with trifluoroacetic acid (0.17 mL, 2.3 mmol). The reaction mixture was stirred at room temperature for 2 h. Upon completion, the reaction was quenched by addition of a saturated solution of sodium bicarbonate (10 mL) and extracted with dichloromethane (3×5 mL). The combined organic layers were separated, dried with sodium sulfate, and concentrated under reduced pressure to afford the crude product, which was purified by preparative TLC to afford (R)-2-amino-N-(2-ethyl-5-methoxy-4-(oxazol-2-yl)phenyl)-4-methylpentanamide (90 mg, 97% yield): $^1$H NMR (400 MHz, $CD_3OD$) δ 8.25 (s, 1H) 7.73 (s, 1H) 7.55 (s, 1H) 7.28 (s, 1H) 4.2 (m, 1H), 3.98 (s, 3H), 2.67 (m, 2H), 1.88 (m, 3H), 1.26 (t, J=7.6 Hz, 3H), 1.11 (m, 6H); LCMS (ESI) m/e 332.2 [(M+H)+, calcd for $C_{18}H_{26}N_3O_3$, 332.2]; LC/MS retention time (method B): $t_R$=1.54 min; HPLC retention time (method L): $t_R$=9.27 min; HPLC retention time (method K): $t_R$=6.8 min.

Example 111

(R)-2-Amino-4-methyl-N-(4-(pyridin-4-yl)-2-(trifluoromethyl)phenyl)pentanamide

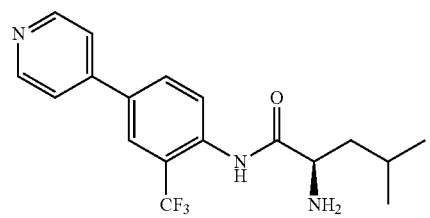

Part A. 4-Bromo-2-(trifluoromethyl)aniline

The procedure was adapted from Lemair, M. et. al. *Tetrahedron*, 2011, 67, 1971-1976. To the solution of 2-(trifluoromethyl)aniline (1.5 g, 9.31 mmol) in acetic acid (15 mL) was added KBr (1.307 g, 10.99 mmol) and sodium perborate monohydrate (0.929 g, 9.31 mmol) and the mixture was stirred for 5 min. To this mixture was added ammonium molybdate tetrahydrate (11.51 g, 9.31 mmol) and the reaction mixture was stirred at room temperature for 3 h. After completion of the reaction as determined by TLC, water was added and the pH was adjusted to 8 using aq. saturated sodium bicarbonate solution. The reaction mixture was extracted with ethyl acetate (3×5 mL). The combined organic extracts were washed with brine solution, dried over sodium sulfate and concentrated under reduced pressure to afford 4-bromo-2-(trifluoromethyl)aniline (800 mg, 36% yield) as a yellow solid. The analytical data was consistent with the literature reference cited above.

Part B. (R)-tert-Butyl(1-((4-bromo-2-(trifluoromethyl)phenyl)amino)-4-methyl-1-oxopentan-2-yl) carbamate To a solution of 4-bromo-2-(trifluoromethyl)aniline (500 mg, 2.083 mmol) in pyridine (10 mL) at −15° C. was added (R)-2-(tert-butoxycarbonylamino)-4-methylpentanoic acid (578 mg, 2.5 mmol). The mixture was stirred for 5 min. To this mixture was added $POCl_3$ (0.233 mL, 2.5 mmol) dropwise over a period of 5 min. The reaction mixture was stirred at −15° C. for 15 min and was then warmed to room temperature and stirred for 15 min. Upon completion of the reaction as determined by TLC, the reaction mixture was concentrated under reduced pressure, quenched with water (10 mL), and the pH adjusted to 3 using 1.5 N aq. HCl solution. The reaction mixture was extracted with ethyl acetate (3×5 mL). The combined organic extracts were washed with brine solution, dried over sodium sulfate and concentrated under reduced pressure to afford (R)-tert-butyl (1-((4-bromo-2-(trifluoromethyl)phenyl)amino)-4-methyl-1-oxopentan-2-yl)carbamate (480 mg, 51% yield) as a brown solid: LCMS (ESI) m/e 453.0 [(M+H)$^+$, calcd for $C_{18}H_{25}BrF_3N_2O_3$, 453.1]; LC/MS retention time (method C): $t_R$=2.21 min.

Part C. (R)-tert-Butyl(4-methyl-1-oxo-1-((4-(pyridin-4-yl)-2-(trifluoromethyl)phenyl)amino)pentan-2-yl)carbamate To a solution of (R)-tert-butyl(1-((4-bromo-2-(trifluoromethyl)phenyl)amino)-4-methyl-1-oxopentan-2-yl)carbamate (300 mg, 0.662 mmol) in 1,4-dioxane (3 mL) and water (1.5 mL) was added cesium carbonate (647 mg, 1.985 mmol) and 4-pyridylboronic acid (163 mg, 1.324 mmol). Nitrogen gas was bubbled through the reaction mixture for 5 min. To this mixture was added Pd(PPh$_3$)$_4$ (61.2 mg, 0.053 mmol) and the mixture was purged with nitrogen for 5 min. The reaction mixture was then heated to 95° C. for 12 h. The reaction mixture was diluted with water and extracted with ethyl acetate (2×5 mL). The combined organic extracts were washed with brine solution (5 mL), dried over sodium sulfate and concentrated under reduced pressure to afford a residue, which was purified using hexane and ethyl acetate gradient to afford (R)-tert-butyl(4-methyl-1-oxo-1-((4-(pyridin-4-yl)-2-(trifluoromethyl)phenyl)amino)pentan-2-yl)carbamate (210 mg, 70% yield) as an orange oil: LCMS (ESI) m/e 452.0 [(M+H)$^+$, calcd for $C_{23}H_{29}F_3N_3O_3$, 452.2]; LC/MS retention time (method C): $t_R$=2.01 min.

Part D. (R)-2-Amino-4-methyl-N-(4-(pyridin-4-yl)-2-(trifluoromethyl)phenyl)-pentanamide To a solution of (R)-tert-butyl(4-methyl-1-oxo-1-((4-(pyridin-4-yl)-2-(trifluoromethyl)phenyl)amino)pentan-2-yl)carbamate (210 mg, 0.465 mmol) in dichloromethane (2 mL) at 0° C. was added HCl (2.326 mL, 2.326 mmol) in diethyl ether dropwise. The reaction was stirred at the same temperature for 10 min and then warmed to room temperature and stirred for 2 h. Upon completion of reaction, the mixture was concentrated under reduced pressure to afford a residue, which was purified by preparative HPLC (Column: Atlantis dc18 (4.6×250 mm) 5 u, MPhase A: 0.05% TFA in water:MeCN (90:10), MPhase B: Methanol, Flow: 1.0 mL/min) to afford product (R)-2-amino-4-methyl-N-(4-(pyridin-4-yl)-2-(trifluoromethyl)phenyl)-pentanamide (40 mg, 25% yield) as an off-white sticky solid (isolated as a HCl salt): $^1$H NMR (400 MHz, CD$_3$OD) δ 8.64 (dd, J=1.6 Hz, J=4.8 Hz, 2H), 8.34 (d, J=8.8 Hz, 1H), 8.08 (m, 2H), 7.78 (dd, J=1.6 Hz, J=4.8 Hz, 2H), 3.56 (m, 1H), 1.9 (m, 1H), 1.86 (m, 1H), 1.76 (m, 1H), 1.01 (m, 6H); $^{19}$F NMR (400 MHz, CD$_3$OD) δ−62.60; LCMS (ESI) m/e 350.2 [(M)$^-$, calcd for $C_{18}H_{19}F_3N_3O$, 350.16]; LC/MS retention time (method C): $t_R$=1.84 min; HPLC retention time (method J): $t_R$=7.29 min; HPLC retention time (method K): $t_R$=8.15 min.

Example 112

(R)—N-(2-(1H-pyrazol-4-yl)-4-(pyridin-4-yl)phenyl)-2-amino-4-methylpentanamide

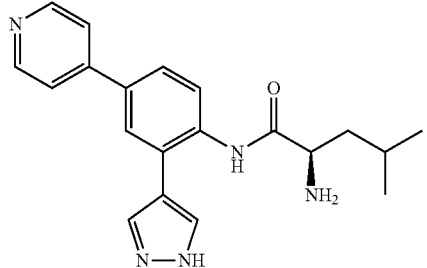 [SMILES: CC(C)C[C@@H](N)C(=O)Nc1ccc(-c2ccncc2)cc1-c1cn[nH]c1]

Part A. N-(4-Bromophenyl)acetamide

To a stirred solution of 4-bromoaniline (30 g, 174 mmol) in dichloromethane (150 mL) was added triethylamine (73.53 mL, 523 mmol) at 0° C. and the mixture was stirred for 15 min. To this mixture was added acetyl chloride (19.12 g, 240 mmol) dropwise and the mixture was stirred at room temperature overnight. The reaction was quenched by addition of water (100 mL). The organic layer was separated, washed with brine solution (100 mL), dried over sodium sulfate, and concentrated under reduced pressure to afford N-(4-bromophenyl)acetamide (35 g, 94% yield): $^1$H NMR (400 MHz, DMSO-d$_6$) δ 10.05 (s, 1H), 7.55 (d, J=9.2 Hz, 2H), 7.46 (dd, J=2 Hz, 6.4 Hz, 2H), 2.05 (s, 3H).

Part B. N-(4-(pyridin-4-yl)phenyl)acetamide

To a stirred solution of N-(4-bromophenyl)acetamide (10.0 g, 46.6 mmol) and pyridin-4-ylboronic acid (11.48 g, 93 mmol) in dioxane (50 mL) and water (10 mL) was added cesium carbonate (45.5 g, 139 mmol) followed by the addition of Pd(PPh$_3$)$_4$ (5.3 g, 4.60 mmol) and the reaction mixture was heated at 95° C. for 14 h. Upon completion of the reaction, the reaction mixture was concentrated under reduced pressure and was diluted with water (100 mL). The product was extracted in dichloromethane (3×50 mL) and the organic layers were separated and washed with water and purified by silica gel column chromatography using a gradient of ethyl acetate in pet ether to afford N-(4-(pyridin-4-yl)phenyl)acetamide (7.1 g, 72% yield): $^1$H NMR (400 MHz, DMSO-$d_6$) δ 10.13 (s, 1H), 8.60 (d, J=6.4 Hz, 2H), 7.79-7.67 (m, 6H), 2.09 (s, 3H).

Part C.
N-(2-bromo-4-(pyridin-4-yl)phenyl)acetamide

To the stirred solution of N-(4-(pyridin-4-yl)phenyl)acetamide (6.00 g, 28.28 mmol) in acetic acid (100 mL) was added NBS (6.56 g, 36.81 mmol) and the mixture was heated at 70° C. for 7 h. Upon completion of the reaction, the reaction mixture was concentrated under reduced pressure and diluted with water (100 mL). The product was extracted with dichloromethane (3×50 mL). The combined organic extracts were dried over sodium sulfate and concentrated under reduced pressure. The residue was subjected to silica gel column chromatography using gradient of ethyl acetate and pet ether to afford N-(2-bromo-4-(pyridin-4-yl)phenyl)acetamide (5.18 g, 63% yield): $^1$H NMR (400 MHz, DMSO-$d_6$) δ 9.55 (s, 1H), 8.65 (dd, J=4.4 Hz, 1.6 Hz, 2H), 8.11 (d, J=1.2 Hz, 1H), 7.82 (m, 2H), 7.75 (dd, J=4.4 Hz, 1.6 Hz, 2H), 2.13 (s, 3H) ppm.

Part D. 2-Bromo-4-(pyridin-4-yl)aniline

To a stirred solution of N-(2-bromo-4-(pyridin-4-yl)phenyl)acetamide (2.00 g, 6.87 mmol) in ethanol (35 mL) and water (10 mL) was added KOH (3.85 g, 68.7 mmol) and the reaction mixture was heated to 90° C. for 12 h. Upon completion of the reaction, the ethanol was concentrated under reduced pressure. Water was added and the aqueous layer was extracted with dichloromethane. The combined organic extracts were washed with water, dried over sodium sulfate and concentrated under reduced pressure. The residue was purified by silica gel column chromatography using 45% EtOAc in hexane to afford 2-bromo-4-(pyridin-4-yl)aniline (1.02 g, 52% yield) as a brown oil. LCMS (ESI) m/e 249.0 [(M+H)$^+$, calcd for $C_{11}H_{10}BrN_2$, 249.0]; LC/MS retention time (method B): $t_R$=0.89 min.

Part E. (R)-tert-Butyl(1-((2-bromo-4-(pyridin-4-yl)phenyl)amino)-4-methyl-1-oxopentan-2-yl)carbamate To a stirred solution of 2-bromo-4-(pyridin-4-yl)aniline (0.2 g, 0.803 mmol) and (R)-2-((tert-butoxycarbonyl)amino)-4-methylpentanoic acid (0.223 g, 0.963 mmol) in pyridine (10 mL) at −15° C. was added POCl$_3$ (0.097 mL, 1.044 mmol) dropwise and the reaction was stirred for 15 min and then warmed to room temperature and stirred for 1 h at room temperature. Upon completion of reaction as determined by TLC, the reaction mixture was concentrated under reduced pressure, quenched with water and the pH adjusted to 3 using 1.5 N aq. HCl solution. The reaction mixture was extracted with dichloromethane (3×5 mL). The combined organic extracts were washed with brine solution, dried over sodium sulfate and concentrated under reduced pressure to afford (R)-tert-butyl(1-((2-bromo-4-(pyridin-4-yl)phenyl)amino)-4-methyl-1-oxopentan-2-yl)carbamate (0.4 g, 90% yield) as a brown oil. The residue was taken to the next step without purification. LCMS (ESI) m/e 462.2 [(M+H)$^+$, calcd for $C_{22}H_{29}BrN_3O_3$, 462.1]; LC/MS retention time (method A): $t_R$=2.10 min.

Part F. tert-Butyl 4-(4,4,5,5-tetramethyl-1,3,2-dioxaborolan-2-yl)-1H-pyrazole-1-carboxylate To a stirred solution of 4-(4,4,5,5-tetramethyl-1,3,2-dioxaborolan-2-yl)-1H-pyrazole (1.00 g, 5.15 mmol) and Boc$_2$O (1.436 mL, 6.18 mmol) in dichloromethane (15 mL) was added triethylamine (1.077 mL, 7.73 mmol) at room temperature and the reaction mixture was stirred for 24 h. After completion of the reaction, as determined by TLC (10% ethyl acetate in hexane), water was added and the aqueous layer was extracted with dichloromethane (50 mL). The organic layer was washed with water, concentrated under reduced pressure to afford tert-butyl 4-(4,4,5,5-tetramethyl-1,3,2-dioxaborolan-2-yl)-1H-pyrazole-1-carboxylate (1.5 g, 99% yield), which was used in the next step without purification. LCMS (ESI) m/e 194.7 (corresponding to de-boc mass under analytical condition) [(M+H−BOC)$^+$, calcd for $C_9H_{15}BN_2O_2$, 194.1]; LC/MS retention time (method C): $t_R$=1.92 min.

Part G. (R)-tert-Butyl 4-(2-(2-((tert-butoxycarbonyl)amino)-4-methylpentanamido)-5-(pyridin-4-yl)phenyl)-1H-pyrazole-1-carboxylate To a stirred solution of (R)-tert-butyl(1-((2-bromo-4-(pyridin-4-yl)phenyl)amino)-4-methyl-1-oxopentan-2-yl)carbamate (0.15 g, 0.324 mmol), tert-butyl 4-(4,4,5,5-tetramethyl-1,3,2-dioxaborolan-2-yl)-1H-pyrazole-1-carboxylate (0.115 g, 0.389 mmol) in dioxane (25 mL) and water (5 mL) was added cesium carbonate (0.317 g, 0.973 mmol) followed by the addition of Pd(PPh$_3$)$_4$ (0.019 g, 0.016 mmol) and the reaction was heated to 95° C. for 18 h. Upon completion of the reaction, ethyl acetate was added and the organic layer was separated and washed with water and purified by column chromatography (50% EtOAc in hexane) (Neutral alumina column) yielding (R)-tert-butyl 4-(2-(2-((tert-butoxycarbonyl)amino)-4-methylpentanamido)-5-(pyridin-4-yl)phenyl)-1H-pyrazole-1-carboxylate (0.1 g, 50% yield) as a light brown solid: LCMS (ESI) m/e 450.3 [(M+H)$^+$, calcd for $C_{25}H_{32}N_5O_3$, 450.2]; LC/MS retention time (method A): $t_R$=1.66 min.

Part H. (R)—N-(2-(1H-pyrazol-4-yl)-4-(pyridin-4-yl)phenyl)-2-amino-4-methylpentanamide To a stirred solution of (R)-tert-butyl 4-(2-(2-((tert-butoxycarbonyl)amino)-4-methylpentanamido)-5-(pyridin-4-yl)phenyl)-1H-pyrazole-1-carboxylate (0.15 g, 0.334 mmol) in MeOH (10 mL) was added TFA (1.500 mL, 19.47 mmol) drop wise at 0° C. and the reaction was warmed to room temperature and stirred for 10 h. Later the reaction was concentrated under reduced pressure, methanolic HCl (10 mL) was added and the mixture was stirred for 15 min, again concentrated under vacuum and purified by preparative HPLC Column: Atlantis dc18 (4.6×250 mm) 5 g, MPhase A: 0.05% TFA in water:MeCN (90:10), MPhase B: Methanol, Flow: 1.0 mL/min) to afford (R)—N-(2-(1H-pyrazol-4-yl)-4-(pyridin-4-yl)phenyl)-2-amino-4-methylpentanamide (60 mg, 51% yield) as a yellow solid isolated as an HCl salt: $^1$H NMR (400 MHz, CD$_3$OD) δ 8.83 (bs, 2H), 8.36 (m, 2H), 8.06-7.94 (m, 5H), 4.10 (m, 1H), 1.76 (m, 3H), 1.05 (m, 6H); LCMS (ESI) m/e 350.2 [(M+H)$^+$, calcd for $C_{20}H_{24}N_5O$, 350.2]; LC/MS retention time (method A): $t_R$=1.29 min; HPLC retention time (method J): $t_R$=6.01 min; HPLC retention time (method K): $t_R$=6.60 min; Chiral HPLC retention time (method CHIRALCEL OJH (250×4.6 mm) 5 micron; Mob. phase: 0.2% DEA in n-hexane:ethanol (85:15): $t_R$=23.88 min.

Example 113

(R)-2-Amino-4-methyl-N-(4-(pyridin-4-yl)-2-(thiophen-3-yl)phenyl)pentanamide

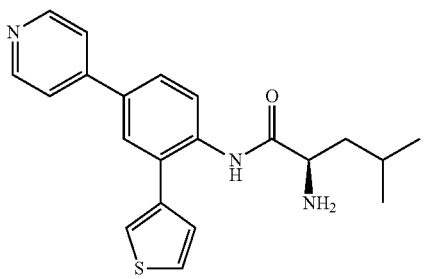 [SMILES: CC(C)C[C@@H](N)C(=O)Nc1ccc(-c2ccncc2)cc1-c1ccsc1]

Part A. (R)-tert-Butyl(4-methyl-1-oxo-1-((4-(pyridin-4-yl)-2-(thiophen-3-yl)phenyl)amino)pentan-2-yl)carbamate To a stirred solution of (R)-tert-butyl(1-((2-bromo-4-(pyridin-4-yl)phenyl)amino)-4-methyl-1-oxopentan-2-yl) carbamate (0.15 g, 0.324 mmol) (prepared as described in Example 112 Parts A-E), 4,4,5,5-tetramethyl-2-(thiophen-3-yl)-1,3,2-dioxaborolane (0.082 g, 0.389 mmol), cesium carbonate (0.317 g, 0.973 mmol) in dioxane (25 mL) and water (5 mL) was added Pd(PPh$_3$)$_4$ (0.019 g, 0.016 mmol) and the reaction was heated to 95° C. for 6 h. After the completion of reaction, the solvent was evaporated; water (5 mL) was added and the aqueous layer was extracted with dichloromethane (3×10 mL). The combined organic layers were washed with water (10 mL) and concentrated under reduced pressure to afford crude product, which was purified by silica gel chromatography (gradient of ethyl acetate in hexanes) to afford (R)-tert-butyl(4-methyl-1-oxo-1-((4-(pyridin-4-yl)-2-(thiophen-3-yl)phenyl)amino)pentan-2-yl)carbamate (0.1 g, 61% yield) as brown oil: LCMS (ESI) m/e 466.2 [(M+H)$^+$, calcd for C$_{26}$H$_{32}$N$_3$O$_3$S 466.2]; LC/MS retention time (method A): t$_R$=2.12 min.

Part B. (R)-2-Amino-4-methyl-N-(4-(pyridin-4-yl)-2-(thiophen-3-yl)phenyl)pentanamide Prepared in a similar fashion as described in Example 1, Parts D using (R)-tert-butyl(4-methyl-1-oxo-1-((4-(pyridin-4-yl)-2-(thiophen-3-yl)phenyl)amino)pentan-2-yl)carbamate (0.1 g, 0.215 mmol) to give (R)-2-amino-4-methyl-N-(4-(pyridin-4-yl)-2-(thiophen-3-yl)phenyl)pentanamide (30 mg, 38% yield) as an off-white solid, which was isolated as a hydrochloride salt: $^1$H NMR (400 MHz, CD$_3$OD) δ 8.81 (m, 2H), 8.31 (m, 2H), 8.00 (m, 3H), 7.62 (m, 2H), 7.31 (m, 1H), 4.04 (m, 1H), 1.71 (m, 3H), 1.00 (m, 6H); LCMS (ESI) m/e 366.2 [(M+H)$^+$, calcd for C$_{21}$H$_{24}$N$_3$OS, 366.2]; LC/MS retention time (method A): t$_R$=1.83 min; HPLC retention time (method J): t$_R$=8.68 min; HPLC retention time (method K): t$_R$=9.59 min; Chiral HPLC retention time (method E3): t$_R$=22.81 min.

Example 114

(R)-2-Amino-N-(2-cyano-4-(pyridin-4-yl)phenyl)-4-methylpentanamide

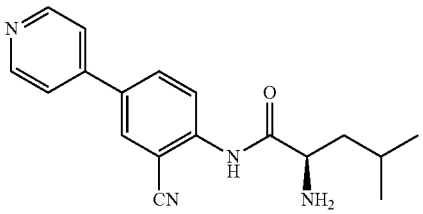 [SMILES: CC(C)C[C@@H](N)C(=O)Nc1ccc(-c2ccncc2)cc1C#N]

Part A: 2-Amino-5-bromobenzonitrile

To a stirred solution of 2-aminobenzonitrile (25 g, 210 mmol) in dichloromethane (500 mL) was added NBS (41.4 g, 230 mmol) portion wise and the mixture was stirred at 0° C. for 2 h. The reaction mixture was gradually warmed to room temperature and was quenched with sodium bicarbonate solution (200 mL). The organic layer was separated, washed with brine, dried over sodium sulfate and concentrated under reduced pressure to afford 2-amino-5-bromobenzonitrile (38 g, 92% yield) as a pale brown solid: $^1$H NMR (400 MHz, DMSO-d$_6$) δ 7.61 (d, J=2.5 Hz, 1H), 7.43 (dd, =9, 2.5 Hz, 1H), 6.75 (d, =9 Hz, 1H), 6.28 (bs, 2H).

Part B: 2-Amino-5-bromobenzamide

To a solution of 2-amino-5-bromobenzonitrile (2 g, 10.2 mmol) in methanol (20 mL) and DMSO (1.5 g, 20 mmol) was added hydrogen peroxide (30% solution in water, 1.4 g, 40 mmol) dropwise followed by the addition of sodium hydroxide (0.2 g, 5 mmol) in water (5 mL). The resultant mixture was heated at 60° C. for 1 h. Upon reaction completion the volatiles were removed under reduced pressure and the residue was diluted with water (5 mL). The solid obtained was filtered, washed with water and dried under vacuum to afford 2-amino-5-bromobenzamide (1.3 g, 60% yield): $^1$H NMR (400 MHz, DMSO-d$_6$) δ 7.84 (bs, 1H), 7.71 (s, 1H), 7.25 (dd, J=2.4 Hz, J=8.8 Hz, 1H), 7.17 (bs, 1H), 6.71 (bs, 2H), 6.66 (d, J=8.8 Hz, 1H).

Part C. (R)-tert-Butyl(1-((4-bromo-2-carbamoylphenyl)amino)-4-methyl-1-oxopentan-2-yl)carbamate To the solution of 2-amino-5-bromobenzamide (2 g, 9.3 mmol) and Boc-D-leucine (4.94 g, 21.4 mmol) in dichloromethane (15 mL) and DMF (4 mL) at room temperature were added disopropylethylamine (5.3 mL, 30 mmol) and HATU (7.6 g, 20 mmol). The resultant mixture was stirred at 50° C. under nitrogen atmosphere for 12 h. Upon completion of the reaction water (10 mL) was added and the aqueous layer was extracted with dichloromethane (2×20 mL). The combined organic layers were separated, dried with sodium sulfate and concentrated under reduced pressure to afford crude product which was purified by silica gel column chromatography (gradient of ethyl acetate in hexanes) to afford (R)-tert-butyl(1-((4-bromo-2-carbamoylphenyl)amino)-4-methyl-1-oxopentan-2-yl)carbamate (2.3 g, 58% yield) as an off-white solid: LCMS (ESI) m/e 428.2 [(M+H)$^+$, calcd for C$_{18}$H$_{27}$BrN$_3$O$_4$ 428.1]; LC/MS retention time (method A): t$_R$=1.92 min.

Part D. (R)-tert-Butyl(1-((4-bromo-2-cyanophenyl)amino)-4-methyl-1-oxopentan-2-yl)carbamate To a solution of (R)-tert-butyl(1-((4-bromo-2-carbamoylphenyl)amino)-4-methyl-1-oxopentan-2-yl)carbamate (1 g, 2.2 mmol) in pyridine (10 mL) cooled at 0° C. was added POCl$_3$ (1.07 g, 7 mmol) under a nitrogen atmosphere. The reaction mixture was stirred at room temperature for 2 h. Upon completion of the reaction, the mixture was concentrated under reduced pressure to dryness and cooled to 0° C. The reaction was quenched with ice and extracted with ethyl acetate (2×30 mL). The combined organic extracts were washed with brine (20 mL), dried over sodium sulfate and concentrated under reduced pressure to afford (R)-tert-butyl (1-((4-bromo-2-cyanophenyl)amino)-4-methyl-1-oxopentan-2-yl)carbamate (0.6 g, 67% yield).

Part E. (R)-tert-Butyl(1-((2-cyano-4-(pyridin-4-yl)phenyl)amino)-4-methyl-1-oxopentan-2-yl)carbamate Prepared by Suzuki coupling reaction in a similar fashion as described in Example 112 Part B using (R)-tert-butyl(1-((4-bromo-2-cyanophenyl)amino)-4-methyl-1-oxopentan-2-yl)carbamate and pyridin-4-ylboronic acid to give the title compound (93 mg, 95% yield) as a yellow solid: LCMS (ESI) m/e 409.9 [(M+H)$^+$, calcd for $C_{23}H_{29}N_4O_3$ 409.2]; LC/MS retention time (method D): $t_R$=0.79 min.

Part F. (R)-2-Amino-N-(2-cyano-4-(pyridin-4-yl)phenyl)-4-methylpentanamide

Prepared in a similar fashion as described in Example 1 Part D using (R)-tert-butyl(1-(2-cyano-4-(pyridin-4-yl)phenyl)amino)-4-methyl-1-oxopentan-2-yl)carbamate to give (R)-2-amino-N-(2-cyano-4-(pyridin-4-yl)phenyl)-4-methylpentanamide (63 mg, 28% yield) as a white solid, which was isolated as a free base: $^1$H NMR (400 MHz, CD$_3$OD) δ 8.65 (d, J=6 Hz, 2H), 8.24 (d, J=8.8 Hz, 1H), 8.19 (s, 1H), 8.11 (dd, J=6 Hz, J=1.2 Hz, 1H), 7.78 (d, J=6.4 Hz, 2H), 3.66 (m, 1H), 1.90 (m, 1H), 1.80 (m, 1H), 1.60 (m, 1H), 1.07 (m, 6H); LCMS (ESI) m/e 309.2 [(M+H)$^+$, calcd for $C_{18}H_{21}N_4O$, 309.2]; LC/MS retention time (method A): $t_R$=1.54 min; HPLC retention time (method J): $t_R$=6.49 min; HPLC retention time (method K): $t_R$=7.13 min; Chiral HPLC retention time (method A2): $t_R$=12.15 min.

Example 115

(R)-2-Amino-4-methyl-N-(4-(pyridin-4-yl)-2-(2H-tetrazol-5-yl)phenyl)pentanamide

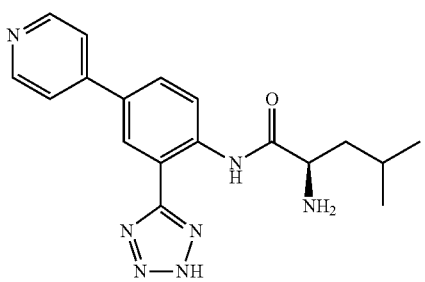 [SMILES: CC(C)C[C@@H](N)C(=O)Nc1ccc(-c2ccncc2)cc1-c1nn[nH]n1]

Part A. (R)-tert-Butyl(1-((4-bromo-2-(2H-tetrazol-5-yl)phenyl)amino)-4-methyl-1-oxopentan-2-yl)carbamate To a solution of (R)-tert-butyl(1-((4-bromo-2-cyanophenyl)amino)-4-methyl-1-oxopentan-2-yl)carbamate (600 mg, 1.46 mmol) (synthesized as described in example 114 Parts A-D) in dry DMF (15 mL) at room temperature under nitrogen was added sodium azide (474 mg, 7.3 mmol) and ammonium chloride (740 mg, 14 mmol). The reaction mixture was heated to 100° C. for 2 h. Upon completion, the reaction mixture was concentrated. The residue was partitioned between dichloromethane (20 mL) and water (15 mL). The organic layer was separated, and the aqueous layer was extracted with dichloromethane (2×20 mL). The combined organic layers were washed with water (10 mL), brine (30 mL), dried (Na$_2$SO$_4$) and concentrated under reduced pressure to afford (R)-tert-butyl(1-((4-bromo-2-(2H-tetrazol-5-yl)phenyl)amino)-4-methyl-1-oxopentan-2-yl)carbamate (0.6 g, 91% yield) as an off-white solid: LCMS (ESI) m/e 453.2 [(M+H)$^+$, calcd for $C_{18}H_{26}BrN_6O_3$, 453.1]; LC/MS retention time (method A): $t_R$=1.58 min.

Part B. (R)-tert-Butyl(4-methyl-1-oxo-1-((4-(pyridin-4-yl)-2-(2H-tetrazol-5-yl)phenyl)amino)pentan-2-yl)carbamate To a stirred solution of (R)-tert-butyl(1-((4-bromo-2-(2H-tetrazol-5-yl)phenyl)amino)-4-methyl-1-oxopentan-2-yl)carbamate (600 mg, 1.32 mmol) and pyridine-4-boronic acid (195 mg, 1.5 mmol) in dioxane (10 mL) and water (2 mL) was added cesium carbonate (1.26 g, 3.9 mmol) followed by the addition of Pd(PPh$_3$)$_4$ (45 mg, 0.039 mmol) and the reaction mixture was heated to 95° C. for 14 h. Upon completion of the reaction, the reaction mixture was concentrated under reduced pressure and diluted with water (20 mL). The product was extracted with ethyl acetate (2×15 mL) and the organic layers were separated and washed with water and purified by silica gel column chromatography using a gradient of chloroform and methanol to afford (R)-tert-butyl(4-methyl-1-oxo-1-((4-(pyridin-4-yl)-2-(2H-tetrazol-5 yl)phenyl)amino)pentan-2-yl)carbamate (0.22 g, 37% yield): LCMS (ESI) m/e 450.2 [(M)$^-$, calcd for $C_{23}H_{28}N_7O_3$, 450.1]; LC/MS retention time (method A): $t_R$=1.64 min.

Part C. (R)-2-Amino-4-methyl-N-(4-(pyridin-4-yl)-2-(2H-tetrazol-5-yl)phenyl)pentanamide Prepared in a similar fashion as described in Example 1 Part D using (R)-tert-butyl(4-methyl-1-oxo-1-((4-(pyridin-4-yl)-2-(2H-tetrazol-5 yl)phenyl)amino)pentan-2-yl)carbamate to give (R)-2-amino-4-methyl-N-(4-(pyridin-4-yl)-2-(2H-tetrazol-5-yl)phenyl)pentanamide (71.6 mg, 40% yield) as a yellow solid, which was isolated as a hydrochloride salt: $^1$H NMR (400 MHz, CD$_3$OD) δ 8.87 (d, J=6.4 Hz, 2H), 8.81 (d, J=8.8 Hz, 1H), 8.74 (s, 1H), 8.38 (d, J=6.8 Hz, 2H), 8.19 (dd, J=2.4 Hz, J=8.8 Hz, 1H), 4.30 (m, 1H), 2.03 (m, 1H), 1.86 (m, 2H), 1.11 (m, 6H); LCMS (ESI) m/e 352.2 [(M+H)$^+$, calcd for $C_{18}H_{22}N_7O$, 352.2]; LC/MS retention time (method B): $t_R$=1.06 min; HPLC retention time (method J): $t_R$=7.42 min; HPLC retention time (method K): $t_R$=7.64 min.

Example 116

(R)-2-Amino-4-methyl-N-(4-(pyridin-4-yl)phenyl) pentanamide

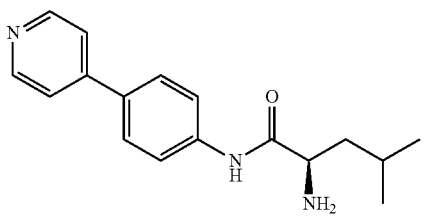 [SMILES: CC(C)C[C@@H](N)C(=O)Nc1ccc(-c2ccncc2)cc1]

Part A. (R)-tert-butyl(1-((4-bromophenyl)amino)-4-methyl-1-oxopentan-2-yl)carbamate To the mixture of 4-bromoaniline (1.00 g, 5.81 mmol) and 2-((tert-butoxycarbonyl)amino)-4-methylpentanoic acid (1.613 g, 6.98 mmol) in pyridine (10 mL) cooled to −15° C. was added $POCl_3$ (0.650 mL, 6.98 mmol). The reaction mixture was stirred at this temperature for 15 min and then warmed to room temperature and stirred for 40 min. After completion of reaction, the reaction mixture was concentrated under reduced pressure, acidified with 1.5N HCl (25 mL) and extracted with ethyl acetate (25 mL×3). The combined organic extracts were washed with brine, dried over sodium sulfate and concentrated under reduced pressure to afford a residue that was purified by preparative TLC on silica gel using 5% methanol in dichloromethane to afford tert-butyl(1-((4-bromophenyl)amino)-4-methyl-1-oxopentan-2-yl)carbamate (800 mg, 33% yield) as a white solid: LCMS (ESI) m/e 385.2 [(M)$^-$, calcd for $C_{17}H_{26}BrN_2O_3$, 385.1]; LC/MS retention time (method A): $t_R$=2.14 min.

Part B. (R)-tert-Butyl(4-methyl-1-oxo-1-((4-(pyridin-4-yl)phenyl)amino)pentan-2-yl)carbamate To a stirred solution of tert-butyl(1-((4-bromophenyl)amino)-4-methyl-1-oxopentan-2-yl)carbamate (700 mg, 1.817 mmol) in dioxane (24 mL) and water (4 mL) was added cesium carbonate (1.776 g, 5.45 mmol) and pyridin-4-ylboronic acid (268 mg, 2.180 mmol). The reaction mixture was purged with nitrogen gas for 10 min. To this mixture was added Pd(PPh$_3$)$_4$ (20.99 mg, 0.018 mmol) and the resultant mixture heated at 100° C. for 12 h. Upon completion of reaction, the reaction was quenched by addition of 50 mL of water and extracted with ethyl acetate (3×10 mL). The combined organic extracts were washed with brine, dried over sodium sulfate and concentrated under reduced pressure to afford an oil which was purified by silica gel column chromatography using 40% ethyl acetate in hexanes to afford (R)-tert-butyl(4-methyl-1-oxo-1-((4-(pyridin-4-yl)phenyl)amino)pentan-2-yl)carbamate (350 mg, 24% yield). LCMS (ESI) m/e 384.2 [(M)$^-$, calcd for $C_{22}H_{30}N_3O_3$, 384.2]; LC/MS retention time (method A): $t_R$=1.88 min.

Part C. (R)-2-Amino-4-methyl-N-(4-(pyridin-4-yl)phenyl)pentanamide

Prepared in a similar fashion as described in Example 1 Part D using (R)-tert-butyl(4-methyl-1-oxo-1-((4-(pyridin-4-yl)phenyl)amino)pentan-2-yl)carbamate from Part B to afford (R)-2-amino-4-methyl-N-(4-(pyridin-4-yl)phenyl) pentanamide (100 mg, 39% yield) as a white solid: $^1$H NMR (400 MHz, CD$_3$OD) δ 8.78 (d, J=6.4 Hz, 2H), 8.23 (d, J=6.8 Hz, 2H), 8.01 (d, J=8.8 Hz, 2H), 7.91 (d, J=8.8 Hz, 2H), 4.09 (m, 1H), 1.83 (m, 3H), 1.07 (d, J=6.4 Hz, 6H); LCMS (ESI) m/e 284.2 [(M+H)$^+$, calcd for $C_{17}H_{22}N_3O$, 284.2]; LC/MS retention time (method A): $t_R$=1.35 min; HPLC retention time (method J): $t_R$=6.78 min; HPLC retention time (method K): $t_R$=7.10 min; Chiral HPLC retention time (method A2): $t_R$=4.61 min.

Example 117

(R)-2-Amino-N-(3-methoxy-4-(pyrimidin-4-yl)phenyl)-4-methylpentanamide

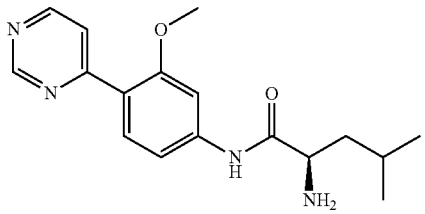 [SMILES: COc1cc(NC(=O)[C@H](N)CC(C)C)ccc1-c1ccncn1]

Part A. 2-Bromo-5-nitrophenol

To a solution of 3-nitrophenol (25.0 g, 179.8 mmol) in acetic acid (250 mL) was added bromine (28.8 g, 179.8 mmol) dropwise and the mixture was heated to 125° C. for 16 h. Upon completion of the reaction the volatiles were carefully removed under reduced pressure to dryness. The residue was partitioned between water (100 mL) and ethyl acetate (150 mL). The organic layer was separated and washed with sodium thiosulfate (100 mL), brine solution (100 mL), dried over sodium sulfate and concentrated under reduced pressure to afford the crude product. This was purified by silica gel column chromatography to afford 2-bromo-5-nitrophenol (20.0 g, 51% yield) as a brown solid: LCMS (ESI) m/e 216.0 [(M)$^-$, calcd for $C_6H_3BrNO_3$, 215.9]; LC/MS retention time (method A): $t_R$=1.52 min.

Part B. 1-Bromo-2-methoxy-4-nitrobenzene

To a solution of 2-bromo-5-nitrophenol (20 g, 92.2 mmol) in THF (300 mL) cooled to 0° C. was added lithium hydroxide (3.87 g, 92.2 mmol) and the mixture was stirred for 1 h. To this mixture dimethylsulfate (17.5 mL, 184.4 mmol) was added dropwise and the mixture was warmed to room temperature. Stirring was continued overnight. Upon completion of the reaction, the mixture was quenched by the addition of water (200 mL) and extracted using ethyl acetate (3×200 mL). The combined organic layers were washed with brine solution (100 mL), dried over sodium sulfate and concentrated under reduced pressure to afford 1-bromo-2-methoxy-4-nitrobenzene (23.0 g, quantitative yield) as a pale yellow solid: GC-MS (EI) m/e 230.9 [(M)$^+$, calcd for $C_7H_6BrNO_3$, 230.9]; GC/MS retention time (method A): $t_R$=7.61 min (GC-MS was performed using Agilent GCMS Module-7890 (GC) 5975C (MSD) fitted with column—HP-5MS, 30 m×0.25 mm ID×0.25 um Film thickness with helium flow of 0.9 mL/min. Column gradient 50° C. for 1 min and raised to 300° C. at the rate of 25° C./min).

Part C. 4-Bromo-3-methoxyaniline

To a solution of 1-bromo-2-methoxy-4-nitrobenzene (23 g, 99.6 mmol) in THF (200 mL) was added ammonium chloride (64 g, 1.2 mol) and zinc dust (78.1 g, 1.2 mol) and the mixture was heated at reflux overnight. The reaction mixture was cooled to room temperature, filtered through a diatomaceous earth (Celite®) bed and the filtrate was concentrated under reduced pressure. The residue was partitioned between water (200 mL) and ethyl acetate (200 mL). The organic layer was washed with brine solution (100 mL), dried over sodium sulfate and concentrated under reduced pressure to afford 4-bromo-3-methoxyaniline (17.4 g, 87% yield) as a yellow solid: $^1$H NMR (DMSO-d$_6$. 400 MHz) δ 7.1 (d, 1H), 6.31 (s, 1H), 6.1 (d. 1H), 5.27 (bs, 2H), 3.72 (s, 3H) ppm.

Part D. Methyl(4-bromo-3-methoxyphenyl)carbamate

To the solution of 4-bromo-3-methoxyaniline (17.4 g, 86.6 mmol) in dichloromethane (117 mL) cooled to 0° C. was added diisopropylethylamine (22.4 g, 173.2 mmol) and the mixture was stirred for 10 min. To this mixture methyl chloroformate (9.8 g, 103.9 mmol) was added dropwise. The reaction mixture was warmed gradually to room temperature and stirring continued for 2 h. Upon completion of the reaction, it was quenched with ice cold water (100 mL) and diluted with ethyl acetate (200 mL). The organic layer was washed with brine solution (100 mL), dried over sodium sulfate and concentrated under reduced pressure to afford methyl(4-bromo-3-methoxyphenyl)carbamate (13 g, 58% yield) as light yellow solid. LCMS (ESI) m/e 258.0 [(M)$^-$, calcd for $C_9H_9BrNO_3$, 258.0]; LC/MS retention time (method A): $t_R$=1.68 min.

Part E. Methyl(3-methoxy-4-(4,4,5,5-tetramethyl-1,3,2-dioxaborolan-2-yl)phenyl)carbamate To the mixture of methyl(4-bromo-3-methoxyphenyl)carbamate (3.00 g, 11.6 mmol), bispinacoloto diboron (8.82 g, 34.6 mmol), and Pd(dppf)Cl$_2$ (0.5 g, 0.6 mmol) was added triethylamine (3.5 g, 34.8 mmol) in dioxane (30 mL). Nitrogen gas was bubbled through the reaction mixture for 5 min and the mixture was heated at 90° C. overnight. Volatiles were removed under reduced pressure to afford the crude product, which was partitioned between water (25 mL) and ethyl acetate (30 mL). The organic layer was separated and washed with brine solution (25 mL), dried over sodium sulfate and concentrated under reduced pressure to afford methyl(3-methoxy-4-(4,4,5,5-tetramethyl-1,3,2-dioxaborolan-2-yl)phenyl)carbamate (1.9 g, 53% yield) as a brown solid: $^1$H NMR (DMSO-d$_6$, 400 MHz) δ 9.77 (s, 1H), 7.45 (d, J=8 Hz, 1H), 7.19 (s, 1H), 7.01 (m, 1H), 3.68 (s, 3H), 3.69 (s, 3H), 1.26 (s, 6H), 1.25 (s, 6H).

Part F. Methyl(3-methoxy-4-(pyrimidin-4-yl)phenyl)carbamate

To the solution of methyl(3-methoxy-4-(4,4,5,5-tetramethyl-1,3,2-dioxaborolan-2-yl)phenyl)carbamate (1.9 g, 6.2 mmol) in DMF (19 mL) was added 4-chloropyrimidine (714 mg, 6.2 mmol), Pd(PPh$_3$)$_4$ (570 mg, 0.5 mmol), potassium phosphate (3.93 g, 18.5 mmol) and the mixture was purged with nitrogen gas for 10 min. The reaction mixture was heated at 95° C. overnight. Upon completion of the reaction, the mixture was diluted with water (10 mL) and extracted with ethyl acetate (2×10 mL). The combined organic layers were washed with brine solution (10 mL), dried over sodium sulfate and concentrated under reduced pressure to afford methyl(3-methoxy-4-(pyrimidin-4-yl)phenyl)carbamate (1.3 g, 81% yield) as a grey solid. LCMS (ESI) m/e 260.0 [(M+H)$^+$, calcd for $C_{13}H_{14}N_3O_3$, 260.1]; LC/MS retention time (method G): $t_R$=1.33 min.

Part G. 3-Methoxy-4-(pyrimidin-4-yl)aniline

To the solution of methyl(3-methoxy-4-(pyrimidin-4-yl)phenyl)carbamate (1.3 g, 5 mmol) in a solvent mixture of methanol (5 mL) and water (15 mL) was added sodium hydroxide (3 g, 75 mmol) and the mixture was heated at 90° C. overnight. The reaction mixture was cooled to room temperature and the volatiles were removed under reduced pressure and extracted with ethyl acetate (3×20 mL). The combined organic layers were washed with brine solution (10 mL), dried over sodium sulfate and concentrated under reduced pressure to afford 3-methoxy-4-(pyrimidin-4-yl)aniline (0.4 g, 40% yield) as a yellow solid: LCMS (ESI) m/e 202.0 [(M+H)$^+$, calcd for $C_{11}H_{12}N_3O$, 202.1]; LC/MS retention time (method G): $t_R$=1.22 min.

Part H. (R)-tert-Butyl(1-((3-methoxy-4-(pyrimidin-4-yl)phenyl)amino)-4-methyl-1-oxopentan-2-yl)carbamate Prepared in a similar fashion as described in Example 1 Part C using 3-methoxy-4-(pyrimidin-4-yl)aniline (0.4 g, 2 mmol) from Part G to give the title compound (0.6 g, 72% yield): LCMS (ESI) m/e 415.2 [(M+H)$^+$, calcd for $C_{22}H_{31}N_4O_4$, 415.2]; LC/MS retention time (method A): $t_R$=1.85 min.

Part I. (R)-2-Amino-N-(3-methoxy-4-(pyrimidin-4-yl)phenyl)-4-methylpentanamide Prepared in a similar fashion as described in Example 1 Part D using (R)-tert-butyl(1-((3-methoxy-4-(pyrimidin-4-yl)phenyl)amino)-4-methyl-1-oxopentan-2-yl)carbamate from Part H to give (R)-2-amino-N-(3-methoxy-4-(pyrimidin-4-yl)phenyl)-4-methylpentanamide (120 mg, 26% yield) as a yellow solid, which was isolated as a hydrochloride salt: $^1$H NMR (400 MHz, CD$_3$OD) δ 9.15 (s, 1H), 8.71 (d, J=5.6 Hz, 1H), 8.11 (dd, J=5.6 Hz, 1.6 Hz, 1H), 8.03 (d, J=8.4 Hz, 1H), 7.4 (d, J=2 Hz, 1H), 7.27 (dd, J=8.4 Hz, 2.0 Hz, 1H), 3.97 (s, 3H), 3.51 (m, 1H), 1.81 (m, 1H), 1.69 (m, 1H), 1.52 (m, 1H), 1.01 (m, 6H); LCMS (ESI) m/e 315.2 [(M+H)$^+$, calcd for $C_{17}H_{23}N_4O_2$, 315.2]; LC/MS retention time (method B): $t_R$=1.42 min; HPLC retention time (method J): $t_R$=9.59 min; HPLC retention time (method K): $t_R$=5.34 min; Chiral HPLC retention time (method CHIRALCEL AD-H (250×4.6) mm 5 micron; Mob. phase: 0.2% DEA in n-hexane:ethanol (80:20): $t_R$=7.14 min.

Example 118

(R)—N-(4-(2-Acetamidopyridin-4-yl)phenyl)-2-amino-4-methylpentanamide

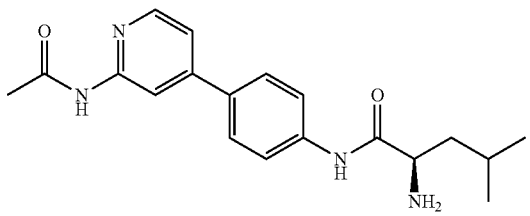 [SMILES: CC(=O)Nc1cc(-c2ccc(NC(=O)[C@H](N)CC(C)C)cc2)ccn1]

Part A. tert-Butyl(4-(trimethylstannyl)phenyl)carbamate

To a solution of tert-butyl(4-bromophenyl)carbamate (1.0 g, 3.67 mmol) in 1,4-dioxane (10 mL) was added hexamethylditin (1.524 mL, 7.35 mmol). The reaction mixture was purged with nitrogen gas and bis(triphenylphosphine)palladium(II) chloride (0.258 g, 0.367 mmol) was added and the mixture was heated at reflux at 95° C. for 16 h. After completion of the reaction, the reaction mixture was diluted with water (50 mL). The aq. layer was extracted with ethyl acetate (3×50 mL). The combined organic layers were dried over $Na_2SO_4$ and concentrated under reduced pressure. The crude product was purified by a neutral alumina column using a gradient of ethyl acetate in hexane to afford tert-butyl(4-(trimethylstannyl)phenyl)-carbamate (0.75 g, 57% yield): $^1$H NMR (400 MHz, $CDCl_3$) δ 7.42 (m, 2H), 7.35 (m, 2H), 6.43 (bs, 1H), 1.54 (s, 9H), 0.27 (s, 9H).

Part B. tert-Butyl(4-(2-Acetamidopyridin-4-yl)phenyl)carbamate

To the solution of tert-butyl(4-(trimethylstannyl)phenyl) carbamate (750 mg, 2.106 mmol) in DMF (7.5 mL) was added N-(4-bromopyridin-2-yl)acetamide (453 mg, 2.106 mmol), $K_2CO_3$ (873 mg, 6.32 mmol) and tetrabutylammonium bromide (1.019 g, 3.16 mmol). The reaction mixture was purged with nitrogen and bis(triphenylphosphine)palladium(II) chloride (148 mg, 0.211 mmol) was added. The reaction mixture was heated at 110° C. for 16 h. The reaction mixture was diluted with water (50 mL). The aq. layer was extracted with ethyl acetate (3×25 mL). The combined organic layers were dried over $Na_2SO_4$ and concentrated under reduced pressure to afford tert-butyl(4-(2-acetamidopyridin-4-yl)phenyl)carbamate (900 mg, 63% yield) as a brown sticky solid, which was used as is in the next step. LCMS (ESI) m/e 328.2 [(M+H)$^+$, calcd for $C_{18}H_{22}N_3O_3$, 328.2]; LC/MS retention time (method B): $t_R$=1.49 min.

Part C. N-(4-(4-aminophenyl)pyridin-2-yl)acetamide

To the solution of tert-butyl(4-(2-acetamidopyridin-4-yl) phenyl)carbamate (900 mg, 2.75 mmol) in dichloromethane (4.5 mL) cooled to 0° C. was added 4 M HCl in dioxane (9 mL, 36.0 mmol). The reaction mixture was stirred at 0° C. for 15 min and then warmed to room temperature and stirred for 2 h. The reaction mixture was concentrated under reduced pressure. The residue was dissolved in water (50 mL). The aqueous layer was washed with ethyl acetate (3×20 mL). The aqueous layer was basified with solid $Na_2CO_3$ and was then extracted with ethyl acetate (3×25 mL). The combined organic layers were dried over $Na_2SO_4$ and concentrated under reduced pressure to afford N-(4-(4-aminophenyl)pyridin-2-yl)acetamide (420 mg, 59% yield). LCMS (ESI) m/e 228.2 [(M+H)$^+$, calcd for $C_{13}H_{14}N_3O$, 228.1]; LC/MS retention time (method B): $t_R$=0.72 min.

Part D. (R)—N-(4-(2-Acetamidopyridin-4-yl)phenyl)-2-amino-4-methylpentanamide Prepared in a similar fashion as described in Example 111 Part B followed by Part D using (R)-2-(tert-butoxycarbonylamino)-4-methylpentanoic acid and N-(4-(4-aminophenyl)pyridin-2-yl)acetamide from Part C to afford (R)—N-(4-(2-acetamidopyridin-4-yl)phenyl)-2-amino-4-methylpentanamide (25 mg, 39% yield) as an off-white solid: $^1$H NMR (400 MHz, $CD_3OD$) δ 8.35 (d, J=6.4 Hz, 1H), 7.95 (s, 1H), 7.88 (m, 4H), 7.71 (d, J=6 Hz, 1H), 4.08 (m, 1H), 2.32 (s, 3H), 1.84 (m, 3H), 1.08 (m, 6H); LCMS (ESI) m/e 341.2 [(M+H)$^+$, calcd for $C_{19}H_{25}N_4O_2$, 341.2]; LC/MS retention time (method C): $t_R$=1.54 min; HPLC retention time (method J): $t_R$=7.53 min; HPLC retention time (method K): $t_R$=8.05 min; Chiral HPLC retention time (method CHIRALPAK AS-H (250×4.6) mm 5 micron; Mob. phase: n-hexane: ethanol (80:20): $t_R$=6.84 min.

Example 119

3-Isopropyl-N-(4-(pyridin-4-yl)phenyl)piperidine-2-carboxamide

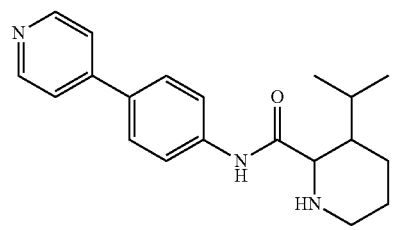 [SMILES: CC(C)C1CCCNC1C(=O)Nc1ccc(-c2ccncc2)cc1]

Prepared in a similar fashion as described in Example 1, Parts C-D using 1-(tert-butoxycarbonyl)-3-isopropylpiperidine-2-carboxylic acid (prepared as described by Subramanyam, C. et al. *Tet. Lett.* 1996, 37, 459) and 4-(pyridin-4-yl) aniline to afford 3-isopropyl-N-(4-(pyridin-4-yl)phenyl) piperidine-2-carboxamid as a diastereomeric mixture (30 mg, 50% yield) as a white solid: $^1$H NMR (400 MHz, $CD_3OD$) δ 8.79 (m, 2H), 8.30 (m, 2H), 8.03 (m, 2H), 7.89 (dd, J=6.8 Hz, 2.0 Hz, 2H), 4.15 (d, J=4 Hz, 1H), 3.8 (m, 1H), 3.15 (m, 1H), 2.20-2.05 (m, 2H), 2.01-1.89 (m, 2H), 1.87-1.75 (m, 2H), 1.01 (m, 6H); LCMS (ESI) m/e 324.0 [(M+H)$^+$, calcd for $C_{20}H_{26}N_3O$, 324.2]; LC/MS retention time (method A): $t_R$=1.39 min; HPLC retention time (method J): $t_R$=7.95 min; HPLC retention time (method K): $t_R$=8.45 min.

Example 120

N-(4-(Pyridin-4-yl)phenyl)-3-(trifluoromethyl)piperidine-2-carboxamide

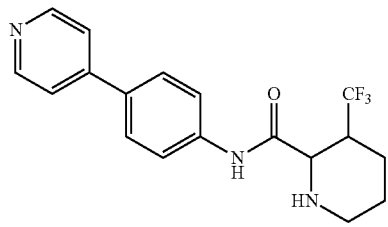 [SMILES: O=C(Nc1ccc(-c2ccncc2)cc1)C1NCCCC1C(F)(F)F]

Prepared in a similar fashion as described in Example 1, Parts C-D using 3-(trifluoromethyl)piperidine-2-carboxylic acid (synthesis described in example 91, Part A) and 4-(pyridin-4-yl)aniline to afford N-(4-(pyridin-4-yl)phenyl)-3-(trifluoromethyl)piperidine-2-carboxamide as a diastereomeric mixture (12 mg, mmol, 8% yield) as a light yellow solid. $^1$H NMR (400 MHz, CD$_3$OD) δ 8.65 (d, J=6.4 Hz, 2H), 7.92-7.80 (m, 6H), 3.85 (d, J=10.4 Hz, 1H), 3.35 (m, 1H), 2.98 (m, 2H), 2.25 (m, 1H), 2.01 (m, 1H), 1.85-1.75 (m, 2H). LCMS (ESI) m/e 350.2 [(M+H)$^+$, calcd for C$_{18}$H$_{19}$F$_3$N$_3$O, 350.2]; LC/MS retention time (method A): t$_R$=1.52 min; HPLC retention time (method P): t$_R$=8.11 min; Chiral HPLC retention time (Method G1, n-Hex: Ethanol—50:50): t$_R$=5.27 min.

Example 121

2-Amino-2-(2-methylcyclohexyl)-N-(4-(pyridin-4-yl)phenyl)acetamide

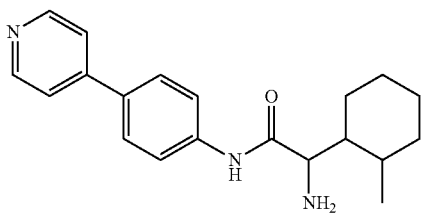 [SMILES: CC1CCCCC1C(N)C(=O)Nc1ccc(-c2ccncc2)cc1]

Prepared in a similar fashion as described in Example 1, Parts C-D using 2-amino-2-(2-methylcyclohexyl)acetic acid (in example 93, Part B) and 4-(pyridin-4-yl)aniline to afford 2-amino-2-(2-methylcyclohexyl)-N-(4-(pyridin-4-yl)phenyl)acetamide as a diastereomeric mixture (14 mg, 23% yield) as a white solid: $^1$H NMR (400 MHz, CD$_3$OD) δ 8.81 (d, J=6.4 Hz, 2H), 8.32 (d, J=6.8 Hz, 2H), 8.05 (dd, J=8.8 Hz, J=2 Hz, 2H), 7.92 (m, 2H), 3.80 (d, J=10.8 Hz, 1H), 2.1-1.2 (m, 10H), 1.1 (d, J=11.2 Hz, 3H); LCMS (ESI) m/e 324.2 [(M+H)$^+$, calcd for C$_{20}$H$_{26}$N$_3$O, 324.2]; LC/MS retention time (method B): t$_R$=1.20 min; HPLC retention time (method J): t$_R$=8.11 min (diastereomeric mixture).

Example 122

2-Amino-N-(4-(pyridin-4-yl)phenyl)-2-(2-(trifluoromethyl)cyclohexyl)acetamide

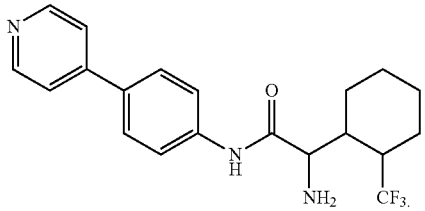

Part A. 2-Acetamido-2-(2-(trifluoromethyl)cyclohexyl)acetic acid

Prepared in the similar fashion as described in example 93 from 2-acetamido-2-(2-(trifluoromethyl)phenyl)acetic acid. The reduction afforded 2-acetamido-2-(2-(trifluoromethyl)cyclohexyl)acetic acid (0.6 g, 73% yield) as a white solid: LCMS (ESI) m/e 268.2 [(M+H)$^+$, calcd for C$_{11}$H$_{17}$F$_3$NO$_3$, 268.1]; LC/MS retention time (method C): t$_R$=1.53 min.

Part B. 2-Amino-2-(2-(trifluoromethyl)cyclohexyl)acetic acid

A stirred solution of 2-acetamido-2-(2-(trifluoromethyl)cyclohexyl)acetic acid (0.5 g, 1.871 mmol) in 6 N HCL (5 ml, 165 mmol) was heated at 100° C. for 14 h. Upon completion of reaction, The reaction mixture was concentrated under reduced pressure under high vacuum to afford 2-amino-2-(2-(trifluoromethyl)cyclohexyl)acetic acid (0.4 g, 95% yield) as a white solid: LCMS (ESI) m/e 226.2 [(M+H)$^+$, calcd for C$_9$H$_{15}$F$_3$NO$_2$, 226.1]; LC/MS retention time (method C): t$_R$=1.45 min.

Part C. 2-((tert-Butoxycarbonyl)amino)-2-(2-(trifluoromethyl)cyclohexyl)acetic acid To a stirred solution of 2-amino-2-(2-(trifluoromethyl)cyclohexyl)acetic acid (0.4 g, 1.78 mmol) in dioxane (4 ml) and water (4 ml) was added NaHCO$_3$ (0.753 g, 7.10 mmol) followed by Boc$_2$O (0.825 ml, 3.55 mmol). The reaction mixture was stirred at room temperature for 14 h. The reaction mixture was concentrated under reduced pressure and acidified with saturated aq. citric acid solution to pH=4 and extracted with ethyl acetate (2×50 mL). The combined organic extracts were dried over Na$_2$SO$_4$, filtered, and concentrated under reduced pressure to afford (0.5 g, 87% yield) as an oil: LCMS (ESI) m/e 324.2 [(M)$^-$, calcd for C$_{14}$H$_{21}$F$_3$NO$_4$, 324.1]; LC/MS retention time (method C): t$_R$=1.75 min.

Part D. 2-Amino-N-(4-(pyridin-4-yl)phenyl)-2-(2-(trifluoromethyl)cyclohexyl)-acetamide Prepared in a similar fashion as described in Example 1, Parts C-D using 2-((tert-butoxycarbonyl)amino)-2-(2-(trifluoromethyl)cyclohexyl)acetic acid from Part C and 4-(pyridin-4-yl)aniline to afford 2-amino-N-(4-(pyridin-4-yl)phenyl)-2-(2-(trifluoromethyl)cyclohexyl)-acetamide as a diastereomeric mixture (10 mg, 13% yield) as a white solid:

NMR (400 MHz, CD$_3$OD) δ 8.78 (d, J=5.6 Hz, 2H), 8.24 (d, J=6.4 Hz, 2H), 8.02 (dd, J=9.2, 1.6 Hz, 2H), 7.93 (d, J=9.6 Hz, 2H), 4.1 (m, 1H), 2.8-1.5 (m, 10H); LCMS (ESI) m/e 378.2 [(M+H)$^+$, calcd for C$_{20}$H$_{23}$F$_3$N$_3$O, 378.2]; LC/MS retention time (method B): t$_R$=1.24 min; HPLC retention time (method J): t$_R$=7.93 min (Diasteriomer 1), 8.05 (Diasteriomer 2). HPLC retention time (method K): t$_R$=9.19 min (Diasteriomer 1) and 9.38 (Diasteriomer 2).

Biological Data

Methods
AAK1 Kinase Assay

The assays were performed in U-bottom 384-well plates. The final assay volume was 30 µl prepared from 15 µl additions of enzyme and substrates (fluoresceinated peptide (5-FAM)-Aha-KEEQSQITSQVTGQIGWR—NH2 and ATP) and test compounds in assay buffer (10 mM Tris-HCL pH 7.4, 10 mM MgCl$_2$, 0.01% Tween-20 and 1.0 mM DTT). The reactions were initiated by the combination of bacterially expressed, GST-Xa-hAAK1 with substrates and test compounds. The reactions were incubated at room temperature for 3 hours and terminated by adding 60 µl of 35 mM EDTA buffer to each sample. The reactions were analyzed on the Caliper LabChip 3000 (Caliper, Hopkinton, Mass.) by electrophoretic separation of the fluorescent substrate and phosphorylated product. Inhibition data were calculated by comparison to EDTA quenched control reactions for 100% inhibition and vehicle-only reactions for 0% inhibition. The final concentration of reagents in the assays are ATP, 22 µM; (5-FAM)-Aha-KEEQSQITSQVTGQIGWR—NH2, 1.5 µM; GST-Xa-hAAK1, 3.5 nM; and DMSO, 1.6%. Dose response curves were generated to determine the concentration required inhibiting 50% of kinase activity (IC$_{50}$). Compounds were dissolved at 10 mM in dimethylsulfoxide (DMSO) and evaluated at eleven concentrations. IC$_{50}$ values were derived by non-linear regression analysis. Results are shown in Table 2.

TABLE 2

| Example | IC$_{50}$ (nM) |
| --- | --- |
| 1 | 36 |
| 2 | 346 |
| 3 | 53 |
| 4 | 136 |
| 5 | 104 |
| 6 | 78 |
| 7 | 64 |
| 8 | 90 |
| 9 | 115 |
| 10 | 5010 |
| 11 | 1,520 |
| 12 | 55 |
| 13 | 248 |
| 14 | 97 |
| 15 | 1,370 |
| 16 | 100 |
| 17 | 66 |
| 18 | 35 |
| 19 | 56 |
| 20 | 63 |
| 21 | 275 |
| 22 | 140 |
| 23 | 5,100 |
| 24 | 19 |
| 25 | 3,250 |
| 26 | 955 |
| 27 | 54 |
| 28 | 709 |
| 29 | 344 |

TABLE 2-continued

| Example | IC$_{50}$ (nM) |
| --- | --- |
| 30 | 590 |
| 31 | 7,320 |
| 32 | 1,140 |
| 33 | 2,100 |
| 34 | 202 |
| 35 | 83 |
| 36 | 48 |
| 37 | 8 |
| 38 | 110 |
| 39 | 29 |
| 40 | 460 |
| 41 | 45 |
| 42 | 860 |
| 43 | 260 |
| 44 | 140 |
| 45 | 150 |
| 46 | 2,200 |
| 47 | 440 |
| 48 | 450 |
| 49 | 90 |
| 50 | 340 |
| 51 | 590 |
| 52 | 530 |
| 53 | 270 |
| 54 | 720 |
| 55 | 130 |
| 56 | 950 |
| 57 | 780 |
| 58 | 4,400 |
| 59 | 2,400 |
| 60 | 210 |
| 61 | 72 |
| 62 | 220 |
| 63 | 540 |
| 64 | 150 |
| 65 | 370 |
| 66 | 110 |
| 67 | 260 |
| 68 | 67 |
| 69 | 280 |
| 70 | 310 |
| 71 | 400 |
| 72 | 1,300 |
| 73 | 1500 |
| 74 | 680 |
| 75 | 5100 |
| 76 | 110 |
| 77 | 810 |
| 78 | 2900 |
| 79 | 130 |
| 80 | 630 |
| 81 | 510 |
| 82 | 1800 |
| 83 | 360 |
| 84 | 240 |
| 85 | 8 |
| 86 | 52 |
| 87 | 280 |
| 88 | 8 |
| 89 | 2000 |
| 90 | 1100 |
| 91 | 417 |
| 92 | 74 |
| 93 | 20 |
| 94 | 750 |
| 95 | 420 |
| 96 | 780 |
| 97 | 630 |
| 98 | 1120 |
| 99 | 780 |
| 100 | 530 |
| 101 | 25 |
| 102 | 6 |
| 103 | 360 |
| 104 | 760 |
| 105 | 620 |
| 106 | 160 |
| 107 | 84 |

TABLE 2-continued

| Example | IC$_{50}$ (nM) |
|---|---|
| 108 | 47 |
| 109 | 790 |
| 110 | 1030 |
| 111 | 300 |
| 112 | 1340 |
| 113 | 500 |
| 114 | 75 |
| 115 | 28 |
| 116 | 25 |
| 117 | 460 |
| 118 | 6 |
| 119 | 33 |
| 120 | 220 |
| 121 | 140 |
| 122 | 64 |

AAK1 Knockout Mice

Mice homozygous (−/−) for the disruption of the AAK1 gene were prepared by two methods; gene trapping and homologous recombination.

Gene trapping is a method of random insertional mutagenesis that uses a fragment of DNA coding for a reporter or selectable marker gene as a mutagen. Gene trap vectors have been designed to integrate into introns or genes in a manner that allows the cellular splicing machinery to splice vector encoded exons to cellular mRNAs. Commonly, gene trap vectors contain selectable marker sequences that are preceded by strong splice acceptor sequences and are not preceded by a promoter. Thus, when such vectors integrate into a gene, the cellular splicing machinery splices exons from the trapped gene onto the 5' end of the selectable marker sequence. Typically, such selectable marker genes can only be expressed if the vector encoding the gene has integrated into an intron. The resulting gene trap events are subsequently identified by selecting for cells that can survive selective culture.

Embryonic stem cells (Lex-1 cells from derived murine strain A129), were mutated by a process involving the insertion of at least a portion of a genetically engineered vector sequence into the gene of interest, the mutated embryonic stem cells were microinjected into blastocysts which were subsequently introduced into pseudopregnant female hosts and carried to term using established methods. See, e.g., "Mouse Mutagenesis", 1998, Zambrowicz et al., eds., Lexicon Press, The Woodlands, Tex. The resulting chimeric animals were subsequently bred to produce offspring capable of germline transmission of an allele containing the engineered mutation in the gene of interest.

AAK1-gene disrupted mice were also made by homologous recombination. In this case, the second coding exon of the murine AAK1 gene (see GenBank Accession Number NM_177762) was removed by methods known in the art. See, e.g., U.S. Pat. Nos. 5,487,992, 5,627,059, and 5,789,215.

Mice homozygous (−/−) for the disruption of the AAK1 gene were studied in conjunction with mice heterozygous (+/−) for the disruption of the AAK1 gene, and wild-type (+/+) litter mates. During this analysis, the mice were subject to a medical work-up using an integrated suite of medical diagnostic procedures designed to assess the function of the major organ systems in a mammalian subject. Homozygous (−/−) "knockout" mice were studied in conjunction with their heterozygous (+/−) and wild-type (+/+) litter mates. Disruption of the AAK1 gene was confirmed by Southern analysis. Expression of the murine homolog of AAK1 was detected by RT-PCR in murine brain; spinal cord; eye; thymus; spleen; lung; kidney; liver; skeletal muscle; bone; stomach, small intestine and colon; heart; adipose; asthmatic lung; LPS liver; blood; banded heart; aortic tree; prostate; and mammary gland (5 week virgin, mature virgin, 12 DPC, 3 day post-partum (lactating), 3 day post-weaning (early involution), and 7 day post-weaning (late involution)).

AAK1 homozygous (−/−) and their wild-type (+/+) littermates were tested using the formalin paw test in order to assess their acute and tonic nociceptive responses. For these tests, Automatic Nociception Analyzers (purchased from the Ozaki lab at University of California, San Diego) were used. A metal band was placed around the left hind paw of each mouse 30 minutes prior to testing. After the 30-minute acclimation period, 20 µl of 5% formalin is subcutaneously injected in the dorsal surface of the left hind paw. Mice were individually housed in cylindrical chambers for 45 minutes. Fresh 5% formalin solution was prepared by diluting formaldehyde (Formalde-fresh 20%, Fisher Scientific, Fair Lawn, N.J.) with distilled water. Investigatory compounds were administered 30 minutes prior to formalin injection.

A computer recorded flinches per minute, total flinches for phase I (acute phase=first 8 minutes), and total flinches for phase II (tonic phase=time between minutes 20-40) through an electromagnetic field. See Yaksh T L, Ozaki G, McCumber D, Rathbun M, Svensson C, Malkmus S, Yaksh M C. An automated flinch detecting system for use in the formalin nociceptive bioassay. J Appl Physiol., 2001; 90:2386-402. Phase 1 and phase 2 data were obtained using homozygous (−/−) mice females (n=16), wild-type females (n=15), homozygous (−/−) mice males (n=9), and wild-type males (n=18). In all groups and in both phases, the AAK1 homozygous (−/−) mice exhibited significantly less recorded paw flinching than their wild-type (+/+) littermates.

Studies of AAK1 knockout mice showed that disruption of the AAK1 gene affects pain response as measured using the formalin paw test described above. The same test was used to confirm that the administration of an AAK1 inhibitor can also affect pain response.

A compound of the disclosure was tested in this assay at different doses. Gabapentin and pregabalin were used as positive controls. Results are shown below in Table 3, wherein the effect of gabapentin at 200 mg/kg is considered a 100% response, the % response for the other compounds is relative to the 200 mg/kg dose of gabapentin, "sc" means subcutaneous administration; "po" means oral administration.

TABLE 3

| Compound | Dose (mg/kg) | Response |
|---|---|---|
| Gabapentin | 50 sc | 60% |
| Gabapentin | 200 sc | 100% |
| Pregabalin | 50 sc | 90% |
| Example 1: (R)-2-Amino-N-(3-methoxy-4-(oxazol-5-yl)phenyl)-4-methylpentanamide | 60 sc | 90% |
| Example 18: (R)-2-Amino-N-(3-(difluoromethoxy)-4-(oxazol-5-yl)phenyl)-4-methylpentanamide | 60 sc | 100% |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

The invention claimed is:

1. A compound of formula (I) or formula (III)

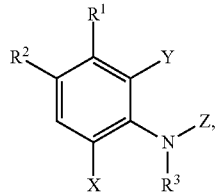
(I)

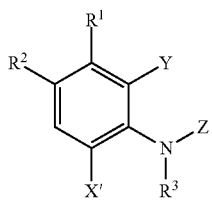
(III)

or a pharmaceutically acceptable salt thereof, wherein:

$R^1$ is $C_1$-$C_3$alkoxy;

$R^2$ is selected from

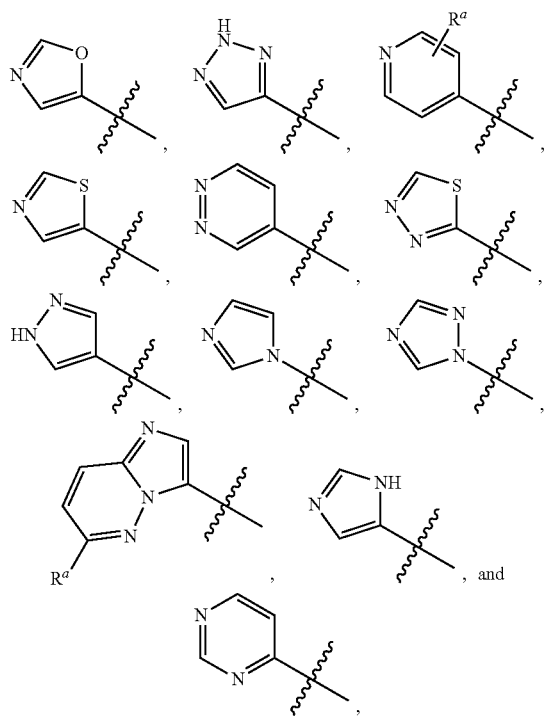

wherein $R^a$ is selected from hydrogen, $C_1$-$C_3$alkoxy, $C_1$-$C_3$alkylamino, $C_1$-$C_3$alkylcarbonylamino, amino, and halo;

$R^3$ is selected from hydrogen and $C_1$-$C_3$alkyl;

X is selected from hydrogen, $C_1$-$C_3$alkoxy, $C_1$-$C_3$alkyl, cyano, halo, and halo$C_1$-$C_3$alkyl, X' is selected from

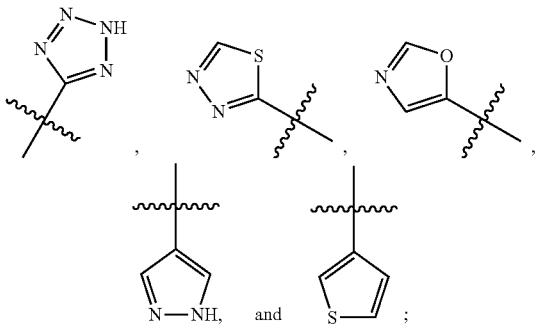

Y is selected from hydrogen and halo;

Z is selected from

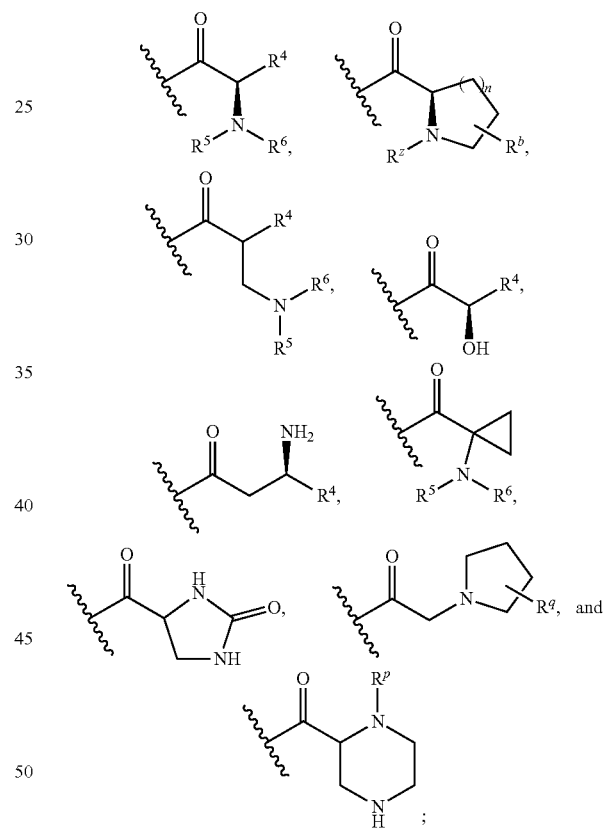

wherein n is 1 or 2;

$R^4$ is selected from $C_2$-$C_6$alkyl, $C_3$-$C_6$cycloalkyl, ($C_3$-$C_6$cycloalkyl)$C_1$-$C_3$alkyl, $C_{1-3}$alkylthio$C_{1-3}$alkyl, hydroxy$C_1$-$C_6$alkyl, and halo$C_1$-$C_6$alkyl;

$R^5$ and $R^6$ are independently selected from hydrogen, $C_1$-$C_3$alkyl, $C_1$-$C_3$alkylsulfonyl, $C_3$-$C_6$cycloalkyl optionally substituted with an amino group, heterocyclyl, heterocyclyl$C_1$-$C_3$alkyl, phenyl$C_1$-$C_3$alkyl, phenyl$C_1$-$C_3$alkylsulfonyl, and phenylsulfonyl; wherein the heterocyclyl, the heterocyclyl part of the heterocyclyl$C_1$-$C_3$alkyl, and the phenyl part of the phenyl$C_1$-$C_3$alkyl, phenyl$C_1$-$C_3$alkylsulfonyl, and the phenylsulfonyl are optionally substituted with one group selected from $C_1$-$C_3$alkyl, halo, hydroxy; or $R^5$ and $R^6$, together with the nitrogen atom to which they are attached, form a five- or six-membered heterocyclic ring optionally containing a second nitrogen atom and optionally substituted with an amino group;

$R^b$ is selected from hydrogen, $C_1$-$C_3$alkoxy, $C_1$-$C_3$alkyl, halo, and halo$C_1$alkyl;

$R^p$ is selected from hydrogen and $C_1$-$C_3$alkyl;

$R^q$ is selected from hydrogen and oxo; and $R^z$ is selected from hydrogen, $C_1$-$C_3$alkyl, and $C_1$-$C_3$alkylcarbonyl;

or a pharmaceutically acceptable salt thereof.

2. A compound of claim 1, or a pharmaceutically acceptable salt thereof, wherein:

X and Y are independently selected from hydrogen and halo; and

Z is

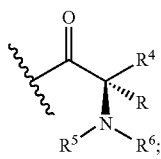

or a pharmaceutically acceptable salt thereof.

3. A composition comprising a compound of claim 1, and a pharmaceutically acceptable salt thereof.

4. A compound selected from:
- (R)-2-Amino-N-(3-methoxy-4-(oxazol-5-yl)phenyl)-4-methylpentanamide;
- (R)—N-(3-Methoxy-4-(oxazol-5-yl)phenyl)pyrrolidine-2-carboxamide;
- (R)-2-Amino-2-cyclopentyl-N-(3-methoxy-4-(oxazol-5-yl)phenyl)acetamide;
- (R)-2-Amino-N-(3-methoxy-4-(oxazol-5-yl)phenyl)-3-methylbutanamide;
- (S)-2-Amino-N-(3-methoxy-4-(oxazol-5-yl)phenyl)-4-methylpentanamide;
- (R)-2-Amino-3-cyclobutyl-N-(3-methoxy-4-(oxazol-5-yl)phenyl)propanamide;
- 2-Amino-N-(3-methoxy-4-(oxazol-5-yl)phenyl)-4-methylpentanamide;
- 2-Amino-N-(3-methoxy-4-(oxazol-5-yl)phenyl)-5-methylhexanamide;
- (R)-2-Amino-3-cyclopropyl-N-(3-methoxy-4-(oxazol-5-yl)phenyl)propanamide;
- (R)-2-Amino-N-ethyl-N-(3-methoxy-4-(oxazol-5-yl)phenyl)-4-methylpentanamide;
- (R)-2-Amino-4-methyl-N-(4-(oxazol-5-yl)-3-(trifluoromethyl)phenyl)pentanamide;
- (R)-2-Amino-N-(3-bromo-4-(oxazol-5-yl)phenyl)-4-methylpentanamide;
- (R)-2-Amino-4-methyl-N-(3-methyl-4-(oxazol-5-yl)phenyl)pentanamide;
- (R)-2-Amino-N-(3-ethyl-4-(oxazol-5-yl)phenyl)-4-methylpentanamide;
- (R)-2-Amino-4-methyl-N-(4-(oxazol-5-yl)-3-(thiophen-3-yl)phenyl)pentanamide;
- (R)-2-Amino-N-(3-hydroxy-4-(oxazol-5-yl)phenyl)-4-methylpentanamide;
- (R)-2-Amino-N-(3-ethoxy-4-(oxazol-5-yl)phenyl)-4-methylpentanamide;
- (R)-2-Amino-N-(3-(difluoromethoxy)-4-(oxazol-5-yl)phenyl)-4-methylpentanamide;
- (R)-2-Amino-N-(3-methoxy-4-(2H-1,2,3-triazol-4-yl)phenyl)-4-methylpentanamide;
- (R)-2-Amino-N-(3-methoxy-4-(pyridin-4-yl)phenyl)-4-methylpentanamide;
- (R)-2-Amino-N-(3-methoxy-4-(thiazol-5-yl)phenyl)-4-methylpentanamide;
- (R)-2-Amino-N-(3-methoxy-4-(pyridazin-4-yl)phenyl)-4-methylpentanamide;
- (R)-2-Amino-N-(3-methoxy-4-(1,3,4-thiadiazol-2-yl)phenyl)-4-methylpentanamide;
- (R)-2-Amino-N-(3-methoxy-4-(1H-pyrazol-4-yl)phenyl)-4-methylpentanamide;
- (R)—N-(4-(1H-Imidazol-1-yl)-3-methoxyphenyl)-2-amino-4-methylpentanamide;
- (R)-2-Amino-N-(3-methoxy-4-(1H-1,2,4-triazol-1-yl)phenyl)-4-methylpentanamide;
- (R)-2-Amino-N-(2-chloro-5-methoxy-4-(oxazol-5-yl)phenyl)-4-methylpentanamide;
- (R)-2-Amino-N-(2-chloro-3-methoxy-4-(oxazol-5-yl)phenyl)-4-methylpentanamide;
- (R)-2-Amino-N-(2,6-dichloro-3-methoxy-4-(oxazol-5-yl)phenyl)-4-methylpentanamide;
- 2-(3-Aminopyrrolidin-1-yl)-N-(3-methoxy-4-(oxazol-5-yl)phenyl)-4-methylpentanamide;
- 2-(trans-4-Aminocyclohexylamino)-N-(3-methoxy-4-(oxazol-5-yl)phenyl)-4-methylpentanamide;
- 2-(Azetidin-3-ylamino)-N-(3-methoxy-4-(oxazol-5-yl)phenyl)-4-methylpentanamide;
- 2-(4-Aminopiperidin-1-yl)-N-(3-methoxy-4-(oxazol-5-yl)phenyl)-4-methylpentanamide;
- (R)-2-Hydroxy-N-(3-methoxy-4-(oxazol-5-yl)phenyl)-4-methylpentanamide;
- 2-(Aminomethyl)-N-(3-methoxy-4-(oxazol-5-yl)phenyl)-4-methylpentanamide;
- 3-Isopropyl-N-(3-methoxy-4-(oxazol-5-yl)phenyl)pyrrolidine-2-carboxamide;
- (R)-2-Amino-N-(3-fluoro-4-(oxazol-5-yl)phenyl)-4-methylpentanamide;
- 2-Amino-N-(3-(difluoromethoxy)-4-(1H-pyrazol-4-yl)phenyl)-4-methylpentanamide;
- 2-amino-N-(3-(dimethylamino)-4-(oxazol-5-yl)phenyl)-4-methylpentanamide;
- (R)-2-Amino-N-(4-(2-chloropyridin-4-yl)-3-methoxyphenyl)-4-methylpentanamide;
- 2-Amino-N-(4-(2-aminopyridin-4-yl)-3-methoxyphenyl)-4-methylpentanamide;
- (R)-2-Amino-N-(4-(imidazo[1,2-b]pyridazin-3-yl)-3-methoxyphenyl)-4-methylpentanamide;
- (R)-2-Amino-N-(4-(6-chloroimidazo[1,2-b]pyridazin-3-yl)-3-methoxyphenyl)-4-methylpentanamide;
- 2-Amino-N-(3-methoxy-4-(2-(methylamino)pyridin-4-yl)phenyl)-4-methylpentanamide;
- (R)-2-Amino-N-(3-methoxy-4-(oxazol-5-yl)phenyl)butanamide;
- (S)-2-Amino-N-(3-methoxy-4-(oxazol-5-yl)phenyl)pentanamide;
- (R)-2-Amino-N-(3-methoxy-4-(oxazol-5-yl)phenyl) hexanamide;
- (S)-2-Amino-N-(3-methoxy-4-(oxazol-5-yl)phenyl) hexanamide;
- (R)-2-Amino-N-(3-methoxy-4-(oxazol-5-yl)phenyl)-4-(methylthio)butanamide;
- (2R,3R)-2-Amino-N-(3-methoxy-4-(oxazol-5-yl)phenyl)-3-methylpentanamide;

(R)-2-Amino-3-cyclohexyl-N-(3-methoxy-4-(oxazol-5-yl)phenyl)propanamide;
N-(3-Methoxy-4-(oxazol-5-yl)phenyl)-2-oxoimidazolidine-4-carboxamide;
N-(3-Methoxy-4-(oxazol-5-yl)phenyl)-1-(methylamino)cyclopropanecarboxamide;
N-(3-Methoxy-4-(oxazol-5-yl)phenyl)-2-(2-oxopyrrolidin-1-yl)acetamide;
(R)-2-((4-Chlorobenzyl)amino)-N-(3-methoxy-4-(oxazol-5-yl)phenyl)-4-methylpentanamide;
(R)—N-(3-Methoxy-4-(oxazol-5-yl)phenyl)-4-methyl-2-(((1-methyl-1H-pyrrol-2-yl)methyl)amino)pentanamide;
(R)-2-((2-Chlorobenzyl)amino)-N-(3-methoxy-4-(oxazol-5-yl)phenyl)-4-methylpentanamide;
(R)—N-(3-Methoxy-4-(oxazol-5-yl)phenyl)-4-methyl-2-((4-methylbenzyl)amino)pentanamide;
(R)—N-(3-Methoxy-4-(oxazol-5-yl)phenyl)-4-methyl-2-(((1-methyl-1H-pyrazol-4-yl)methyl)amino)pentanamide;
(R)—N-(3-Methoxy-4-(oxazol-5-yl)phenyl)-4-methyl-2-((thiophen-3-ylmethyl)amino)pentanamide;
(R)—N-(3-Methoxy-4-(oxazol-5-yl)phenyl)-4-methyl-2-(((3-methylthiophen-2-yl)methyl)amino)pentanamide;
(R)-2-(((1,2,3-Thiadiazol-4-yl)methyl)amino)-N-(3-methoxy-4-(oxazol-5-yl)phenyl)-4-methylpentanamide;
(R)—N-(3-methoxy-4-(oxazol-5-yl)phenyl)-4-methyl-2-(methyl sulfonamido)pentanamide;
(R)-2-(Ethylsulfonamido)-N-(3-methoxy-4-(oxazol-5-yl)phenyl)-4-methylpentanamide;
(R)—N-(3-Methoxy-4-(oxazol-5-yl)phenyl)-4-methyl-2-(propylsulfonamido)pentanamide;
(R)—N-(3-methoxy-4-(oxazol-5-yl)phenyl)-4-methyl-2-(phenylsulfonamido)pentanamide;
(R)—N-(3-Methoxy-4-(oxazol-5-yl)phenyl)-4-methyl-2-(phenylmethylsulfonamido)pentanamide;
(S)—N-(3-Methoxy-4-(oxazol-5-yl)phenyl)piperidine-2-carboxamide;
(R)-2-Amino-N-(3-methoxy-4-(oxazol-5-yl)phenyl)-4,4-dimethylpentanamide;
(R)-2-Amino-3-hydroxy-N-(3-methoxy-4-(oxazol-5-yl)phenyl)propanamide;
2-Amino-5,5,5-trifluoro-N-(3-methoxy-4-(oxazol-5-yl)phenyl)pentanamide;
(2R,3S)-2-Amino-3-hydroxy-N-(3-methoxy-4-(oxazol-5-yl)phenyl)butanamide;
(2R,4S)-4-Methoxy-N-(3-methoxy-4-(oxazol-5-yl)phenyl)pyrrolidine-2-carboxamide;
(R)-3-Amino-N-(3-methoxy-4-(oxazol-5-yl)phenyl)-4-methylpentanamide;
1-Isobutyryl-N-(3-methoxy-4-(oxazol-5-yl)phenyl)piperidine-2-carboxamide;
(S)-1-Isopropyl-N-(3-methoxy-4-(oxazol-5-yl)phenyl)pyrrolidine-2-carboxamide;
(S)-1-Isobutyryl-N-(3-methoxy-4-(oxazol-5-yl)phenyl)pyrrolidine-2-carboxamide;
1-Isopropyl-N-(3-methoxy-4-(oxazol-5-yl)phenyl)piperidine-2-carboxamide;
2-Amino-4-fluoro-N-(3-methoxy-4-(oxazol-5-yl)phenyl)-4-methylpentanamide;
3-Isopropyl-N-(3-methoxy-4-(oxazol-5-yl)phenyl)piperidine-2-carboxamide;
1-Isopropyl-N-(3-methoxy-4-(oxazol-5-yl)phenyl)piperazine-2-carboxamide;
3-Isopropyl-N-(3-methoxy-4-(oxazol-5-yl)phenyl)piperidine-2-carboxamide;
(2R,3R)-3-Isopropyl-N-(3-methoxy-4-(oxazol-5-yl)phenyl)piperidine-2-carboxamide;
(2R,4S)-4-Fluoro-N-(3-methoxy-4-(oxazol-5-yl)phenyl)pyrrolidine-2-carboxamide;
(2R,4R)-4-Fluoro-N-(3-methoxy-4-(oxazol-5-yl)phenyl)pyrrolidine-2-carboxamide;
N-(3-Methoxy-4-(oxazol-5-yl)phenyl)-3-(trifluoromethyl)piperidine-2-carboxamide;
2-Amino-N-(3-methoxy-4-(oxazol-5-yl)phenyl)-2-(2-methylcyclohexyl)acetamide;
2-Amino-3-cyclobutyl-N-(2-fluoro-5-methoxy-4-(oxazol-5-yl)phenyl)propanamide;
2-Amino-3-cyclopropyl-N-(2-fluoro-5-methoxy-4-(oxazol-5-yl)phenyl)propanamide;
(R)-2-Amino-N-(2-fluoro-5-methoxy-4-(oxazol-5-yl)phenyl)-3-methylbutanamide;
2-Amino-N-(2-fluoro-5-methoxy-4-(oxazol-5-yl)phenyl)-4,4-dimethylpentanamide;
(R)-2-Amino-N-(2-fluoro-5-methoxy-4-(oxazol-5-yl)phenyl)-4-methylpentanamide;
(S)-2-Amino-N-(2-fluoro-5-methoxy-4-(oxazol-5-yl)phenyl)-4-methylpentanamide;
(R)-2-Amino-2-cyclopentyl-N-(2-fluoro-5-methoxy-4-(oxazol-5-yl)phenyl)acetamide;
(R)-2-Amino-N-(2-cyano-5-methoxy-4-(oxazol-5-yl)phenyl)-4-methylpentanamide;
(R)-2-Amino-N-(5-methoxy-4-(oxazol-5-yl)-2-(2H-tetrazol-5-yl)phenyl)-4-methylpentanamide;
(R)-2-Amino-N-(5-methoxy-4-(oxazol-5-yl)-2-(1,3,4-thiadiazol-2-yl)phenyl)-4-ethylpentanamide;
(R)-2-Amino-N-(5-methoxy-2,4-bis(oxazol-5-yl)phenyl)-4-methylpentanamide;
(R)-2-Amino-N-(2,5-difluoro-4-(oxazol-5-yl)phenyl)-4-methylpentanamide;
(R)-2-Amino-4-methyl-N-(4-(oxazol-5-yl)-3-(trifluoromethoxy)phenyl)pentanamide;
(R)-2-Amino-N-(5-fluoro-2-methoxy-4-(oxazol-5-yl)phenyl)-4-methylpentanamide;
(R)-2-Amino-N-(3-cyano-4-(oxazol-5-yl)phenyl)-4-methylpentanamide;
(R)—N-(4-(1H-Imidazol-5-yl)-3-methoxyphenyl)-2-amino-4-methylpentanamide;
(R)-2-Amino-N-(2-ethyl-5-methoxy-4-(oxazol-2-yl)phenyl)-4-methylpentanamide; and
(R)-2-Amino-N-(3-methoxy-4-(pyrimidin-4-yl)phenyl)-4-methylpentanamide;
or a pharmaceutically acceptable salt thereof.

5. A method of inhibiting adaptor associated kinase 1 (AAK1) activity, comprising contacting AAK1 with a compound of formula (II)

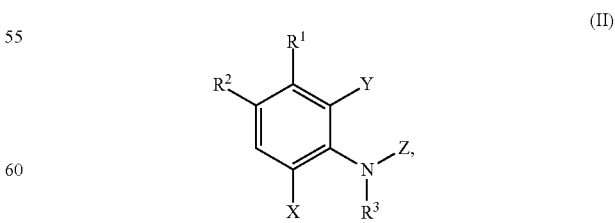

or a pharmaceutically acceptable salt thereof, wherein:
$R^1$ is selected from hydrogen, $C_1$-$C_3$alkoxy, $C_1$-$C_3$alkyl, cyano, $diC_1$-$C_3$alkylamino, halo, $haloC_1$-$C_3$alkoxy, $haloC_1$-$C_3$alkyl, hydroxy, and thienyl;

$R^2$ is selected from

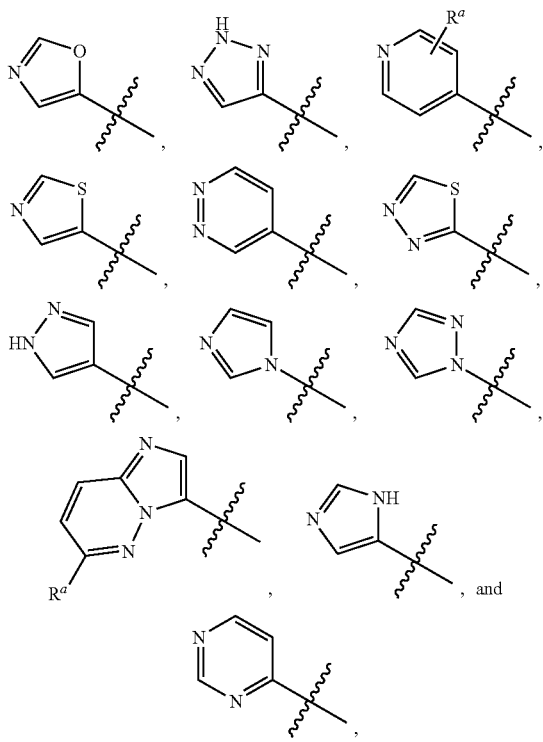

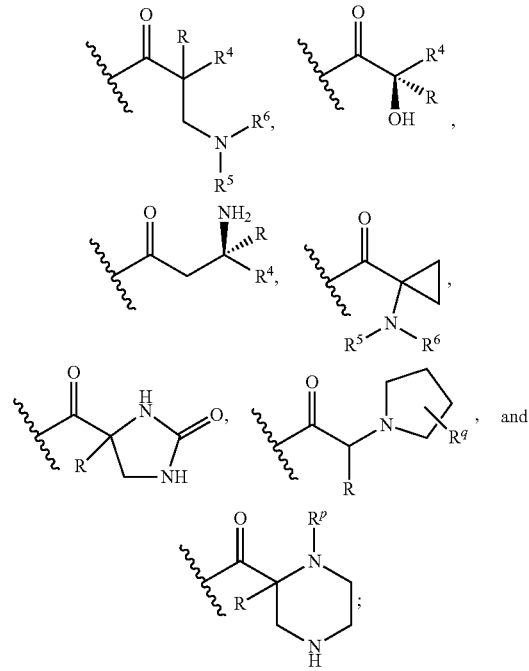

wherein $R^a$ is selected from hydrogen, $C_1$-$C_3$alkoxy, $C_1$-$C_3$alkylamino, $C_1$-$C_3$alkylcarbonylamino, amino, and halo;

$R^3$ is selected from hydrogen and $C_1$-$C_3$alkyl;

X is selected from hydrogen, $C_1$-$C_3$alkoxy, $C_1$-$C_3$alkyl, cyano, halo, halo$C_1$-$C_3$alkyl,

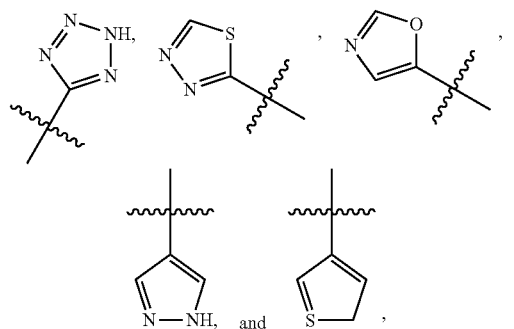

Y is selected from hydrogen and halo;

Z is selected from

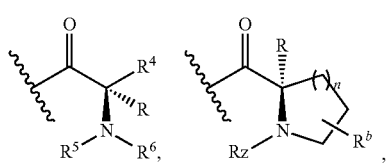

wherein n is 1 or 2;

R is selected from hydrogen and $C_1$-$C_3$alkyl;

$R^4$ is selected from $C_2$-$C_6$alkyl, $C_3$-$C_6$cycloalkyl, ($C_3$-$C_6$cycloalkyl)$C_1$-$C_3$alkyl, $C_{1-3}$alkylthio$C_{1-3}$alkyl, hydroxy$C_1$-$C_6$alkyl, and halo$C_1$-$C_6$alkyl;

$R^5$ and $R^6$ are independently selected from hydrogen, $C_1$-$C_3$alkyl, $C_1$-$C_3$alkylsulfonyl, $C_3$-$C_6$cycloalkyl optionally substituted with an amino group, heterocyclyl, heterocyclyl$C_1$-$C_3$alkyl, phenyl$C_1$-$C_3$alkyl, phenyl$C_1$-$C_3$alkylsulfonyl, and phenylsulfonyl; wherein the heterocyclyl, the heterocyclyl part of the heterocyclyl$C_1$-$C_3$alkyl, and the phenyl part of the phenyl$C_1$-$C_3$alkyl, phenyl$C_1$-$C_3$alkylsulfonyl, and the phenylsulfonyl are optionally substituted with one group selected from $C_1$-$C_3$alkyl, halo, hydroxy; or $R^5$ and $R^6$, together with the nitrogen atom to which they are attached, form a five- or six-membered heterocyclic ring optionally containing a second nitrogen atom and optionally substituted with an amino group;

$R^b$ is selected from hydrogen, $C_1$-$C_3$alkoxy, $C_1$-$C_3$alkyl, halo, and halo$C_1$alkyl;

$R^p$ is selected from hydrogen and $C_1$-$C_3$alkyl;

$R^q$ is selected from hydrogne and oxo; and $R^z$ is selected from hydrogen, $C_1$-$C_3$alkyl, and $C_1$-$C_3$alkylcarbonyl;

or a pharmaceutically acceptable salt thereof.

6. A method for inhibiting the activity of AAK1, the method comprising administering to a patient in need thereof a therapeutically effective amount of a compound of formula (II)

(II)

or a pharmaceutically acceptable salt thereof, wherein:

$R^1$ is selected from hydrogen, $C_1$-$C_3$alkoxy, $C_1$-$C_3$alkyl, cyano, di$C_1$-$C_3$alkylamino, halo, halo$C_1$-$C_3$alkoxy, halo$C_1$-$C_3$alkyl, hydroxy, and thienyl;

$R^2$ is selected from wherein $R^a$ is selected from hydrogen, $C_1$-$C_3$alkoxy, $C_1$-$C_3$alkylamino, $C_1$-$C_3$alkylcarbonylamino, amino, and halo;

$R^3$ is selected from hydrogen and $C_1$-$C_3$alkyl;

X is selected from hydrogen, $C_1$-$C_3$alkoxy, $C_1$-$C_3$alkyl, cyano, halo, halo$C_1$-$C_3$alkyl, Y is selected from hydrogen and halo;
Z is selected from wherein
n is 1 or 2;
R is selected from hydrogen and $C_1$-$C_3$alkyl;
R is selected from hydrogen and $C_1$-$C_3$alkyl;
$R^4$ is selected from $C_2$-$C_6$alkyl, $C_3$-$C_6$cycloalkyl, ($C_3$-$C_6$cycloalkyl)$C_1$-$C_3$alkyl, $C_{1-3}$alkylthio$C_{1-3}$alkyl, hydroxy$C_1$-$C_6$alkyl, and halo$C_1$-$C_6$alkyl;
$R^5$ and $R^6$ are independently selected from hydrogen, $C_1$-$C_3$alkyl, $C_1$-$C_3$alkylsulfonyl, $C_3$-$C_6$cycloalkyl optionally substituted with an amino group, heterocyclyl, heterocyclyl$C_1$-$C_3$alkyl, phenyl$C_1$-$C_3$alkyl, phenyl$C_1$-$C_3$alkylsulfonyl, and phenylsulfonyl; wherein the heterocyclyl, the heterocyclyl part of the heterocyclyl$C_1$-$C_3$alkyl, and the phenyl part of the phenyl$C_1$-$C_3$alkyl, phenyl$C_1$-$C_3$alkylsulfonyl, and the phenylsulfonyl are optionally substituted with one group selected from $C_1$-$C_3$alkyl, halo, hydroxy; or
$R^5$ and $R^6$, together with the nitrogen atom to which they are attached, form a five- or six-membered heterocyclic ring optionally containing a second nitrogen atom and optionally substituted with an amino group;
$R^b$ is selected from hydrogen, $C_1$-$C_3$alkoxy, $C_1$-$C_3$alkyl, halo, and halo$C_1$alkyl;

$R^p$ is selected from hydrogen and $C_1$-$C_3$alkyl;
$R^q$ is selected from hydrogne and oxo; and
$R^z$ is selected from hydrogen, $C_1$-$C_3$alkyl, and $C_1$-$C_3$alkylcarbonyl;
or a pharmaceutically acceptable salt thereof.

* * * * *

UNITED STATES PATENT AND TRADEMARK OFFICE
CERTIFICATE OF CORRECTION

PATENT NO. : 10,253,027 B2
APPLICATION NO. : 14/902868
DATED : April 9, 2019
INVENTOR(S) : Richard Hartz et al.

Page 1 of 2

It is certified that error appears in the above-identified patent and that said Letters Patent is hereby corrected as shown below:

In the Claims

In Claim 2, Column 197, Line 20-26:

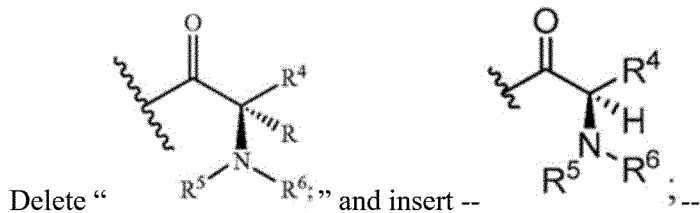

Delete " " and insert -- ; --

In Claim 4, Column 198, Line 55:
Below "methylpentanamide;" insert -- (R)-2-Amino-N-(3-(methoxy)-4-(6-(methylamino)imidazo[1,2-b]pyridazin-3-yl)phenyl)-4-methylpentanamide; --

In Claim 4, Column 199, Line 29:
Delete "(methyl sulfonamido)" and insert -- (methylsulfonamido) --

In Claim 5, Column 201, Line 49-55:

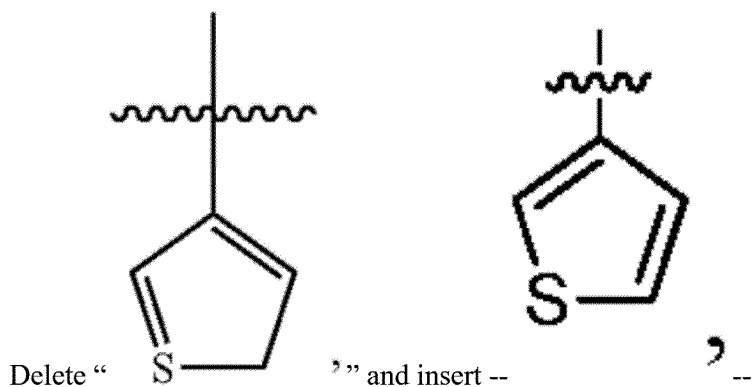

Delete " " and insert -- ; --

Signed and Sealed this
Second Day of February, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,253,027 B2

In Claim 5, Column 202, Line 57:
Delete "hydrogne" and insert -- hydrogen --

In Claim 6, Column 204, Line 2-8:

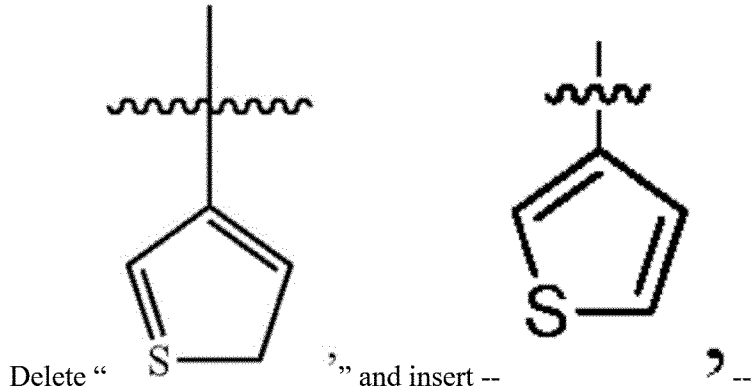

Delete " " and insert -- --

In Claim 6, Column 204, Line 14-20:

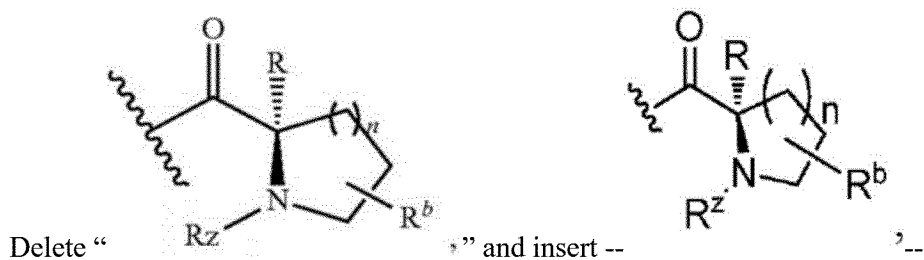

Delete " " and insert -- --

In Claim 6, Column 204, Line 47-48:
Delete "R is selected from hydrogen and $C_1$-$C_3$alkyl; R is selected from hydrogen and $C_1$-$C_3$alkyl;"
and insert -- R is selected from hydrogen and $C_1$-$C_3$alkyl; --

In Claim 6, Column 205, Line 2:
Delete "hydrogne" and insert -- hydrogen --